(12) United States Patent
Getman et al.

(10) Patent No.: US 6,683,210 B2
(45) Date of Patent: *Jan. 27, 2004

(54) BIS-AMINO ACID HYDROXYETHYLAMINO SULFONAMIDE RETROVIRAL PROTEASE INHIBITORS

(75) Inventors: Daniel P Getman, Chesterfield, MO (US); Gary A DeCrescenzo, St. Charles, MO (US); John N Freskos, Clayton, MO (US); Michael L Vazquez, Gurnee, IL (US); James A Sikorski, Des Peres, MO (US); Balekudru Devadas, Chesterfield, MO (US); Srinivasan Raj Nagarajan, Chesterfield, MO (US); David L Brown, Chesterfield, MO (US); Joseph J McDonald, Ballwin, MO (US)

(73) Assignee: G. D. Searle & Co., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/097,642

(22) Filed: Mar. 15, 2002

(65) Prior Publication Data

US 2003/0204097 A1 Oct. 30, 2003

Related U.S. Application Data

(63) Continuation of application No. 09/694,783, filed on Oct. 24, 2000, now Pat. No. 6,388,132, which is a continuation of application No. 09/495,334, filed on Feb. 1, 2000, now Pat. No. 6,316,496, which is a continuation of application No. 08/913,096, filed on Jan. 21, 1998, now Pat. No. 6,143,788, which is a continuation of application No. 08/479,071, filed on Jun. 7, 1995, now Pat. No. 6,150,556, which is a continuation-in-part of application No. 08/402,450, filed on Mar. 10, 1995, now abandoned.

(51) Int. Cl.[7] .................. C07C 311/03; C07C 311/16; A61K 31/18

(52) U.S. Cl. ............... 564/92; 564/90; 560/13; 549/366; 549/434; 549/437; 549/443; 549/467; 548/179; 548/309.7; 546/169; 514/311; 514/367; 514/394; 514/456; 514/464; 514/466; 514/467; 514/487; 514/602; 514/604

(58) Field of Search ............................ 514/311, 367, 514/394, 456, 464, 466, 467, 487, 602, 604; 546/169; 548/179, 309.7; 549/366, 434, 437, 443, 467; 560/13; 564/90, 92

(56) References Cited

U.S. PATENT DOCUMENTS

| | | |
|---|---|---|
| 4,450,164 A | 5/1984 | Bristol et al. |
| 4,477,441 A | 10/1984 | Boger et al. |
| 4,514,391 A | 4/1985 | Gordon et al. |
| 4,548,926 A | 10/1985 | Matsueda et al. |
| 4,595,407 A | 6/1986 | Carter |
| 4,599,198 A | 7/1986 | Hoover |
| 4,616,088 A | 10/1986 | Ryono et al. |
| 4,634,465 A | 1/1987 | Ehrenfreund et al. |
| 4,668,769 A | 5/1987 | Hoover |
| 4,668,770 A | 5/1987 | Boger et al. |
| 4,757,050 A | 7/1988 | Natarajan et al. |
| 4,880,938 A | 11/1989 | Freidinger |
| H725 H | 1/1990 | Gordon |
| 4,963,530 A | 10/1990 | Hemmi et al. |
| 4,977,277 A | 12/1990 | Rosenberg et al. |
| 5,585,397 A | 12/1996 | Tung et al. .................. 514/473 |
| 5,744,481 A | 4/1998 | Vezquez et al. ............. 514/311 |
| 5,968,942 A | 10/1999 | Vazquez et al. |
| 6,060,476 A | 5/2000 | Vazquez et al. |
| 6,143,788 A | 11/2000 | Getman et al. |
| 6,150,556 A | 11/2000 | Getman et al. |
| 6,316,496 B1 | 11/2001 | Getman et al. |
| 6,388,132 B1 * | 5/2002 | Getman et al. ............... 564/92 |

FOREIGN PATENT DOCUMENTS

| | | |
|---|---|---|
| EP | 0 114 993 | 8/1984 |
| EP | 0 172 347 | 2/1986 |
| EP | 0 223 437 | 5/1987 |
| EP | 0 264 795 | 4/1988 |
| EP | 0 337 714 | 10/1989 |
| EP | 0 342 541 | 11/1989 |
| EP | 0 346 847 | 12/1989 |
| EP | 0 356 223 | 2/1990 |
| EP | 0 389 898 | 10/1990 |
| EP | 0 393 445 | 10/1990 |
| EP | 0 393 457 | 10/1990 |
| EP | 0 402 646 | 12/1990 |
| EP | 0468 641 | 1/1992 |
| GB | 2184730 | 7/1987 |
| GB | 2200115 | 7/1988 |
| GB | 2209752 | 5/1989 |
| WO | WO 84/03044 | 8/1984 |
| WO | 92/08699 | 5/1992 |
| WO | WO 94 04492 | 3/1994 |
| WO | WO 94 04493 | 3/1994 |
| WO | 94/05639 | 3/1994 |
| WO | WO 94 10134 | 11/1994 |
| WO | WO 95 06030 | 2/1995 |
| WO | WO 95 33464 | 12/1995 |
| WO | WO 00 42060 | 7/2000 |

OTHER PUBLICATIONS

European Search Report dated Jan. 29, 2002.

(List continued on next page.)

*Primary Examiner*—Shailendra Kumar
(74) *Attorney, Agent, or Firm*—Banner & Witcoff, Ltd.

(57) ABSTRACT

Selected bis-amino acid hydroxyethylamino sulfonamide compounds are effective as retroviral protease inhibitors, and in particular as inhibitors of HIV protease. The present invention relates to such retroviral protease inhibitors and, more particularly, relates to selected novel compounds, composition and method for inhibiting retroviral proteases, such as human immunodeficiency virus (HIV) protease prophylactically preventing retroviral infection or the spread of a retrovirus, and treatment of a retroviral infection.

28 Claims, No Drawings

OTHER PUBLICATIONS

International Search Report of PCT/US96/02685 dated Jul. 25, 1996.
Roberts et al., *Science*, 248, 358 (1990).
Erickson et al., *Science*, 249, 527 (1990).
Pearl et al., *Nature*, 328 (1987).
Martin, *Drugs of the Future*, 1991, 16(3), 210–212.
Meek et al., *Science*, 343:90–92, (1990).
Rich et al., Pept. Struct., Funct. Proc. Am. Pept. Sym., $8^{th}$ ed. pp. 511–520 (1983).
Rosenberg et al., *J. Med. Chem.*, 30, 122401228 (1987).
Fittkau, *J. Prakt. Chem.*, 315, 1037 (1973).
Hirsh et al., *N. Eng. J. Med.*, 328, 1686 (1993).
E.E. Gilbert, "*Recent Developments in Preparative Sulfonation and Sulfation*", Sunthesis, 3 (1969).
Silcox et al., *J. Heterocycle. Chem.*, 4, 166–67 (1967).
Cabiddu et al., *Synthesis*, 797–798 (1976).
Ncube et al., *Tet. Lett.* 26, 2345, 2348 (1978).
Ncube et al., *Tet., Let.*, 3, 255–256 (1977).
Cole et al., *Aust. J. Chem.*, 33, 657–80 (1980).

* cited by examiner

BIS-AMINO ACID HYDROXYETHYLAMINO SULFONAMIDE RETROVIRAL PROTEASE INHIBITORS

CROSS-REFERENCE TO RELATED APPLICATIONS

This is a continuation of Ser. No. 09/694,783, filed Oct. 24, 2000, now U.S. Pat. No. 6,388,132, which is a continuation of Ser. No. 09/495,334, filed Feb. 1, 2000, now U.S. Pat. No. 6,316,496 B1, which is a continuation of Ser. No. 08/913,096, filed Jan. 21, 1998, now U.S. Pat. No. 6,143,788 B1, which is a continuation of Ser. No. 08/479,071, filed Jun. 7, 1995, now U.S. Pat. No. 6,150,556, which is a continuation-in-part of Ser. No. 08/402,450, filed Mar. 10, 1995, now abandoned, all of which are incorporated by reference herein in their entirety.

BACKGROUND OF THE INVENTION

The present invention relates to retroviral protease inhibitors and, more particularly, relates to novel compounds, composition and method for inhibiting retroviral proteases, such as human immunodeficiency virus (HIV) protease. This invention, in particular, relates to bis-amino acid hydroxyethylamine sulfonamide protease inhibitor compounds, composition and method for inhibiting retroviral proteases, prophylactically preventing retroviral infection or the spread of a retrovirus, and treatment of a retroviral infection, e.g., an HIV infection. The subject invention also relates to processes for making such compounds as well as to intermediates useful in such processes.

During the replication cycle or gene transcription products are translated as proteins. These proteins are subsequently processed by a virally encoded protease (or proteinase) to yield viral enzymes and structural proteins of the virus core. Most commonly, the gag precursor proteins are processed into the core proteins and the pal precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pal gene of HIV prevents processing of the gag precursor protein. It has also been shown through site-directed mutagenesis of an aspartic acid residue in the HIV protease active site that processing of the gag precursor protein is prevented. Thus, attempts have been made to inhibit viral replication by inhibiting the action of retroviral proteases.

Retroviral protease inhibition typically involves a transition-state mimetic whereby the retroviral protease is exposed to a mimetic compound which binds (typically in a reversible manner) to the enzyme in competition with the gag and gag-pol proteins to thereby inhibit specific processing of structural proteins and the release of retroviral protease itself. In this manner, retroviral replication proteases can be effectively inhibited.

Several classes of compounds have been proposed, particularly for inhibition of proteases, such as for inhibition of HIV protease. Such compounds include hydroxyethylamine isosteres and reduced amide isosteres. See, for example, EP O 346 847; EP O 342,541; Roberts et al, "Rational Design of Peptide-Based Proteinase Inhibitors," Science, 248, 35 (1990); and Erickson et al, "Design Activity, and 2.8 Å Crystal Structure of a C₂ Symmetric Inhibitor Complexed to HTV-1 Protease," Science, 249, 527 (1990). U.S. Pat. No. 5,157,041, WO 94/04491, WO 94/04492, WO 94/64493, WO 9/05639, WO 92/08701 and U.S. patent application Ser. No. 08/294,468, filed Aug. 23, 1994, (each of which is incorporated herein by reference in its entirety) for example describe hydroxyethylamine, hydroxyethylurea or hydroxyethyl sulfonamide isostere containing retroviral protease inhibitors.

Several classes of compounds are known to be useful as inhibitors of the proteolytic enzyme renin. See, for example, U.S. Pat. No. 4,599,198; U.K. 2,184,730; G.B. 2,209,752; EP 0 264 795; G.B. 2,200,115 and U.S. SIR H725. Of these, G.B. 2,200,115, GB 2,209,752, EP O 264,795, U.S. SIR H725 and U.S. Pat. No. 4,599,198 disclose urea-containing hydroxyethylamine renin inhibitors. EP 468 641 discloses renin inhibitors and intermediates for the preparation of the inhibitors which include sulfonamide-containing hydroxyethylamine compounds, such as 3-(t-butoxycarbonyl)amino-cyclohexyl-1-(phenylsulfonyl)amino-2(5)-butanol. G.B. 2,200,115 also discloses sulfamoyl-containing hydroxyethylamine renin inhibitors, and EP 0264 795 discloses certain sulfonamide-containing hydroxyethylamine renin inhibitors. However, it is known that, although renin and HIV proteases are both classified as aspartyl proteases, compounds which are effective renin inhibitors generally are not predictive for effective HIV protease inhibition.

BRIEF DESCRIPTION OF THE INVENTION

The present invention relates to selected retroviral protease inhibitor compounds, analogs and pharmaceutically acceptable salts, esters and prodrugs thereof. The subject compounds are characterized as bis amino acid hydroxyethylamine sulfonamide inhibitor compounds. The invention compounds advantageously inhibit retroviral proteases, such as human immunodeficiency virus (HIV) protease. Therefore, this invention also encompasses pharmaceutical compositions, methods for inhibiting retroviral proteases and methods for treatment or prophylaxis of a retroviral infection, such as an HIV infection. The subject invention also relates to processes for making such compounds as well as to intermediates useful in such processes.

DETAILED DESCRIPTION OF THE INVENTION

In accordance with the present invention, there is provided a retroviral protease inhibiting compound of the formula:

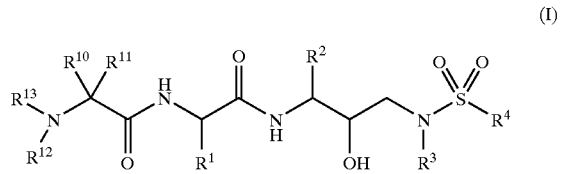

(I)

or a pharmaceutically acceptable salt, prodrug or ester thereof, wherein $R^1$ represents alkyl, alkenyl, alkynyl, hydroxyalkyl, alkoxyalkyl, cyanoalkyl, imidazolylmethyl, —CH$_2$CONH$_2$, —CH$_2$CH$_2$CONH$_2$, —CH$_2$S(O)$_2$NH$_2$, —CH$_2$SCH$_3$, —CH$_2$S(O)CH$_3$, —CH$_2$S(O)$_2$CH$_3$, —C(CH$_3$)$_2$SCH$_3$, —C(CH$_3$)$_2$S(O)CH$_3$ or —C(CH$_3$)$_2$S(O)$_2$CH$_3$ radicals; preferably, $R^1$ represents alkyl of 1–5 carbon atoms, alkenyl of 2–5 carbon atoms, alkynyl of 2–5 carbon atoms, hydroxyalkyl of 1–3 carbon atoms, alkoxyalkyl of 1–3 alkyl and 1–3 alkoxy carbon atoms, cyanoalkyl of 1–3 alkyl carbon atoms, imidazolylmethyl, —CH$_2$CONH$_2$, —CH$_2$CH$_2$CONH$_2$, —CH$_2$S(O)$_2$NH$_2$, —CH$_2$SCH$_3$, —CH$_2$S(O)CH$_3$, —CH$_2$S(O)$_2$CH$_3$, —C(CH$_3$)$_2$SCH$_3$, —C(CH$_3$)$_2$S(O)CH$_3$ or —C(CH$_3$)$_2$S(O)$_2$CH$_3$ radicals; more preferably, $R^1$ represents alkyl of 1–4 carbon atoms, alkenyl of 2–3 carbon atoms, aryl of 3–4 carbon atoms, cyanomethyl, imidazolylmethyl, —CH$_2$CONH$_2$, —CH$_2$CH$_2$CONH$_2$, —CH$_2$S(O)$_2$NH$_2$, —CH$_2$SCH$_3$, —CH$_2$S(O)CH$_3$, —CH$_2$S(O)$_2$CH$_3$, —C(CH$_3$)$_2$SCH$_3$, —C(CH$_3$)$_2$S(O) CH$_3$ or —C(CH$_3$)$_2$S(O)$_2$CH$_3$ radicals; and most preferably, $R^1$ represents sec-butyl, tert-butyl, isopropyl, 3-propynyl, cyanomethyl or —C(CH$_3$)$_2$S(O)$_2$ CH$_3$ radicals;

$R^2$ represents alkyl, aralkyl, alkylthioalkyl, arylthioalkyl or cycloalkylalkyl radicals; preferably, $R^2$ represents radicals of alkyl of 1–5 carbon atoms, aralkyl of 1–3 alkyl carbon atoms, alkylthioalkyl of 1–3 alkyl carbon atoms, arylthioalkyl of 1–3 alkyl carbon atoms or cycloalkylalkyl of 1–3 alkyl carbon atoms and 3–6 ring member carbon atoms; more preferably, $R^2$ represents radicals of alkyl of 3–5 carbon atoms, arylmethyl, alkylthioalkyl of 1–3 alkyl carbon atoms, arylthiomethyl or cycloalkylmethyl of 5–6 ring member carbon atoms radicals; even more preferably, $R^2$ represents isobutyl, n-butyl, CH$_3$5CH$_2$CH$_2$—, benzyl, phenylthiomethyl, (2-naphthylthio)methyl, 4-methoxyphenylmethyl, 4-hydroxyphenylmethyl, 4-fluorophenylmethyl or cyclohexylmethyl radicals; even more preferably, $R^2$ represents benzyl, 4-fluorophenylmethyl or cyclohexylmethyl radicals; most preferably, $R^2$ represents benzyl;

$R^3$ represents alkyl, cycloalkyl or cycloalkylalkyl radicals; preferably, $R^3$ represents radicals of alkyl radical of 1–5 carbon atoms, cycloalkyl of 5–8 ring members or cycloalkylmethyl radical of 3–6 ring members; more preferably, $R^3$ represents propyl, isoamyl, isobutyl, butyl, cyclopentylmethyl, cyclohexylmethyl, cyclohexyl or cycloheptyl radicals; more preferably $R^3$ represents isobutyl or cyclopentylmethyl radicals;

$R^4$ represents aryl, heteroaryl or heterocyclo radicals provided $R^{11}$ is other than a hydrogen radical and $R^4$ represents heterocyclo or benzo fused heteroaryl radicals provided $R^{11}$ is a hydrogen radical; preferably, $R^4$ represents aryl, benzo fused 5 to 6 ring member heteroaryl or benzo fused 5 to 6 ring member heterocyclo radicals provided $R^{11}$ is other than a hydrogen radical and $R^4$ represents benzo fused 5 to 6 ring member heteroaryl or benzo fused 5 to 6 ring member heterocyclo radicals provided $R^{11}$ is a hydrogen radical; or $R^4$ represents a radical of the formula

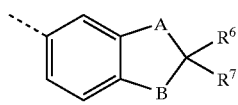

wherein A and B each independently represent O, S, SO or SO$_2$; preferably, A and H each represent O;

$R^6$ represents deuterium, alkyl or halogen radicals; preferably, $R^6$ represents deuterium, alkyl of 1–5 carbon atoms, fluoro or chloro radicals; more preferably $R^6$ represents deuterium, methyl, ethyl, propyl, isopropyl or fluoro radicals;

$R^7$ represents hydrogen, deuterium, alkyl or halogen radicals; preferably, $R^7$ represents hydrogen, deuterium, alkyl of 1–3 carbon atoms, fluoro or chloro radicals; more preferably, $R^7$ represents hydrogen, deuterium, methyl or fluoro radicals; or $R^6$ and $R^7$ each independently represent fluoro or chloro radicals; and preferably, $R^6$ and $R^7$ each represent a fluoro radical; or $R^4$ represents a radical of the formula

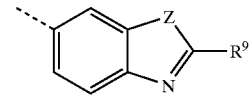

wherein Z represents O, S or NH; and $R^9$ represents a radical of formula

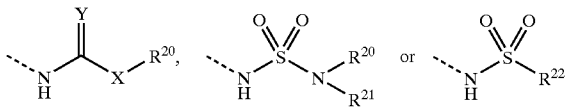

wherein Y represents O, S or NH; X represents a bond, O or NR$^{21}$;

$R^{20}$ represents hydrogen, alkyl, alkenyl, alkynyl, aralkyl, heteroaralkyl, heterocycloalkyl, aminoalkyl, N-monosubstituted or N,N-disubstituted aminoalkyl wherein said substituents are alkyl or aralkyl radicals, carboxyalkyl, alkoxycarbonylalkyl, cyanoalkyl or hydroxyalkyl radicals; preferably, $R^{20}$ represents hydrogen, alkyl of 1 to 5 carbon atoms, alkenyl of 2 to 5 carbon atoms, alkynyl of 2 to 5 carbon atoms, aralkyl of 1 to 5 alkyl carbon atoms, heteroaralkyl of 5 to 6 ring members and 1 to 5 alkyl carbon atoms, heterocycloalkyl of 5 to 6 ring members and 1 to 5 alkyl carbon atoms, aminoalkyl of 2 to 5 carbon atoms, N-monosubstituted or N,N-disubstituted aminoalkyl of 2 to 5 alkyl carbon atoms wherein said substituents are radicals of alkyl of 1 to 3 carbon atoms, aralkyl of 1 to 3 alkyl carbon atoms radicals, carboxyalkyl of 1 to 5 carbon atoms, alkoxycarbonylalkyl of 1 to 5 alkyl carbon atoms, cyanoalkyl of 1 to 5 carbon atoms or hydroxyalkyl of 2 to 5 carbon atoms; more preferably, $R^{20}$ represents hydrogen, alkyl of 1 to 5 carbon atoms, phenylalkyl of 1 to 3 alkyl carbon atoms, heterocycloalkyl of 5 to 6 ring members and 1 to 3 alkyl carbon atoms, or N-mono-substituted or N,N-disubstituted aminoalkyl of 2 to 3 carbon atoms wherein said substituents are alkyl radicals of 1 to 3 carbon atoms; and most preferably, $R^{20}$ represents hydrogen, methyl, ethyl, propyl, isopropyl, isobutyl, benzyl, 2-(1-pyrrolidinyl)ethyl, 2-(1-piperidinyl)ethyl, 2-(1-piperazinyl)ethyl, 2-(4-methylpiperazin-1-yl)ethyl, 2-(1-morpholinyl)ethyl, 2-(1-thiamorpholinyl) ethyl or 2-(N,N-dimethylamino)ethyl radicals;

$R^{21}$ represents hydrogen or alkyl radicals; preferably, $R^{21}$ represents hydrogen radical or alkyl radical of 1 to 3 carbon atoms; more preferably, $R^{21}$ represents hydrogen or methyl radicals; and most preferably, $R^{21}$ represents a hydrogen radical; or the radical of formula —NR$^{20}$R$^{21}$ represents a heterocyclo radical; preferably, the radical of formula —NR$^{20}$R$^{21}$ represents a 5 to 6 ring member heterocyclo radical; more preferably, the radical of formula —NR$^{20}$R$^{21}$ represents pyrrolidinyl, piperidinyl, piperazinyl, 4-methylpiperazinyl, 4-benzylpiperazinyl, morpholinyl or thiamorpholinyl radicals; and $R^{22}$ represents alkyl or $R^{20}R^{21}$N-alkyl radicals; preferably, $R^{22}$ represents alkyl or $R^{20}R^{21}$N-alkyl radicals wherein alkyl is 1 to 3 carbon atoms; and more preferably, $R^{22}$ represents alkyl radical of 1 to 3 carbon atoms; and preferably $R^4$ represents phenyl, 2-naphthyl, 4-methoxyphenyl, 4-hydroxyphenyl, 3,4-dimethoxyphenyl, 3-aminophenyl or 4-aminophenyl radicals provided $R^{11}$ is other than a hydrogen radical, or $R^4$ represents benzothiazol-5-yl, benzothiazol-6-yl, 2-amino-benzothiazol-5-yl, 2-(methoxycarbonylamino)benzothiazol-5-yl, 2-amino-benzothiazol-6-yl, 2-(methoxycarbonylamino)benzothiazol-6-yl, 5-benzoxazolyl, 6-benzoxazolyl, 6-benzopyranyl, 3,4-dihydrobenzofuran-6-yl, 7-benzopyranyl, 3,4-dihydrobenzofuran-7-yl, 2,3-dihydrobenzofuran-5-yl, benzofuran-5-yl, 1,3-benzodioxol-5-yl, 2-methyl-1,3-benzodioxol-5-yl, 2,2-dimethyl-1,3-benzodioxol-5-yl, 2,2-dideutero-1,3-benzodioxol-5-yl, 2,2-difluoro-1,3-benzodioxol-5-yl, 1,4-benzodioxon-6-yl, 5-benzimidazolyl, 2-(methoxycarbonylamino) benzimidazol-5-yl, 6-quinolinyl, 7-quinolinyl, 6-isoquinolinyl or 7-isoquinolinyl radicals; more preferably, $R^4$ represents phenyl, 2-naphthyl, 4-methoxyphenyl or 4-hydroxyphenyl radicals provided $R^{11}$ is other than a hydrogen radical, or $R^4$ represents benzothiazol-5-yl, benzothiazol-6-yl, benzoxazol-5-yl, 2,3-dihydrobenzofuran-5-yl, benzofuran-5-yl, 1,3-benzodioxol-5-yl, 2-methyl-1,3-benzodioxol-5-yl, 2,2-dimethyl-1,3-benzodioxol-5-yl, 2,2-dideutero-1,3-benzodioxol-5-yl, 2,2-difluoro-1,3-benzodioxol-5-yl, 1,4-benzodioxan-6-yl, 2-(methoxycarbonylamino)benzothiazol-5-yl, 2-(methoxycarbonylamino)benzothiazol-6-yl or 2-(methoxycarbonylamino)benzimidazol-5-yl radicals; and most preferably, $R^4$ represents phenyl, 4-methoxyphenyl or 4-hydroxyphenyl radicals provided $R^{11}$ is other than a hydrogen radical, or $R^4$ represents benzothiazol-5-yl, benzothiazol-6-yl, 2,3-dihydrobenzofuran-5-yl, benzofuran-5-yl, 1,3-benzodioxol-5-yl, 2-methyl-1,3-benzodioxol-5-yl, 2,2-dimethyl-1,3-benzodioxol-5-yl, 2,2-dideutero-1,3-benzodioxol-5-yl, 2,2-difluoro-1,3-benzodioxol-5-yl, 1,4-benzodioxon-6-yl, 2-(methoxycarbonylamino) benzothiazol-6-yl or 2-(methoxycarbonylamino) benzimidazol-5-yl radicals;

$R^{10}$ represents hydrogen, alkyl, hydroxyalkyl or alkoxyalkyl radicals; preferably, $R^{10}$ represents hydrogen, alkyl, hydroxyalkyl or alkoxyalkyl radicals, wherein alkyl and alkoxy are each 1–3 carbon atoms; more preferably, $R^{10}$ represents hydrogen, methyl, ethyl, propyl, hydroxymethyl, hydroxyethyl, methoxymethyl or methoxyethyl radicals; most preferably, $R^{10}$ represents hydrogen, methyl or ethyl radicals;

$R^{11}$ represents hydrogen, alkyl, hydroxyalkyl, alkoxyalkyl, aralkyl, heteroaralkyl, alkylthioalkyl or the sulfone or sulfoxide derivatives thereof, —$CH_2CH_2CONH_2$ or —$CH_2CONH_2$ radicals; preferably, $R^{11}$ represents hydrogen, alkyl of 1–5 carbon atoms, hydroxyalkyl of 1–4 carbon atoms, alkoxyalkyl of 1–4 alkyl carbon atoms, benzyl, imidazolylmethyl, —$CH_2CH_2CONH_2$, —$CH_2CONH_2$, —$CH_2CH_2SCH_3$ or —$CH_2SCH_3$ radicals or the sulfone or sulfoxide derivatives thereof; more preferably, $R^{11}$ represents hydrogen, methyl, ethyl, propyl, isopropyl, butyl, secbutyl, isobutyl, tertbutyl, hydroxymethyl, hydroxyethyl, methoxymethyl or methoxyethyl radicals; most preferably, $R^{11}$ represents hydrogen, methyl or ethyl radicals; and $R^{12}$ and $R^{13}$ each independently represent hydrogen, alkyl, aralkyl, heteroaralkyl, cycloalkyl, cycloalkylalkyl, hydroxyalkyl, alkoxyalkyl, aryl or heteroaryl radicals; preferably, $R^{12}$ and $R^{13}$ each independently represent hydrogen, alkyl, aralkyl, heteroaralkyl, cycloalkyl, cycloalkylalkyl, hydroxyalkyl, alkoxyalkyl, aryl or heteroaryl radicals, wherein alkyl is 1–5 carbon atoms, cycloalkyl is 3–6 ring member cycloalkyl optionally benzo fused, and heteroaryl is 5 to 6 ring member heteroaryl optionally benzo fused; more preferably, $R^{12}$ and $R^{13}$ each independently represent hydrogen, alkyl of 1–5 carbon atoms, phenylalkyl of 1–3 alkyl carbon atoms, 5 to 6 ring member heteroaralkyl of 1–3 alkyl carbon atoms, cycloalkyl of 3–6 ring members, cycloalkylmethyl of 3–6 ring members, hydroxyalkyl of 1–3 carbon atoms, methoxyalkyl of 1–3 alkyl carbon atoms or phenyl radicals; even more preferably, $R^{12}$ and $R^{13}$ each independently represent hydrogen, methyl, ethyl, propyl, isopropyl, cyclopropyl, cyclobutyl, cyclopentyl, cyclohexyl, cyclohexylmethyl, benzyl, phenylethyl, 2-pyridylmethyl, 3-pyridylmethyl, 4-pyridylmethyl, 2-(2-pyridyl)ethyl, 2-(3-pyridyl)ethyl, 2-(4-pyridyl) ethyl, furylmethyl, 2-furylethyl, 2-hydroxyethyl, 2-methoxyethyl or phenyl radicals; east preferably, $R^{12}$ represents hydrogen or methyl radicals; and most preferably, $R^{13}$ represents hydrogen, methyl, ethyl, propyl, cyclopropyl, isopropyl, benzyl, 2-phenylethyl, 2-pyridylmethyl, 3-pyridylmethyl, 4-pyridylmethyl, 2-(2-pyridyl)ethyl, 2-(3-pyridyl)ethyl, 2-(4-pyridyl) ethyl, furylmethyl, 2-furylethyl or 2-methoxyethyl radicals.

Another family of compounds of interest within Formula I as defined above wherein $R^4$ represents aryl, heteroaryl or heterocyclo radicals provided $R^{11}$ is other than hydrogen or alkyl radicals, and $R^4$ represents heterocyclo or benzo fused heteroaryl radicals provided $R^{11}$ is a hydrogen or alkyl radical; preferably, $R^4$ represents aryl, benzo fused 5 to 6 ring member heteroaryl or benzo fused 5 to 6 ring member heterocyclo radicals provided $R^{11}$ is other than hydrogen or alkyl radicals, and $R^4$ represents benzo fused 5 to 6 ring member heteroaryl or benzo fused 5 to 6 ring member heterocyclo radicals provided $R^{11}$ is a hydrogen or alkyl radical.

The absolute stereochemistry of the carbon atom of —CH(OH)— group is preferably (R). The absolute stereochemistry of the carbon atom of —CH($R^1$)— group is preferably (S). The absolute stereochemistry of the carbon atom of —CH($R^2$)— groups is preferably (S).

A family of compounds of particular interest within Formula I are compounds embraced by the formula

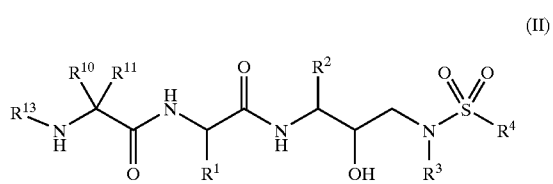

(II)

or a pharmaceutically acceptable salt, prodrug or ester thereof, wherein n, $R^1$, $R^2$, $R^3$, $R^9$, $R^{10}$, $R^{11}$, and $R^{13}$ are as defined above.

A family of compounds of further interest within Formula II are compounds embraced by the formula

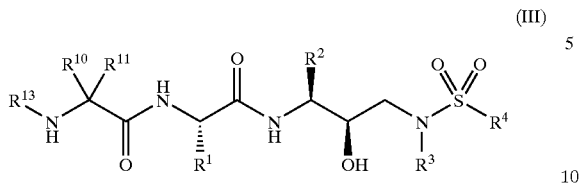

(III)

or a pharmaceutically acceptable salt, prodrug or ester thereof, wherein $R^1$, $R^2$, $R^3$, $R^9$, $R^{10}$, $R^{11}$, and $R^{13}$ are as defined above.

A more preferred family of compounds within Formula III consists of compounds or a pharmaceutically acceptable salt, prodrug or ester thereof, wherein $R^1$ represents sec-butyl, tert-butyl, iso-propyl, 3-propynyl, cyanomethyl or —$C(CH_3)_2S(O)_2CH_3$ radicals;

$R^2$ represents a benzyl radical;

$R^3$ represents propyl, isoamyl, isobutyl, butyl, cyclohexyl, cycloheptyl, cyclopentylmethyl or cyclohexylmethyl radicals; and $R^4$ is as defined above;

$R^{10}$ represents hydrogen, methyl, ethyl, propyl, hydroxymethyl or hydroxyethyl radicals;

$R^{11}$ represents hydrogen, methyl, ethyl, propyl, isopropyl, butyl, secbutyl, isobutyl, tertbutyl, hydroxymethyl, hydroxyethyl, methoxymethyl or methoxyethyl radicals; and $R^{13}$ represents hydrogen, methyl, ethyl, propyl, isopropyl, cyclopropyl, cyclobutyl, cycloheptyl, cyclohexyl, cyclohexylmethyl, benzyl, phenylethyl, 2-pyridylmethyl, 3-pyridylmethyl, 4-pyridylmethyl, 2-(2-pyridyl)ethyl, 2-(3-pyridyl)ethyl, 2-(4-pyridyl) ethyl, furylethyl, 2-furylethyl, 2-hydroxyethyl, 2-methoxyethyl or phenyl radicals.

Compounds of interest include the following:

2S-[[(N-methylamino)acetyl]amino]-N-[2R-hydroxy-3-[[(1,3-benzodioxol-5-yl)sulfonyl](2-methylpropyl) amino]-1S-(phenylmethyl)propyl]-3,3-dimethyl-butanamide;

2S-[[(N-methylamino)acetyl]amino]-N-[2R-hydroxy-3-[[(1,3-benzodioxol-5-yl)sulfonyl](2-methylpropyl) amino]-1S-(phenylmethyl)propyl]-3-methyl-butanamide;

2S-[[(N-methylamino)acetyl]amino]-N-[2R-hydroxy-3-[[(1,3-benzodioxol-5-yl)sulfonyl](2-methylpropyl) amino]-1S-(phenylmethyl)propyl]-3-cyanopropanamide;

2S-[[(N-methylamino)acetyl]amino]-N-[2R-hydroxy-3-[[(1,3-benzodioxol-5-yl)sulfonyl](2-methylpropyl) amino]-1S-(phenylmethyl)propyl]-3S-methyl-pentanamide;

2S-[[(N-methylamino)acetyl]amino]-N-[2R-hydroxy-3-[[(1,3-benzodioxol-5-yl)sulfonyl](2-methylpropyl) amino]-1S-(phenylmethyl)propyl]-4-pentynamide;

2S-[[(N-methylamino)acetyl]amino]-N-[2R-hydroxy-3-[[(benzofuran-5-yl)sulfonyl](2-methylpropyl)amino]-1S-(phenylmethyl)propyl]-3,3-dimethyl-butanamide;

2S-[[(N-methylamino)acetyl]amino]-N-[2R-hydroxy-3-[[(benzofuran-5-yl)sulfonyl](2-methylpropyl)amino]-1S-(phenylmethyl)propyl]-3-methyl-butanamide;

2S-[[(N-methylamino)acetyl]amino]-N-[2R-hydroxy-3-[[(benzofuran-5-yl)sulfonyl](2-methylpropyl)amino]-1S-(phenylmethyl)propyl]-3-cyanopropanamide;

2S-[[(N-methylamino)acetyl]amino]-N-[2R-hydroxy-3-[[(benzofuran-5-yl)sulfonyl](2-methylpropyl)amino]-1S-(phenylmethyl)propyl]-3S-methyl-pentanamide;

2S-[[(N-methylamino)acetyl]amino]-N-[2R-hydroxy-3-[[(benzofuran-5-yl)sulfonyl](2-methylpropyl)amino]-1S-(phenylmethyl)propyl]-4-pentynamide;

2S-[[(N-methylamino)acetyl]amino]-N-[2R-hydroxy-3-[[(2-methyl-1,3-benzodioxol-5-yl)sulfonyl](2-methylpropyl)amino]-1S-(phenylmethyl)propyl]-3,3-dimethyl-butanamide;

2S-[[(N-methylamino)acetyl]amino]-N-[2R-hydroxy-3-[[(2-methyl-1,3-benzodioxol-5-yl)sulfonyl](2-methylpropyl)amino]-1S-(phenylmethyl)propyl]-3-methyl-butanamide;

2S-[[(N-methylamino)acetyl]amino]-N-[2R-hydroxy-3-[[(2-methyl-1,3-benzodioxol-5-yl)sulfonyl](2-methylpropyl)amino]-1S-(phenylmethyl)propyl]-3-cyanopropanemide;

2S-[[(N-methylamino)acetyl]amino]-N-[2R-hydroxy-3-[[(2-methyl-1,3-benzodioxol-5-yl)sulfonyl](2-methylpropyl)amino]-1S-(phenylmethyl)propyl]-3S-methyl-pentanamide;

2S-[[(N-methylamino)acetyl]amino]-N-[2R-hydroxy-3-[[(2-methyl-1,3-benzodioxol-5-yl)sulfonyl](2-methylpropyl)amino]-1S-(phenylmethyl)propyl]-4-pentynamide;

2S-[[(N-methylamino)acetyl]amino]-N-[2R-hydroxy-3-[[(2,3-dihydrobenzofuran-5-yl)sulfonyl](2-methylpropyl)amino]-1S-(phenylmethyl)propyl]-3,3-dimethyl-butanamide;

2S-[[(N-methylamino)acetyl]amino]-N-[2R-hydroxy-3-[[(2,3-dihydrobenzofuran-5-yl)sulfonyl](2-methylpropyl)amino]-1S-(phenylmethyl)propyl]-3-methyl-butanamide;

2S-[[(N-methylamino)acetyl]amino]-N-[2R-hydroxy-3-[[(2,3-dihydrobenzofuran-5-yl)sulfonyl](2-methylpropyl)amino]-1S-(phenylmethyl)propyl]-3-cyanopropanamide;

2S-[[(N-methylamino)acetyl]amino]-N-[2R-hydroxy-3-[[(2,3-dihydrobenzofuran-5-yl)sulfonyl](2-methylpropyl)amino]-1S-phenylmethyl)propyl]-3S-methyl-pentanamide;

2S-[[(N-methylamino)acetyl]amino]-N-[2R-hydroxy-3-[[(2,3-dihydrobenzofuran-5-yl)sulfonyl](2-methylpropyl)amino]-1S-phenylmethyl)propyl]-4-pentynamide;

2S-[[(N-methylamino)acetyl]amino]-N-[2R-hydroxy-3-[[(benzothiazol-6-yl)sulfonyl](2-methylpropyl) amino]-1S-(phenylmethyl)propyl]-3,3-dimethyl-butanamide;

2S-[[(N-methylamino)acetyl]amino]-N-[2R-hydroxy-3-[[(benzothiazol-6-yl)sulfonyl](2-methylpropyl) amino]-1S-(phenylmethyl)propyl]-3-methyl-butanamide;

2S-[[(N-methylamino)acetyl]amino]-N-[2R-hydroxy-3-[[(benzothiazol-6-yl)sulfonyl](2-methylpropyl) amino]-1S-(phenylmethyl)propyl]-3-cyanopropanamide;

2S-[[(N-methylamino)acetyl]amino]-N-[2R-hydroxy-3-[[(benzothiazol-6-yl)sulfonyl](2-methylpropyl) amino]-1S-(phenylmethyl)propyl]-3S-methyl-pentanamide;

2S-[[(N-methylamino)acetyl]amino]-N-[2R-hydroxy-3-[[(benzothiazol-6-yl)sulfonyl](2-methylpropyl)amino]-1S-(phenylmethyl)propyl]-4-pentynamide;

2S-[[(N-methylamino)acetyl]amino]-N-[2R-hydroxy-3-[[(2,2-difluoro-1,3-benzodioxol-5-yl)sulfonyl](2-methylpropyl)amino]-1S-(phenylmethyl)propyl]-3,3-dimethyl-butanamide;

2S-[[(N-methylamino)acetyl]amino]-N-[2R-hydroxy-3-[[(2,2-difluoro-1,3-benzodioxol-5-yl)sulfonyl](2-methylpropyl)amino]-1S-(phenylmethyl)propyl]-3-methyl-butanamide;

2S-[[(N-methylamino)acetyl]amino]-N-[2R-hydroxy-3-[[(2,2-difluoro-1,3-benzodioxol-5-yl)sulfonyl](2-methylpropyl)amino]-1S-(phenylmethyl)propyl]-3-cyanopropanamide;

2S-[[(N-methylamino)acetyl]amino]-N-[2R-hydroxy-3-[[(2,2-difluoro-1,3-benzodioxol-5-yl)sulfonyl](2-methylpropyl)amino]-1S-(phenylmethyl)propyl]-3S-methyl-pentanamide;

2S-[[(N-methylamino)acetyl]amino]-N-[2R-hydroxy-3-[[(2,2-difluoro-1,3-benzodioxol-5-yl)sulfonyl](2-methylpropyl)amino]-1S-(phenylmethyl)propyl]-4-pentynamide;

2S-[[(N-methylamino)acetyl]amino]-N-[2R-hydroxy-3-[[(1,4-benzodioxan-6-yl)sulfonyl](2-methylpropyl)amino]-1S-(phenylmethyl)propyl]-3,3-dimethyl-butanamide;

2S-[[(N-methylamino)acetyl]amino]-N-[2R-hydroxy-3-[[(1,4-benzodioxan-6-yl)sulfonyl](2-methylpropyl)amino]-1S-(phenylmethyl)propyl]-3-methyl-butanamide;

2S-[[(N-methylamino)acetyl]amino]-N-[2R-hydroxy-3-[[(1,4-benzodioxan-6-yl)sulfonyl](2-methylpropyl)amino]-1S-(phenylmethyl)propyl]-3-cyanopropanamide;

2S-[[(N-methylamino)acetyl]amino]-N-[2R-hydroxy-3-[[(1,4-benzodioxan-6-yl)sulfonyl](2-methylpropyl)amino]-1S-(phenylmethyl)propyl]-3S-methyl-pentanamide;

2S-[[(N-methylamino)acetyl]amino]-N-[2R-hydroxy-3-[[(1,4-benzodioxan-6-yl)sulfonyl](2-methylpropyl)amino]-1S-(phenylmethyl)propyl]-4-pentynamide;

2S-[[(N,N-dimethylamino)acetyl]amino]-N-[2R-hydroxy-3-[[(1,3-benzodioxol-5-yl)sulfonyl](2-methylpropyl)amino]-1S-(phenylmethyl)propyl]-3,3-dimethyl-butanamide;

2S-[[(N,N-dimethylamino)acetyl]amino]-N-[2R-hydroxy-3-[[(1,3-benzodioxol-5-yl)sulfonyl](2-methylpropyl)amino]-1S-(phenylmethyl)propyl]-3-methyl-butanamide;

2S-[[(N,N-dimethylamino)acetyl]amino]-N-[2R-hydroxy-3-[[(1,3-benzodioxol-5-yl)sulfonyl](2-methylpropyl)amino]-1S-(phenylmethyl)propyl]-3-cyanopropanimide;

2S-[[(N,N-dimethylamino)acetyl]amino]-N-[2R-hydroxy-3-[[(1,3-benzodioxol-5-yl)sulfonyl](2-methylpropyl)amino]-1S-(phenylmethyl)propyl]-3S-methyl-pentanamide;

2S-[[(N,N-dimethylamino)acetyl]amino]-N-[2R-hydroxy-3-[[(1,3-benzodioxol-5-yl)sulfonyl](2-methylpropyl)amino]-1S-(phenylmethyl)propyl]-4-pentynamide;

2S-[[(N,N-dimethylamino)acetyl]amino]-N-[2R-hydroxy-3-[[(benzofuran-5-yl)sulfonyl](2-methylpropyl)amino]-1S-(phenylmethyl)propyl]-3,3-dimethyl-butanamide;

2S-[[(N,N-dimethylamino)acetyl]amino]-N-[2R-hydroxy-3-[[(benzofuran-5-yl)sulfonyl](2-methylpropyl)amino]-1S-(phenylmethyl)propyl]-3-methyl-butanamide;

2S-[[(N,N-dimethylamino)acetyl]amino]-N-[2R-hydroxy-3-[[(benzofuran-5-yl)sulfonyl](2-methylpropyl)amino]-1S-(phenylmethyl)propyl]-3-cyanopropanamide;

2S-[[(N,N-dimethylamino)acetyl]amino]-N-[2R-hydroxy-3-[[(benzofuran-5-yl)sulfonyl](2-methylpropyl)amino]-1S-(phenylmethyl)propyl]-3S-methyl-pentanamide;

2S-[[(N,N-dimethylamino)acetyl]amino]-N-[2R-hydroxy-3-[[(benzofuran-5-yl)sulfonyl](2-methylpropyl)amino]-1S-(phenylmethyl)propyl]-4-pentynamide;

2S-[[(N,N-dimethylamino)acetyl]amino]-N-[2R-hydroxy-3-[[(2-methyl-1,3-benzodioxol-5-yl)sulfonyl](2-methylpropyl)amino]-1S-(phenylmethyl)propyl]-3,3-dimethylbutanamide;

2S-[[(N,N-dimethylamino)acetyl]amino]-N-[2R-hydroxy-3-[[(2-methyl-1,3-benzodioxol-5-yl)sulfonyl](2-methylpropyl)amino]-1S-(phenylmethyl)propyl]-3-methylbutanamide;

2S-[[(N,N-dimethylamino)acetyl]amino]-N-[2R-hydroxy-3-[[(2-methyl-1,3-benzodioxol-5-yl)sulfonyl](2-methylpropyl)amino]-1S-(phenylmethyl)propyl]-3-cyanopropanamide;

2S-[[(N,N-dimethylamino)acetyl]amino]-N-[2R-hydroxy-3-[[(2-methyl-1,3-benzodioxol-5-yl)sulfonyl](2-methylpropyl)amino]-1S-(phenylmethyl)propyl]-3S-methylpentanamide;

2S-[[(N,N-dimethylamino)acetyl]amino]-N-[2R-hydroxy-3-[[(2-methyl-1,3-benzodioxol-5-yl)sulfonyl](2-methylpropyl)amino]-1S-(phenylmethyl)propyl]-4-pentynamide;

2S-[[(N,N-dimethylamino)acetyl]amino]-N-[2R-hydroxy-3-[[(2,3-dihydrobenzofuran-5-yl)sulfonyl](2-methylpropyl)amino]-1S-(phenylmethyl)propyl]-3,3-dimethyl-butanamide;

2S-[[(N,N-dimethylamino)acetyl]amino]-N-[2R-hydroxy-3-[[(2,3-dihydrobenzofuran-5-yl)sulfonyl](2-methylpropyl)amino]-1S-(phenylmethyl)propyl]-3-methyl-butanamide;

2S-[[(N,N-dimethylamino)acetyl]amino]-N-[2R-hydroxy-3-[[(2,3-dihydrobenzofuran-5-yl)sulfonyl](2-methylpropyl)amino]-1S-(phenylmethyl)propyl]-3-cyanopropanamide;

2S-[[(N,N-dimethylamino)acetyl]amino]-N-[2R-hydroxy-3-[[(2,3-dihydrobenzofuran-5-yl)sulfonyl](2-methylpropyl)amino]-1S-phenylmethyl)propyl]-3S-methyl-pentanamide;

2S-[[(N,N-dimethylamino)acetyl]amino]-N-[2R-hydroxy-3-[[(2,3-dihydrobenzofuran-5-yl)sulfonyl](2-methylpropyl)amino]-1S-phenylmethyl)propyl]-4-pentynamide;

2S-[[(N,N-dimethylamino)acetyl]amino]-N-[2R-hydroxy-3-[[(benzothiazol-6-yl)sulfonyl](2-methylpropyl)amino]-1S-(phenylmethyl)propyl]-3,3-dimethyl-butanamide;

2S-[[(N,N-dimethylamino)acetyl]amino]-N-[2R-hydroxy-3-[[(benzothiazol-6-yl)sulfonyl](2- methylpropyl)amino]-1S-(phenylmethyl)propyl]-3-methyl-butanamide;

2S-[[(N,N-dimethylamino)acetyl]amino]-N-[2R-hydroxy-3-[[(benzothiazol-6-yl)sulfonyl](2-methylpropyl)amino]-1S-(phenylmethyl)propyl]-3-cyanopropanamide;

2S-[[(N,N-dimethylamino)acetyl]amino]-N-[2R-hydroxy-3-[[(benzothiazol-6-yl)sulfonyl](2-methylpropyl)amino]-1S-(phenylmethyl)propyl]-3S-methyl-pentanamide;

2S-[[(N,N-dimethylamino)acetyl]amino]-N-[2R-hydroxy-3-[[(benzothiazol-6-yl)sulfonyl](2-methylpropyl)amino]-1S-(phenylmethyl)propyl]-4-pentynamide;

2S-[[(N,N-dimethylamino)acetyl]amino]-N-[2R-hydroxy-3-[[(2,2-difluoro-1,3-benzodioxol-5-yl)sulfonyl](2-methylpropyl)amino]-1S-(phenylmethyl)propyl]-3,3-dimethyl-butanamide;

2S-[[(N,N-dimethylamino)acetyl]amino]-N-[2R-hydroxy-3-[[(2,2-difluoro-1,3-benzodioxol-5-yl)sulfonyl](2-methylpropyl)amino]-1S-(phenylmethyl)propyl]-3-methyl-butanamide;

2S-[[(N,N-dimethylamino)acetyl]amino]-N-[2R-hydroxy-3-[[(2,2-difluoro-1,3-benzodioxol-5-yl)sulfonyl](2-methylpropyl)amino]-1S-(phenylmethyl)propyl]-3-cyanopropanamide;

2S-[[(N,N-dimethylamino)acetyl]amino]-N-[2R-hydroxy-3-[[(2,2-difluoro-1,3-benzodioxol-5-yl)sulfonyl](2-methylpropyl)amino]-1S-(phenylmethyl)propyl]-3S-methyl-pentanamide;

2S-[[(N,N-dimethylamino)acetyl]amino]-N-[2R-hydroxy-3-[[(2,2-difluoro-1,3-benzodioxol-5-yl)sulfonyl](2-methylpropyl)amino]-1S-(phenylmethyl)propyl]-4-pentynamide;

2S-[[(N,N-dimethylamino)acetyl]amino]-N-[2R-hydroxy-3-[[(1,4-benzodioxon-6-yl)sulfonyl](2-methylpropyl)amino]-1S-(phenylmethyl)propyl]-3,3-dimethyl-butanamide;

2S-[[(N,N-dimethylamino)acetyl]amino]-N-[2R-hydroxy-3-[[(1,4-benzodioxon-6-yl)sulfonyl](2-methylpropyl)amino]-1S-(phenylmethyl)propyl]-3-methyl-butanamide;

2S-[[(N,N-dimethylamino)acetyl]amino]-N-[2R-hydroxy-3-[[(1,4-benzodioxon-6-yl)sulfonyl](2-methylpropyl)amino]-1S-(phenylmethyl)propyl]-3-cyanopropanamide;

2S-[[(N,N-dimethylamino)acetyl]amino]-N-[2R-hydroxy-3-[[(1,4-benzodioxon-6-yl)sulfonyl](2-methylpropyl)amino]-1S-(phenylmethyl)propyl]-3S-methyl-pentanamide;

2S-[[(N,N-dimethylamino)acetyl]amino]-N-[2R-hydroxy-3-[[(1,4-benzodioxon-6-yl)sulfonyl](2-methylpropyl)amino]-1S-(phenylmethyl)propyl]-4-pentynamide;

2S-[[(N-benzylamino)acetyl]amino]-N-[2R-hydroxy-3-[[(1,3-benzodioxol-5-yl)sulfonyl](2-methylpropyl)amino]-1S-(phenylmethyl)propyl]-3,3-dimethyl-butanamide;

2S-[[(N-benzylamino)acetyl]amino]-N-[2R-hydroxy-3-[[(1,3-benzodioxol-5-yl)sulfonyl](2-methylpropyl)amino]-1S-(phenylmethyl)propyl]-3-methyl-butanamide;

2S-[[(N-benzylamino)acetyl]amino]-N-[2R-hydroxy-3-[[(1,3-benzodioxol-5-yl)sulfonyl](2-methylpropyl)amino]-1S-(phenylmethyl)propyl]-3S-methyl-pentanamide;

2S-[[(N-benzylamino)acetyl]amino]-N-[2R-hydroxy-3-[[phenylsulfonyl](2-methylpropyl)amino]-1S-(phenylmethyl)propyl]-3,3-dimethyl-butanamide;

2S-[[(N-benzylamino)acetyl]amino]-N-[2R-hydroxy-3-[[phenylsulfonyl](2-methylpropyl)amino]-1S-(phenylmethyl)propyl]-3-methyl-butanamide;

2S-[[(N-benzylamino)acetyl]amino]-N-[2R-hydroxy-3-[[phenylsulfonyl](2-methylpropyl)amino]-1S-(phenylmethyl)propyl]-3S-methyl-pentanamide;

2S-[[(N-benzylamino)acetyl]amino]-N-[2R-hydroxy-3-[[(4-methoxyphenyl)sulfonyl](2-methylpropyl)amino]-1S-(phenylmethyl)propyl]-3,3-dimethyl-butanamide;

2S-[[(N-benzylamino)acetyl]amino]-N-[2R-hydroxy-3-[[(4-methoxyphenyl)sulfonyl](2-methylpropyl)amino]-1S-(phenylmethyl)propyl]-3-methyl-butanamide;

2S-[[(N-benzylamino)acetyl]amino]-N-[2R-hydroxy-3-[[(4-methoxyphenyl)sulfonyl](2-methylpropyl)amino]-1S-(phenylmethyl)propyl]-3S-methyl-pentanamide;

2S-[[(N-benzylamino)acetyl]amino]-N-[2R-hydroxy-3-[[(2,3-dihydrobenzofuran-5-yl)sulfonyl](2-methylpropyl)amino]-1S-(phenylmethyl)propyl]-3,3-dimethyl-butanamide;

2S-[[(N-benzylamino)acetyl]amino]-N-[2R-hydroxy-3-[[(2,3-dihydrobenzofuran-5-yl)sulfonyl](2-methylpropyl)amino]-1S-(phenylmethyl)propyl]-3-methyl-butanamide;

2S-[[(N-benzylamino)acetyl]amino]-N-[2R-hydroxy-3-[[(2,3-dihydrobenzofuran-5-yl)sulfonyl](2-methylpropyl)amino]-1S-(phenylmethyl)propyl]-3S-methyl-pentanamide;

2S-[[(N-benzylamino)acetyl]amino]-N-[2R-hydroxy-3-[[(benzothiazol-6-yl)sulfonyl](2-methylpropyl)amino]-1S-(phenylmethyl)propyl]-3,3-dimethyl-butanamide;

2S-[[(N-benzylamino)acetyl]amino]-N-[2R-hydroxy-3-[[(benzothiazol-6-yl)sulfonyl](2-methylpropyl)amino]-1S-(phenylmethyl)propyl]-3-methyl-butanamide;

2S-[[(N-benzylamino)acetyl]amino]-N-[2R-hydroxy-3-[[(benzothiazol-6-yl)sulfonyl](2-methylpropyl)amino]-1S-(phenylmethyl)propyl]-3S-methyl-pentanamide;

2S-[[(N-benzylamino)acetyl]amino]-N-[2R-hydroxy-3-[[(2-naphthyl)sulfonyl](2-methylpropyl)amino]-1S-(phenylmethyl)propyl]-3,3-dimethyl-butanamide;

2S-[[(N-benzylamino)acetyl]amino]-N-[2R-hydroxy-3-[[(2-naphthyl)sulfonyl](2-methylpropyl)amino]-1S-(phenylmethyl)propyl]-3-methyl-butanamide;

2S-[[(N-benzylamino)acetyl]amino]-N-[2R-hydroxy-3-[[(2-naphthyl)sulfonyl](2-methylpropyl)amino]-1S-(phenylmethyl)propyl]-3S-methyl-pentanamide;

2S-[[(N-benzylamino)acetyl]amino]-N-[2R-hydroxy-3-[[(1,4-benzodioxan-6-yl)sulfonyl](2-methylpropyl)amino]-1S-(phenylmethyl)propyl]-3,3-dimethyl-butanamide;

2S-[[(N-benzylamino)acetyl]amino]-N-[2R-hydroxy-3-[[(1,4-benzodioxan-6-yl)sulfonyl](2-methylpropyl)amino]-1S-(phenylmethyl)propyl]-3-methyl-butanamide;

2S-[[(N-benzylamino)acetyl]amino]-N-[2R-hydroxy-3-[[(1,4-benzodioxan-6-yl)sulfonyl](2-methylpropyl)amino]-1S-(phenylmethyl)propyl]-3S-methyl-pentanamide;

2S-[[(N-benzylamino)acetyl]amino]-N-[2R-hydroxy-3-[[(1,3-benzodioxol-5-yl)sulfonyl](2-methylpropyl)amino]-1S-(phenylmethyl)propyl]pent-4-ynamide;

2S-[[(N-benzylamino)acetyl]amino]-N-[2R-hydroxy-3-[[phenylsulfonyl](2-methylpropyl)amino]-1S-(phenylmethyl)propyl]pent-4-ynamide;

2S-[[(N-benzylamino)acetyl]amino]-N-[2R-hydroxy-3-[[(4-methoxyphenyl)sulfonyl](2-methylpropyl)amino]-1S-(phenylmethyl)propyl]pent-4-ynamide;

2S-[[(N-benzylamino)acetyl]amino]-N-[2R-hydroxy-3-[[benzothiazol-6-yl)sulfonyl](2-methylpropyl)amino]-1S-(phenylmethyl)propyl]pent-4-ynamide;

2S-[[(N-benzylamino)acetyl]amino]-N-[2R-hydroxy-3-[[(2,3-dihydrobenzofuran-5-yl)sulfonyl](2-methylpropyl)amino]-1S-(phenylmethyl)propyl]pent-4-ynamide;

2S-[[(N-benzylamino)acetyl]amino]-N-[2R-hydroxy-3-[[(2-naphthyl)sulfonyl](2-methylpropyl)amino]-1S-(phenylmethyl)propyl]pent-4-ynamide;

2S-[[(N-benzylamino)acetyl]amino]-N-[2R-hydroxy-3-[[(1,4-benzodioxan-6-yl)sulfonyl](2-methylpropyl)amino]-1S-(phenylmethyl)propyl]pent-4-ynamide;

2S-[[(N-benzylamino)acetyl]amino]-N-[2R-hydroxy-3-[[(1,3-benzodioxol-5-yl)sulfonyl](2-methylpropyl)amino]-1S-(phenylmethyl)propyl]pent-4-ynamide;

2S-[[(N-cyclopropylamino)acetyl]amino]-N-[2R-hydroxy-3-[[(1,3-benzodioxol-5-yl)sulfonyl](2-methylpropyl)amino]-1S-(phenylmethyl)propyl]-3,3-dimethyl-butanamide;

2S-[[(N-cyclopropylamino)acetyl]amino]-N-[2R-hydroxy-3-[[(1,3-benzodioxol-5-yl)sulfonyl](2-methylpropyl)amino]-1S-(phenylmethyl)propyl]-3-methyl-butanamide;

2S-[[(N-cyclopropylamino)acetyl]amino]-N-[2R-hydroxy-3-[[(1,3-benzodioxol-5-yl)sulfonyl](2-methylpropyl)amino]-1S-(phenylmethyl)propyl]-3S-methyl-pentanamide;

2S-[[(N-cyclopropylamino)acetyl]amino]-N-[2R-hydroxy-3-[[phenylsulfonyl](2-methylpropyl)amino]-1S-(phenylmethyl)propyl]-3,3-dimethyl-butanamide;

2S-[[(N-cyclopropylamino)acetyl]amino]-N-[2R-hydroxy-3-[[phenylsulfonyl](2-methylpropyl)amino]-1S-(phenylmethyl)propyl]-3-methyl-butanamide;

2S-[[(N-cyclopropylamino)acetyl]amino]-N-[2R-hydroxy-3-[[phenylsulfonyl](2-methylpropyl)amino]-1S-(phenylmethyl)propyl]-3S-methyl-pentanamide;

2S-[[(N-cyclopropylamino)acetyl]amino]-N-[2R-hydroxy-3-[[(4-methoxyphenyl)sulfonyl](2-methylpropyl)amino]-1S-(phenylmethyl)propyl]-3,3-dimethyl-butanamide;

2S-[[(N-cyclopropylamino)acetyl]amino]-N-[2R-hydroxy-3-[[(4-methoxyphenyl)sulfonyl](2-methylpropyl)amino]-1S-(phenylmethyl)propyl]-3-methyl-butanamide;

2S-[[(N-cyclopropylamino)acetyl]amino]-N-[2R-hydroxy-3-[[(4-methoxyphenyl)sulfonyl](2-methylpropyl)amino]-1S-(phenylmethyl)propyl]-3S-methyl-pentanamide;

2S-[[(N-cyclopropylamino)acetyl]amino]-N-[2R-hydroxy-3-[[(2,3-dihydrobenzofuran-5-yl)sulfonyl](2-methylpropyl)amino]-1S-(phenylmethyl)propyl]-3,3-dimethyl-butanamide;

2S-[[(N-cyclopropylamino)acetyl]amino]-N-[2R-hydroxy-3-[[(2,3-dihydrobenzofuran-5-yl)sulfonyl])2-methylpropyl)amino]-1S-(phenylmethyl)propyl]-3-methyl-butanamide;

2S-[[(N-cyclopropylamino)acetyl]amino]-N-[2R-hydroxy-3-[[(2,3-dihydrobenzofuran-5-yl)sulfonyl](2-methylpropyl)amino]-1S-(phenylmethyl)propyl]-3S-methyl-pentanamide;

2S-[[(N-cyclopropylamino)acetyl]amino]-N-[2R-hydroxy-3-[[(benzothiazol-6-yl)sulfonyl](2-methylpropyl)amino]-1S-(phenylmethyl)propyl]-3,3-dimethyl-butanamide;

2S-[[(N-cyclopropylamino)acetyl]amino]-N-[2R-hydroxy-3-[[(benzothiazol-6-yl)sulfonyl](2-methylpropyl)amino]-1S-(phenylmethyl)propyl]-3-methyl-butanamide;

2S-[[(N-cyclopropylamino)acetyl]amino]-N-[2R-hydroxy-3-[[(benzothiazol-6-yl)sulfonyl](2-methylpropyl)amino]-1S-(phenylmethyl)propyl]-3S-methyl-pentanamide;

2S-[[(N-cyclopropylamino)acetyl]amino]-N-[2R-hydroxy-3-[[(2-naphthyl)sulfonyl](2-methylpropyl)amino]-1S-(phenylmethyl)propyl]-3,3-dimethyl-butanamide;

2S-[[(N-cyclopropylamino)acetyl]amino]-N-[2R-hydroxy-3-[[(2-naphthyl)sulfonyl](2-methylpropyl)amino]-1S-(phenylmethyl)propyl]-3-methyl-butanamide;

2S-[[(N-cyclopropylamino)acetyl]amino]-N-[2R-hydroxy-3-[[(2-naphthyl)sulfonyl](2-methylpropyl)amino]-1S-(phenylmethyl)propyl]-3S-methyl-pentanamide;

2S-[[(N-cyclopropylamino)acetyl]amino]-N-[2R-hydroxy-3-[[(1,4-benzodioxan-6-yl)sulfonyl](2-methylpropyl)amino]-1S-(phenylmethyl)propyl]-3,3-dimethyl-butanamide;

2S-[[(N-cyclopropylamino)acetyl]amino]-N-[2R-hydroxy-3-[[(1,4-benzodioxan-6-yl)sulfonyl](2-methylpropyl)amino]-1S-(phenylmethyl)propyl]-3-methyl-butanamide;

2S-[[(N-cyclopropylamino)acetyl]amino]-N-[2R-hydroxy-3-[[(1,4-benzodioxan-6-yl)sulfonyl](2-methylpropyl)amino]-1S-(phenylmethyl)propyl]-3S-methyl-pentanamide;

2S-[[(N-cyclopropylamino)acetyl]amino]-N-[2R-hydroxy-3-[[(1,3-benzodioxal-5-yl)sulfonyl](2-methylpropyl)amino]-1S-(phenylmethyl)propyl]pent-4-ynamide;

2S-[[(N-cyclopropylamino)acetyl]amino]-N-[2R-hydroxy-3-[[phenylsulfonyl](2-methylpropyl)amino]-1S-(phenylmethyl)propyl]pent-4-ynamide;

2S-[[(N-cyclopropylamino)acetyl]amino]-N-[2R-hydroxy-3-[[(4-methoxyphenyl)sulfonyl](2-methylpropyl)amino]-1S-(phenylmethyl)propyl]pent-4-ynamide;

2S-[[(N-cyclopropylamino)acetyl]amino]-N-[2R-hydroxy-3-[[benzothiazol-6-yl)sulfonyl](2-methylpropyl)amino]-1S-(phenylmethyl)propyl]pent-4-ynamide;

2S-[[(N-cyclopropylamino)acetyl]amino]-N-[2R-hydroxy-3-[[(2,3-dihydrobenzofuran-5-yl)sulfonyl](2-methylpropyl)amino]-1S-(phenylmethyl)propyl]pent-4-ynamide;

2S-[[(N-cyclopropylamino)acetyl]amino]-N-[2R-hydroxy-3-[[2-naphthyl)sulfonyl](2-methylpropyl)amino]-1S-(phenylmethyl)propyl]pent-4-ynamide;

2S-[[(N-cyclopropylamino)acetyl]amino]-N-[2R-hydroxy-3-[[(1,4-benzodioxan-6-yl)sulfonyl](2-methylpropyl)amino]-1S-(phenylmethyl)propyl]pent-4-ynamide;

2S-[[(N-cyclopropylamino)acetyl]amino]-N-[2R-hydroxy-3-[[(1,3-benzodioxol-5-yl)sulfonyl](2-methylpropyl)amino]-1S-(phenylmethyl)propyl]pent-4-ynamide;

2S-[[(N-2-methoxyethylamino)acetyl]amino]-N-[2R-hydroxy-3-[[(1,3-benzodioxol-5-yl)sulfonyl](2-methylpropyl)amino]-1S-(phenylmethyl)propyl]-3,3-dimethyl-butanamide;

2S-[[(N-2-methoxyethylamino)acetyl]amino]-N-[2R-hydroxy-3-[[(1,3-benzodioxol-5-yl)sulfonyl](2-methylpropyl)amino]-1S-(phenylmethyl)propyl]-3-methyl-butanamide;

2S-[[(N-2-methoxyethylamino)acetyl]amino]-N-[2R-hydroxy-3-[[(1,3-benzodioxol-5-yl)sulfonyl](2-methylpropyl)amino]-1S-(phenylmethyl)propyl]-3S-methyl-pentanamide;

2S-[[(N-2-methoxyethylamino)acetyl]amino]-N-[2R-hydroxy-3-[[phenylsulfonyl](2-methylpropyl)amino]-1S-(phenylmethyl)propyl]-3,3-dimethyl-butanamide;

2S-[[(N-2-methoxyethylamino)acetyl]amino]-N-[2R-hydroxy-3-[[phenylsulfonyl](2-methylpropyl)amino]-1S-(phenylmethyl)propyl]-3-methyl-butanamide;

2S-[[(N-2-methoxyethylamino)acetyl]amino]-N-[2R-hydroxy-3-[[phenylsulfonyl](2-methylpropyl)amino]-1S-(phenylmethyl)propyl]-3S-methyl-pentanamide;

2S-[[(N-2-methoxyethylamino)acetyl]amino]-N-[2R-hydroxy-3-[[(4-methoxyphenyl)sulfonyl](2-methylpropyl)amino]-1S-(phenylmethyl)propyl]-3,3-dimethyl-butanamide;

2S-[[(N-2-methoxyethylamino)acetyl]amino]-N-[2R-hydroxy-3-[[(4-methoxyphenyl)sulfonyl](2-methylpropyl)amino]-1S-(phenylmethyl)propyl]-3-methyl-butanamide;

2S-[[(N-2-methoxyethylamino)acetyl]amino]-N-[2R-hydroxy-3-[[(4-methoxyphenyl)sulfonyl](2-methylpropyl)amino]-1S-(phenylmethyl)propyl]-3S-methyl-pentanamide;

2S-[[(N-2-methoxyethylamino)acetyl]amino]-N-[2R-hydroxy-3-[[(2,3-dihydrobenzofuran-5-yl)sulfonyl](2-methylpropyl)amino]-1S-(phenylmethyl)propyl]-3,3-dimethyl-butanamide;

2S-[[(N-2-methoxyethylamino)acetyl]amino]-N-[2R-hydroxy-3-[[(2,3-dihydrobenzofuran-5-yl)sulfonyl](2-methylpropyl)amino]-1S-(phenylmethyl)propyl]-3-methyl-butanamide;

2S-[[(N-2-methoxyethylamino)acetyl]amino]-N-[2R-hydroxy-3-[[(2,3-dihydrobenzofuran-5-yl)sulfonyl](2-methylpropyl)amino]-1S-(phenylmethyl)propyl]-3S-methyl-pentanamide;

2S-[[(N-2-methoxyethylamino)acetyl]amino]-N-(2R-hydroxy-3-[[(benzothiazol-6-yl)sulfonyl](2-methylpropyl)amino]-1S-(phenylmethyl)propyl]-3,3-dimethyl-butanamide;

2S-[[(N-2-methoxyethylamino)acetyl]amino]-N-[2R-hydroxy-3-[[(benzothiazol-6-yl)sulfonyl](2-methylpropyl)amino]-1S-(phenylmethyl)propyl]-3-methyl-butanamide;

2S-[[(N-2-methoxyethylamino)acetyl]amino]-N-[2R-hydroxy-3-[[(benzothiazol-6-yl)sulfonyl](2-methylpropyl)amino]-1S-(phenylmethyl)propyl]-3S-methyl-pentanamide;

2S-[[(N-2-methoxyethylamino)acetyl]amino]-N-[2R-hydroxy-3-[[(2-naphthyl)sulfonyl](2-methylpropyl)amino]-1S-(phenylmethyl)propyl]-3,3-dimethyl-butanamide;

2S-[[(N-2-methoxyethylamino)acetyl]amino]-N-[2R-hydroxy-3-[[(2-naphthyl)sulfonyl](2-methylpropyl)amino]-1S-(phenylmethyl)propyl]-3-methyl-butanamide;

2S-[[(N-2-methoxyethylamino)acetyl]amino]-N-[2R-hydroxy-3-[[(2-naphthyl)sulfonyl](2-methylpropyl)amino]-1S-(phenylmethyl)propyl]-3S-methyl-pentanamide, 2S-[[(N-2-methoxyethylamino)acetyl]amino]-N-[2R-hydroxy-3-[[(1,4-benzodioxan-6-yl)sulfonyl](2-methylpropyl)amino]-1S-(phenylmethyl)propyl]-3,3-dimethyl-butanamide;

2S-[[(N-2-methoxyethylamino)acetyl]amino]-N-[2R-hydroxy-3-[[(1,4-benzodioxan-6-yl)sulfonyl](2-methylpropyl)amino]-1S-(phenylmethyl)propyl]-3-methyl-butanamide;

2S-[[(N-2-methoxyethylamino)acetyl]amino]-N-[2R-hydroxy-3-[[(1,4-benzodioxan-6-yl)sulfonyl](2-methylpropyl)amino]-1S-(phenylmethyl)propyl]-3S-methyl-pentanamide;

2S-[[(N-2-methoxyethylamino)acetyl]amino]-N-[2R-hydroxy-3-[[(1,3-benzodioxal-5-yl)sulfonyl](2-methylpropyl)amino]-1S-(phenylmethyl)propyl]pent-4-ynamide;

2S-[[(N-2-methoxyethylamino)acetyl]amino]-N-[2R-hydroxy-3-[[phenylsulfonyl](2-methylpropyl)amino]-1S-(phenylmethyl)propyl]pent-4-ynamide;

2S-[[(N-2-methoxyethylamino)acetyl]amino]-N-[2R-hydroxy-3-[[(4-methoxyphenyl)sulfonyl](2-methylpropyl)amino]-1S-(phenylmethyl)propyl]pent-4-ynamide;

2S-[[(N-2-methoxyethylamino)acetyl]amino]-N-[2R-hydroxy-3-[[benzothiazol-6-yl)sulfonyl](2-methylpropyl)amino]-1S-(phenylmethyl)propyl]pent-4-ynamide;

2S-[[(N-2-methoxyethylamino)acetyl]amino]-N-[2R-hydroxy-3-[[(2,3-dihydrobenzofuran-5-yl)sulfonyl](2-methylpropyl)amino]-1S-(phenylmethyl)propyl]pent-4-ynamide;

2S-[[(N-2-methoxyethylamino)acetyl]amino]-N-[2R-hydroxy-3-[[2-naphthyl)sulfonyl](2-methylpropyl)amino]-1S-(phenylmethyl)propyl]pent-4-ynamide;

2S-[[(N-2-methoxyethylamino)acetyl]amino]-N-[2R-hydroxy-3-[[(1,4-benzodioxan-6-yl)sulfonyl](2-methylpropyl)amino]-1S-(phenylmethyl)propyl]pent-4-ynamide; and 2S-[[(N-2-methoxyethylamino)acetyl]amino]-N-[2R-hydroxy-3-[[(1,3-benzodioxol-5-yl)sulfonyl](2-methylpropyl)amino]-1S-(phenylmethyl)propyl]pent-4-ynamide.

As utilized herein, the term "alkyl", alone or in combination, means a straight-chain or branched-chain alkyl radical containing preferably from 1 to 8 carbon atoms, more preferably from 1 to 5 carbon atoms, most preferably 1 to 3 carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "hydroxyalkyl", alone or in combination, means a alkyl radical as defined above wherein at least one hydrogen atom has been replaced by a hydroxyl group, but no more than one hydrogen atom per carbon atom; preferably, 1 to 4 hydrogen atoms have been replaced by hydroxyl groups; more preferably, 1 to 2 hydrogen atoms have been replaced by hydroxyl groups; and most preferably, one hydrogen atom has been replaced by a hydroxyl group. The term "alkenyl", alone or in combination, means a straight chain or branched-chain hydrocarbon radical having one or more double bonds and containing preferably from 2 to 10 carbon atoms, more preferably from 2 to 8 carbon atoms, most preferably from 2 to 5 carbon atoms. Examples of suitable alkenyl radicals include ethenyl, propynyl, 2-methylpropenyl, 1,4-butadienyl and the like. The term "alkynyl", alone or in combination, means a straight chain or branched chain hydrocarbon radical having one or more triple bonds and containing preferably from 2 to 10 carbon atoms, more preferably from 2 to 5 carbon atoms. Examples of alkynyl radicals include ethynyl, propynyl (propargyl), butynyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "alkoxyalkyl", alone or in combination, means a alkyl radical as defined above wherein at least one hydrogen atom has been replaced by a alkoxy group, but no more than one hydrogen atom per carbon atom; preferably, 1 to 4 hydrogen atoms have been replaced by alkoxy groups; more preferably, 1 to 2 hydrogen atoms have teen replaced by alkoxy groups; and most preferably, one hydrogen atom has been replaced by a alkoxy group. The term "cycloalkyl", alone or in combination, means a saturated or partially saturated monocyclic, bicyclic or tricyclic alkyl radical wherein each cyclic moiety contains preferably from 3 to 8 carbon atom ring members, more preferably from 3 to 7 carbon atom ring members, most preferably from 5 to 6 carbon atom ring members, and which may optionally be a benzo fused ring system which is optionally substituted as defined herein with respect to the definition of aryl. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as naphthyl and β-carbolinyl, and substituted ring systems, such as biphenyl, phenylpyridyl, naphthyl and diphenylpiperazinyl. The term "cycloalkylalkyl" means an alkyl radical as defined above which is substituted by a cycloalkyl radical as defined above. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like. The term "benzo", alone or in combination, means the divalent radical $C_6H_4=$ derived from benzene. The term "aryl", alone or in combination, means a phenyl or naphthyl radical which is optionally substituted with one or more substituents selected from alkyl, alkoxy, halogen, hydroxy, amino, nitro, cyano, haloalkyl, carboxy, alkoxycarbonyl, cycloalkyl, heterocyclo, alkanoylamino, amido, amidino, alkoxycarbonylamino, N-alkylamidino, alkylamino, dialkylamino, N-alkylamino, N,N-dialkylamino, aralkoxycarbonylamino, alkylthio, alkylsulfinyl, alkylsulfonyl and the like. Examples of aryl radicals are phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 4-$CF_3$-phenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl, piperazinylphenyl and the like. The terms "aralkyl" and "aralkoxy", alone or in combination, means an alkyl or alkoxy radical as defined above in which at least one hydrogen atom is replaced by an aryl radical as defined above, such as benzyl, benzyloxy, 2-phenylethyl, dibenzylmethyl, hydroxyphenylmethyl, methylphenylmethyl, diphenylmethyl, diphenylmethoxy, 4-methoxyphenylmethoxy and the like. The term "aralkoxycarbonyl", alone or in combination, means a radical of the formula aralkyl-O—C(O)— in which the term "aralkyl" has the significance given above. Examples of an aralkoxycarbonyl radical are benzyloxycarbonyl and 4-methoxyphenylmethoxycarbonyl. The term "aryloxy" means a radical of the formula aryl-O— in which the term aryl has the significance given above. The term "alkanoyl", alone or in combination, means an aryl radical derived from an alkanecarboxylic acid, examples of which include acetyl, propionyl, butyryl, valeryl, 4-methylvaleryl, and the like. The term "cycloalkylcarbonyl" means an aryl radical of the formula cycloalkyl-C(O)— in which the term "cycloalkyl" has the significance give above, such as cyclopropylcarbonyl, cyclohexylcarbonyl, adamantylcarbonyl, 1,2,3,4-tetrahydro-2-naphthoyl, 2-acetamido-1,2,3,4-tetrahydro-2-naphthoyl, 1-hydroxy-1,2,3,4-tetrahydro-6-naphthoyl and the like. The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like. The term "amyl" means an acyl radical derived from an arylcarboxylic acid, "aryl" having the meaning given above. Examples of such aroyl radicals include substituted and unsubstituted benzoyl or napthoyl such as benzoyl, 4-chlorobenzoyl, 4-carboxybenzoyl, 4-(benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like. The terms "heterocyclo," alone or in combination, means a saturated or partially unsaturated monocyclic, bicyclic or tricyclic heterocycle radical containing at least one nitrogen, oxygen or sulfur atom ring member and having preferably 3 to 8 ring members in each ring, more preferably 3 to 7 ring members in each ring and most preferably 5 to 6 ring members in each ring. "Heterocyclo" is intended to include sulfones, sulfoxides, N-oxides of tertiary nitrogen ring members, and carbocyclic fused and benzo fused ring systems. Such heterocyclo radicals may be optionally substituted on one or more carbon atoms by halogen, alkyl, alkoxy, hydroxy, oxo, aryl, aralkyl, heteroaryl, heteroaralkyl, amidino, N-alkylamidino, alkoxycarbonylamino, alkylsulfonylamino and the like, and/or on a secondary nitrogen atom (i.e., —NH—) by hydroxy, alkyl, aralkoxycarbonyl, alkanoyl, heteroaralkyl, phenyl or phenylalkyl and/or on a tertiary nitrogen atom (i.e., =N—) by oxido. "Heterocycloalkyl" means an alkyl radical as defined above in which at least one hydrogen atom is replaced by a heterocyclo radical as defined above, such as pyrrolidinylmethyl, tetrahydrothienylmethyl, pyridylmethyl and the like. The term "heteroaryl", alone or in combination, means an aromatic heterocyclo radical as defined above, which is optionally substituted as defined above with respect to the definitions of aryl and heterocyclo. Examples of such heterocyclo and heteroaryl groups are pyrrolidinyl, piperidinyl, piperazinyl, morpholinyl, thiamorpholinyl, pyrrolyl, imidazolyl (e.g., imidazol 4-yl, 1-benzyloxycarbonylimidazol-4-yl, etc.), pyrazolyl, pyridyl, (e.g., 2-(1-piperidinyl)pyridyl and 2-(4-benzyl piperazin-1-yl-1-pyridinyl, etc.), pyrazolyl, pyrimidinyl, furyl, tetrahydrofuryl, thienyl, tetrahydrothienyl and its sulfoxide and sulfone derivatives, triazolyl, oxazolyl, thiazolyl, indolyl (e.g., 2-indolyl, etc.), quinolinyl, (e.g., 2-quinolinyl, 3-quinolinyl, 1-oxido-2-quinolinyl, etc.), isoquinolinyl (e.g., 1-isoquinolinyl, 3-isoquinolinyl, etc.), tetrahydroquinolinyl (e.g., 1,2,3,4-tetrahydro-2-quinolyl, etc.), 1,2,3,4-tetrahydroisoquinolinyl (e.g., 1,2,3,4-tetrahydro-1-oxo-isoquinolinyl, etc.), quinoxalinyl, β-carbolinyl, 2-benzofurancarbonyl, 1-, 2-, 4- or 5-benzimidazolyl, methylenedioxyphen-4-yl, methylenedioxyphen-5-yl, ethylenedioxyphenyl, benzothiazolyl, benzopyranyl, benzofuryl, 2,3-dihydrobenzofuryl, benzoxazolyl, thiophenyl and the like. The term "cycloalkylalkoxycarbonyl" means an acyl group derived from a cycloalkylalkoxycarboxylic acid of the formula cycloalkylalkyl-O—COOH wherein cycloalkylalkyl has the meaning given above. The term "aryloxyalkanoyl" means an acyl radical of the formula aryl-O-alkanoyl wherein aryl and alkanoyl have the meaning given above. The term "heterocycloalkoxycarbonyl" means an acyl group derived from heterocycloalkyl-O—COOH wherein heterocycloalkyl is as defined above. The term "heterocycloalkanoyl" is an acyl radical derived from a heterocycloalkylcarboxylic acid wherein heterocyclo has the meaning given above. The term "heterocyclo alkoxycarbonyl" means an acyl radical derived from a heterocycloalkyl-O—COOH wherein heterocyclo has the meaning given above. The term "heteroaryloxycarbonyl" means an acyl radical derived from a carboxylic acid represented by heteroaryl-O—COOH wherein heteroaryl has the meaning given above. The term "aminocarbonyl" alone or in combination, means an amino-substituted carbonyl (carbamoyl) group wherein the amino group can be a primary, secondary or tertiary amino group containing substituents selected from alkyl, aryl, aralkyl, cycloalkyl, cycloalkylalkyl radicals and the like. The term "aminoalkanoyl" means an acyl group derived from an amino-substituted alkylcarboxylic acid wherein the amino group can be a primary, secondary or tertiary amino group containing substituents selected from alkyl, aryl, aralkyl, cycloalkyl, cycloalkylalkyl radicals and the like. The term "halogen" means fluorine, chlorine, bromine or iodine. The term "haloalkyl" means an alkyl radical having the meaning as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like. The term "leaving group" (L or W) generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

Procedures for preparing the compounds of Formula I are set forth below. It should be noted that the general procedure is shown as it relates to preparation of compounds having the specified stereochemistry, for example, wherein the absolute stereochemistry about the hydroxyl group is designated as (R). However, such procedures are generally applicable to those compounds of opposite configuration, e.g., where the stereochemistry about the hydroxyl group is (S). In addition, the compounds having the (R) stereochemistry can be utilized to produce those having the (S) stereochemistry. For example, a compound having the (R) stereochemistry can be inverted to the (S) stereochemistry using well-known methods.

Preparation of Compounds of Formula I

The compounds of the present invention represented by Formula I above can be prepared utilizing the following general procedures as schematically shown in Schemes I and II.

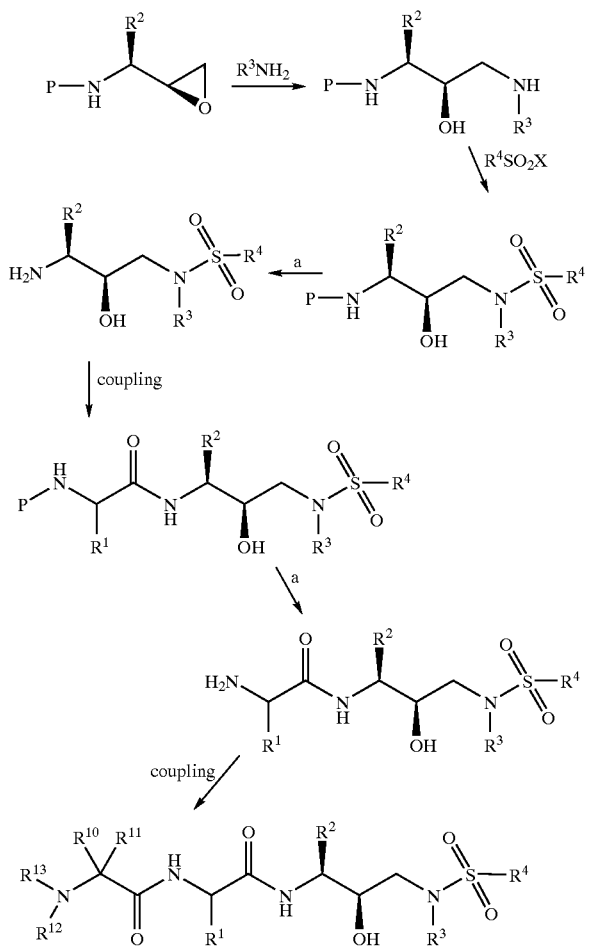

a) deprotection; X=Cl or Br;

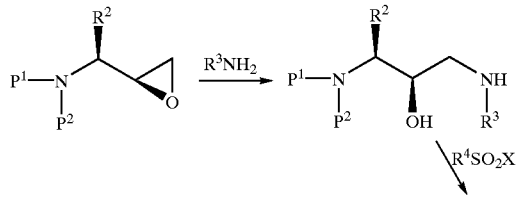

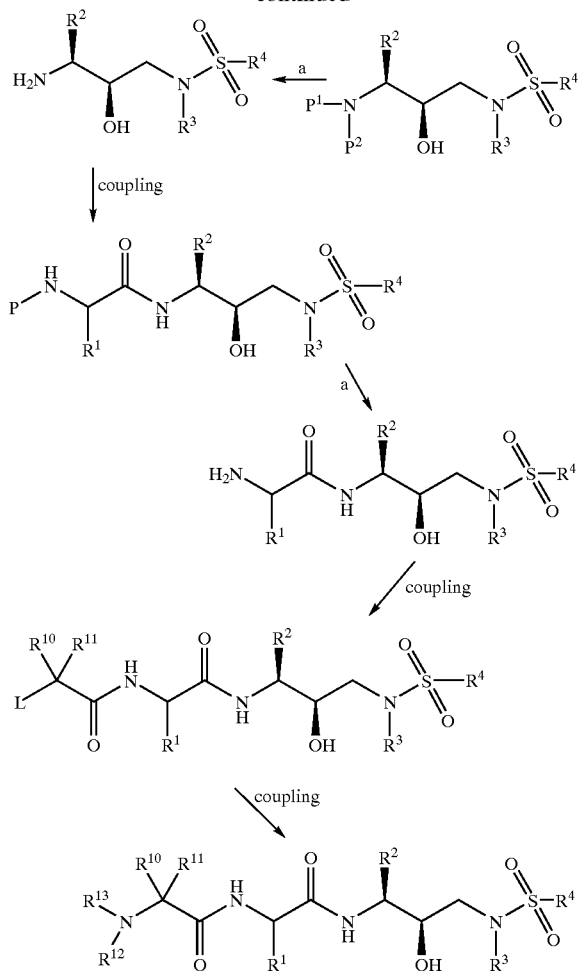

a) deprotection; X=Cl or Br; L=leaving group.

An N-protected chloroketone derivative of an amino acid having the formula:

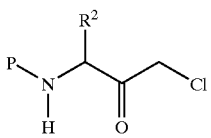

wherein P represents an amino protecting group, and $R^2$ is as defined above, is reduced to the corresponding alcohol utilizing an appropriate reducing agent. Suitable amino protecting groups are well known in the art and include carbobenzoxy, t-butoxycarbonyl, and the like. A preferred amino protecting group is carbobenzoxy. A preferred N-protected chloroketone is N-benzyloxycarbonyl-L-phenylalanine chloromethyl ketone. A preferred reducing agent is sodium borohydride. The reduction reaction is conducted at a temperature of from −10° C. to about 25° C., preferably at about 0° C., in a suitable solvent system such as, for example, tetrahydrofuran, and the like. The N-protected chloroketones are commercially available, e.g., such as from Bachem, Inc., Torrance, Calif. Alternatively, the chloroketones can be prepared by the procedure set forth in S. J. Fittkau, *J. Prakt. Chem.*, 315, 1037 (1973), and subsequently N-protected utilizing procedures which are well known in the art.

The halo alcohol can be utilized directly, as described below, or, preferably, is reacted, preferably at room temperature, with a suitable base in a suitable solvent system to produce an N-protected amino epoxide of the formula:

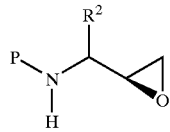

wherein P and $R^2$ are as defined above. Suitable solvent systems for preparing the amino epoxide include ethanol, methanol, isopropanol, tetrahydrofuran, dioxane, and the like including mixtures thereof. Suitable bases for producing the epoxide from the reduced chloroketone include potassium hydroxide, sodium hydroxide, potassium t-butoxide, DBU and the like. A preferred base is potassium hydroxide.

Alternatively, a protected amino epoxide can be prepared, such as in co-owned and co-pending PCT patent application Ser. No. PCT/US93/04804 (WO 93/23388) and PCT/US94/12201, and U.S. patent application Attorney Docket No. C-2860, each of which is incorporated herein by reference in their entirety) disclose methods of preparing chiral epoxide, chiral cyanohydrin, chiral amine and other chiral intermediates useful in the preparation of retroviral protease inhibitors, starting with a DL-, D- or L-amino acid which is reacted with a suitable amino-protecting group in a suitable solvent to produce an amino-protected amino acid ester. For the purposes of illustration, a protected L-amino acid with the following formula will be used to prepare the inhibitors of this invention:

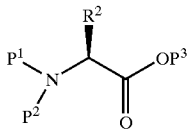

wherein $P^3$ represents carboxyl-protecting group, e.g., methyl, ethyl, benzyl, tertiary-butyl, 4-methoxyphenylmethyl and the like; $R^2$ is as defined above; and $P^1$ and $P^2$ independently are selected from amine protecting groups, including but not limited to, aralkyl, substituted aralkyl, cycloalkenylalkyl and substituted cycloalkenylalkyl, allyl, substituted allyl, aryl, alkoxycarbonyl, aralkoxycarbonyl and silyl. Examples of aralkyl include, but are not limited to benzyl, ortho-methylbenzyl, trityl and benzhydryl, which can be optionally substituted with halogen, alkyl of $C_1$—$C_8$, alkoxy, hydroxy, nitro, alkylene, amino, alkylamino, acylamino and aryl, or their salts, such as phosphonium and ammonium salts. Examples of aryl groups include phenyl, naphthalenyl, indanyl, anthracenyl, durenyl, 9-(9-phenylfluorenyl) and phenanthrenyl, cycloalkenylalkyl or substituted cycloalkylenylalkyl radicals containing cycloalkyls of $C_6$-$C_{10}$. Suitable acyl groups include carbobenzoxy, t-butoxycarbonyl, iso-butoxycarbonyl, benzoyl, substituted benzoyl, butyryl, acetyl, tri-fluoroacetyl, tri-chloroacetyl, phthaloyl and the like. Preferably $P^1$ and $P^2$ are independently selected from aralkyl and substituted aralkyl. More preferably, each of $P^1$ and $P^2$ is benzyl.

Additionally, the P¹ and/or P² protecting groups can form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, e.g., nitrophthalimidyl. The term silyl refers to a silicon atom optionally substituted by one or more alkyl, aryl and aralkyl groups.

Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of the amine functions to provide mono- or bis-disilylamine can provide derivatives of the aminoalcohol, amino acid, amino acid esters and amino acid amide in the case of amino acids, amino acid esters and amino acid amides, reduction of the carbonyl function provides the required mono- or bis-silyl aminoalcohol. Silylation of the aminoalcohol can lead to the N,N,O-tri-silyl derivative. Removal of the silyl function from the silyl ether function is readily accomplished by treatment with, for example, a metal hydroxide or ammonium fluoride reagent, either as a discrete reaction step or in situ during the preparation of the amino aldehyde reagent. Suitable silylating agents are, for example, trimethylsilyl chloride, tert-buty-dimethylsilyl chloride, phenyldimethylsilyl chloride, diphenylmethylsilyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

The amino-protected L-amino acid ester is then reduced, to the corresponding alcohol. For example, the amino-protected L-amino acid ester can be reduced with diisobutylaluminum hydride at −78° C. in a suitable solvent such as toluene. Preferred reducing agents include lithium aluminium hydride, lithium borohydride, sodium borohydride, borane, lithium tri-ter-butoxyaluminum hydride, borane/THF complex. Most preferably, the reducing agent is diisobutylaluminum hydride (DiBAL-H) in toluene. The resulting alcohol is then converted, for example, by way of a Swern oxidation, to the corresponding aldehyde of the formula:

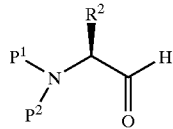

wherein P¹, P² and R² are as defined above. Thus, a dichloromethane solution of the alcohol is added to a cooled (−75 to −68° C.) solution of oxalyl chloride in dichloromethane and DMSO in dichloromethane and stirred for 35 minutes.

Acceptable oxidizing reagents include, for example, sulfur trioxide-pyridine complex and DMSO, oxalyl chloride and DMSO, acetyl chloride or anhydride and DMSO, trifluoroacetyl chloride or anhydride and DMSO, methanesulfonyl chloride and DMSO or tetrahydro thiaphene-S-oxide, toluenesulfonyl bromide and DMSO, trifluoromethanesulfonyl anhydride (triflic anhydride) and DMSO, phosphorus pentachloride and DMSO, dimethylphosphoryl chloride and DMSO and isobutyl chloroformate and DMSO. The oxidation conditions reported by Reetz et al [*Angew Chem.*, 99, p. 1186, (1987)], *Angew Chem. Int. Ed. Engl.*, 26, p. 1141, 1987) employed oxalyl chloride and DMSO at −78° C.

The preferred oxidation method described in this invention is sulfur trioxide pyridine complex, triethylamine and DMSO at room temperature. This system provides excellent yields of the desired chiral protected amino aldehyde usable without the need for purification i.e., the need to purify kilograms of intermediates by chromatography is eliminated and large scale operations are made less hazardous. Reaction at room temperature also eliminated the need for the use of low temperature reactor which makes the process more suitable for commercial production.

The reaction may be carried out under an inert atmosphere such as nitrogen or argon, or normal or dry air, under atmospheric pressure or in a sealed reaction vessel under positive pressure. Preferred is a nitrogen atmosphere. Alternative amine bases include, for example, tri-butyl amine, tri-isopropyl amine, N-methylpiperidine, N-methyl morpholine, azabicyclononane, diisopropylethylamine, 2,2,6,6-tetramethylpiperidine, N,N-dimethylaminopyridine, or mixtures of these bases. Triethylamine is a preferred base. Alternatives to pure DMSO as solvent include mixtures of DMSO with non-protic or halogenated solvents such as tetrahydrofuran, ethyl acetate, toluene, xylene, dichloromethane, ethylene dichloride and the like. Dipolar aprotic co-solvents include acetonitrile, dimethylformamide, dimethylacetamide, acetamide, tetramethyl urea and its cyclic analog, N-methylpyrrolidone, sulfolane and the like. Rather than N,N-dibenzylphenylalaninol as the aldehyde precursor, the phenylalaninol derivatives discussed above can be used to provide the corresponding N-monosubstituted [either P¹ or P²=H] or N,N-disubstituted aldehyde.

In addition, hydride reduction of an amide or ester derivative of the corresponding benzyl for other suitable protecting group) nitrogen protected phenylalanine, substituted phenylalanine or cycloalkyl analog of phenylalanine derivative can be carried out to provide the aldehydes. Hydride transfer is an additional method of aldehyde synthesis under conditions where aldehyde condensations are avoided, cf, Oppenauer oxidation.

The aldehydes of this process can also be prepared by methods of reducing protected phenylalanine and phenylalanine analogs or their amide or ester derivatives by, e.g., sodium amalgam with HCl in ethanol or lithium or sodium or potassium or calcium in ammonia. The reaction temperature may be from about −20° C. to about 45° C., and preferably from about 5° C. to about 25° C. Two additional methods of obtaining the nitrogen protected aldehyde include oxidation of the corresponding alcohol with bleach in the presence of a catalytic amount of 2,2,6,6-tetramethyl-1-pyridyloxy free radical. In a second method, oxidation of the alcohol to the aldehyde is accomplished by a catalytic amount of tetrapropylammonium perruthenate in the presence of N-methylmorpholine-N-oxide.

Alternatively, an acid chloride derivative of a protected phenylalanine or phenylalanine derivative as disclosed above can be reduced with hydrogen and a catalyst such as Pd on barium carbonate or barium sulphate, with or without an additional catalyst moderating agent such as sulfur or a thiol (Rosenmund Reduction).

The aldehyde resulting from the Swern oxidation is then reacted with a halomethyllithium reagent, which reagent is generated in situ by reacting an alkyllithium or arylithium compound with a dihalomethane represented by the formula $X^1CH_2X^2$ wherein $X^1$ and $X^2$ independently represent I, Br or Cl. For example, a solution of the aldehyde and chloroiodomethane in THF is cooled to −78° C. and a solution of n-butyllithium in hexane is added. The resulting product is a mixture of diastereomers of the corresponding amino-protected epoxides of the formulas:

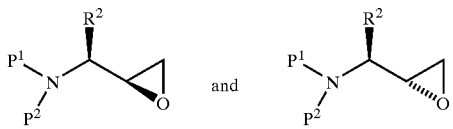

The diastereomers can be separated e.g., by chromatography, or, alternatively, once reacted in subsequent steps the diastereomeric products can be separated. A D-amino acid can be utilized in place of the L-amino acid in order to prepare compounds having an (S) stereochemistry at the carbon bonded to $R^2$.

The addition of chloromethyllithium or bromomethyllithium to a chiral amino aldehyde is highly diastereoselective. Preferably, the chloromethyllithium or bromomethyllithium is generated in-situ from the reaction of the dihalomethane and n-butyllithium. Acceptable methyleneating halomethanes include chloroiodomethane, bromofluoromethane, dibromomethane, diiodomethane, bromofluoromethane and the like. The sulfonate ester of the addition product of, for example, hydrogen bromide to formaldehyde is also a methyleneating agent. Tetrahydrofuran is the preferred solvent, however alternative solvents such as toluene, dimethoxyethane, ethylene dichloride, methylene chloride can be used as pure solvents or as a mixture. Dipolar aprotic solvents such as acetonitrile, DMF, N-methylpyrrolidone are useful as solvents or as part of a solvent mixture. The reaction can be carried out under an inert atmosphere such as nitrogen or argon. For n-butyl lithium can be substituted other organometalic reagents reagents such as methyllithium, tert-butyl lithium, sec-butyl lithium, phenyllithium, phenyl sodium and the like. The reaction can be carried out at temperatures of between about −80° C. to 0° C. but preferably between about −80° C. to −20° C. The most preferred reaction temperatures are between −40° C. to −15° C. Reagents can be added singly but multiple additions are preferred in certain conditions. The preferred pressure of the reaction is atmospheric however a positive pressure is valuable under certain conditions such as a high humidity environment.

Alternative methods of conversion to the epoxides of this invention include substitution of other charged methylenation precurser species followed by their treatment with base to form the analogous anion. Examples of these species include trimethylsulfoxonium tosylate or triflate, tetramethylammonium halide, methyldiphenylsulfoxonium halide wherein halide is chloride, bromide or iodide.

The conversion of the aldehydes of this invention into their epoxide derivative can also be carried out in multiple steps. For example, the addition of the anion of thioanisole prepared from, for example, a butyl or aryl lithium reagent, to the protected aminoaldehyde, oxidation of the resulting protected aminosulfide alcohol with well known oxidizing agents such as hydrogen peroxide, tert-butyl hypochlorite, bleach or sodium periodate to give a sulfoxide. Alkylation of the sulfoxide with, for example, methyl iodide or bromide, methyl tasylate, methyl mesylate, methyl triflate, ethyl bromide, isopropyl bromide, benzyl chloride or the like, in the presence of an organic or inorganic base Alternatively, the protected aminosulfide alcohol can be alkylated with, for example, the alkylating agents above, to provide a sulfonium salts that are subsequently converted into the subject epoxides with tert-amine or mineral bases.

The desired epoxides formed, using most preferred conditions, diastereoselectively in ratio amounts of at least about an 85:15 ratio (S:R). The product can be purified by chromatography to give the diastereomerically and enantiomerically pure product but it is more conveniently used directly without purification to prepare retroviral protease inhibitors. The foregoing process is applicable to mixtures of optical isomers as well as resolved compounds. If a particular optical isomer is desired, it can be selected by the choice of starting material, e.g., L-phenylalanine, D-phenylalanine, L-phenylalaninol, D-phenylalaninol, D-hexahydrophenylalaninol and the like, or resolution can occur at intermediate or final steps. Chiral auxiliaries such as one or two equivilants of camphor sulfonic acid, citric acid, camphoric acid, 2-methoxyphenylacetic acid and the like can be used to form salts, esters or amides of the compounds of this invention. These compounds or derivatives can be crystallized or separated chromatographically using either a chiral or achiral column as is well known to those skilled in the art.

The amino epoxide is then reacted, in a suitable solvent system, with an equal amount, or preferably an excess of, a desired amine of the formula $R^3NH_2$, wherein $R^3$ is hydrogen or is as defined above. The reaction can be conducted over a wide range of temperatures, e.g., from about 10° C. to about 100° C., but is preferably, but not necessarily, conducted at a temperature at which the solvent begins to reflux. Suitable solvent systems include protic, non-protic and dipolar aprotic organic solvents such as, for example, those wherein the solvent is an alcohol, such as methanol, ethanol, isopropanol, and the like, ethers such as tetrahydrofuran, dioxane and the like, and toluene, N,N-dimethylformamide, dimethyl sulfoxide, and mixtures thereof. A preferred solvent is isopropanol. The resulting product is a 3-(N-protected amino)-3-($R^2$)-1-(NH$R^3$)-propan-2-ol derivative (hereinafter referred to as an amino alcohol) can be represented by the formulas:

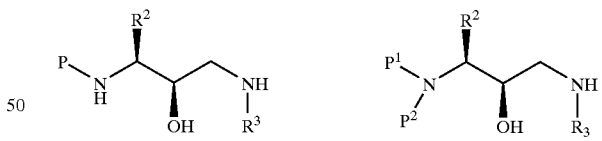

wherein P, $P^1$, $P^2$, $R^2$ and $R^3$ are as described above. Alternatively, a haloalcohol can be utilized in place of the amino epoxide.

The amino alcohol defined above is then reacted in a suitable solvent with the sulfonyl chloride $R^4SO_2Cl$, the sulfonyl bromide $R^4SO_2Br$ or the corresponding sulfonyl anhydride, preferably in the presence of an acid scavenger. Suitable solvents in which the reaction can be conducted include methylene chloride, tetrahydrofuran and the like. Suitable acid scavengers include triethylamine, pyridine and the like. The resulting sulfonamide derivative can be represented, depending on the epoxide utilized by the formulas

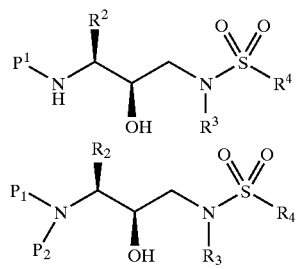

wherein P, P¹, P², R², R³ and R⁴ are as defined above. These intermediates are useful for preparing inhibitor compounds of the present invention.

The sulfonyl halides of the formula $R^4SO_2X$ can be prepared by the reaction of a suitable aryl, heteroaryl and benzo fused heterocyclo Grignard or lithium reagents with sulfuryl chloride, or sulfur dioxide followed by oxidation with a halogen, preferably chlorine. Aryl, heteroaryl and benzo fused heterocyclo Grignard or lithium reagents can be prepared from their corresponding halide (such as chloro or bromo) compounds which are commercially available or readily prepared from commercially available starting materials using known methods in the art. Also, thiols may be oxidized to sulfonyl chlorides using chlorine in the presence of water under carefully controlled conditions. Additionally, sulfonic acids, such as arylsulfonic acids, may be converted to sulfonyl halides using reagents such as $PCl_5$, $SOCl_2$, ClC(O)C(O)Cl and the like, and also to anhydrides using suitable dehydrating reagents. The sulfonic acids may in turn be prepared using procedures well known in the art. Some sulfonic acids are commercially available. In place of the sulfonyl halides, sulfinyl halides ($R^4SOX$) or sulfenyl halides ($R^4SX$) can be utilized to prepare compounds wherein the —$SO_2$— moiety is replaced by an —SO— or —S— moiety, respectively. Arylsulfonic acids, benzo fused heterocyclo sulfonic acids or heteroaryl sulfonic acids can be prepared by sulfonation of the aromatic ring by well known methods in the art, such as by reaction with sulfuric acid, $SO_3$, $SO_3$ complexes, such as $DMF(SO_3)$, pyridine ($SO_3$), N,N-dimethylacetamide($SO_3$), and the like. Preferably, arylsulfonyl halides are prepared from aromatic compounds by reaction with $DMF(SO_3)$ and $SOCl_2$ or ClC(O)C(O)Cl. The reactions may be performed stepwise or in a single pot.

Arylsulfonic acids, benzo fused heterocycle sulfonic acids, heteroaryl sulfonic acids, arylmercaptans, benzo fused heterocyclo mercaptans, heteroarylmercaptans, arylhalides, benzo fused heterocyclo halides, heteroarylhalides, and the like are commercially available or can be readily prepared from starting materials commercially available using standard methods well known in the art. For example, a number of sulfonic acids ($R^4SO_3H$) represented by the formulas

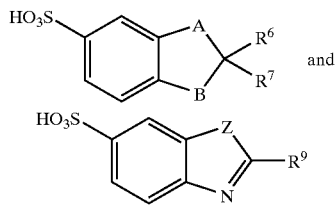

wherein A, B, Z, R⁶, R⁷ and R⁹ are as defined above, have been prepared from 1,2-benzenedithiol, 2-mercaptanphenol, 1,2-benzenediol, 2-aminobenzothiazole, benzothiazole, 2-aminobenzimidazole, benzimidazole, and the like, which are commercially available, by Carter, U.S. Pat. No. 4,595,407; Ehrenfreund et al., U.S. Pat. No. 4,634,465; Yoder et al., J. Heterocycl. Chem. 4:166–167 (1967); Cole et al., Aust. J. Chem. 33:675–680 (1980); Cabiddu et al., Synthesis 797–798 (1976); Ncube et al., Tet. Letters 2345–2348 (1978); Ncube et al., Tet. Letters 255–256 (1977); Ansink & Cerfontain, Rec. Trav. Chim. Pays-Bas 108:395–403 (1989); and Kajihara & Tsuchiya, EP 638564 A1, each of which are incorporated herein by reference in their entirety. For example, 1,2-benzenedithiol, 2-mercaptanphenol or 1,2-benzenediol can be reacted with $R^6R^7C(L')_2$, where L' is as defined below, preferably, Br or I, in the presence of a base, such as hydroxide, or $R^6R^7C=O$ in the presence of acid, such as toluenesulfonic acid, or $P_2O_5$, to prepare the substituted benzo fused heterocycle of formula

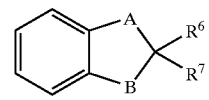

which can then be sulfonylated to the sulfonic acid above For example, $CF_2Br_2$ or $CD_2Br_2$ can be reacted with 1,2-benzenedithiol, 2-mercaptanphenol or 1,2-benzenediol in the presence of base to produce the compounds

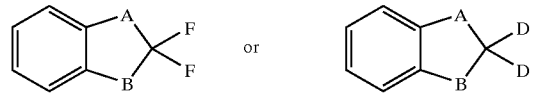

respectively, wherein A and B are O or S and D is a deuterium atom. Also, when A and/or B represent S, the sulfur can be oxidized using the methods described below to the sulfone or sulfoxide derivatives.

Following preparation of the sulfonamide derivative, the amino protecting group P or P¹ and P² amino protecting groups are removed under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a suitable solvent system such as an alcohol, acetic acid, and the like or mixtures thereof. Where the protecting group is a t-butoxycarbonyl group, it can be removed utilizing an inorganic or organic acid, e.g., HCl or trifluoroacetic acid, in a suitable solvent system, e.g., dioxane or methylene chloride. The resulting product is the amine salt derivative.

Following neutralization of the salt, the amine is then coupled to the DL-, D-, or L-amino acid corresponding to the formula $PNHCH(R^1)COOH$, wherein P and R¹ are as defined above, followed by deprotection of the amine as described above, and coupling to

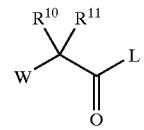

wherein R¹⁰ and R¹¹ are as defined above, W is a leaving group, such as mesylate, bromo or chloro, and L is leaving group such as halide, anhydride, active ester, and the like. For example when $R^{10}$ and $R^{11}$ are both hydrogen radical, bromoacetyl halide, chloroacetyl halide or the corresponding anhydride can be used. Finally, reacting the above intermediate with the amine $R^{12}R^{13}NH$ can produce the antiviral compounds of the present invention having the formula

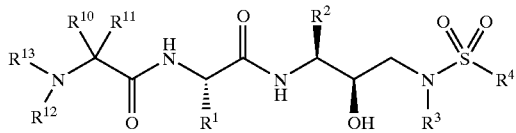

wherein $R^1$, $R^2$, $R^3$, $R^4$, $R^{10}$, $R^{11}$, $R^{12}$ and $R^{13}$ are as defined above. Amines of the formula $R^{12}R^{13}NH$ are commercially available, such as dimethylamine, isobutylamine, isopropylamine, benzylamine, and the like; or can readily be prepared from commercially available starting materials using standard methods well known in the art.

Alternatively, following neutralization of the salt, the amine of formula

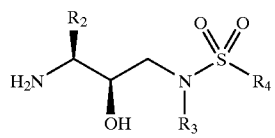

is then coupled to the DL-, D-, or L-amino acid corresponding to the formula PNHCH($R^1$)COOH, wherein P and $R^1$ are as refined above, followed by deprotection of the amine as described above and then coupling the deprotected amine to the amino acid of formula

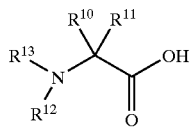

or specific stereoisomer thereof, wherein $R^{10}$, $R^{11}$, $R^{12}$, and $R^{13}$ are as defined above, such as N-methylalanine, N,N-dimethylalanine, N,N,2,2-tetramethylglycine, N-benzylserine and the like, to produce the antiviral compounds of the present invention. The amino acids are commercially available or are readily prepared from a protected carboxylic acid with a leaving group W (defined above), W—$(R^{10})(R^{11})C$—$CO_2P^3$, by reaction with the amine $R^{12}R^{13}NH$ as shown in Scheme III, wherein $P^3$, $R^{10}$, $R^{11}$, $R^{12}$, and $R^{13}$ are as defined above.

Scheme III

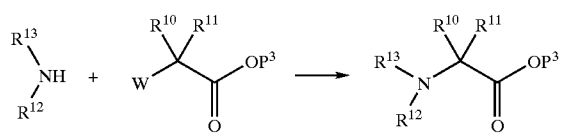

Alternatively, following neutralization of the salt, the amine of formula

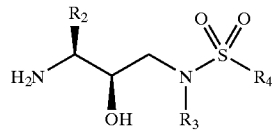

is then coupled to the DL-, D-, or L-amino acid corresponding to the formula

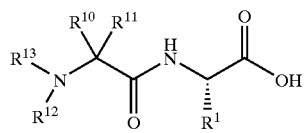

wherein $R^1$, $R^{10}$, $R^{11}$, $R^{12}$, and $R^{13}$ are as defined above, which can be prepared in a similar fashion to the coupling methods described above from DL-, D-, or L-amino acid corresponding to the formula $NH_2CH(R^1)COOP^3$, wherein $P^3$ and $R^1$ are as defined above.

The DL-, D-, or L-amino acid corresponding to the formula PNHCH($R^1$)COOH or $NH_2CH(R^1)COOP^3$, wherein P, $P^3$ and $R^1$ are as defined above, are commercially available (Sigma Chemical Co.), or readily prepared using standard methods well known in the art from readily available starting materials. Preferably, P is a benzyloxycarbonyl or t-butoxycarbonyl radical and $P^3$ is benzyl or tert-butyl radicals. Standard coupling procedures can be used to couple the amino acids and amines. The carboxylic acid group is reacted to form an anhydride, mixed anhydride, acid halide, such as chloride or bromide, or active ester, such as esters of N-hydroxysuccinimide, HOBT and the like, using well known procedures and conditions. Appropriate solvent systems include tetrahydrofuran, ethylether, methyl-tert-butylether, methylene chloride, N,N-dimethylformamide and the like, including mixtures thereof.

Alternatively, the protected amino alcohol from the epoxide opening can be further protected at the newly introduced amino group with a protecting group P' which is not removed with the removal of the amino protecting groups P or $P^1$ and $P^2$. One skilled in the art can choose appropriate combinations of P', P, $P^1$ and $P^2$. For example, suitable combinations are P=Cbz and P'=Boc; P'=Cbz and P=Boc; $P^1$=Cbz, $P^2$=benzyl and P'=Boc; and $P^1$=$P^2$=benzyl and P'=Boc. The resulting compound represented by the formula

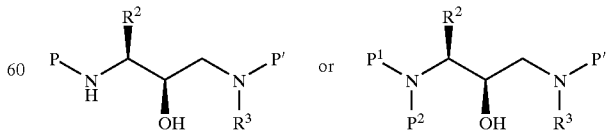

can be carried through the remainder of the synthesis to provide a compound of the formula

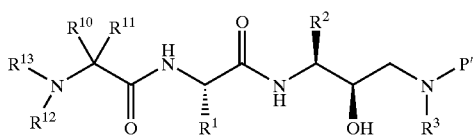

wherein P', $R^1$, $R^2$, $R^3$, $R^{10}$, $R^{11}$, $R^{12}$, and $R^{13}$ are as defined above. The protecting group P' is then selectively removed and the resulting amine is reacted with the sulfonyl chloride $R^4SO_2Cl$, the sulfonyl bromide $R^4SO_2Br$ or the corresponding sulfonyl anhydride, preferably in the presence of an acid scavenger, to form the compounds of the present invention. This selective deprotection and conversion to the sulfonamide can be accomplished at either the end of the synthesis or at any appropriate intermediate step if desired.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on either a Varian VXR-300 or VXR-400 nuclear magnetic resonance spectrometer.

The following Examples illustrate the preparation of inhibitor compounds of the present invention and intermediates useful in preparing the inhibitor compounds of the present invention.

EXAMPLE 1

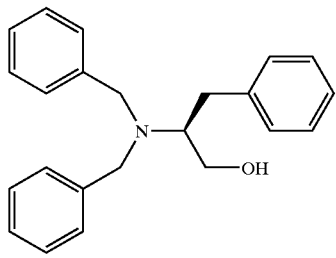

Preparation of 2S-[bis(Phenylmethyl)amino]benzenepropanol

Method 1: 2S-[bis(Phenylmethyl)amino]benzenepropanol from the DIBAL Reduction of N,N-bis(Phenylmethyl)-L-phenylalanine Phenylmethyl Ester Step 1:

A solution of L-phenylalanine (50.0 g, 0.302 mol), sodium hydroxide (24.2 g, 0.605 mol) and potassium carbonate (83.6 g, 0.605 mol) in water (500 mL) was heated to 97° C. Benzyl bromide (108.5 mL, 0.605 mol) was then slowly added (addition time—25 min). The mixture was stirred at 97° C. for 30 minutes under a nitrogen atmosphere. The solution was cooled to room temperature and extracted with toluene (2×250 mL). The combined organic layers were washed with water and brine, dried over magnesium sulfate, filtered and concentrated to an oil. The identity of the product was confirmed as follows. Analytical TLC (10% ethyl acetate/hexane, silica gel) showed major component at Rf value=0.32 to be the desired tribenzylated compound, N,N-bis(phenylmethyl)-L-phenylalanine phenylmethyl ester. This compound can be purified by column chromatography (silica gel, 15% ethyl acetate/hexane). Usually the product is pure enough to be used directly in the next step without further purification. $^1$H NMR spectrum was in agreement with published literature. 1H NMR (CDCL$_3$) $\partial$, 3.00 and 3.14 (ABX-system, 2H, $J_{AB}$=14.1 Hz, $J_{AX}$=7.3 Hz and $J_{BX}$=5.9 Hz), 3.54 and 3.92 (AB-System, 4H, $J_{AB}$=13.9 Hz), 3.71 (t, 1H, J=7.6 Hz), 5.11 and 5.23 (AB-System, 2H, $J_{AB}$=12.3 Hz), and 7.18 (m, 20H). EIMS: m/z 434 (M−1).

Step 2:

The benzylated phenylalanine phenylmethyl ester (0.362 mol) from the previous reaction was dissolved in toluene (750 mL) and cooled to) −55° C. A 1.5 M solution of DIBAL in toluene (443.9 mL, 0.666 mol), was added at a rate to maintain the temperature between −55 to −50° C. (addition time—1 hr). The mixture was stirred for 20 minutes under a nitrogen atmosphere and then quenched at −55° C. by the slow addition of methanol (37 ml). The cold solution was then poured into cold (5° C.) 1.5 N HCl solution (1.8 L). The precipitated solid (approx. 138 g) was filtered off and washed with toluene. The solid material was suspended in a mixture of toluene (400 mL) and water (100 ml). The mixture was cooled to 5° C. and treated with 2.5 N NaOH (186 mL) and then stirred at room temperature until solid dissolved. The toluene layer was separated from the aqueous phase and washed with water and brine, dried over magnesium sulfate, filtered and concentrated to a volume of 75 mL (89 g). Ethyl acetate (25 mL) and hexane (25 mL) were added to the residue upon which the desired alcohol product began to crystallize. After 30 min, an additional 50 mL hexane were added to promote further crystallization. The solid was filtered off and washed with 50 mL hexane to give 34.9 g of first crop product. A second crop of product (5.6 g) was isolated by refiltering the mother liquor. The two crops were combined and recrystallized from ethyl acetate (20 mL) and hexane (30 mL) to give 40 g of βS-2-[Bis(phenylmethyl)amino]benzenepropanol, 40% yield from L-phenylalanine. An additional 7 g (7%) of product can be obtained from recrystallization of the concentrated mother liquor. TLC of product Rf=0.23 (10% ethyl acetate/hexane, silica gel); $^1$H NMR (CDCl$_3$) $\partial$ 2.44 (m, 1H,), 3.09 (m, 2H), 3.33 (m, 1H), 3.48 and 3.92 (AB-System, 4H, $J_{AB}$=13.3 Hz), 3.52 (m, 1H) and 7.23 (m, 15H); $[\alpha]_D^{25}$ +42.4 (c 1.45, CH$_2$Cl$_2$); DSC 77.67° C.; Anal. Calcd. for $C_{23}H_{25}ON$: C, 83.34; H, 7.60; N, 4.23. Found: C, 83.43; H, 7.59; N, 4.22. HPLC on chiral stationary phase: Cyclobond I SP column (250×4.6 mm I.D.), mobile phase: methanol/triethyl ammonium acetate buffer pH 4.2 (58:42, v/v), flow-rate of 0.5 ml/min, detection with detector at 230 nm and a temperature of 0° C. Retention time: 11.25 min., retention time of the desired product enantiomer: 12.5 min.

Method 2: Preparation of βS-2-[bis(Phenylmethyl)amino] benzene-propanol From the N,N-Dibenzylation of L-phenylalaninol L-phenylalaninol (176.6 g, 1.168 mol) was added to a stirred solution of potassium carbonate (484.6 g, 3.506 mol) in 710 mL of water. The mixture was heated to 65° C. under a nitrogen atmosphere. A solution of benzyl bromide (400 g, 2.339 mol) in 3A ethanol (305 mL) was added at a rate that maintained the temperature between 60–68° C. The biphasic solution was stirred at 65° C. for 55 min and then allowed to cool to 10° C. with vigorous stirring. The oily product solidified into small granules. The product was diluted with 2.0 L of tap water and stirred for 5 minutes to dissolve the inorganic by products. The product was isolated by filtration under reduced pressure and washed with water until the pH is 7. The crude product obtained was air dried overnight to give a semi-dry solid (407 g) which was recrystallized from 1.1 L of ethyl acetate/heptane (1:10 by volume). The product was isolated by filtration (at −8° C.), washed with 1.6 L of cold (−10° C.) ethyl acetate/heptane (1:10 by volume) and air-dried to give 339 g (88% yield) of βS-2-[Bis (phenylmethyl)amino]benzene-propanol, Mp=71.5–73.0° C. More product can be obtained from the mother liquor if necessary. The other analytical characterization was identical to compound prepared as described in Method 1.

EXAMPLE 2

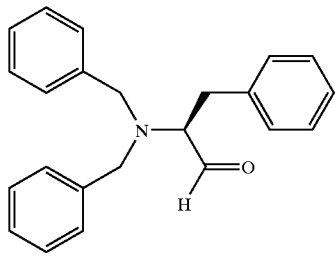

Preparation of 2S-[bis(Phenylmethyl)amino] benzenepropanaldehyde

Method 1:

2S-[Bis(phenylmethyl)amino]benzene-propanol (200 g, 0.604 mol) was dissolved in triethylamine (300 mL, 2.15 mol). The mixture was cooled to 12° C. and a solution of sulfur trioxide/pyridine complex (380 g, 2.39 mol) in DMSO (1.6 L) was added at a rate to maintain the temperature between 8–17° C. (addition time—1.0 h). The solution was stirred at ambient temperature under a nitrogen atmosphere for 1.5 hour at which time the reaction was complete by TLC analysis (33% ethyl acetate/hexane, silica gel). The reaction mixture was cooled with ice water and quenched with 1.6 L of cold water (10–15° C.) over 45 minutes. The resultant solution was extracted with ethyl acetate (2.0 L), washed with 5% citric acid (2.0 L), and brine (2.2 L), dried over MgSO$_4$ (280 g) and filtered. The solvent was removed on a rotary evaporator at 35–40° C. and then dried under vacuum to give 198.8 g of 2S-[Bis-(phenylmethyl)amino] benzenepropanaldehyde as a pale yellow oil (99.9%). The crude product obtained was pure enough to be used directly in the next step without purification. The analytical data of the compound were consistent with the published literature. [α]$_D^{25}$=−92.9° (c 1.87, CH$_2$Cl$_2$); $^1$H NMR (400 MHz, CDCl$_3$) ∂, 2.94 and 3.15 (ABX-System, 2H, J$_{AB}$=13.9 Hz, J$_{AX}$=7.3 Hz and J$_{BX}$=6.2 Hz), 3.56 (t, 1H, 7.1 Hz), 3.69 and 3.82 (AB-System, 4H, J$_{AB}$=13.7 Hz), 7.25 (m, 15H) and 9.72 (s, 1H); HRMS Calcd for (M+1) C$_{23}$H$_{24}$NO 330.450, found: 330.1836. Anal. Calcd. for C$_{23}$H$_{23}$ON: C, 83.86; H, 7.04; N, 4.25. Found: C, 83.64; H, 7.42; N, 4.19. HPLC on chiral stationary phase: (S,S) Pirkle-Whelk-O 1 column (250×4.6 mm I.D.), mobile phase: hexane/ isopropanol (99.5:0.5, v/v), flow-rate: 1.5 ml/min, detection with UV detector at 210 nm. Retention time of the desired S-isomer: 8.75 min., retention time of the R-enantiomer 10.62 min.

Method 2:

A solution of oxalyl chloride (8.4 ml, 0.096 mol) in dichloromethane (240 ml) was cooled to −74° C. A solution of DMSO (12.0 ml, 0.155 mol) in dichloromethane (50 ml) was then slowly added at a rate to maintain the temperature at −74° C. (addition time ~1.25 hr). The mixture was stirred for 5 min. followed by addition of a solution of βS-2-[bis (phenylmethyl)amino]benzene-propanol 0.074 mol) in 100 ml of dichloromethane (addition time—20 min., temp. −75° C. to −68° C.). The solution was stirred at −78° C. for 35 minutes under a nitrogen atmosphere. Triethylamine (41.2 ml, 0.295 mol) was then added over 10 min. (temp. −78° to −68° C.) upon which the ammonium salt precipitated. The cold mixture was stirred for 30 min. and then water (225 ml) was added. The dichloromethane layer was separated from the aqueous phase and washed with water, brine, dried over magnesium sulfate, filtered and concentrated. The residue was diluted with ethyl acetate and hexane and then filtered to further remove the ammonium salt. The filtrate was concentrated to give αS-[bis(phenylmethyl)amino] benzenepropanaldehyde The aldehyde was carried on to the next step without purification.

Method 3:

To a mixture of 1.0 g(3.0 mmoles) of βS-2[bis (phenylmethyl)amino]benzenepropanol 0.531 g(4.53 mmoles) of N-methyl morpholine, 2.27 g of molecular sieves(4A) and 9.1 mL of acetonitrile was added 53 mg (0.15 mmoles) of tetrapropylammonium perruthenate (TPAP). The mixture was stirred for 40 minutes at room temperature and concentrated under reduced pressure. The residue was suspended in 15 mL of ethyl acetate, filtered through a pad of silica gel. The filtrate was concentrated under reduced pressure to give a product containing approximately 50% of αS-2[bis(phenylmethyl)amino]benzene pro- panaldehyde as a pale yellow oil.

Method 4:

To a solution of 1.0 g (3.02 mmoles) of βS-2[bis (phenylmethyl)amino]benzenepropanol in 9.0 mL of toluene was added 4.69 mg(0.03 mmoles) of 2,2,6,6-tetramethyl-1- piperidinyloxy, free radical (TEMPO), 0.32 g(3.11 mmoles) of sodium bromide, 9.0 mL of ethyl acetate and 1.5 mL of water. The mixture was cooled to 0° C. and an aqueous solution of 2.87 mL of 5% household bleach containing 0.735 g(8.75 mmoles) of sodium bicarbonate and 8.53 mL of water was added slowly over 25 minutes. The mixture was stirred at 0° C. for 60 minutes. Two more additions (1.44 mL each) of bleach was added followed by stirring for 10 minutes. The two phase mixture was allowed to separate. The aqueous layer was extracted twice with 20 mL of ethyl acetate. The combined organic layer was washed with 4.0 mL of a solution containing 25 mg of potassium iodide and water (4.0 mL), 20 mL of 10% aqueous sodium thiosulfate solution and then brine solution. The organic solution was dried over magnesium sulfate, filtered and concentrated under reduced pressure to give 1.34 g of crude oil containing a small amount of the desired product aldehyde, αS-[bis (phenylmethyl)amino]benzenepropanaldehyde.

Method 5:

Following the same procedures as described in Method 1 of this Example except 3.0 equivalents of sulfur trioxide pyridine complex was used and αS-[bis(phenylmethyl) amino]benzenepropanaldehyde was isolated in comparable yields.

EXAMPLE 3

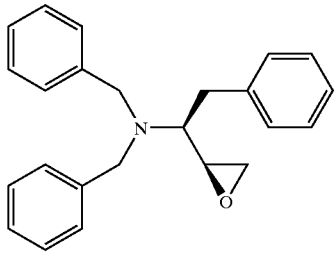

Preparation of N,N-Dibenzyl-3(S)-amino-1,2-(S)-epoxy-4-phenylbutane

Method 1:

A solution of αS-[Bis(phenylmethyl)amino] benzenepropanaldehyde (191.7 g, 0.58 mol) and chloroiodomethane (56.4 mL, 0.77 mol) in tetrahydrofuran (1.8 L) was cooled to −30 to −35° C. (colder temperature such as −70° C. also worked well but warmer temperatures are more readily achieved in large scale operations) in a stainless steel reactor under a nitrogen atmosphere. A solution of n-butyl lithium in hexane (1.6 M, 365 mL, 0.58 mol) was then added at a rate that maintained the temperature below −25° C. After addition the mixture was stirred at −30 to −35° C. for 10 minutes. More additions of reagents were carried out in the following manner: (1) additional chloroiodomethane (17 mL) was added, followed by n-butyl lithium (110 mL) at <−25° C. After addition the mixture was stirred at −30 to −35° C. for 10 minutes. This was repeated once. (2) Additional chloroiodomethane (8.5 mL, 0.11 mol) was added, followed by n-butyl lithium (55 mL, 0.088 mol) at <−25° C. After addition the mixture was stirred at −30 to −35° C. for 10 minutes. This was repeated 5 times. (3) Additional chloroiodomethane (8.5 mL, 0.11 mol) was added, followed by n-butyl lithium (37 mL, 0.059 mol) at <−25° C. After addition the mixture was stirred at −30 to −35° C. for 10 minutes. This was repeated once. The external cooling was stopped and the mixture warned to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material. (The crude product weight was >100%. Due to the relative instability of the product on silica gel, the crude product is usually used directly in the next step without purification). The diastereomeric ratio of the crude mixture was determined by proton NMR: (2S)/(2R): 86:14. The minor and major epoxide diastereomers were characterized in this mixture by tlc analysis (silica gel, 10% ethyl acetate/hexane), Rf=0.29 & 0.32, respectively. An analytical sample of each of the diastereomers was obtained by purification on silica-gel chromatography (3% ethyl acetate/hexane) and characterized as follows:

N,N,αS-Tris(phenylmethyl)-2S-oxiranemethanamine $^1$H NMR (400 MHz, CDCl$_3$) ∂ 2.49 and 2.51 (AB-System, 1H, J$_{AB}$=2.82), 2.76 and 2.77 (AB-System, 1H, J$_{AB}$=4.03), 2.83 (m, 2H), 2.99 & 3.03 (AB-System, 1H, J$_{AB}$=10.1 Hz), 3.15 (m, 1H), 3.73 & 3.84 (AB-System, 4H, J$_{AB}$=14.00), 7.21 (m, 15H); $^{13}$C NMR (400 MHz, CDCl$_3$) ∂ 139.55, 129.45, 128.42, 128.14, 128.09, 126.84, 125.97, 60.32 54.23, 52.13, 45.99, 33.76; HRMS Calcd for C$_{24}$H$_{26}$NO (M+1) 344.477, found 344.2003.

N,N,αS-Tris(phenylmethyl)-2R-oxiranemethanamine $^1$H NMR (300 MHz, CDCl$_3$) ∂ 2.20 (m, 1H), 2.59 (m, 1H), 2.75 (m, 2H), 2.97 (m, 1H), 3.14 (m, 1H), 3.85 (AB-System, 4H), 7.25 (m, 15H).HPLC on chiral stationary phase: Pirkle-Whelk-O 1 column (250×4.6 mm I.D.), mobile phase: hexane/isopropanol (99.5:0.5, v/v), flow rate: 1.5 ml/min, detection with UV detector at 210 m. Retention time of (8): 9.38 min., retention time of enantiomer of (4): 13.75 min.

Method 2:

A solution of the crude aldehyde 0.074 mol and chloroiodomethane (7.0 ml, 0.096 mol) in tetrahydrofuran (285 ml) was cooled to −78° C., under a nitrogen atmosphere. A 1.6 M solution of n-butyl lithium in hexane (25 ml, 0.040 mol) was then added at a rate to maintain the temperature at −75° C. (addition time—15 min.). After the first addition, additional chloroiodomethane 11.6 ml, 0.022 mol) was added again, followed by n-butyl lithium (23 ml, 0.037 mol), keeping the temperature at −75° C. The mixture was stirred for 15 min. Each of the reagents, chloroiodomethane (0.70 ml, 0.010 mol) and n-butyl lithium (5 ml, 0.008 mol) were added 4 more times over 45 min. at −75° C. The cooling bath was then removed and the solution warmed to 22° C. over 1.5 hr. The mixture was poured into 300 ml of saturated aq. ammonium chloride solution. The tetrahydrofuran layer was separated. The aqueous phase was extracted with ethyl acetate (1×300 ml). The combined organic layers were washed with brine, dried over magnesium sulfate, filtered and concentrated to give a brown oil (27.4 g). The product could be used in the next step without purification. The desired diastereomer can be purified by recrystallization at a subsequent step. The product could also be purified by chromatography.

Method 3:

A solution of αS-[bis(phenylmethyl)amino] benzenepropanaldehyde (178.84 g, 0.54 mol) and bromochloromethane (46 mL, 0.71 mol) in tetrahydrofuran (1.8 L) was cooled to −30 to −35° C. (colder temperature such as −70° C. also worked well but warmer temperatures are more readily achieved in large sale operations) in a stainless steel reactor under a nitrogen atmosphere. A solution of n-butyl lithium in hexane (1.6 M, 340 mL, 0.54 mol) was then added at a rate that maintained the temperature below −25° C. After addition the mixture was stirred at −30 to −35° C. for 10 minutes. More additions of reagents were carried out in the following manner: (1) additional bromochloromethane (14 mL) was added, followed by n-butyl lithium (102 mL) at <−25° C. After addition the mixture was stirred at −30 to −35° C. for 10 minutes. This was repeated once. (2) Additional bromochloromethane (7 mL, 0.11 mol) was added, followed by n-butyl lithium (51 mL, 0.082 mol) at <−25° C. After addition the mixture was stirred at −30 to −35° C. for 10 minutes. This was repeated 5 times. (3) Additional bromochloromethane (7 mL, 0.11 mol) was added, followed by n-butyl lithium (51 mL, 0.082 mol) at <−25° C. After addition the mixture was stirred at −30 to −35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C in vacuo (0.8 bar) for 1 h to give 222.8 g of crude material.

Method 4:

Following the same procedures as described in Method 3 of this Example except the reaction temperatures were at −20° C. The resulting N,N,αS-tris(phenylmethyl)-2S-oxiranemethanamine was a diastereomeric mixture of lesser purity then that of Method 3.

Method 5:

Following the same procedures as described in Method 3 of this Example except the reaction temperatures were at −70—−78° C. The resulting N,N,αs-tris(phenylmethyl)-2S-oxiranemethanamine was a diastereomeric mixture, which was used directly in the subsequent steps without purification.

Method 6:

Following the same procedures as described in Method 3 of this Example except a continuous addition of bromochloromethane and n-butyl lithium was used at −30 to −35° C. After the reaction and work up procedures as described in Method 3 of this Example, the desired N,N,αS-tris(phenylmethyl)-2S-oxiranemethanamine was isolated in comparable yields and purities.

Method 7:

Following the same procedures as described in Method 2 of this Example except dibromomethane was used instead of chloroiodomethane. After the reaction and work up procedures as described in Method 2 of this Example, the desired N,N,αS-tris(phenylmethyl)-2S-oxirane-methanamine was isolated.

EXAMPLE 4

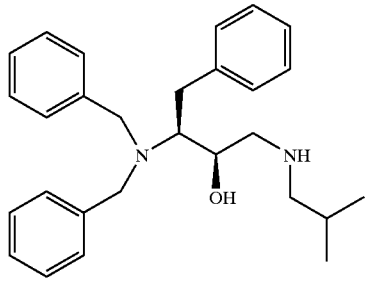

Preparation of N-[3(S)-[N,N-bis(Phenylmethyl) amino]-2(R)-hydroxy-4-phenylbutyl]-N-isobutylamine To a solution of crude N,N-dibenzyl-3(S)-amino-1,2(S)-epoxy-4-phenylbutane (388.5 g, 1.13 mol) in isopropanol (2.7 L) (or ethyl acetate) was added isobutylamine (1.7 kgm, 23.1 mol) over 2 min. The temperature increased from 25° C. and to 30° C. The solution was heated to 82° C. and stirred at this temperature for 1.5 hours. The warm solution was concentrated under reduced pressure at 65° C., The brown oil residue was transferred to a 3-L flask and dried in vacuo (0.8 mm Hg) for 16 h to give 450 g of 3S-(N,N-bis(phenylmethyl)amino-4-phenylbutan-2R-ol as a crude oil.

An analytical sample of the desired major diastereomeric product was obtained by purifying a small sample of crude product by silica gel chromatography (40% ethyl acetate/hexane). Tlc analysis: silica gel, 40% ethyl acetate/hexane; Rf=0.28; HPLC analysis: ultrasphere ODS column, 25% triethylamino-/phosphate buffer pH 3-acetonitrile, flow rate 1 mL/min, UV detector; retention time 7.49 min.; HRMS Calcd for $C_{28}H_{27}N_2O$ (M+1) 417.616, found 417.2887. An analytical sample of the minor diastereomeric product, 3S-[N,N-bis(phenylmethyl)amino]1-(2-methylpropyl)amino-4-phenylbutan-2S-ol was also obtained by purifying a small sample of crude product by silica gel chromatography (40% ethyl acetate/hexane).

EXAMPLE 5

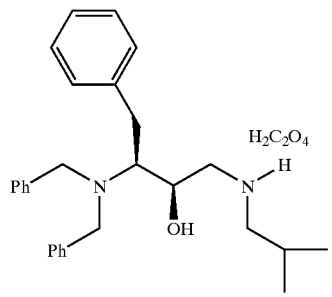

Preparation of N-[3(S)-[N,N-bis(Phenylmethyl) amino]-2(R)-hydroxy-4-phenylbutyl]-N-isobutylamine.oxalic Acid Salt To a solution of oxalic acid (8.08 g, 89.72 mmol) in methanol (76 mL) was added a solution of crude 3(S)-[N,N-bis(phenylmethyl)amino]-1-(2-methylpropyl)amino-4-phenylbutan-2(R)-ol {39.68 g, which contains about 25.44 g (61.06 mmol) of 3(S),2(R) isomer and about 4.49 g (10.78 mmol) of 3(S),2(S) isomer} in ethyl acetate (90 mL) over 15 minutes. The mixture was stirred at room temperature for about 2 hours. Solid was isolated by filtration, washed with ethyl acetate (2×20 mL) and dried in vacuo for about 1 hour to yield 21.86 g (70.78 isomer recovery) of 97% diastereomerically pure salt (based on HPLC peak areas). HPLC analysis: Vydec-peptide/protein C18 column, UV detector 254 nm, flow rate 2 mL/min., gradient {A=0.05% trifluoroacetic acid in water, B=0.05% trifluoroacetic acid in acetonitrile, 0 min. 75% A/25% B, 30 min. 10% A/90% B, 35 min. 10% A/90% B, 37 min. 75% A/25% B}; Retention time 10.68 min. (3(S),2(R) isomer) and 9.73 min. (3(S),2(S) isomer). Mp=174.99° C.; Microanalysis: Calc.: C 71.05%, H 7.50%, N 5.53%; Found: C 71.71%, H 7.75%, N 5.39%.

Alternatively, oxalic acid dihydrate (119 g, 0.94 mole) was added to a 5000 mL round bottom flask fitted with a mechanical stirrer and a dropping funnel. Methanol (1000 ml) was added and the mixture stirred until dissolution was complete. A solution of crude 3(S)-[N,N-bis(phenylmethyl) amino]-1-(2-methylpropyl) amino-4-phenylbutan-2(R)-ol in ethyl acetate 1180 ml, 0.212 g amino alcohol isomers/mL, 0.9160 moles) was added over a twenty minute period. The mixture was stirred for 18 hours and the solid product was isolated by centrifugation in six portions at 400G. Each portion was washed with 125 mL of ethyl acetate. The salt was then collected and dried overnight at 1 torr to yield 336.3 g of product (71% based upon total amino alcohol). HPLC/MS (electrospray) was consistent with the desired product (m/z 417 [M+H]$^+$).

Alternatively, crude 3(S)-[N,N-bis(phenylmethyl)amino]-1-(2-methylpropyl)amino-4-phenylbutan-2(R)-ol (5 g) was dissolved in methyl-tert-butylether (MTBE) (10 mL) and oxalic acid (1 g) in methanol (4 mL) was added. The mixture was stirred for about 2 hours. The resulting solid was filtered, washed with cold MTBE and dried to yield 2.1 g of white solid of about 98.9% diastereomerically pure (based on HPLC peak areas).

EXAMPLE 6

Preparation of N-[3(S)-[N,N-bis(Phenylmethyl) amino]-2(R)-hydroxy-4-phenylbutyl]-N-isobutylamine.acetic Acid Salt To a solution of crude 3(S)-[N,N-bis(phenylmethyl)amino]-1-(2-methylpropyl)amino-4-phenylbutan-2(R)-ol in methyl-tert-butylether (MTBE) (45 mL, 1.1 g amino alcohol isomers/mL) was added acetic acid (6.9 mL) dropwise. The mixture was stirred for about 1 hour at room temperature. The solvent was removed in vacuo to yield a brown oil about 85% diastereomerically pure product (based on HPLC peak areas). The brown oil was crystallized as follows: 0.2 g of the oil was dissolved in the first solvent with heat to obtain a clear solution, the second solvent was added until the solution became cloudy, the mixture was heated again to clarity, seeded with about 99% diastereomerically pure product, cooled to room temperature and then stored in a refrigerator overnight. The crystals were filtered, washed with the second solvent and dried. The diastereomeric purity of the crystals was calculated from the HPLC peak areas. The results are shown in Table 1.

TABLE 1

| First Solvent | Second Solvent | Solvent Ratio | Recovery Weight (g) | Diastereomeric Purity (%) |
|---|---|---|---|---|
| MTBE | Heptane | 1:10 | 0.13 | 98.3 |
| MTBE | Hexane | 1:10 | 0.03 | 99.6 |
| Methanol | Water | 1:1.5 | 0.05 | 99.5 |
| Toluene | Heptane | 1:10 | 0.14 | 98.7 |
| Toluene | Hexane | 1:10 | 0.10 | 99.7 |

Alternatively, crude 3(S)-[N,N-bis(phenylmethyl)amino]-1-(2-methylpropyl)amino-4-phenylbutan-2(R)-ol (50.0 g, which contains about 30.06 g (76.95 mmol) of 3(S),2(R) isomer and about 5.66 g (13.58 mmol) of 3(S),2(S) isomer) was dissolved in methyl-tert-butylether (45.0 mL). To this solution was added acetic acid (6.90 mL, 120.6 mmol) over a period of about 10 min. The mixture was stirred at room temperature for about 1 hour and concentrated under reduced pressure. The oily residue was purified by recrystallization from methyl tert-butylether (32 mL) and heptane (320 mL). Solid was isolated by filtration, washed with cold heptane and dried in vacuo for about 1 hour to afford 21.34 g (58.2% isomer recovery) of 96% diastereomerically pure monoacetic acid salt (based on HPLC peak areas). Mp=105–106° C.; Microanalysis: Calc.: C 75.53%, H 8.39%, N 5.87%; Found: C 75.05%, H 8.759, N 5.71%.

EXAMPLE 7

Preparation of N-[3(S)-[N,N-bis(Phenylmethyl) amino]-2(R)-hydroxy-4-phenylbutyl]-N-isobutylamine.L-tartaric Acid Salt Crude 3(S)-[N,N-bis(phenylmethyl)amino]-1-(2-methylpropyl)amino-4-phenylbutan-2(R)-ol (10.48 g, which contains about 6.72 g (16.13 mmol) of 3(S),2(R) isomer and about 1.19 g (2.85 mmol) of 3(S),2(S) isomer} was dissolved in tetrahydrofuran (10.0 mL). To this solution was added a solution of L-tartaric acid (2.85 g, 19 mmol) in methanol (5.0 mL) over a period of about 5 min. The mixture was stirred at room temperature for about 10 min. and concentrated under reduced pressure. Methyl-tert-butylether (20.0 mL) was added to the oily residue and the mixture was stirred at room temperature for about 1 hour. Solid was isolated by filtration to afford 7.50 g of crude salt. The crude salt was purified by recrystallization from ethyl acetate and heptane at room temperature to yield 4.13 g (45.2% isomer recovery) of 95% diastereomerically pure L-tartaric acid salt (based on HPLC peak areas). Microanalysis: talc.: C 67.76%, H 7.41%, N 4.94%; Found: C 70.06%, H 7.47%, N 5.07%.

EXAMPLE 8

Preparation of N-[3(S)-[N,N-bis(Phenylmethyl) amino]-2(R)-hydroxy-4-phenylbutyl]-N-isobutylamine.dihydrochloric Acid Salt Crude 3(S)-[N,N-bis(phenylmethyl)amino]-1-(2-methylpropyl)amino-4-phenylbutan-2(R)-ol (10.0 g, which contains about 6.41 g (15.39 mmol) of 3(S),2(R) isomer and about 1.13 g (2.72 mmol) of 3(S),2(S) isomer} was dissolved in tetrahydrofuran (20.0 mL). To this solution was added hydrochloric acid (20 mL, 6.0 N) over a period of about 5 min. The mixture was stirred at room temperature for about 1 hour and concentrated under reduced pressure. The residue was recrystallized from ethanol at 0° C. to yield 3.20 g (42.7% isomer recovery) of 98% diastereomerically pure dihydrochloric acid salt (based on HPLC peak areas). Microanalysis: Calc.: C 68.64%, H 7.76%, N 5.72% ; Found: C 68.79%, H 8.07%, N 5.55%.

EXAMPLE 9

Preparation of N-[3(S)-[N,N-bis(Phenylmethyl) amino]-2(R)-hydroxy-4-phenylbutyl]-N-isobutylamine.toluenesulfonic Acid Salt Crude 3(S)-[N,N-bis(phenylmethyl)amino]-1-(2-methylpropyl)amino-4-phenylbutan-2(R)-ol (5.0 g, which contains about 3.18 g (7.63 mmol) of 3(S),2(R) isomer and about 0.56 g (1.35 mmol) of 3(S),2(S) isomer} was dissolved in methyl-tert-butylether (10.0 mL). To this solution was added a solution of toluenesulfonic acid (2.28 g, 12 mmol) in methyl-tert-butylether (2.0 mL) and methanol (2.0 mL) over a period of about 5 min. The mixture was stirred at room temperature for about 2 hours and concentrated under reduced pressure. The residue was recrystallized from methyl-tert-butylether and heptane at 0° C., filtered, washed with cold heptane and dried in vacuo to yield 1.85 g (40.0% isomer recovery) of 97% diastereomerically pure monotoluenesulfonic acid salt (based on HPLC peak areas).

EXAMPLE 10

Preparation of N-[3(S)-[N,N-bis(Phenylmethyl) amino]-2(R)-hydroxy-4-phenylbutyl]-N-isobutylamine.methanesulfonic Acid Salt Crude 3(S)-[N,N-bis(phenylmethyl)amino]-1-(2-methylpropyl)amino-4-phenylbutan-2(R)-ol (10.68 g, which contains about 6.85 g (16.44 mmol) of 3(S),2(R) isomer and about 1.21 g (2.90 mmol) of 3(S),2(S) isomer} was dissolved in tetrahydrofuran (10.0 mL). To this solution was added methanesulfonic acid (1.25 mL, 19.26 mmol). The mixture was stirred at room temperature for about 2 hours and concentrated under reduced pressure. The oily residue was recrystallized from methanol and water at 0° C., filtered, washed with cold methanol/water (1:4) and dried in vacuo to yield 2.40 g (28.5% isomer recovery) of 98% diastereomerically pure monomethanesulfonic acid salt (based on HPLC peak areas).

EXAMPLE 11

Preparation of N-Benzyl-L-phenylalaninol

Method 1:

L-Phenylalaninol (89.51 g, 0.592 moles) was solved in 375 mL of methanol under inert atmosphere, 35.52 g (0.592 moles) of glacial acetic acid and 50 mL of methanol was added followed by a solution of 62.83 g (0.592 moles) of benzaldehyde in 100 mL of methanol. The mixture was cooled to approximately 15° C. and a solution of 134.6 g (2.14 moles) of sodium cyanoborohydride in 700 mL of methanol was added in approximately 40 minutes, keeping the temperature between 15° C. and 25° C. The mixture was stirred at room temperature for 18 hours. The mixture was concentrated under reduced pressure and partitioned between 1 L of 2M ammonium hydroxide solution and 2 L of ether. The ether layer was washed with 1 L of 1M ammonium hydroxide solution, twice with 500 mL water, 500 mL of brine and dried over magnesium sulfate for 1 hour. The ether layer was filtered, concentrated under reduced pressure and the crude solid product was recrystallized from 110 mL of ethyl acetate and 1.3 L of hexane to give 115 g (81% yield) of N-benzyl-L-phenylalaninol as a white solid.

Method 2:

L-Phenylalaninol (5 g, 33 mmoles) and 3.59 g (33.83 mmoles) of benzaldehyde were dissolved in 55 mL of 3A ethanol under inert atmosphere in a Parr shaker and the mixture was warmed to 60° C. for 2.7 hours. The mixture was cooled to approximately 25° C. and 0.99 g of 5% platinum on carbon was added and the mixture was hydrogenated at 60 psi of hydrogen and 40° C. for 10 hours. The catalyst was filtered off, the product was concentrated under reduced pressure and the crude solid product was recrystallized from 150 mL of heptane to give 3.83 g (48% yield) of N-benzyl-L-phenylalaninol as a white solid.

EXAMPLE 12

Preparation of N-(t-Butoxycarbonyl)-N-benzyl-L-phenylalaninol

N-benzyl-L-phenylalaninol (2.9 g, 12 mmoles) was dissolved in 3 mL of triethylamine and 27 mL of methanol and 5.25 g (24.1 mmoles) of di-tert-butyl dicarbonate was added. The mixture was warned to 60° C. for 35 minutes and concentrated under reduced pressure. The residue was dissolved in 150 mL of ethyl acetate and washed twice with 10 mL of cold (0–5° C.), dilute hydrochloric acid (pH 2.5 to 3), 15 mL of water, 10 mL of brine, dried over magnesium sulfate, filtered and concentrated under reduced pressure. The crude product oil was purified by silica gel chromatography (ethyl acetate:hexane, 12:3 as eluting solvent) to give 3.98 g (97% yield) of colorless oil.

EXAMPLE 13

Preparation of N-(t-Butoxycarbonyl)-N-benzyl-L-phenylalaninal

Method 1:

To a solution of 0.32 g (0.94 moles) of N-(t-butoxycarbonyl)-N-benzyl-L-phenylalaninol in 2.8 mL of toluene was added 2.4 mg (0.015 mmoles) of 2,2,6,6-tetramethyl-1-piperidinyloxy, free radical (TEMPO), 0.1 g (0.97 moles) of sodium bromide, 2.8 mL of ethyl acetate and 0.34 mL of water. The mixture was cooled to 0° C. and an aqueous solution of 4.2 mL of 5% household bleach containing 0.23 g (3.0 mL, 2.738 moles) of sodium bicarbonate was added slowly over 30 minutes. The mixture was stirred at 0° C. for 10 minutes. Three more additions (0.4 mL each) of bleach was added followed by stirring for 10 minutes after each addition to consume all the stating material. The two phase mixture was allowed to separate. The aqueous layer was extracted twice with 8 mL of toluene. The combined organic layer was washed with 1.25 mL of a solution containing 0.075 g of potassium iodide, sodium bisulfate (0.125 g) and water(1.1 mL), 1.25 mL of 10% aqueous sodium thiosulfate solution, 1.25 mL of pH 7 phosphate buffer and 1.5 mL of brine solution. The organic solution was dried over magnesium sulfate, filtered and concentrated under reduced pressure to give 0.32 g (100% yield) of N-(t-butoxycarbonyl)-N-benzyl-L-phenylalaninal.

Method 2:

To a solution of 2.38 g (6.98 moles) of N-(t-butoxycarbonyl)-N-benzyl-L-phenylalaninol in 3.8 mL (27.2 moles) of triethylamine at 10° C. was added a solution of 4.33 g (27.2 moles) of sulfur trioxide pyridine complex in 17 mL of dimethyl sulfoxide. The mixture was warmed to room temperature and stirred for one hour. Water (16 mL) was added and the mixture was extracted with 20 mL of ethyl acetate. The organic layer was washed with 20 mL of 5% citric acid, 20 mL of water, 20 mL of brine, dried over magnesium sulfate and filtered. The filtrate was concentrated under reduced pressure to give 2.37 g (100% yield) of N-(t-Butoxycarbonyl)-N-benzyl-L-phenylalaninal.

EXAMPLE 14

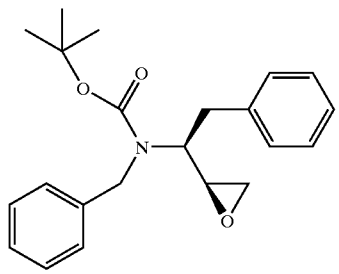

Preparation of 3(S)-[N-(t-Butoxycarbonyl)-N-benzylamino]-1,2-(S)-epoxy-4-phenylbutane Method 1:

A solution of 2.5 g (7.37 mmoles) of N-(t-butoxycarbonyl)-N-benzyl-L-phenylalaninal and 0.72 mL of chloroiodomethane in 35 mL of THF was cooled to −78° C. A 4.64 mL of a solution of n-butyllithium (1.6 M in hexane, 7.42 mmoles) was added slowly, keeping the temperature below −70° C. The mixture was stirred for 10 minutes between −70 to −75° C. Two additional portions of 0.22 mL of chloroiodomethane and 1.4 mL of n-butyllithium was added sequentially and the mixture was stirred for 10 minutes between −70 to −75° C. after each addition. Four additional portions of 0.11 mL of chloroiodomethane and 0.7 mL of n-butyllithium was added sequentially and the mixture was stirred for 10 minutes between −70 to −75° C. after each addition. The mixture was warmed to room temperature for 3.5 hours. The product was quenched at below 5° C. with 24 mL of ice-cold water. The biphasic layers were separated and the aqueous layer was extracted twice with 30 mL of ethyl acetate. The combined organic layers was washed three times with 10 ml water, then with 10 mL brine, dried over sodium sulfate, filtered and concentrated under reduced pressure to give 2.8 g of a yellow crude oil. This crude oil (>100% yield) is a mixture of the diastereomeric epoxides N-αS-bis(phenylmethyl)-N-(t-butoxycarbonyl)-2S-oxiranemethanamine and N,αS-bis(phenylmethyl)-N-(t-butoxycarbonyl)-2R-oxiranemethanamine. The crude mixture is used directly in the next step without purification.

Method 2:

To a suspension of 2.92 g (13.28 mmoles) of trimethylsulfoxonium iodide in 45 mL of acetonitrile was added 1.49 g (13.28 mmoles) of potassium t-butoxide. A solution of 3.0 g (8.85 mmoles) of N-(t-butoxycarbonyl)-N-benzyl-L-phenylalaninal in 18 mL of acetonitrile was added and the mixture was stirred at room temperature for one hour. The mixture was diluted with 150 mL of water and extracted twice with 200 mL of ethyl acetate. The organic layers were combined and washed with 100 mL water, 50 mL brine, dried over sodium sulfate, filtered and concentrated under reduced pressure to give 3.0 g of a yellow crude oil. The crude product was purified by silica gel chromatography (ethyl acetate/hexane: 1:8 as eluting solvent) to give 1.02 g (32.7% yield) of a mixture of the two diastereomers N,αS-bis(phenylmethyl)-N-(t-butoxycarbonyl)-2S-oxiranemethanamine and N,αS-bis(phenylmethyl)-N-(t-butoxycarbonyl)-2R-oxiranemethanamine.

Method 3:

To a suspension of 0.90 g (4.42 mmoles) of trimethylsulfonium iodide in 18 mL of acetonitrile was added 0.495 g (4.42 mmoles) of potassium t-butoxide. A solution of 1.0 g (2.95 moles) of N-(t-butoxycarbonyl)-N-benzyl-L-phenylalaninal in 7 mL of acetonitrile was added and the mixture was stirred at room temperature for one hour. The mixture was diluted with 80 mL of water and extracted twice with 80 mL of ethyl acetate. The organic layers were combined and washed with 100 mL water, 30 mL brine, dried over sodium sulfate, filtered and concentrated under reduced pressure to give 1.04 g of a yellow crude oil. The crude product was a mixture of the two diastereomers N,αs-bis(phenylmethyl)-N-(t-butoxycarbonyl)-2S-oxiranemethanamine and N,αS-bis(phenylmethyl)-N-(t-butoxycarbonyl)-2-oxiranemethanamine.

EXAMPLE 15

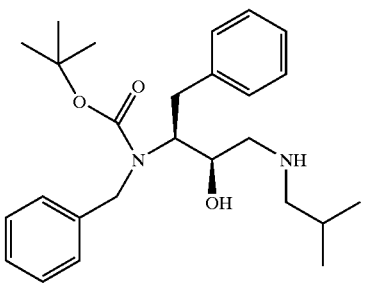

Preparation of 3(S)-[N-(t-Butoxycarbonyl)-N-(phenylmethyl)amino]-1-(2-methylpropyl)-amino-4-phenylbutan-2R-ol To a solution of 500 mg (1.42 mmoles) of the crude epoxide (a mixture of the two diastereomers N,αS-bis(phenylmethyl)-N-(t-butoxycarbonyl)-2S-oxiranemethanamine and N,αS-bis(phenylmethyl)-N-(t-butoxycarbonyl)-2R-oxiranemethanamine) in 0.98 mL of isopropanol was added 0.71 mL (7.14 mmoles) of isobutylamine. The mixture was warmed to reflux at 85° C. to 90° C. for 1.5 hours. The mixture was concentrated under reduced pressure and the product oil was purified by silica gel chromatography (chloroform:methanol, 100:6 as eluting solvents) to give 330 mg of 3S-[N-(t-butoxycarbonyl)-N-(phenylmethyl)amino]-1-(2-methylpropyl)amino-4-phenylbutan-2R-ol as a colorless oil (54.5% yield). 3S-[N-(t-butoxycarbonyl)-N-(phenylmethyl)amino]-1-(2-methylpropyl)amino-4-phenylbutan-2S-ol was also isolated. When purified N,αS-bis(phenylmethyl)-N-(t-butoxycarbonyl)-2S-oxiranemethanamine was used as starting material, 3S-[N-(t-butoxycarbonyl)-N-(phenylmethyl)amino]-1-(2-methylpropyl)amino-4-phenylbutan-2R-ol was isolated after purification by chromatography in an 86% yield.

EXAMPLE 16

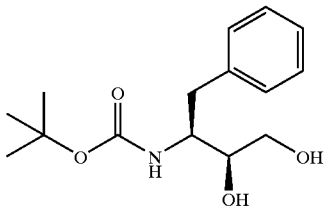

Preparation of 3S-(N-(t-Butoxycarbonyl)amino-4-phenylbutan-1,2R-diol

To a solution of 1 g (3.39 mmoles) of 2S-(N-t-butoxycarbonyl)amino-1S-hydroxy-3-phenylbutanoic acid (commercially available from Nippon Kayaku, Japan) in 50 mL of THF at 0° C. was added 50 mL of borane-THF complex (liquid, 1.0 M in THF), keeping the temperatures below 5° C. The reaction mixture was warmed to room temperature and stirred for 16 hours. The mixture was cooled to 0° C. and 20 mL of water was added slowly to destroy the excess $BH_3$ and to quench the product mixture, keeping the temperature below 12° C. The quenched mixture was stirred for 20 minutes and concentrated under reduced pressure. The product mixture was extracted three times with 60 mL of ethyl acetate. The organic layers were combined and washed with 20 mL of water, 25 mL of saturated sodium chloride solution and concentrated under reduced pressure to give 1.1 g of crude oil. The crude product was purified by silica gel chromatography (chloroform/methanol, 10:6 as eluting solvents) to give 900 mg (94.4% yield) of 3S-(N-t-butoxycarbonyl)amino-4-phenylbutan-1,2R-diol as a white solid.

EXAMPLE 17

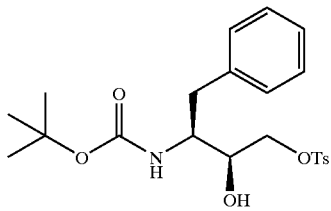

Preparation of 3S-(N-(t-Butoxycarbonyl)amino-3R-hydroxy-4-phenylbut-1-yl Toluenesulfonate To a solution of 744.8 mg (2.65 mmoles) of 3S-(N-t-butoxycarbonyl)amino-4-phenylbutan-1,2R-diol in 13 mL of pyridine at 0° C. was added 914 mg of toluenesulfonyl chloride in one portion. The mixture was stirred at 0° C. to 5° C. for 5 hours. A mixture of 6.5 mL of ethyl acetate and 15 mL of 5% aqueous sodium bicarbonate solution was added to the reaction mixture and stirred for 5 minutes. The product mixture was extracted three times with 50 mL of ethyl acetate. The organic layers were combined and washed with 15 mL of water, 10 mL of saturated sodium chloride solution and concentrated under reduced pressure to give about 1.1 g of a yellow chunky solid. The crude product was purified by silica gel chromatography (ethyl acetate/hexane 1:3 as eluting solvents) to give 850 mg (74% yield) of 3S-(N-t-butoxycarbonyl)amino-2R-hydroxy-4-phenylbut-1-yl toluenesulfonate as a white solid.

EXAMPLE 18

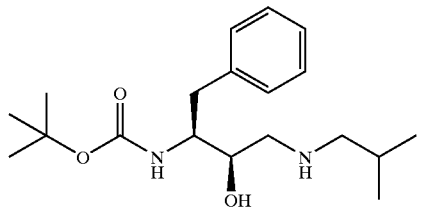

Preparation of 3S-[N-(t-Butoxycarbonyl)amino]-1-(2-methylpropyl)amino-4-phenylbutan-2R-ol To a solution of 90 mg (0.207 mmoles) of 3S-(N-t-butoxycarbonyl)amino-2R-hydroxy-4-phenylbut-1-yl toluenesulfonate in 0.143 mL of isopropanol and 0.5 mL of toluene was added 0.103 mL (1.034 mmoles) of isobutylamine. The mixture was warmed to 80 to 85° C. and stirred for 1.5 hours. The product mixture was concentrated under reduced pressure at 40 to 50° C. and purified by silica gel chromatography (chloroform/methanol, 10:1 as eluting solvents) to give 54.9 mg (76.8% yield) of 3S-[N-(t-butoxycarbonyl)amino]-1-(2-methylpropyl)amino-4-phenylbutan-2R-ol as a white solid.

EXAMPLE 19

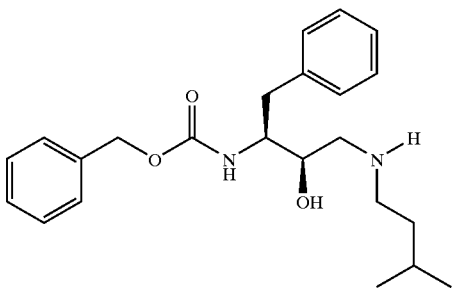

Preparation of N-[3(S)-Benzyloxycarbonylamino-2(R)-hydroxy-4-phenylbutyl]-N-isoamylamine Part A:

To a solution of 75.0 g (0.226 mol) of N-benzyloxycarbonyl-L-phenylalanine chloromethyl ketone in a mixture of 807 mL of methanol and 807 mL of tetrahydrofuran a −2° C., was added 13.17 g (0.348 mol, 1.54 equiv.) of solid sodium borohydride over one hundred minutes. The solvents were removed under reduced pressure at 40° C. and the residue dissolved in ethyl acetate (approx. 1 L). The solution was washed sequentially with 1M potassium hydrogen sulfate, saturated sodium bicarbonate and then saturated sodium chloride solutions. After drying over anhydrous magnesium sulfate and filtering, the solution was removed under reduced pressure. To the resulting oil was added hexane (approx. 1 L) and the mixture warmed to 60° C. with swirling. After cooling to room temperature, the solids were collected and washed with 2 L of hexane. The resulting solid was recrystallized from hot ethyl acetate and hexane to afford 32.3 g (43% yield) of N-benzyloxycarbonyl-3(S)-amino-1-chloro-4-phenyl-2(S)-butanol, mp 150–151° C. and M+Li$^+$=340.

Part B:

To a solution of 6.52 g (0.116 mol, 1.2 equiv.) of potassium hydroxide in 968 mL of absolute ethanol at room temperature, was added 32.3 g (0.097 mol) of N-CBZ-3(S)-amino-1-chloro-4-phenyl-2(S)-butanol. After stirring for fifteen minutes, the solvent was removed under reduced pressure and the solids dissolved in methylene chloride. After washing with water, drying over magnesium sulfate, filtering and stripping, one obtains 27.9 g of a white solid. Recrystallization from hot ethyl acetate and hexane afforded 22.3 g (77% yield) of N-benzyloxycarbonyl-3(S)-amino-1,2(S)-epoxy-4-phenylbutane, mp 102–103° C. and MH$^+$298.

Part C:

A solution of N-benzyloxycarbonyl-3(S)-amino-1,2(S)-epoxy-4-phenylbutane (1.00 g, 3.36 mmol) and isoamylamine (4.90 g, 67.2 mmol, 20 equiv.) in 10 mL of isopropyl alcohol was heated to reflux for 1.5 hours. The solution was cooled to room temperature, concentrated in vacuo and then poured into 100 mL of stirring hexane whereupon the product crystallized from solution. The product was isolated by filtration and air dried to give 1.18 g, 95% of N=[[3(S)-phenylmethylcarbamoyl)amino-2(R)-hydroxy-4-phenylbutyl]N-[(3-methylbutyl)]amine mp 108.0–109.5° C., MH$^+$ m/z=371.

EXAMPLE 20

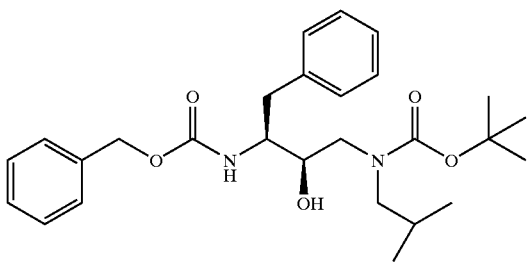

Preparation of N-[(1,1-Dimethylethoxyl)carbonyl]-N-[2-methylpropyl]-3S-[N¹-(phenylmethoxycarbonyl)amino]-2R-hydroxy-4-phenylbutylamine To a solution of 7.51 g (20.3 mmol) of N-[3S-[(phenylmethoxycarbonyl)amino]-2R-hydroxy-4-phenylbutyl]-2-methylpropylamine in 67 mL of anhydrous tetrahydrofuran was added 2.25 g (22.3 mmol) of triethylamine. After cooling to 0° C., 4.4 g (20.3 mmol) of di-tert-butyldicarbonate was added and stirring continued at room temperature for 21 hours. The volatiles were removed in vacuo, ethyl acetate added, then washed with 5% citric acid, saturated sodium bicarbonate, brine, dried over magnesium sulfate, filtered and concentrated to afford 9.6 g of crude product. Chromatography on silica gel using 30% ethyl acetate/hexane afforded 8.2 g of pure N-[[3S-(phenylmethylcarbamoyl)amino]-2R-hydroxy-4-phenyl]-1-[(2-methylpropyl)amino-2-(1,1-dimethylethoxyl)carbonyl]butane, mass spectum m/e=477 (M+Li).

EXAMPLE 21

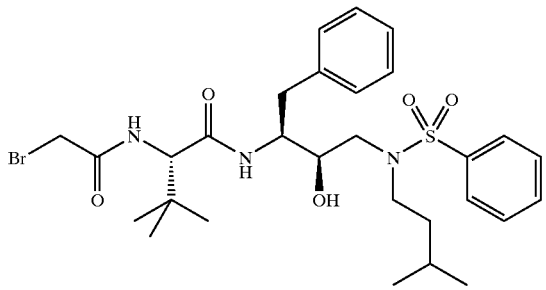

Preparation of 2S-[[Bromoactyl]amino]-N-[2R-hydroxy-3-[N¹-methyl-butyl)-N¹-(phenylsulfonyl)amino]-1S-(phenylmethyl)propyl]-3,3-dimethylbutaneamide Part A:

To a solution of N-CBZ-L-tert-leucine (450 mg, 1.7 mmol) and N-hydroxybenzotriazole (260 mg, 1.7 mmol) in DMF (10 mL) was added EDC (307 mg, 1.6 mmol). The solution was stirred for 60 minutes at room temperature and then 2R-hydroxy-3-[N-(3-methylbutyl)-N-(phenylsulfonyl)amino]-1S-(phenylmethyl)propylamine (585 mg, 1.5 mmol) in DMF (2 mL) was added. The reaction was stirred for 16 hours at room temperature, then poured into a 50% saturated solution of sodium bicarbonate (200 mL). The aqueous mixture was extracted thrice with ethyl acetate (50 mL). The combined ethyl acetate layers were washed with water (50 mL) and saturated NaCl solution (50 mL), then dried over magnesium sulfate. Filtration and concentration produced an oil which was chromatographed on silica gel (50 gm) eluting with 20% ethyl acetate in hexane. The phenylmethyl [1S-[[[2R-hydroxy-3-[(3-methylbutyl)(phenylsulfonyl)amino]-1S-(phenylmethyl)propyl]amino]carbonyl]-2,2-dimethylpropyl]carbamate was obtained as a solid Anal. Calcd for $C_{35}H_{47}N_3O_6S$: C, 65.91; H, 7.43; N, 6.59. Found: C, 65.42; H, 7.24; N, 6.55.

Part B:

A solution of phenylmethyl [1S-[[[2R-hydroxy-3-[(3-methylbutyl)(phenylsulfonyl)-amino]-1S-(phenylmethyl)propyl]amino]carbonyl]-2,2-dimethylpropyl]carbamate (200 mg, 0.31 mmol) in methanol (15 mL) was hydrogenated over 10% palladium on carbon for 2 hours. The reaction was filtered through diatomaceous earth and concentrated to an oil.

Part C:

The resulting free amine from part B (150 mg, 0.3 mmol) was combined with diisopropylethylamine (114 uL, 0.33 mmol) in dichloromethane (5 mL). To this was added bromoacetyl chloride (27 uL, 0.33 mmol) dropwise. The reaction was stirred for 30 minutes at room temperature, then diluted with dichloromethane (30 mL) and extracted with 1 N HCl, water, and then saturated NaCl solution (25 mL each). The organic solution was dried over MgSO₄ and concentrated to a solid. The 2S-[[bromoacetyl]amino]-N-[2R-hydroxy-3-[(3-methylbutyl)(phenylsulfonyl)amino]-1S-(phenylmethyl)propyl]-3,3-dimethylbutaneamide was sufficiently pure for use in the next step. This material can also be prepared by substituing bromoacetic anhydride for bromoacetyl chloride, or one can use chloroacetyl chloride or chloracetic anhydride.

EXAMPLE 22

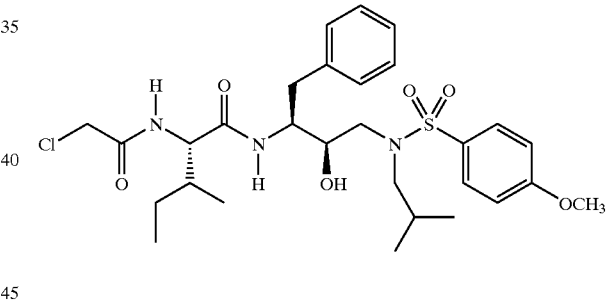

Preparation of 2S-[Chloroactylamino]-N-[2R-hydroxy-3-[N¹-methylpropyl)-N¹-(4-methoxyphenylsulfonyl)amino]-1S-(phenylmethyl)propyl]-3S-methylpentanamide Part A:

To a solution of 2R-hydroxy-3-[(2-methylpropyl)(4-methoxyphenylsulfonyl)amino]-1S-(phenylmethyl) propylamine (1.70 g, 4.18 mmol) in 40 mL of dichloromethane was added N-carbobenzyloxy-L-isoleucine-N-hydroxysuccinamide ester (1.51 g, 4.18 mmol) and the solution stirred under nitrogen atmosphere for 16 hours. The contents were concentrated in vacuo and the residue was redissolved in ethyl acetate. The ethyl acetate solution was washed with an aqueous solution of 5% KHSO₄, saturated sodium bicarbonate, and saturated sodium chloride, dried over magnesium sulfate, filtered, and concentrated to yield 2.47 g of crude product. The product was purified by silica gel chromatography using 1 2:1 hexane:ethyl acetate eluant to yield 2.3 g. (84% yield) of 2S-[(carbobenzyloxy)amino]-N-[2R-hydroxy-3-[(3-methylpropyl)(4-methoxyphenylsulfonyl)amino]-1S-(phenylmethyl)propyl]-3S-methylpentanamide.

Part B:

(1.18 g, 1.8 mmol) of the product from Part A was dissolved in 50 mL of methanol, and to this was added 250 mg of 10% Palladium on Carbon while under a stream of nitrogen. The suspension was hydrogenated using 50 psig of hydrogen for 20 hours. The contents were purged with nitrogen and filtered through celite, and concentrated in vacuo to yield 935 mg of 2S-(amino)-N-[2R-hydroxy-3-[(3-methylpropyl)(4-methoxyphenylsulfonyl)amino]-1S-(phenylmethyl)propyl]-3S-methylpentanamide, which was used without further purification.

Part C:

(0.935 g, 1.8 mmol) of the amine from Part B was dissolved in 15 mL of dioxane and to this was added (190 mg, 1.85 mmol) of 4-methylmorpholine followed by (0.315 g, 1.8 mmol) of chloroacetic anhydride. The reaction mixture was stirred under nitrogen atmosphere for 3 hours, concentrated in vacuo, and redissolved in ethyl acetate. The ethyl acetate solution was washed with 50 mL of 5% aqueous $KHSO_4$, saturated $NaHCO_3$, and saturated NaCl solution, dried over $MgSO_4$, filtered and concentrated to yield 613 mg, (68% yield) of 2S-[(chloroacetyl)amino]-N-[2R-hydroxy-3-[(3-methylpropyl)(4-methoxyphenylsulfonyl)amino]-1S-(phenylmethyl)propyl]-3S-methylpentanamide, after purification by silica gel chromatography using 1:1 hexane:ethyl acetate.

EXAMPLE 23

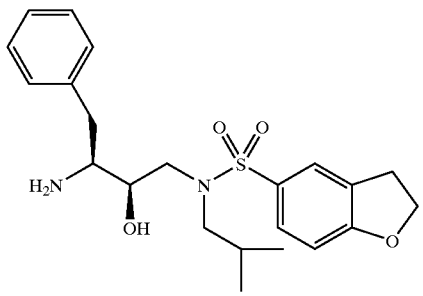

Preparation of 2R-Hydroxy-3-[[2,3-dihydrobenzofuran-5-yl)sulfonyl](2-methylpropyl) amino]-1S-(phenylmethyl)propylamine Part A: Preparation of 5-(2,3-Dihydrobenzofuranyl) Sulfonyl Chloride To a solution of 3.35 g of anhydrous N,N-dimethylformamide at 0° C. under nitrogen was added 6.18 g of sulfuryl chloride, whereupon a solid formed. After stirring for 15 minutes, 4.69 g of 2,3-dihydrobenzofuran was added, and the mixture heated at 100° C. for 2 hours. The reaction was cooled, poured into ice water, extracted with methylene chloride, dried over magnesium sulfate, filtered and concentrated the crude material. This was recrystallized from ethyl acetate to afford 2.45 g of 5-(2,3-dihydrobenzofuranyl)sulfonyl chloride.

Part B: Preparation of Carbamic Acid, 2R-Hydroxy-3-[[(2, 3-dihydrobenzofuran-5-yl)sulfonyl](2-methylpropyl) amino]-1S-(phenylmethyl)propyl-, Phenylmethyl Ester To a solution of 1.11 g (3.0 mmol) of N-[3S-benzyloxycarbonylamino-2R-hydroxy-4-phenyl]-N-isobutylamine in 20 mL of anhydrous methylene chloride, was added 1.3 mL (0.94 g, 9.3 mmol) of triethylamine. The solution was cooled to 0° C. and 0.66 g of 5-(2,3-dihydrobenzofuranyl) sulfonyl chloride was added, stirred for 15 minutes at 0° C., then for 2 hour at room temperature. Ethyl acetate was added, washed with 5% citric acid, saturated sodium bicarbonate, brine, dried and concentrated to yield 1.62 g of crude material. This was recrystallized from diethyl ether to afford 1.17 g of pure carbamic acid, [2R-hydroxy-3-[[(2,3-dihydrobenzofuran-5-yl)sulfonyl](2-methylpropyl)amino]-1S-(phenylmethyl)propyl-, phenylmethyl ester.

Part C: Preparation of [2R-Hydroxy-3-[[(2,3-dihydrobenzofuran-5-yl)sulfonyl](2-methylpropyl)amino]-1S-(phenylmethyl)propylamine A solution of 2.86 g of carbamic acid, [2R-hydroxy-3-[[(2,3-dihydrobenzofuran-5-yl)sulfonyl](2-methylpropyl) amino]-1S-(phenylmethyl)propyl-, phenylmethyl ester in 30 mL of tetrahydrofuran was hydrogenated 0.99 g of 10% palladium-on-carbon under 50 psig of hydrogen for 16 hours. The catalyst was removed by filtration and the filtrate concentrated to afford 1.99 g of the desired [2R-hydroxy-3-[[(2,3-dihydrobenzofuran-5-yl)sulfonyl](2-methylpropyl) amino]-1S-(phenylmethyl)propylamine.

EXAMPLE 24

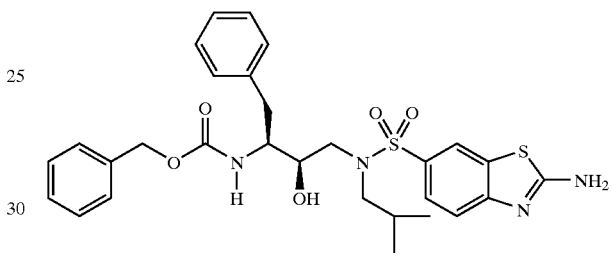

Preparation of Carbamic Acid, 2R-Hydroxy-3-[[(2-aminobenzothiazol-6-yl)sulfonyl](2-methylpropyl) amino]-1S-(phenylmethyl)propyl-, Phenylmethyl Ester Carbamic acid, 2R-hydroxy-3-[[(4-aminophenyl) sulfonyl](2-methylpropyl)amino]-1S-(phenylmethyl) propyl-, phenylmethyl ester 0.30 g (0.571 mmol) was added to a well mixed powder of anhydrous copper sulfate (1.20 g) and potassium thiocyanate (1.50 g) followed by dry methanol (6 mL) and the resulting black-brown suspension was heated at reflux for 2 hrs. The reaction mixture was filtered and the filtrate was diluted with water (5 mL) and heated at reflux. Ethanol was added to the reaction mixture, cooled and filtered. The filtrate upon concentration afforded a residue which was chromatographed (ethyl acetate:hexane 80:20) to afford 0.26 g (78%) of the desired compound as a solid.

EXAMPLE 25

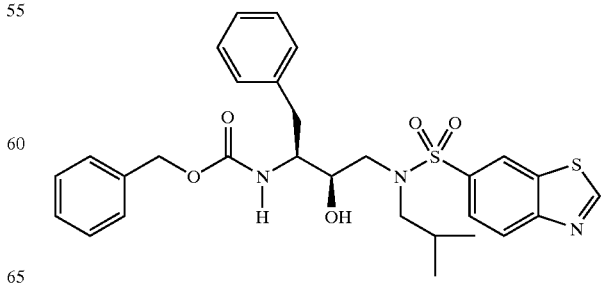

Preparation of Carbamic Acid, 2R-Hydroxy-3-[[(benzothiazol-6-yl)sulfonyl](2-methylpropyl)amino]-1S-(phenylmethyl)propyl-, Phenylmethyl Ester Method 1:

Carbamic acid, 2R-hydroxy-3-[[(2-aminobenzothiazol-6-yl)sulfonyl](2-methylpropyl)amino]-1S-(phenylmethyl)propyl-, phenylmethyl ester (0.25 g, 0.429 mmol) was added to a solution of isoamylnitrite (0.116 mL, 0.858 mmol) in dioxane (5 mL) and the mixture was heated at 85° C. After the cessation of evolution of nitrogen, the reaction mixture was concentrated and the residue was purified by chromatography (hexane:ethyl acetate 5:3) to afford 0.130 g (53%) of the desired product as a solid.

Method 2:

Crude benzothiazole-6-sulfonyl chloride in ethyl acetate (100 mL) was added to N-[3S-benzyloxycarbonylamino-2R-hydroxy-4-phenyl]-N-isobutylamine (1.03 g, 2.78 mmol) followed by N-methylmorpholine (4 mL). After stirring at room temperature for 18 hr., the reaction mixture was diluted with ethyl acetate (100 mL), washed with citric acid (5%, 100 mL), sodium bicarbonate (saturated, 100 mL) and brine (100 mL), dried (MgSO$_4$) and concentrated in vacuo. The residue was chromatographed (silica gel, ethyl acetate:hexane 1:1) to afford 0.340 g (23%) of desired product.

EXAMPLE 26

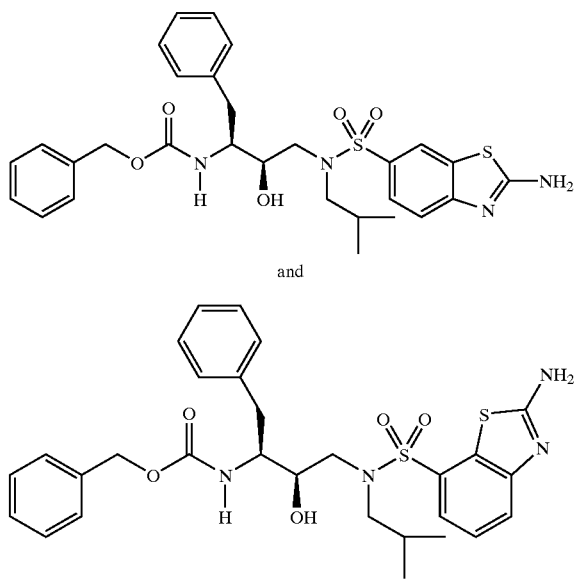

and

Preparation of Carbamic Acid, 2R-Hydroxy-3-[[(2-aminobenzothiazol-5-yl)sulfonyl](2-methylpropyl)amino]-1S-(phenylmethyl)propyl-, Phenylmethyl Ester; and Carbamic Acid, 2R-Hydroxy-3-[[(2-aminobenzothiazol-7-yl)sulfonyl](2-methylpropyl)amino-1S-(phenylmethyl)propyl-, Phenylmethyl Ester The carbamic acid, 2R-hydroxy-3-[(3-aminophenylsulfonyl)(2-methylpropyl)amino]-1S-(phenylmethyl)propyl-, phenylmethyl ester 0.36 g (0.685 mmol) was added to a well mixed powder of anhydrous copper sulfate (1.44 g) and potassium thiocyanate (1.80 g) followed by dry methanol (10 mL) and the resulting black-brown suspension was heated at reflux for 2 hrs. The reaction mixture was filtered and the filtrate was diluted with water (5 mL) and heated at reflux. Ethanol was added to the reaction mixture, cooled and filtered. The filtrate upon concentration afforded a residue which was chromatographed (ethyl acetate:hexane 1:1) to afford 0.18 g (45%) of the 7-isomer as a solid. Further elution of the column with (ethyl acetate:hexane 3:2) afforded 0.80 g (20% ) afforded the 5-isomer as a solid.

EXAMPLE 27

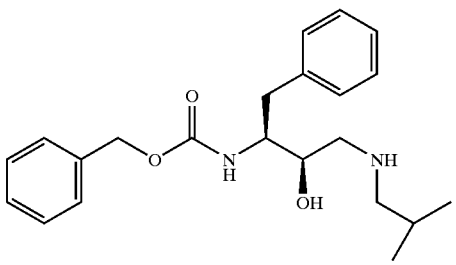

Preparation of N-[3(S)-Benzyloxycarbonylamino-2(R)-hydroxy-4-phenyl]N-isobutylamine Part A: N-Benzyloxycarbonyl-3(S)-amino-1-chloro-4-phenyl-2(S)-butanol To a solution of N-benzyloxycarbonyl-L-phenylalanine chloromethyl ketone (75 g, 0.2 mol) in a mixture of 800 mL of methanol and 800 mL of tetrahydrofuran was added sodium borohydride (13.17 g, 0.348 mol, 1.54 equiv.) over 100 min. The solution was stirred at room temperature for 2 hours and then concentrated in vacuo. The residue was dissolved in 1000 ml, of ethyl acetate and washed with 1N KHSO$_4$, saturated aqueous NaHCO$_3$, saturated aqueous NaCl, dried over anhydrous MgSO4, filtered and concentrated in vacuo to give an oil. The crude product was dissolved in 1000 mL of hexanes at 60° C. and allowed to cool to room temperature where upon crystals formed that were isolated by filtration and washed with copious amounts of hexanes. This solid was then recrystallized from hot ethyl acetate and hexanes to provide 32.3 g 43% of N-benzyloxycarbonyl-3(S)-amino-1-chloro-4-phenyl-2(S)-butanol, mp 150–151° C., FAB MS: MLi$^+$=340.

Part B: 3(S)-[N-(Benzyloxycarbonyl)amino]-1,2(S)-epoxy-4-phenylbutane

A solution of potassium hydroxide (6.52 g. 0.116 mol, 1.2 equiv.) in 970 mL of absolute ethanol was treated with N-benzyloxycarbonyl-3(S)-amino-1-chloro-4-phenyl-2(S)-butanol (32.3 g, 0.097 mol). This solution was stirred at room temperature for 15 minutes and then concentrated in vacuo to give a white solid. The solid was dissolved in dichloromethane and washed with water, dried over anhyd MgSO$_4$, filtered and concentrated in vacuo to give a white solid. The solid was crystallized from hexanes and ethyl acetate to give 22.3 g, 77% of 3(S)-[N-(benzyloxycarbonyl)amino]-1,2(S)-epoxy-4-phenylbutane, up 102–103° C., FAB MS: MH$^+$=298.

Part C: N-[3(S)-Benzyloxycarbonylamino-2(R)-hydroxy-4-phenyl]N-isobutylamine

A solution of N-benzylcarbonyl-3(S)-amino-1,2-(S)-epoxy-4-phenyl butane (50.0 g, 0.168 mol) and isobutylamine (246 g, 3.24 mol, 20 equivalents) in 650 mL of isopropyl alcohol was heated to reflux for 1.25 hours. The solution was cooled to room temperature, concentrated in vacuo and then poured into 1 L of stirring hexane whereupon the product crystallized from solution. The product was isolated by filtration and air dried to give 57.56 g, 92% of N[3(s)-benzyloxycarbonylamino-2(R)-hydroxy-4-phenyl]-N-isobutylamine, mp 108.0–109.5° C., MH+m/z=371.

EXAMPLE 28

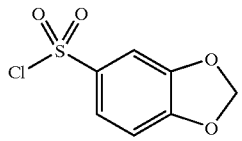

Preparation of 1,3-Benzodioxole-5-sulfonyl Chloride

Method 1:

To a solution of 4.25 g of anhydrous N,N-dimethylformamide at 0° C. under nitrogen was added 7.84 g of sulfuryl chloride, whereupon a solid formed. After stirring for 15 minutes, 6.45 g of 1,3-benzodioxole was added, and the mixture heated at 100° C. for 2 hours. The reaction was cooled, poured into ice water, extracted with methylene chloride, dried over magnesium sulfate, filtered and concentrated to give 7.32 g of crude material as a black oil. This was chromatographed an silica gel using 20% methylene chloride/hexane to afford 1.9 g of (1,3-benzodioxol-5-yl)sulfonyl chloride.

Method 2:

To a 22 liter round bottom flask fitted with a mechanical stirrer, a cooling condenser, a heating mantle and a pressure equalizing dropping funnel was added sulfur trioxide DMF complex (2778 g, 18.1 moles). Dichloroethane (4 liters) was then added and stirring initiated. 1,3-Benzodioxole (1905 g, 18.1 moles) as then added through the dropping funnel over a five minute period. The temperature was then raised to 75° C. and held for 22 hours (NMR indicated that the reaction was done after 9 hours.) The reaction was cooled to 26° and oxalyl chloride (2290 g, 18.1 moles) was added at a rate so as to maintain the temperature below 40° C. (1.5 hours). The mixture was heated to 67° C. for 5 hours followed by cooling to 16° C. with an ice bath. The reaction was quenched with water (5 l) at a rate which kept the temperature below 20° C. After the addition of water was complete, the mixture was stirred for 10 minutes. The layers were separated and the organic layer was washed again twice with water (5 l). The organic layer was dried with magnesium sulfate (500 g) and filtered to remove the drying agent. The solvent was removed under vacuum at 50° C. The resulting warm liquid was allowed to cool at which time a solid began to form. After one hour, the solid was washed with hexane (400 mL), filtered and dried to provide the desired sulfonyl chloride (2823 g). The hexane wash was concentrated and the resulting solid washed with 400 mL hexane to provide additional sulfonyl chloride (464 g). The total yield was 3287 g (95.5% based upon 1,3-benzodioxole).

Method 3:

1,4-benzodioxan-6-sulfonyl chloride was prepared according to the procedure disclosed in EP 583960, incorporated herein by reference.

EXAMPLE 29

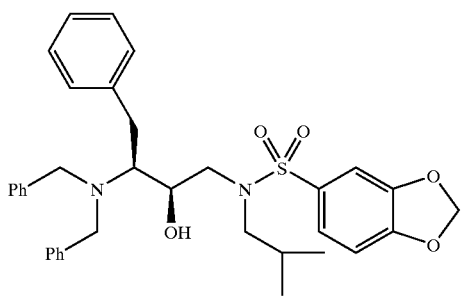

Preparation of 1-[N-[(1,3-Benzodioxol-5-yl) sulfonyl]-N-(2-methylpropyl)amino]-3(S)-[bis (phenylmethyl)amino]-4-phenyl-2(R)-butanol Method 1:

To a 5000 mL, 3-necked flask fitted with a mechanical stirrer was added N-[3(S)-[N,N-bis(phenylmethyl)amino]-2(R)-hydroxy-4-phenylbutyl]-N-isobutylamine.oxalic acid salt (354.7 g, 0.7 mole) and 1,4-dioxane (2000 mL). A solution of potassium carbonate (241.9 g, 1.75 moles) in water (250 mL) was then added. The resultant heterogeneous mixture was stirred for 2 hours at room temperature followed by the addition of 1,3-benzodioxole-5-sulfonyl chloride (162.2 g, 0.735 mole) dissolved in 1,4-dioxane (250 mL) over 15 minutes. The reaction mixture was stirred at room temperature for 18 hours. Ethyl acetate (1000 mL) and water (500 mL) were charged to the reactor and stirring continued for another 1 hour. The aqueous layer was separated and further extracted with ethyl acetate (200 mL). The combined ethyl acetate layers were washed with 25% brine solution (500 mL) and dried over anhydrous magnesium sulfate. After filtering and washing the magnesium sulfate with ethyl acetate (200 mL), the solvent in the filtrate was removed under reduced pressure yielding the desired sulfonamide as an viscous yellow foamy oil (440.2 g 105% yield). HPLC/MS (electrospray) (m/z 601 [M+H]+).

EXAMPLE 30

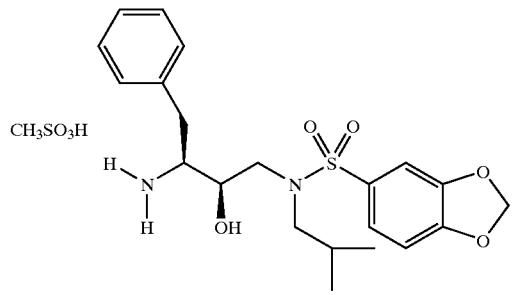

Preparation of 1-[N-[(1,3-Benzodioxol-5-yl) sulfonyl]-N-(2-methylpropyl)amino]-3(S)-amino-4-phenyl-2(R)-butanol.methanesulfonic Acid Salt Method 1:

Crude 1-[N-[(1,3-benzodioxol-5-yl)sulfonyl]-N-(2-methylpropyl)amino]-3(S)-[bis(phenylmethyl)amino]-4-phenyl-2(R)-butanol (6.2 g, 0.010 moles) was dissolved in methanol (40 mL). Methanesulfonic acid (0.969 g, 0.010 moles) and water (5 mL) were then added to the solution. The mixture was placed in a 500 mL Parr hydrogenation bottle containing 20% Pd(OH)$_2$ on carbon (255 mg, 50% water content). The bottle was placed in the hydrogenator and purged 5 times with nitrogen and 5 times with hydrogen. The reaction was allowed to proceed at 35° C. with 63 PSI hydrogen pressure for 18 hours. Additional catalyst (125 mg) was added and, after purging, the hydrogenation continued for and additional 20 hours. The mixture was filtered through celite which was washed with methanol (2×10 mL). Approximately one third of the methanol was removed under reduced pressure. The remaining methanol was removed by aziotropic distillation with toluene at 80 torr. Toluene was added in 15, 10, 10 and 10 mL portions. The product crystallized from the mixture and was filtered and washed twice with 10 mL portions of toluene. The solid was dried at room temperature at 1 torr for 6 hours to yield the amine salt (4.5 g, 84%). HPLC/MS (electrospray) was consistent with the desired product (m/z 421 [M+H]$^+$).

Method 2:

Part A: N-[3(S)-[N,N-bis(phenylmethyl)amino]-2(R)-hydroxy-4-phenylbutyl]-N-isobutylamine.oxalic acid salt (2800 g, 5.53 moles) and THF (4 L) were added to a 22 L round bottom flask fitted with a mechanical stirrer. Potassium carbonate (1921 g, 13.9 moles) was dissolved in water (2.8 L) and added to the THF slurry. The mixture was then stirred for one hour. 1,3-benzodioxole-5-sulfonyl chloride (1281 g, 5.8 moles) was dissolved in THF (1.4 L) and added to the reaction mixture over 25 minutes. An additional 200 ml, of THF was used to rinse the addition funnel. The reaction was allowed to stir for 14 hours and then water (4 L) was added. This mixture was stirred for 30 minutes and the layers allowed to separate. The layers was removed and the aqueous layer washed twice with THF (500 mL). The combined THF layers were dried with magnesium sulfate (500 g) for one hour. This solution was then filtered to remove the drying agent and used in subsequent reactions.

Part B: To the THF solution of crude 1-[N-[(1,3-benzodioxol-5-yl)sulfonyl]-N-(2-methylpropyl)amino]-3(S)-[bis(phenylmethyl)amino]-4-phenyl-2(R)-butanol was added water (500 mL) followed by methane sulfonic acid (531 g, 5.5 moles). The solution was stirred to insure complete mixing and added to a 5 gallon autoclave. Pearlman's catalyst (200 g of 20% Pd(OH)$_2$ on C/50% water) was added to the autoclave with the aid of THF (500 mL). The reactor was purged four times with nitrogen and four times with hydrogen. The reactor was charged with 60 psig of hydrogen and stirring at 450 rpm started. After 16 hours, HPLC analysis indicated that a small amount of the monobenzyl intermediate was still present. Additional catalyst (50 g) was added and the reaction was allowed to run overnight. The solution was then filtered through celite (500 g) to remove the catalyst and concentrated under vacuum in five portions. To each portion, toluene (500 mL) was added and removed under vacuum to azectropically removed residual water. The resulting solid was divided into three portions and each washed with methyl t-butyl ether (2 L) and filtered. The residual solvent was removed at room temperature in a vacuum oven at less than 1 torr to yield the 2714 g of the expected salt.

If desired, the product can be further purified by the following procedure. A total of 500 mL of methanol and 170 g of material from above was heated to reflux until it all dissolved. The solution was cooled, 200 mL of isopropanol added and then 1000–1300 mL of hexane, whereupon a white solid precipitated. After cooling to 0° C., this precipitate was collected and washed with hexane to afford 123 g of the desired material. Through this procedure, the original material which was a 95:5 mixture of alcohol diastereomers was greater than 99:1 of the desired diastereomer.

EXAMPLE 31

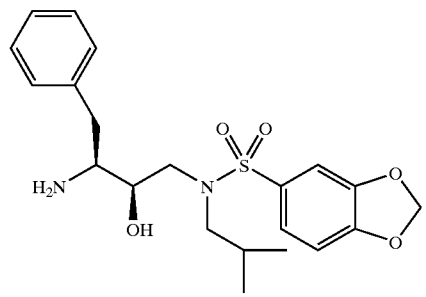

Preparation of 2R-Hydroxy-3-[[(1,3-benzodioxol-5-yl)sulfonyl](2-methylpropyl)amino]-1S-(phenylmethyl)propylamine Part A: Preparation of 2R-Hydroxy-3-[[(1,3-benzodioxol-5-yl)sulfonyl](2-methylpropyl)amino]-1S-(phenylmethyl)propylcarbamic Acid Phenylmethyl Ester To a solution of 3.19 g (8.6 mmol) of N-[3S-benzyloxycarbonylamino-2R-hydroxy-4-phenyl]-N-isobutylamine in 40 mL of anhydrous methylene chloride, was added 0.87 g of triethylamine. The solution was cooled to 0° C. and 1.90 g of (1,3-benzodioxol-5-yl)sulfonyl chloride was added, stirred for 15 minutes at 0° C., then for 17 hours at room temperature. Ethyl acetate was added, washed with 5% citric acid, saturated sodium bicarbonate, brine, dried and concentrated to yield crude material. This was recrystallized from diethyl ether/hexane to afford 4.77 g of pure 2R-hydroxy-3-[[(1,3-benzodioxol-5-yl)sulfonyl](2-methylpropyl)amino]-1S-(phenylmethyl)propylcarbamic acid phenylmethyl ester.

Part B: Preparation of 2R-Hydroxy-3-[[(1,3-benzodioxol-5-yl)sulfonyl](2-methylpropyl)amino]-1S-(phenylmethyl)propylamine A solution of 4.11 g of carbamic acid, 2R-hydroxy-3-[[(1, 3-benzodioxol-5-yl)sulfonyl](2-methylpropyl)amino]-1S-(phenylmethyl)propyl-, phenylmethyl ester in 45 mL of tetrahydrofuran and 25 mL of methanol was hydrogenated over 1.1 g of 10% palladium-on-carbon under 50 psig of hydrogen for 16 hours. The catalyst was removed by filtration and the filtrate concentrated to afford 1.82 g of the desired 2R-hydroxy-3-[[(1,3-benzodioxol-5-yl)sulfonyl](2-methylpropyl)amino]-l5-(phenylmethyl)propylamine.

EXAMPLE 32

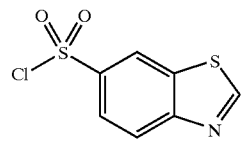

Preparation of Benzothiazole-6-sulfonyl Chloride

Part A: Preparation of N-(4-Sulfonamidophenyl)thiourea

A mixture of sulfanilamide (86 g, 0.5 mole), ammonium thiocyanate (76.0 g, 0.5 mole) and dilute hydrochloric acid (1.5 N, 1 L) was mechanically stirred and heated at reflux for 2 hr. About 200 mL of water was distilled off and concentration of the reaction mixture afforded a solid. The solid was filtered and was washed with cold water and air dried to afford 67.5 g (59%) of the desired product as a white powder.

Part B: Preparation of 2-Amino-6-sulfonamidobenzothiazole

Bromine (43.20 g, 0.27 mol) in chloroform (200 mL) was a added over 1 hr. to a suspension of N-(4-sulfonamidophenyl)-thiourea (27.72, 0.120 mol) in chloroform (800 mL). After the addition, the reaction mixture was heated at reflux for 4.5 hr. The chloroform was removed in vacuo and the residue was repeatedly distilled with additional amounts of chloroform. The solid obtained was treated with water (600 mL) followed by ammonium hydroxide (to make it basic), then was heated at reflux for 1 hr. The cooled reaction mixture was filtered, washed with water and air dried to afford 22.0 g (80%) of the desired product as a white powder.

Part C: Preparation of Benzothiazole-6-sulfonic Acid

A suspension of 2-amino-6-sulfonamido-benzothiazole (10.0 g, 43.67 mmol) in dioxane (300 mL) was heated at reflux. Isoamylnitrite (24 mL) was added in two portions to the reaction mixture. Vigorous evolution of gas was observed (the reaction was conducted behind a shield as a precaution) and after 2 hr., a red precipitate was deposited in the reaction vessel. The reaction mixture was filtered hot, and the solid was washed with dioxane and was dried. The solid was recrystallized from methanol-water. A small amount of a precipitate was formed after 2 days. The precipitate was filtered off and the mother liquor was concentrated in vacuo to afford a pale red-orange solid (8.0 g, 85%) of pure product.

Part D: Preparation of 6-Chlorosulfonylbenzothiazole

Thionyl chloride (4 mL) was added to a suspension of the benzothiazole-6-sulfonic acid (0.60 g, 2.79 mmol) in dichloroethane (15 mL) and the reaction mixture was heated at reflux and dimethylformamide (5 mL) was added to the reaction mixture to yield a clear solution. After 1.5 hr. at reflux, the solvent was removed in vacuo and excess HCl and thionyl chloride was chased by evaporation with dichloroethane.

EXAMPLE 33

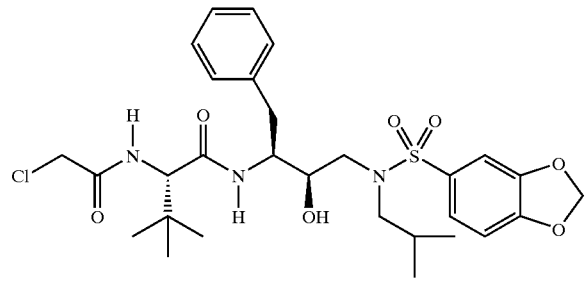

Preparation of N-[2R-Hydroxy-3-[[(1,3-benzodioxol-5-yl)sulfonyl](2-methylpropyl)amino]-1S-(phenylmethyl)propyl]-2S-[(chloroacetyl)amino]-3,3-dimethylbutanamide Part A: Preparation of N-[2R-Hydroxy-3-[[(1,3-benzodioxol-5-yl)sulfonyl](2-methylpropyl)amino]-1S-(phenylmethyl)propyl]-2S-[(phenylmethoxycarbonyl)amino]-3,3-dimethylbutanamide

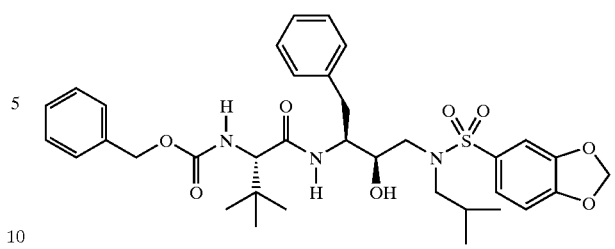

To a solution of 118.8 g (0.776 mol) of N-hydroxybenzotriazole and 137.1 g (0.52 mol) of N-carbobenzyloxycarbonyl-L-tert-leucine in 750 mL of anhydrous DMF at 0° C. under a nitrogen atmosphere, was added 109.1 g (0.57 mol) of EDC. After stirring at 0° C. for 2 hours, a solution of 273 g (0.53 mol) of 2R-hydroxy-3-[[(1,3-benzodioxol-5-yl)sulfonyl](2-methylpropyl)amino]-1S-(phenylmethyl)propylamine methanesulfonate, previously neutralized with 228 mL (210 g, 2.08 mol) of 4-methylmorpholine, in 250 mL of anhydrous DMF was added. After stirring at 0° C. for 30 minutes, the mixture stirred at room temperature for 18 hours. The solvents were removed under reduced pressure at 45° C., 1.5 L of ethyl acetate added, washed with 5% citric acid, saturated sodium bicarbonate, brine, dried over anhydrous magnesium sulfate, filtered and concentrated to afford 400 g of crude material. This was chromatographed in 3 batches on a Prep 2000 Chromatogram on silica gel using 20%–50% ethyl acetate/hexane as eluent to yield 320 g of purified material, m/e=674 (M+Li), 98% by HPLC.

Part B: Preparation of N-[2R-Hydroxy-3-[[(1,3-benzodioxol-5-yl)sulfonyl](2-methylpropyl)amino]-1S-(phenylmethyl)propyl]-2S-amino-3,3-dimethylbutanamide

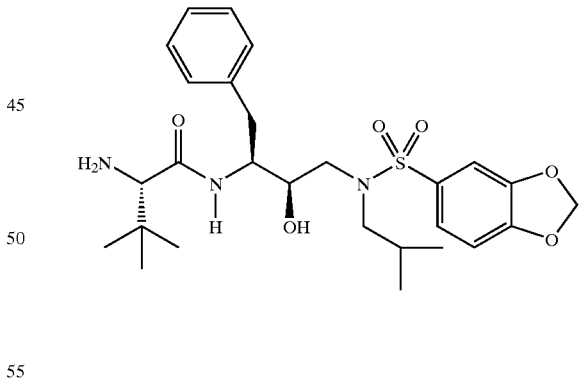

A solution of 312 g of the Cbz compound from above in 1 L of tetrahydrofuran was hydrogenated in the presence of 100 g of 4% palladium-on-carbon catalyst under 60 psig of hydrogen for 6 hours at room temperature. The catalyst was removed by filtration and the solvents removed under reduced pressure to afford 240 g of the desired compound.

Part C: Preparation of N-[2R-Hydroxy-3-[[(1,3-benzodioxol-5-yl)sulfonyl](2-methylpropyl)amino]-1S-(phenylmethyl)propyl]-2S-[(chloroacetyl)amino]-3,3-dimethylbutanamide

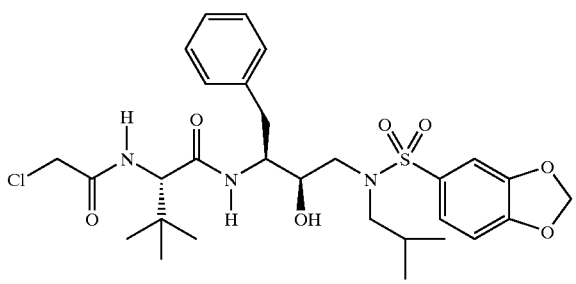

To a solution of 234.3 g (0.439 mol) of the amine from above in 1 L of methylene chloride, was added 80 mL (59.5 g, 0.46 mol) of diisopropylethylamine, followed by the slow addition at room temperature of 78.8 g (0.46 mol) of chloroacetic anhydride while maintaining the temperature below 35° C. After stirring for an additional 1 hour, analysis by HPLC indicated a small amount of starting material was still present, and 1.5 g of chloroacetic anhydride was added. After 10 minutes, the solvents were removed under reduced pressure, 1 L ethyl acetate added, washed with 5% citric acid, saturated sodium bicarbonate, brine, dried over anhydrous magnesium sulfate, filtered and concentrated to yield 314 g of crude material. This was chromatographed in 3 portions on a Prep 2000 Chromatogram on silica gel using 20–50% ethyl acetate/hexane to afford 165 g of the desired compound, m/e=616 (M+Li), 98% by HPLC.

EXAMPLE 34

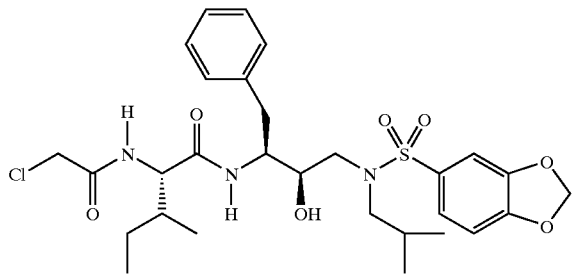

Preparation of N-[2R-Hydroxy-3-[[(1,3-benzodioxol-5-yl)sulfonyl](2-methylpropyl)amino]-1S-(phenylmethyl)propyl]-2S-[(chloroacetyl)amino]-3S-methylpentanamide Part A: Preparation of N-[2R-Hydroxy-3-[[(1,3-benzodioxol-5-yl)sulfonyl](2-methylpropyl)amino]-1S-(phenylmethyl)propyl]-2S-[[(1,1-dimethylethoxy)carbonyl]amino]-3S-methylpentanamide

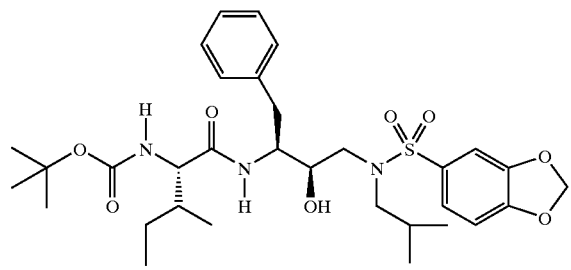

To a cooled solution of N-t-Boc-L-isoleucine 2.02 g (8.74 mmol) and 2.00 g (13.11 mmol) of N-hydroxybenzotriazole in 17 mL of N,N-dimethylformamide was added 1.84 g (9.61 mmol) of EDC and stirred at 0° C. for one hour. To this was added a solution of 3.67 g (8.74 mmol) of 2R-hydroxy-3-[[(1,3-benzodioxol-5-yl)sulfonyl](2-methylpropyl)amino]-1S-(phenylmethyl)propyl amine in 6 mL of N,N-dimethylformamide and the solution stirred for 16 hours. The solvent was removed in vacuo, replaced with ethyl acetate, and washed with saturated sodium bicarbonate, 5% citric acid and brine. The organic layers were dried over magnesium sulfate, filtered and concentrated to yield 6.1 grams of crude product, which was chromatoraphed on silica gel using 1:1 ethyl acetate:hexane eluant to produce 4.3 g (78% yield) of N-[2R-hydroxy-3-[[(1,3-benzodioxol-5-yl)sulfonyl](2-methylpropyl)amino]-1S-(phenylmethyl)propyl]-2S-[[(1,1-dimethylethoxy)carbonyl]amino]-3S-methylpentanamide.

Part B: Preparation of N-[2R-Hydroxy-3-[[(1,3-benzodioxol-5-yl)sulfonyl](2-methylpropyl)amino]-1S-(phenylmethyl)propyl]-2S-amino-3S-methylpentanamide.hydrochloride Salt

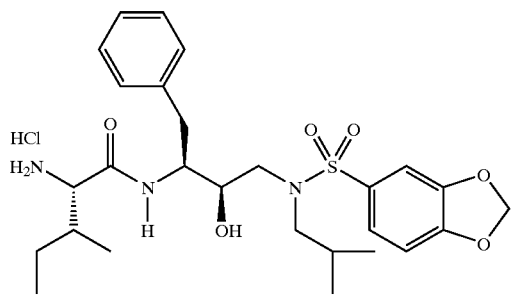

N-[2R-hydroxy-3-[[(1,3-benzodioxol-5-yl)sulfonyl](2-methylpropyl)amino]-1S-(phenylmethyl)propyl]-2S-[[(1,1-dimethylethoxy)carbonyl]amino]-3S-methylpentanamide (4.29 g, 6.77 mmol) was dissolved in 20 mL of 4N HCl in dioxane and stirred for 20 minutes. The precipitated product was stripped two times from diethyl ether and the crude hydrochloride salt was used in subsequent reactions.

Part C: Preparation of N-[2R-Hydroxy-3-[[(1,3-benzodioxol-5-yl)sulfonyl](2-methylpropyl)amino]-1S-(phenylmethyl)propyl]-2S-[(chloroacetyl)amino]-3S-methylpentanamide

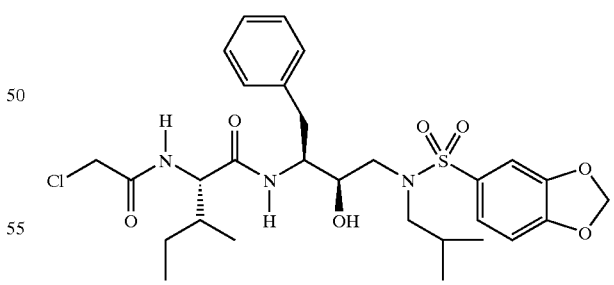

N-[2R-hydroxy-3-[[(1,3-benzodioxol-5-yl)sulfonyl](2-methylpropyl)amino]-1S-(phenylmethyl)propyl]-2S-amino-3S-methylpentanamide.hydrochloride salt (3.62 g, 6.77 mmol) was dissolved in 45 mL of methylene chloride and to this was added 1.3 g (10.15 mmol) of N,N-diisopropylethyl amine to neutralllize the salt, and another 0.923 g (7.10 mmol) of diisopropylethyl amine followed by 1.22 g (7.11 mmol) of chloroacetic anhydride. The solution was stirred at room temperature for 30 minutes. The contents were concentrated on a rotory evaporator and the residue was partitioned between ethyl acetate and water. The organic layer was washed with 5% citric acid and then saturated sodium bicarbonate and brine. The organic layers were dried over magnesium sulfate filtered and concentrated to yield 4.12 g of crude product. Recrystallization from ethyl acetate hexane yielded 3.5 g (85% yield) of N-[2R-hydroxy-3-[[(1,3-benzodioxol-5-yl)sulfonyl](2-methylpropyl)amino]-1S-(phenylmethyl)propyl]-2S-[(chloroacetyl)amino]-3S-methylpentanamide, as a white solid; mass spectrum m/z= 616 (M+Li).

EXAMPLE 35

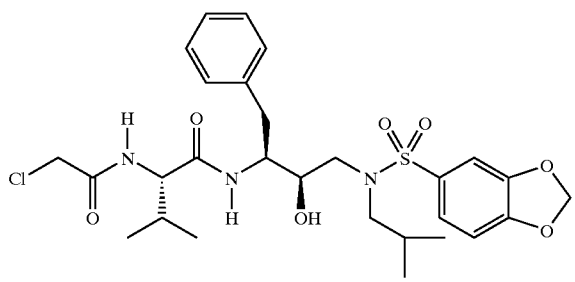

Preparation of N-[[2R-Hydroxy-3-[(1,3-benzodioxol-5-yl)sulfonyl](2-methylpropyl)amino]-1S-(phenylmethyl)propyl]-2S-[(chloroacetyl)amino]-3-methylbutaneamide Part A: Preparation of N-[[2R-Hydroxy-3-[(1,3-benzodioxol-5-yl)sulfonyl](2-methylpropyl)amino]-1S-(phenylmethyl)propyl]-2S-[(phenylmethoxycarbonyl)amino]-3-methylbutaneamide

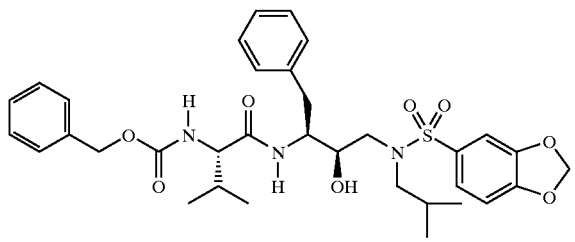

A 250 mL round bottom flask equipped with magnetic stir bar was charged with N-Cbz-L-Valine (4.22 g, 16.8 mmol) in 20 mL DMF. The solution was cooled to 0° C. and charged with HoBt (2.96, 21.9 mmol) and EDC (3.22 g, 16.8 mmol) and stirred 1 hour. The reaction was then charged with N-methylmorpholine (1.7 g, 16.8 mmol), 2R-hydroxy-3-[[(1,3-benzodioxol-5-yl)sulfonyl](2-methylpropyl)amino]-1S-(phenylmethyl)propylamine (7.55 g, 14.6 mmol) in 30 mL of DMF. The reaction was stirred overnight at room temperature then concentrated in vacuo and partioned between ethyl acetate and 5% Citric acid. The combined organic layers were washed with saturated sodium bicarbonate and brine, and dried over sodium sulfate. Concentration in vacuo yielded 10 g crude product. Purification by Prep HPLC (20–40% ethyl acetate/hexane) yielded 5.8 g (61%) of the desired compound.

Part B: Preparation of N-[[2R-Hydroxy-3-[(1,3-benzodioxol-5-yl)sulfonyl](2-methylpropyl)amino]-1S-(phenylmethyl)propyl]-2S-amino-3-methylbutaneamide

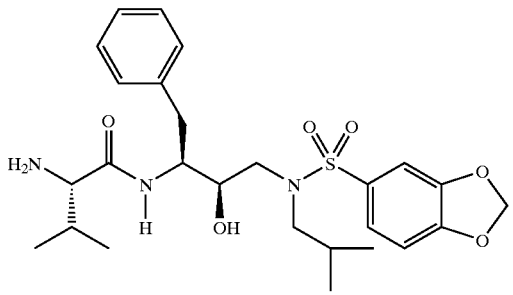

A 300 mL Fisher-Porter vessel equipped with magnetic stir bar was charged with N-[[2R-hydroxy-3-[(1,3-benzodioxol-5-yl)sulfonyl](2-methylpropyl)amino]-1S-(phenylmethyl)propyl]-2S-[(phenylmethoxycarbonyl)amino]-3-methylbutaneamide (5.8 g), 2.3 g of 10% Pd—C in 75 mL tetrahydrofuran. The reaction was charged with 50 psi H₂ and hydrogenated overnight. The reaction mixture was filtered thru Celite and concentrated in vacuo to yield 4.4 g of white foam that was used in subsequent reactions without further purification.

Part C: Preparation of N-[[2R-Hydroxy-3-[(1,3-benzodioxol-5-yl)sulfonyl](2-methylpropyl)amino]-1S-(phenylmethyl)propyl]-2S-[(chloroacetyl)amino]-3-methylbutaneamide

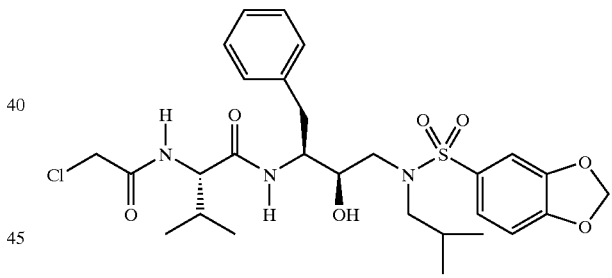

A 250 mL round bottom flask equipped with magnetic stir bar was charged with crude N-[[2R-hydroxy-3-[(1,3-benzodioxol-5-yl)sulfonyl](2-methylpropyl)amino]-1S-(phenylmethyl)propyl]-2S-amino-3-methylbutaneamide (4.35 g) in 60 mL CH₂Cl₂. The reaction was charged with 1.19 g diisopropylamine followed by 1.5 g of chloroacetic anhydride and stirred until TLC indicated no remaining starting material (about 1.5 hours). The reaction was concentrated in vacuo and partioned between ethyl acetate and saturated sodium bicarbonate. The combined organic layers were washed with brine, and dried over sodium sulfate. Concentration in vacuo yielded 5.17 g of desired product that was used in subsequent reactions without further purification.

EXAMPLE 36

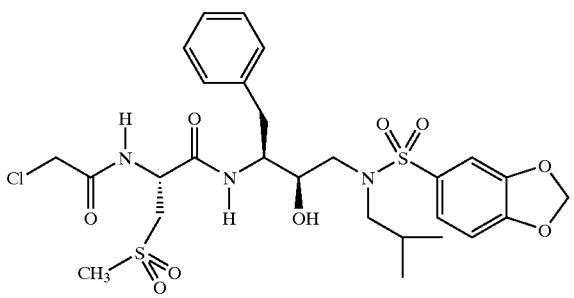

Preparation of N-[[2R-Hydroxy-3-[(1,3-benzodioxol-5-yl)sulfonyl](2-methylpropyl)amino]-1S-(phenylmethyl)propyl]-2S-[(chloroacetyl)amino]-3-(methylsulfonyl)propaneamide Part A: Preparation of N-[[2R-Hydroxy-3-[(1,3-benzodioxol-5-yl)sulfonyl](2-methylpropyl)amino]-1S-(phenylmethyl)propyl]-2S-[[(1,1-dimethylethoxy)carbonyl]amino]-3-(methylthio)propaneamide

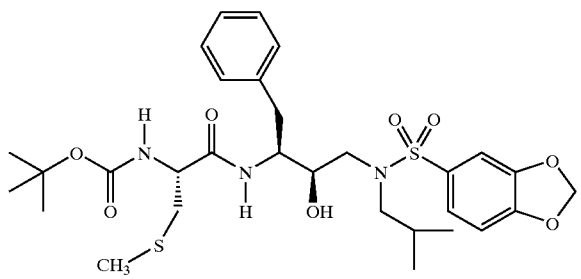

N-t-Boc-S-methyl-(L)-cysteine (2.80 g, 11.9 mmol), 1-Hydroxybenzotriazole hydrate (1.92 g, 12.5 mmol), and 1-(3-dimethylaminopropyl)-3-ethylcarbodiimide hydrochloride (2.27 g, 11.9 mmol) were mixed in N,N-dimethylformamide (30.0 mL) at 0° C. for 10 min. N-Methylmorpholine (3.03 g, 33.0 mmol) was addled and the solution stirred an additional 10 min at 0° C. 2R-Hydroxy-3-[[(1,3-benzodioxol-5-yl)sulfonyl](2-methylpropyl)amino]-1S-(phenylmethyl)propylamine (5.00 g, 11.9 mmol) was added and the solution was warmed to room temperature and stirred for 2 hours. The reaction mixture was poured into ethyl acetate (500 mL) and washed with 10% aqueous hydrochloric acid (3×100 mL), saturated aqueous sodium bicarbonate (3×100 mL) and brine (2×100 mL). The organic layer was dried over sodium sulfate and percolated through a bed of silica gel (50 g). The desired product (7.13 g, 11.19 mmol, 93% yield) was obtained as a while solid by removal of the solvent at reduced pressure; m/e calcd 637; found (M+Li) 644.

Part B: Preparation of N-[[2R-Hydroxy-3-[(1,3-benzodioxol-5-yl)sulfonyl](2-methylpropyl)amino]-1S-(phenylmethyl)propyl]-2S-[[(1,1-dimethylethoxy)carbonyl]amino]-3-(methylsulfonyl)propaneamide

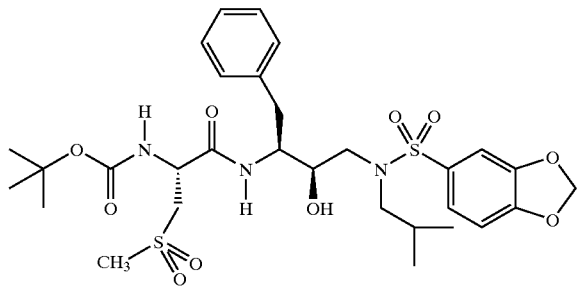

N-[[2R-hydroxy-3-[(1,3-benzodioxol-5-yl)sulfonyl](2-methylpropyl)amino]-1S-(phenylmethyl)propyl]-2S-[[(1,1-dimethylethoxy)carbonyl]amino]-3-(methylthio)propaneamide (7.10 g, 11.1 mmol) was dissolved in methanol (150 mL). A solution of oxone® (20.8 g, 33.9 mmol) in water (150 mL) was added dropwise to the solution at room temperature over 1.5 hours. The solution became cloudy and a precipitate formed during the addition. The reaction was stirred for an additional 1 hour and tetrahydrofuran (200 mL) was added. After an additional 1 hour of mixing the solution was poured into ethyl acetate (1000 mL) and washed with water (3×200 mL) followed by brine (2×300 ml). The organic layer was dried over anhydrous sodium sulfate and solvent removed at reduced pressure. The desired product (5.75 g, 8.86 mmol, 79% yield) was obtained as an off white solid; m/e calcd 669; found (M+H) 670.

Part C: Preparation of N-[[2R-Hydroxy-3-[(1,3-benzodioxol-5-yl)sulfonyl](2-methylpropyl)amino]-1S-(phenylmethyl)propyl]-2S-amino-3-(methylsulfonyl)propaneamide.hydrochloride Salt

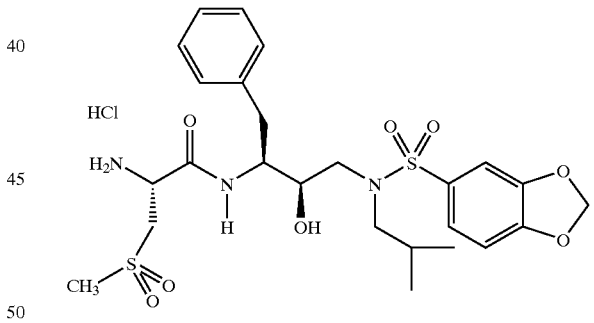

N-[[2R-hydroxy-3-[(1,3-benzodioxol-5-yl)sulfonyl](2-methylpropyl)amino]-1S-(phenylmethyl)propyl]-2S-[[(1,1-dimethylethoxy)carbonyl]amino]-3-(methylsulfonyl)propaneamide (5.5 g, 8.20 mmol) was dissolved in dichloromethane (100 mL) at room temperature. Anhydrous hydrochloric acid was bubbled through the solution for 15 min. The solution was stirred at room temperature for 2 hours and the solvent was removed at reduced pressure. The desired product (4.91 g, 8.10 mmol, 99% yield) was obtained as a white solid; m/e calcd 569; found (M+Li) 576.

Part D: Preparation of N-[[2R-Hydroxy-3-[(1,3-benzodioxol-5-yl)sulfonyl](2-methylpropyl)amino]-1S-(phenylmethyl)propyl]-2S-[(chloroacetyl)amino]-3-(methylsulfonyl)propaneamide

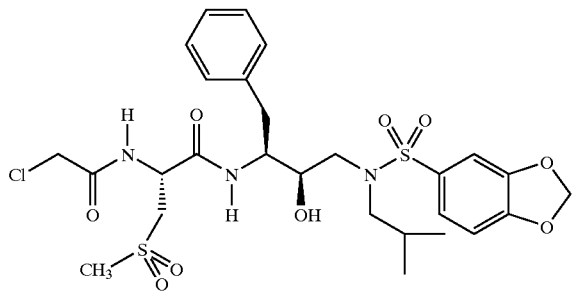

N-[[2R-hydroxy-3-[(1,3-benzodioxol-5-yl)sulfonyl](2-methylpropyl)amino]-1S-(phenylmethyl)propyl]-2S-amino-3-(methylsulfonyl)propaneamide.hydrochloride salt (4.00 g, 6.59 mmole) was mixed at room temperature in acetonitrile (40 mL). Triethylamine (2.10 g, 21.0 mmol) and chloroacetic anhydride (1.12 g, 6.59 mmol) were added. The solution was stirred at room temperature for 16 hours and poured into ethyl acetate (250 mL). The solution was washed with 10% aqueous acetic acid (2×100 mL), saturated aqueous sodium bicarbonate (2×100 mL), and brine (2×100 mL). The organic layer was dried over anhydrous sodium sulfate and solvent removed at reduced pressure. The product (1.20 g, 1.85 mmol, 28% yield) was obtained as a white solid by crystallization from ethyl acetate and hexanes; m/e calcd 645; found (M+Li) 652.

EXAMPLE 37

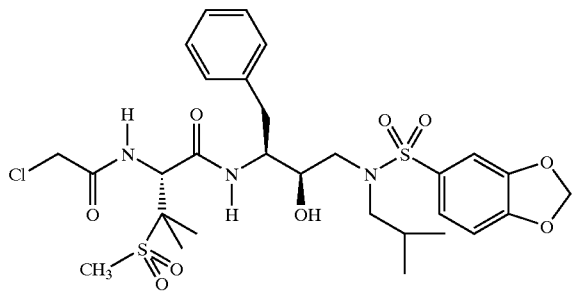

Preparation of N-[[2R-Hydroxy-3-[(1,3-benzodioxol-5-yl)sulfonyl](2-methylpropyl)amino]-1S-(phenylmethyl)propyl]-2S-[(chloroacetyl)amino]-3-methyl-3-(methylsulfonyl)butaneamide Part A: Preparation of N-[[2R-Hydroxy-3-[(1,3-benzodioxol-5-yl)sulfonyl](2-methylpropyl)amino]-1S-(phenylmethyl)propyl]-2S-[[(1,1-dimethylethoxy)carbonyl]amino]-3-methyl-3-(methylthio)butaneamide

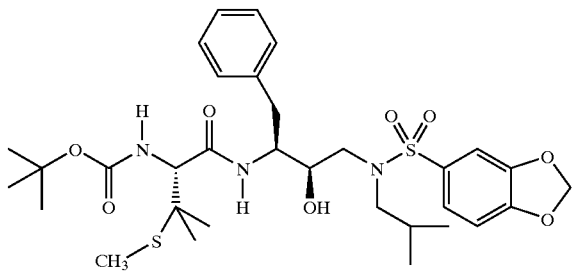

The N-t-boc-S-methyl-L-penicillamine dicyclohexylamine salt (4.00 g, 9.00 mmol), 1-Hydroxybenzotriazole hydrate (1.69 g, 11.00 mmol), and 1-(3-dimethylaminopropyl)-3-ethylcarbodiimide hydrochloride (1.71 g, 9.00 mmol) were mixed in dimethylformamide (60.0 mL) at room temperature. The heterogeneous mixture was stirred for 1 hour and 2R-hydroxy-3-[[(1,3-benzodioxol-5-yl)sulfonyl](2-methylpropyl)amino]-1S-(phenylmethyl)propylamine (3.78 g, 9.00 mmol) was added and the heterogenous mixture was stirred for 16 hours. The solution was poured into ethyl acetate (600 mL) and washed with 10% aqueous acetic acid (2×300 mL), saturated aqueous sodium bicarbonate (2×300 mL) and brine (300 mL). The solution was dried over sodium sulfate and the solvent was removed in vacuo. The desired product was purified by flash chromatography (0–80% ethyl acetate/hexanes on silica gel). The product (5.21 g, 7.83 mmol, 87% yield) was obtained as a white foam; m/e calcd 665; found (M+Li) 672.

Part B: Preparation of N-[[2R-Hydroxy-3-[(1,3-benzodioxol-5-yl)sulfonyl](2-methylpropyl)amino]-1S-(phenylmethyl)propyl]-2S-[[(1,1-dimethylethoxy)carbonyl]amino]-3-methyl-3-(methylsulfonyl)butaneamide

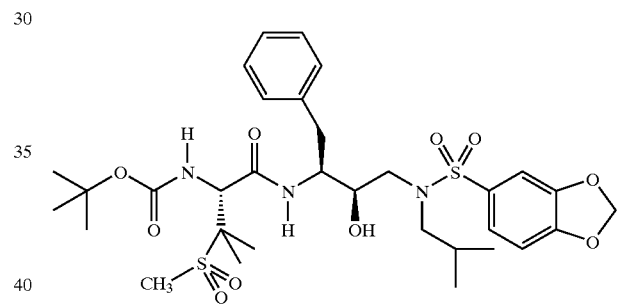

N-[[2R-hydroxy-3-[(1,3-benzodioxol-5-yl)sulfonyl](2-methylpropyl)amino]-1S-(phenylmethyl)propyl]-2S-[[(1,1-dimethylethoxy)carbonyl]amino]-3-methyl-3-(methylthio)butaneamide (5.01 g, 7.53 mmol) was dissolved in tetrahydrofuran (250 mL). A solution of oxone® (13.8 g, 22.6 mmol) in water (250 mL) was added dropwise to the solution at room temperature over 2 hours. The solution became cloudy and a precipitate formed during the addition. The solution was poured into ethyl acetate (500 mL) and wasted with water (3×200 mL) followed by brine (2×300 mL). The organic layer was dried over anhydrous sodium sulfate and solvent removed in vacuo. The product (4.72 g, 6.77 mmol, 89% yield) was obtained as a white foam; m/e calcd 697; found (M+Li) 704.

Part C: Preparation of N-[[2R-Hydroxy-3-[(1,3-benzodioxol-5-yl)sulfonyl](2-methylpropyl)amino]-1S-(phenylmethyl)propyl]-2S-amino-3-methyl-3-(methylsulfonyl)butaneamide.hydrochloride Salt

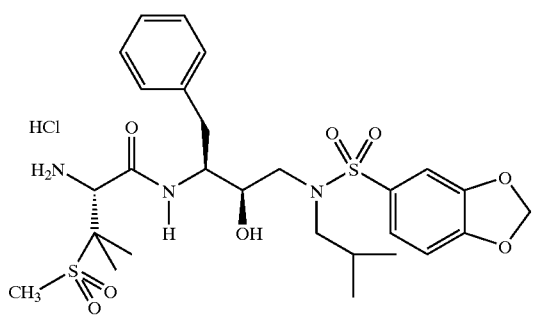

N-[[2R-hydroxy-3-[(1,3-benzodioxol-5-yl)sulfonyl](2-methylpropyl)amino]-1S-(phenylmethyl)propyl]-2S-[[(1,1-dimethylethoxy)carbonyl]amino]-3-methyl-3-(methylsulfonyl)butaneamide (4.51 g, 6.46 mmol) was dissolved in dichloromethane (200 mL) at room temperature. Anhydrous hydrochloric acid was bubbled through the solution for 30 min. The solution was stirred at room temperature for 1 hour and the solvent was removed in vacuo. The product (4.02 g, 6.35 mmol, 99% yield) was obtained as a white solid; m/e calcd 697; found (M+Li) 704.

Part D: Preparation of N-[[2R-Hydroxy-3-[(1,3-benzodioxol-5-yl)sulfonyl](2-methylpropyl)amino]-1S-(phenylmethyl)propyl]-2S-[(chloroacetyl)amino]-3-methyl-3-(methylsulfonyl)butaneamide

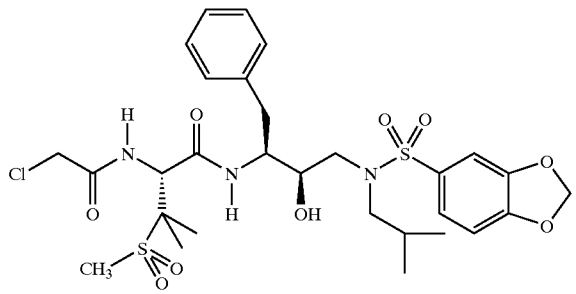

N-[[2R-hydroxy-3-[(1,3-benzodioxol-5-yl)sulfonyl](2-methylpropyl)amino]-1S-(phenylmethyl)propyl]-2S-amino-3-methyl-3-(methylsulfonyl)butaneamide.hydrochloride salt (3.90 g, 6.15 mmole) was mixed at room temperature in acetonitrile (40 mL). Triethylamine (1.86 g, 18.45 mmol) and chloroacetic anhydride (1.05 g, 6.15 mmol) were added. The solution was stirred at room temperature for 16 hours and poured into ethyl acetate (250 mL). The solution was washed with 10% aqueous acetic acid (2×100 mL), saturated aqueous sodium bicarbonate (2×100 mL), and brine (2×100 mL). The organic layer was dried over anhydrous sodium sulfate and solvent was removed in vacuo. A yellow oil (4.3 g) was obtained and purified by flash chromatography (silica gel, 50–75% ethyl acetates in hexanes. The product (2.15 g, 3.18 mmol, 52% Yield) was obtained as a white foam; m/e calcd 674; found (M+Li) 681.

EXAMPLE 38

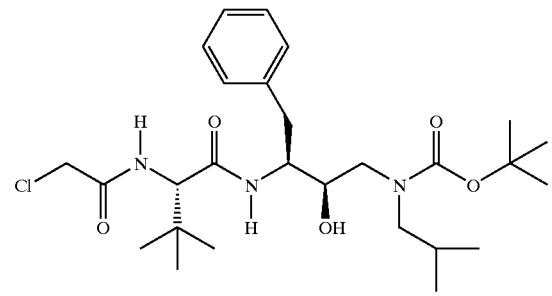

Preparation of N-[2R-Hydroxy-3-[[(1,1-dimethylethoxy)carbonyl](2-methylpropyl)amino]-1S-(phenylmethyl)propyl]-2S-[(chloroacetyl)amino]-3,3-dimethylbutanamide Part A: Preparation of N-[(1,1-Dimethylethoxyl)carbonyl]-N-[2-methylpropyl]-3S-[N$^1$-(phenylmethoxycarbonyl)amino]-2R-hydroxy-4-phenylbutylamine

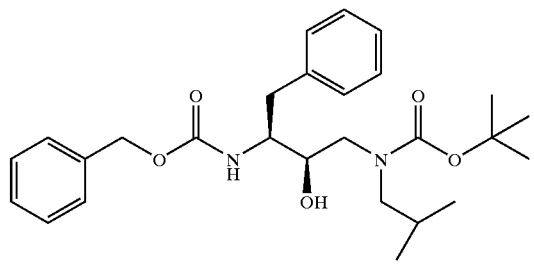

A solution of N-[3S-[N$^1$-(benzyloxycarbonyl)amino]-2R-hydroxy-4-phenylbutyl]-N-(2-methylpropyl)amine (18.5 g, 50 mmol), BOC-ON (12.35 g, 50 mmol) and triethylamine (7 mL) in tetrahydrofuran (400 mL) was stirred at room temperature for 18 hours and then concentrated in vacuo. The residue was dissolved in dichloromethane (1 L) and washed with sodium hydroxide (5%, 2×200 mL) and brine, dried (MgSO4) and then concentrated in vacuo to afford 23.5 g (quantitative yield) of the pure desired product.

Part B: Preparation of N-[2R-Hydroxy-3-[[(1,1-dimethylethoxy)carbonyl](2-methylpropyl)amino]-1S-(phenylmethyl)propyl]-2S-[(phenylmethoxycarbonyl)amino]-3,3-dimethylbutanamide

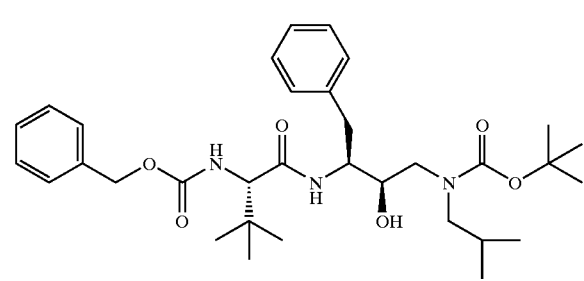

N-[(1,1-dimethylethoxyl)carbonyl]-N-[2-methylpropyl]-3S-[N¹-(phenylmethoxycarbonyl)amino]-2R-hydroxy-4-phenylbutylamine in ethanol was hydrogenated at 45 psig of hydrogen in the presence of 5% pd(C) catalyst to yield N-[(1,1-dimethylethoxyl)carbonyl]-N-[2-methylpropyl]-3S-[N¹-(phenylmethoxycarbonyl)amino]-2R-hydroxy-4-phenylbutylamine. Following standard workup, the crude amine (12.24 g, 36.42 mmol) was added to a mixture of N-carbobenzyloxycarbonyl-L-tert-leucine (9.67 g, 36.42 mmol), HOBT (4.92 g, 36.42 mmol) and EDC (6.98 g, 36.42 mmol) in DMF (300 mL) after the mixture was stirred at room temperature for 1 hour. The mixture was stirring for an additional 18 hours. The DMF was removed in vacuo, the residue was dissolved in dichloromethane (500 mL), washed with sodium hydroxide (5%, 2×200 mL) and brine (200 mL), dried and concentrated to afford 21 g (quantitative) of the desired product.

Part C: Preparation of N-[2R-Hydroxy-3-[[(1,1-dimethylethoxy)carbonyl](2-methylpropyl)amino]-1S-(phenylmethyl)propyl]-2S-amino-3,3-dimethylbutanamide

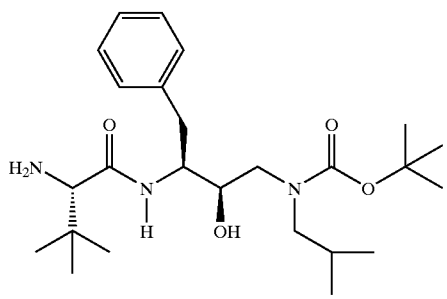

N-[2R-hydroxy-3-[[(1,1-dimethylethoxy)carbonyl](2-methylpropyl)amino]-1S-(phenylmethyl)propyl]-2S-[(phenylmethoxycarbonyl)amino]-3,3-dimethylbutanamide (20 g, 34.29 mmol) in methanol (250 mL) was hydrogenated at room temperature in the presence of Pd/C (10%, 5 g). The catalyst was filtered off and the filtrate was concentrated to afford 13.8 g (90%) of the pure desired product.

Part D: Preparation of N-[2R-Hydroxy-3-[[(1,1-dimethylethoxy)carbonyl](2-methylpropyl)amino]-1S-(phenylmethyl)propyl]-2S-[(chloroacetyl)amino]-3,3-dimethylbutanamide

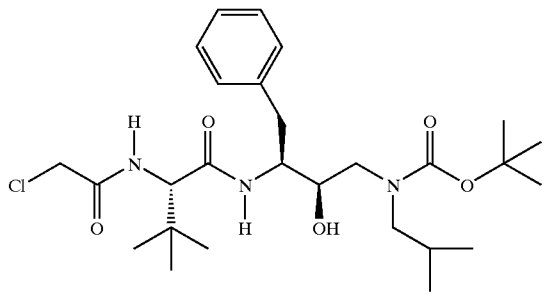

To N-[2R-hydroxy-3-[[(1,1-dimethylethoxy)carbonyl](2-methylpropyl)amino]-1S-(phenylmethyl)propyl]-2S-amino-3,3-dimethylbutanamide (12.45 g, 27.70 mmol) in dichloromethane (200 mL) was added chloroacetic anhydride (5.21 g, 30.48 mmol) and the reaction mixture was stirred for 18 hours. The reaction mixture was washed with citric acid (5%, 100 mL), sodium bicarbonate (saturated, 100 mL) and brine, dried (MgSO4) and concentrated to afford 12.0 g (82%) of the pure desired product.

EXAMPLE 39

Preparation of 2R-Hydroxy-3-[[(1,4-benzodioxan-6-yl)sulfonyl](2-methylpropyl)amino]-1S-(phenylmethyl)propylcarbamic Acid Phenylmethyl Ester

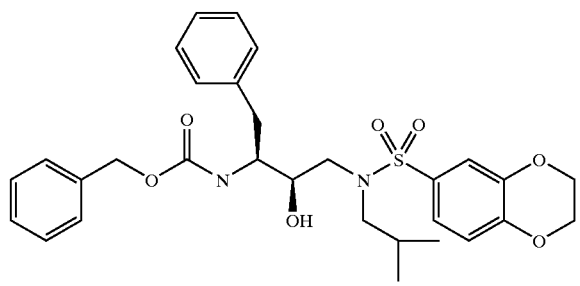

To a solution of the N-[3S-[(phenylmethoxycarbonyl)amino]-2R-hydroxy-4-phenylbutyl]-N-(2-methylpropyl) amine (0.5 g, 1.35 mmol) in CH₂Cl₂ (5.0 mL) containing Et₃N (0.35 mL, 2.5 mmol) was added 1,4-benzodioxan-6-sulfonyl chloride (0.34 g, 1.45 mmol) and stirred at 0° C. for 30 min. After stirring at room temperature for 1 hour, the reaction mixture was diluted with CH₂Cl₂ (20 mL), washed with cold 1N HCl (3×20 mL), water (2×20 mL), satd. NaHCO₃ (2×20 mL) and water (3×20 mL), dried (Na₂SO₄) and concentrated under reduced pressure. The resulting residue was purified by flash chromatography using 35% EtOAc in hexane to give the desired product as a white amorphous solid which crystallized from MeOH as a white powder (0.65 g 84% yield): m.p. 82–84° C., HRMS-FAB: calcd for $C_{30}H_{37}N_2O_7S$ 569.2321 (MH⁺), found 569.2323.

EXAMPLE 40

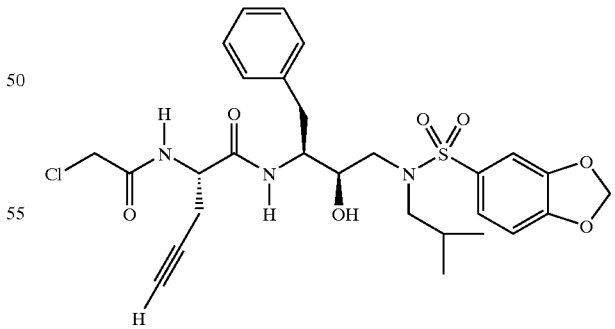

Preparation of 2S-[(Chloroacetyl)amino]-N-[2R-hydroxy-3-[[(1,3-benzodioxol-5-yl)sulfonyl](2-methylpropyl)amino]-1S-(phenylmethyl)propyl] pent-4-ynamide Part A. Preparation of 2S-[[(1,1-Dimethylethoxy)carbonyl]amino]-N-[2R-hydroxy-3-[[(1,3-benzodioxol-5-yl)sulfonyl](2-methylpropyl)amino]-1S-(phenylmethyl)propyl]pent-4-ynamide

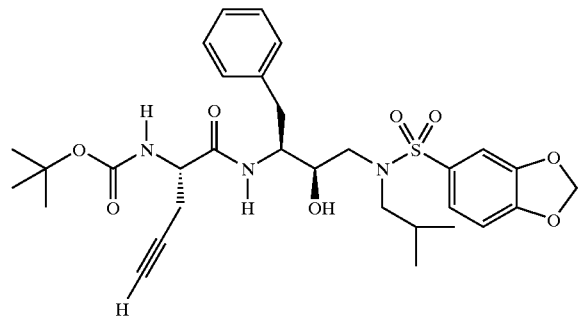

To a cooled solution of N-t-Boc-L-propargyl glycine (5.0 g, 23.4 mmol) and 4.7 g (1.5 equiv.) of N-hydroxybenzotriazole in 40 mL of N,N-dimethylformamide was added 4.6 g (23.4 mmol) of EDC and stirred at 0° C. for one hour. To this was added a solution of 12.10 g (23.4 mmol) of 2R-hydroxy-3-[[(1,3-benzodioxol-5-yl)sulfonyl](2-methylpropyl)amino]-1S-(phenylmethyl)propylamine in 6 mL of N,N-dimethylformamide and the solution stirred for 16 hours. The solvent was removed by rotory evaporation, replaced with ehtyl acetate, and washed with saturated sodium bicarbonate, 5% citric acid and brine. The organics were dried over magnesium sulfate, filtered and concentrated to yield 13.3 grams of crude product, which crystallized from diethyl ether: ethyl acetate to yield 6.9 g of 2S-[[(1,1-dimethylethoxy)carbonyl]amino]-N-[2R-hydroxy-3-[[(1,3-benzodioxol-5-yl)sulfonyl](2-methylpropyl)amino]-1S-(phenylmethyl)propyl]pent-4-ynamide.

Part B. Preparation of 2S-Amino-N-[2R-hydroxy-3-[[(1,3-benzodioxol-5-yl)sulfonyl](2-methylpropyl)amino]-1S-(phenylmethyl)propyl]pent-4-ynamide

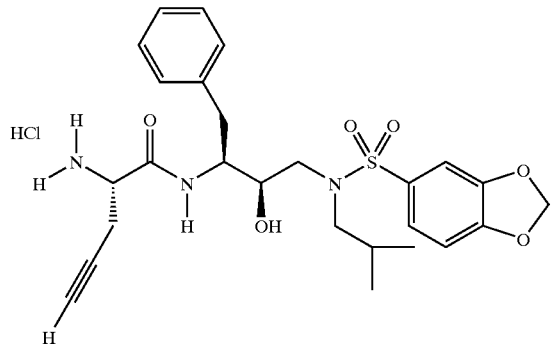

5.0 g (8.12 mmol) of the product from Part A. was dissolved in 20 mL of 4N HCl in dioxane and stirred for 30 minutes. The precipitated product was stripped two times from diethyl ether and this crude hydrochloride salt was used in Part C.

Part C. Preparation of 2S-[(Chloroacetyl)amino]-N-[2R-hydroxy-3-[[(1,3-benzodioxol-5-yl)sulfonyl](2-methylpropyl)amino]-1S-(phenylmethyl)propyl]pent-4-ynamide

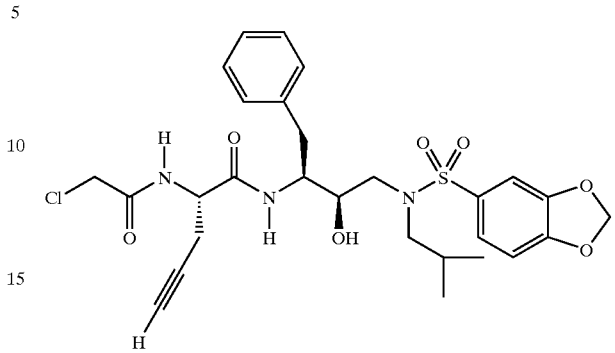

4.4 g (8.12 mmol) of amine hydrochloride from Part B was dissolved in 60 mL of methylene chloride and to this was added 3.0 g (24 mmol) of N,N-diisopropylethyl amine, followed by 1.38 g (8.1 mmol) of chloroacetic anhydride. The solution was stirred at room temperature overnight. The contents were concentrated on a rotory evaporator and the residue was partitioned between ethyl acetate and water. The organic layer was washed with 5% citric acid and then saturated sodium bicarbonate and brine. The organics were dried over magnesium sulfate filtered and concentrated to yield 4.3 g of crude product. Recrystallization from ethyl acetate hexane yielded 3.6 g (75% yield) of 2S-[(chloroacetyl)amino]-N-[2R-hydroxy-3-[[(1,3-benzodioxol-5-yl)sulfonyl](2-methylpropyl)amino]-1S-(phenylmethyl)propyl]pent-4-ynamide as a white solid.

EXAMPLE 41

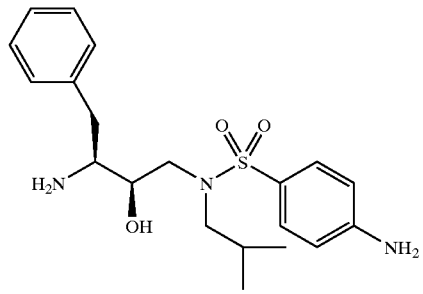

Preparation of 2R-Hydroxy-3-[[(4-aminophenyl)sulfonyl](2-methylpropyl)amino]-1S-(phenylmethyl)propylamine Part A: Preparation of 2R-Hydroxy-3-[[(4-nitrophenyl)sulfonyl](2-methylpropyl)amino]-1S-(phenylmethyl)propylcarbamic Acid Phenylmethyl Ester To a solution of 4.0 g (10.8 mmol) of N-[3S-benzyloxycarbonylamino-2R-hydroxy-4-phenyl]-N-isobutylamine in 50 mL of anhydrous methylene chloride, was added 4.5 mL (3.27 g, 32.4 mmol) of triethylamine. The solution was cooled to 0° C. and 2.63 g (11.9 mmol) of 4-nitrobenzene sulfonyl chloride was added, stirred for 30 minutes at 0° C., then for 1 hour at room temperature. Ethyl acetate was added, washed with 5% citric acid, saturated sodium bicarbonate, brine, dried and concentrated to yield 5.9 g of crude material. This was recrystallized from ethyl acetate/hexane to afford 4.7 g of pure [2R-hydroxy-3-[[(4- nitrophenyl)sulfonyl](2-methylpropyl)amino]-1S-(phenylmethyl)propylcarbamic acid phenylmethyl ester, m/e=556 (M+H).

Part B: Preparation of 2R-Hydroxy-3-[[(4-aminophenyl)sulfonyl](2-methylpropyl)amino]-1S-(phenylmethyl)propylamine A solution of 3.0 g (5.4 mmol) of 2R-hydroxy-3-[[(4-nitrophenyl)sulfonyl](2-methylpropyl)amino]-1S-(phenylmethyl)propylcarbamic acid phenylmethyl ester in 20 mL of ethyl acetate was hydrogenated over 1.5 g of 10% palladium-on-carbon catalyst under 35 psig of hydrogen for 3.5 hours. The catalyst was removed by filtration and the solution concentrated to afford 2.05 g of the desired 2R-hydroxy-3-[[(4-aminophenyl)sulfonyl](2-methylpropyl)amino]-1S-(phenylmethyl)propylamine, m/e=392 (M+H).

EXAMPLE 42

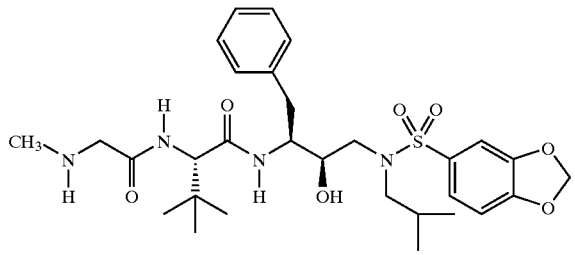

Preparation of 2S-[[(N-Methylamino)acetyl]amino]-N-[2R-hydroxy-3-[[(1,3-benzodioxol-5-yl)sulfonyl](2-methylpropyl)amino]-1S-(phenylmethyl)propyl]-3,3-dimethylbutanamide To 6.55 g (10.7 mmol) of N-[2R-hydroxy-3-[[(1,3-benzodioxol-5-yl)sulfonyl](2-methylpropyl)amino]-1S-(phenylmethyl)propyl]-2S-[(chloroacetyl)amino]-3,3-dimethylbutanamide was added 25 mL of tetrahydrofuran, the solvent removed under reduced pressure to remove any ethyl acetate, and then 25 mL of tetrahydrofuran was added. To this solution at 10° C. was added 19 mL (214 mmol) of 40% aqueous methylamine. After 2 hours, the solvents were removed under reduced pressure, added 1 L ethyl acetate, washed with saturated sodium bicarbonate, brine, dried over anhydrous magnesium sulfate, filtered and concentrated to afford 6.0 g of crude material, which was assayed by HPLC to be 98% purity.

EXAMPLE 43

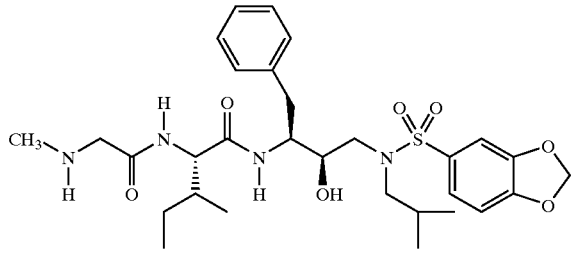

Preparation of N-[2R-Hydroxy-3-[[(1,3-benzodioxol-5-yl)sulfonyl](2-methylpropyl)amino]-1S-(phenylmethyl)propyl]-2S-[[(N-methylamino)acetyl]amino]-3S-methylpentanamide To 3.47 g (5.7 mmol) of N-[2R-hydroxy-3-[[(1,3-benzodioxol-5-yl)sulfonyl](2-methylpropyl)amino]-1S-(phenylmethyl)propyl]-2S-[(chloroacetyl)amino]-3S-methylpentanamide was added 50 mL of tetrahydrofuran. To this solution was added 12 mL (135 mmol) of 40% aqueous methylamine. After 6 hours, the solvents were removed under reduced pressure, added ethyl acetate, washed with saturated sodium bicarbonate, brine, dried over anhydrous magnesium sulfate, filtered and concentrated to afford 3.5 g of crude material, which was assayed by HPLC to be 96% purity. The product was chromatographically purified on basic alumina using methanol and ethyl acetate eluants to yield 2.88 g (85%) pure desired product (100% by HPLC); m/e $C_{30}H_{44}N_4O_7S$ calcd 604.77; found (M+Li) 611.

EXAMPLE 44

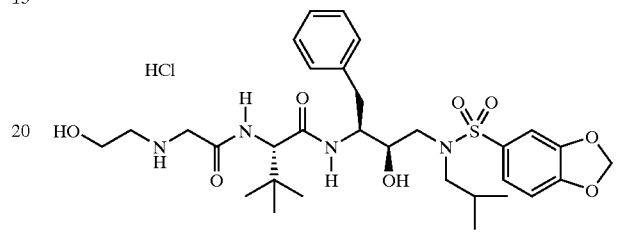

Preparation of 2S-[[N-(2-Hydroxyethyl)aminoacetyl]amino]-N-[2R-hydroxy-3-[[(1,3-benzodioxol-5-yl)sulfonyl](2-methylpropyl)amino]-1S-(phenylmethyl)propyl]-3,3-dimethylbutanamide.hydrochloride A solution of 2.0 g 2S-[(chloroacetyl)amino]-N-[2R-hydroxy-3-[[(1,3-benzodiox-5-yl)sulfonyl](2-methylpropyl)amino]-1S-(phenylmethyl)propyl]-3,3-dimethyl-butanamide and 4.0 g 2-hydroxyethyl amine (20 eq.) in 8 mL tetrahydrofuran was stirred 6 hours at room temperature. The reaction was concentrated in vacuo and partitioned between ethyl acetate and saturated aqueous sodium bicarbonate. The combined organics were washed with brine, dried, and concentrated in vacuo to the crude free base. The product was dissolved in 25 mL acetonitrile and 2.0 eq. aqueous HCl was added. After 10 minutes the reaction was concentrated in vacuo and chased with 30 ml water and vacumn dried over $P_2O_5$.

EXAMPLE 45

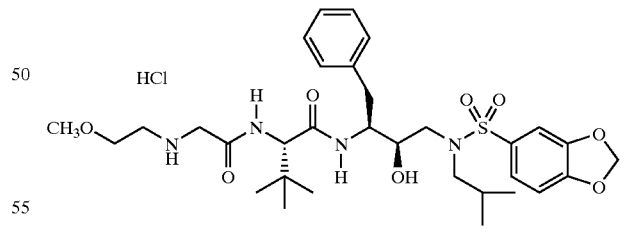

Preparation of 2S-[[N-(2-Methoxyethyl)aminoacetyl]amino]-N-[2R-hydroxy-3-[[(1,3-benzodioxol-5-yl)sulfonyl](2-methylpropyl)amino]-1S-(phenylmethyl)propyl]-3,3-dimethylbutanamide.hydrochloride A solution of 2.0 g of 2S-[(chloroacetyl)amino]-N-[2R-hydroxy-3-[[(1,3-benzodiox-5-yl)sulfonyl](2-methylpropyl)amino]-1S-(phenylmethyl)propyl]-3,3-dimethyl-butanamide and 4.8 mL 2-methoxyethyl amine (20 eq.) in 8 mL tetrahydrofuran was stirred 4 hours at room temperature. The reaction was concentrated in vacuo and partitioned between ethyl acetate and saturated aqueous sodium bicarbonate. The combined organics were washed with brine, dried, and concentrated in vacuo to the crude free base. The product was taken up in 25 mL acetonitrile and 2.0 eq. aqueous HCl was added. After 10 minutes the reaction was concentrated in vacuo and chased with 30 ml water and vacumn dried over $P_2O_5$.

EXAMPLE 46

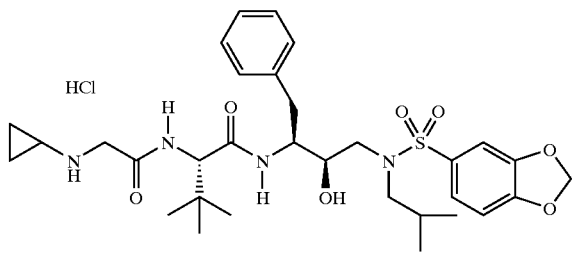

Preparation of 2S-[[(N-Cyclopropylamino)acetyl] amino]-N-[2R-hydroxy-3-[[(1,3-benzodioxol-5-yl) sulfonyl](2-methylpropyl)amino]-1S-(phenylmethyl) propyl]-3,3-dimethylbutanamide.hydrochloride A solution of 2.0 g of 2S-[(chloroacetyl)amino]-N-[2R-hydroxy-3-[[(1,3-benzodiox-5-yl)sulfonyl](2-methylpropyl)amino]-1S-(phenylmethyl)propyl]-3,3-dimethyl-butanamide and 4.5 mL cyclopropyl amine (20 eq.) in 8 mL tetrahydrofuran was stirred 24 hours at room temperature. The reaction was concentrated in vacuo and partitioned between ethyl acetate and saturated aqueous sodium bicarbonate. The combined organics were washed with brine, dried, and concentrated in vacuo to the crude free base. The product was taken up in 25 mL acetonitrile and 2.0 eq. aqueous HCl was added. After 10 minutes the reaction was concentrated in vacuo and chased with 30 ml water and vacumn dried over $P_2O_5$ to yield 1.5 g white solid.

EXAMPLE 47

Preparation of 5-Chlorosulfonyl-2-carbomethoxyamino-benzimidazole

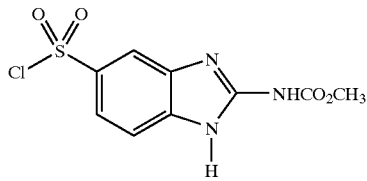

A solution of 2-carbomethoxyamino-benzimidazole (5.0 g, 0.026 mole) in chlorosulfonic acid (35.00 mL) was stirred at 0° C. for 30 minutes and at room temperature for 3 hours. The resulting dark colored reaction mixture was poured into an ice-water mixture (200 mL), and stirred at room temperature for 30 minutes. The resulting precipitate was filtered and washed with cold water (500 mL). The solid was dried overnight under high vacuum in a desiccator over NaOH pellets to give 5-chlorosulfonyl-2-carbomethoxyamino-benzimidazole (5.9 g, 78%) as a grey powder. $^1$H NMR (DMSO-$d_6$) d: 3.89 (s, 3H), 7.55 (d, J=8.4 Hz, 1H), 7.65 (d, J=8.4 Hz, 1H), 7.88 (s, 1H).

EXAMPLE 48

Preparation of N-[2R-Hydroxy-3-[N$^1$-[(2-carbomethoxyamino-benzimidazol-5-yl)sulfonyl]-N$^1$-(2-methylpropyl)amino]-1S-(phenylmethyl) propyl]carbamic Acid Phenylmethyl Ester

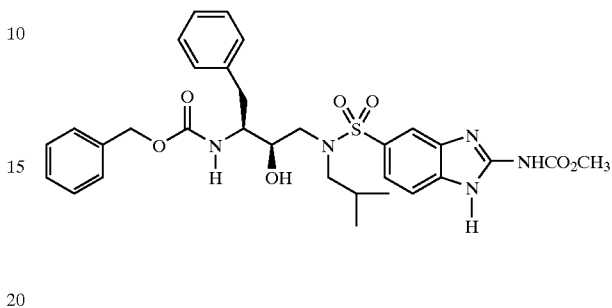

To a cold solution of N-[3S-[(phenylmethoxycarbonyl) amino]-2R-hydroxy-4-phenylbutyl]-N-(2-methylpropyl) amine (5.0 g, 13.5 mmol) in dichloromethane (70 mL) was added triethylamine (5.95 g, 54.0 mmol) followed by the addition of 5-chlorosulfonyl-2-carbomethoxyamino-benzimidazole (4.29 g, 14.85 mmol) in small portions as a solid. The reaction mixture was stirred at 0° C. for 30 minutes and at room temperature for 2.5 hours when reaction of the amino alcohol was complete. The mixture was cooled and filtered, and the filtrate was concentrated. The resulting residue was dissolved in EtOAc (200 mL), washed successively with cold 5% citric acid (3×50 mL), saturated aqueous sodium bicarbonate (3×50 mL) and water, (3×100 mL), then dried (Na$_2$SO$_4$), concentrated and dried under vacuum. The residue was triturated with methanol, cooled, filtered, washed with MeOH-EtOAc (1:1, v/v) and dried in a desiccator to give pure N-[2R-hydroxy-3-[[(2-carbomethoxyamino-benzimidazol-5-yl)sulfonyl](2-methylpropyl)-amino]-1S-(phenylmethyl)propyl]carbamic acid phenylmethyl ester (6.02 g, 72%) as a light brown powder: FABMS: m/z=630 (M+Li); HRMS: calcd. for $C_{32}H_{38}N_5O_7S$ (M+H) 624.2492, found 624.2488.

EXAMPLE 49

Preparation of 2R-Hydroxy-3-[[(2-amino-benzimidazol-5-yl)sulfonyl](2-methyl-propyl) amino]-1S-(phenylmethyl)propylamine

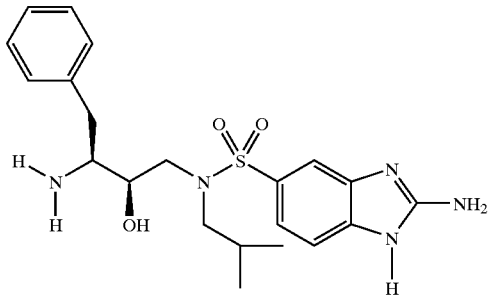

A solution of N-[2R-hydroxy-3-[[(2-carbomethoxyamino-benzimidazol-5-yl)sulfonyl](2-methylpropyl)amino]-1S-(phenylmethyl)propyl]carbamic acid phenylmethyl ester (0.36 g, 0.58 mmol) in 2.5 N methanolic KOH (2.00 mL) was heated at 70° C. under a nitrogen atmosphere for 3 hours. The reaction mixture was diluted with water (10 mL) and extracted with EtOAc (3×15 mL). The combined organic extracts were washed with brine, dried ($Na_2SO_4$) and concentrated. The resulting residue was purified by reverse-phase HPLC using a 10–90% $CH_3CN/H_2O$ gradient (30 min) at a flow rate of 70 mL/min. The appropriate fractions were combined and freeze dried to give pure 2R-hydroxy-3-[[(2-amino-benzimidazol-5-yl)sulfonyl](2-methylpropyl)amino]-1S-(phenyl-methyl)propylamine (0.22 g, 58%) as a white powder: FAB-MS m/z=432 (M+H); HRMS: calcd. for $C_{21}H_{30}N_5O_3S$ (M+H) 432.2069, found 432.2071.

EXAMPLE 50

Preparation of N-[2R-Hydroxy-3-[[(2-amino-benzimidazol-5-yl)sulfonyl](2-methylpropyl)-amino]-1S-(phenylmethyl)propyl]carbamic Acid Phenylmethyl Ester

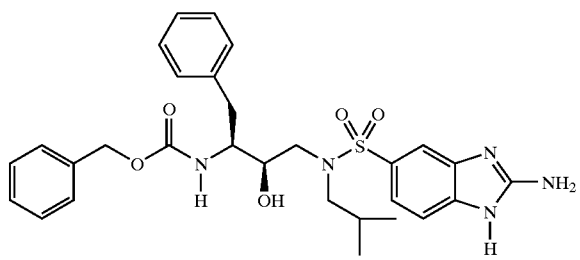

To a solution of 2R-hydroxy-3-[[(2-amino-benzimidazol-5-yl)sulfonyl](2-methyl-propyl)amino]-1S-(phenylmethyl)propylamine (0.22 g, 0.33 mmol) in THF (3.00 mL), triethylamine (0.11 g, 1.1 mmol) and benzyloxycarbonyl succinimide (0.09 g, 0.36 mmol) were added, and the reaction mixture was stirred at room temperature for 16 hours. The solution was concentrated, and the residue was partitioned between EtOAc (15 mL) and saturated aqueous sodium bicarbonate. The organic phase was washed with brine, dried ($Na_2SO_4$), and concentrated. The resulting residue was purified by reverse-phase HPLC using a 10–90% $CH_3CN/H_2O$ gradient (30 min) at a flow rate of 70 mL/min. The appropriate fractions were combined and freeze dried to give pure N-[2R-hydroxy-3-[[(2-amino-benzimidazol-5-yl)sulfonyl](2-methylpropyl)amino]-1S-(phenylmethyl)propyl]carbamic acid phenylmethyl ester (0.12 g, 61%) as a white powder: FAB-MS m/z=566 (M+H); HRMS: calcd. for $C_{29}H_{36}N_5O_5S$ 566.2437 (M+H), found 566.2434.

EXAMPLE 51

Preparation of 2R-Hydroxy-3-[[(2-carbomethoxyamino-benzimidazol-5-yl)sulfonyl](2-methylpropyl)amino]-1S-(phenylmethyl) propylamine

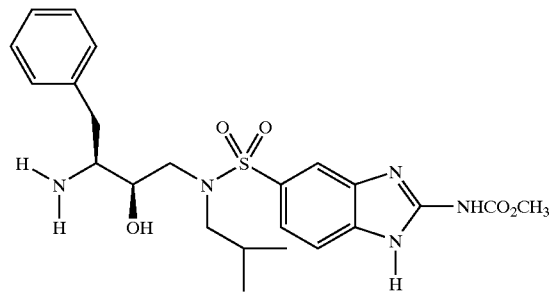

A solution of N-[2R-hydroxy-3-[[(2-carbomethoxyamino-benzimidazole-5-yl)sulfonyl](2-methylpropyl)-amino]-1S-(phenylmethyl)propyl]carbamic acid phenylmethyl ester (2.5 g, 0.4 mmol) in MeOH (10 mL) and THF (50 mL) was hydrogenated in the presence of 10% Pd/C (1.2 g) at room temperature at 60 psi for 16 hours. The catalyst was removed by filtration, and the filtrate was concentrated under reduced pressure. The resulting residue was triturated with ether and filtered. The solid substance thus obtained was washed with ether and dried in vacuo to afford pure 2R-hydroxy-3-[[(2-carbomethoxyamino-benzimidazol-5-yl)sulfonyl](2-methylpropyl)amino]-1S-(phenylmethyl)propylamine (1.5 g, 77%) as an off white powder: $R_t$=12.8 min; FAB-MS m/z=490 (M+H); HRMS: calcd. for $C_{23}H_{32}N_5O_5S$ 490.2124 (M+H), found 490.2142.

EXAMPLE 52

Preparation of N-[2R-Hydroxy-3-[[(2-carbomethoxyamino-benzimidazol-5-yl)sulfonyl](2-methylpropyl)amino]-1S-(phenylmethyl)propyl]-2S-amino-3,3-dimethylbutanamide

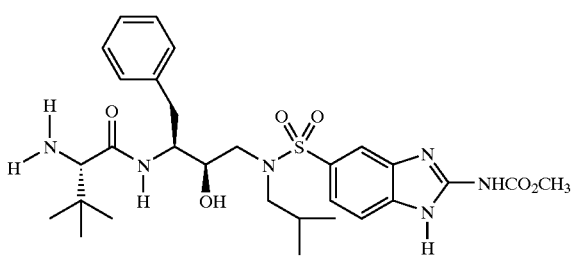

Part A: Preparation of N-[2R-Hydroxy-3-[N¹-[(2-carbomethoxyamino-benzimidazol-5-yl)sulfonyl]-N¹-(2-methylpropyl)amino]-1S-(phenylmethyl)propyl-2S-[(phenylmethoxy-carbonyl)amino]-3,3-dimethylbutanamide methylpropyl)amino]-1S-(phenylmethyl)propyl]-2S-amino-3,3-dimethylbutanamide (2.9 g, 88%) as a pale yellow powder. A portion of the material was purified by reverse-phase HPLC using a 10–90% $CH_3CN/H_2O$ gradient (30 min) at a flow rate of 70 mL/min. The appropriate fractions pressure. The resulting residue was triturated with ether and filtered. The solid residue was washed with ether and dried in vacuo to afford N-[2R-hydroxy-3-[[(2-carbomethoxyamino-benzimidazol-5-yl)sulfonyl](2-were combined and freeze dried to give pure N-[2R-hydroxy-3-[[(2-carbomethoxyamino-benzimidazol-5-yl)sulfonyl](2-methylpropyl)amino]-1S-(phenylmethyl)propyl-2S-amino-3,3-dimethylbutanamide as a white powder: $R_t$=13.9 min; FAB-MS m/z=609 (M+Li), 603 (M+H); HRMS: calcd. for $C_{29}H_{43}N_6O_6S$ 603.2965 (M+H), found 603.2972.

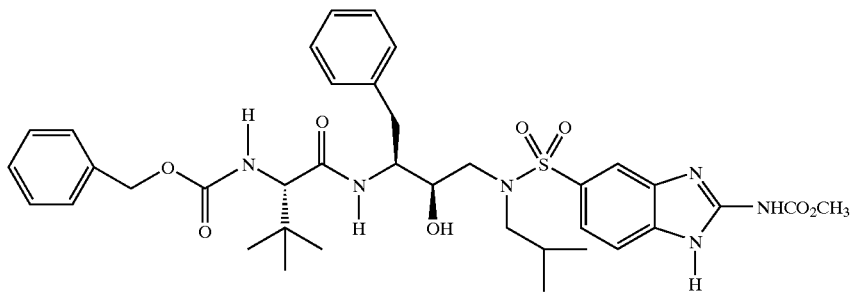

To a solution of N-carbobenzyloxycarbonyl-L-tert-leucine (0.65 g, 2.45 mmol) in DMF (10 mL) was added HOBt (0.5 g, 3.22 mmol) and EDC (0.49 g, 2.55 mmol), and the resulting mixture was stirred at 0° C. for 2 hours. Then a solution of 2R-hydroxy-3-[[(2-carbomethoxyamino-benzimidazol-5-yl)sulfonyl](2-methylpropyl)amino]-1S-(phenylmethyl)propylamine (1.2 g, 2.45 mmol) in DMF (4 mL) and N-methyl morpholine (0.74 g, 7.3 mmol) was added, and the mixture was stirred at room temperature for 16 hours. The DMF was then distilled away in vacuo, and the remaining residue was partitioned between cold 1N aqueous HCl (100 mL) and EtOAc (200 mL). The organic phase was washed successively with cold 1N HCl (2×50 mL), brine (2×50 mL), 0.25 N NaOH (3×50 mL), brine, dried ($Na_2SO_4$) and concentrated in vacuo. The resulting residue was purified by silica gel flash column chromatography using EtOAc as the eluent to afford 1.5 g (83%) of pure N-[2R-hydroxy-3-[[(2-carbomethoxyamino-benzimidazol-5-yl)sulfonyl](2-methylpropyl)amino]-1S-(phenylmethyl)propyl-2S-[(phenylmethoxy-carbonyl)amino]-3,3-dimethylbutanamide: $R_t$=21.2 min; FAB-MS m/z=737 (M+H), HRMS: calcd. for $C_{37}H_{49}N_6O_8S$ 737.3333 (M+H), found 737.3334.

Part B: Preparation of N-[2R-Hydroxy-3-[[(2-carbomethoxyamino-benzimidazol-5-yl)sulfonyl](2-methylpropyl)amino]-1S-(phenylmethyl)propyl]-2S-amino-3,3-dimethylbutanamide A solution of N-[2R-hydroxy-3-[[(2-carbomethoxyamino-benzimidazol-5-yl)sulfonyl](2-methylpropyl)amino]-1S-(phenylmethyl)propyl-2S-[(phenylmethoxycarbonyl)amino]-3,3-dimethylbutanamide (4.0 g, 5.4 mmol) in MeOH (15 mL) and THF (65 mL) was hydrogenated in the presence of 10% Pd/C (2.0 g) at room temperature at 50 psi for 16 hours. The catalyst was removed by filtration, and the filtrate was concentrated under reduced

EXAMPLE 53

Preparation of N-[2R-Hydroxy-3-[[(2-carbomethoxyamino-benzimidazol-5-yl)sulfonyl](2-methylpropyl)amino]-1S-(phenylmethyl)propyl-2S-[(chloroacetyl)amino]-3,3-dimethylbutanamide

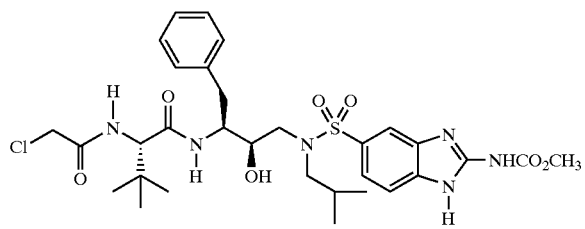

A mixture of chloroacetic acid (0.32 g, 3.39 mmol), HOBt (0.78 g, 5.0 mmol), and EDC (0.65 g, 3.39 mmol) in DMF (5 mL) was stirred at 0° C. for 1 hour, and was then added to a solution of N-[2R-hydroxy-3-[[(2-carbomethoxyamino-benzimidazol-5-yl)sulfonyl](2-methylpropyl)amino]-1S-(phenylmethyl)propyl]-2S-amino-3,3-dimethylbutanamide (2.0 g, 3.3 mmol) in DMF (5 mL). The resulting mixture was stirred at 0° C. for 2 hours, and at room temperature for 1 hour when the reaction was complete. The DMF was removed in vacuo. The resulting residue was dissolved in EtOAc (50 mL) and washed successively with saturated aqueous sodium bicarbonate (3×25 mL), brine, dried ($Na_2SO_4$), and concentrated under reduced pressure. The resulting material was crystallized from EtOAc to give 1.2 g (53%) of pure N-[2R-hydroxy-3-[[(2-carbomethoxyamino-benzimidazol-5-yl)sulfonyl](2-methylpropyl)amino]-1S-(phenylmethyl)propyl]-2S-[(chloroacetyl)amino]-3,3-dimethylbutanamide as a white powder: m.p. 253° C. (decomp); $R_t$=18.1 min; FAB-MS m/z=679 (M+H), HRMS: calcd. for $C_{31}H_{44}N_6O_7SCl$ 679.2681 (M+H), found 679.2690.

EXAMPLE 54

Preparation of N-[2R-Hydroxy-3-[[(2-carbomethoxyamino-benzimidazol-5-yl)sulfonyl](2-methylpropyl)amino]-1S-(phenylmethyl)propyl-2S-[(N-methylaminoacetyl)amino]-3,3-dimethylbutanamide

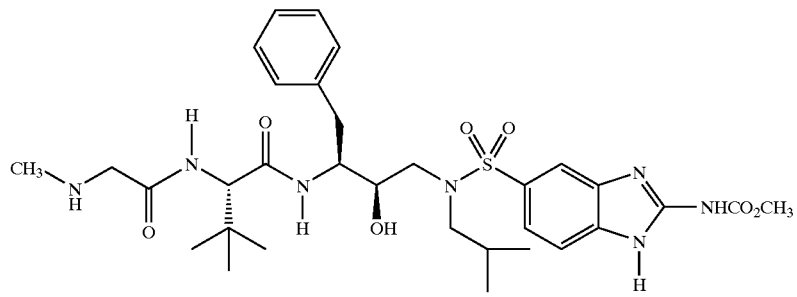

N-[2R-hydroxy-3-[[(2-carbomethoxyamino-benzimidazol-5-yl)sulfonyl](2-methylpropyl)amino]-1S-(phenylmethyl)propyl]-2S-[(chloroacetyl)amino]-3,3-dimethylbutanamide (0.7 g, 1.03 mmol) was dissoved in THF (3.00 mL). Methylamine (0.8 mL, 40% solution in water) was added and the reaction was stirred at room temperature for 2 hours. The mixture was diluted with water (10 mL), and extracted with ethyl acetate (2×20 mL). The combined organic extracts were washed with brine, dried ($Na_2SO_4$), and concentrated in vacuo. The resulting residue was purified by reverse-phase HPLC using a 5–70% $CH_3CN/H_2O$ gradient (30 min) at a flow rate of 70 mL/min. The appropriate fractions were combined and freeze dried to give pure N-[2R-hydroxy-3-[[(2-carbomethoxyamino-benzimidazol-5-yl)sulfonyl](2-methylpropyl)amino]-1S-(phenylmethyl)propyl-2S-[(N-methylaminoacetyl)amino]-3,3-dimethylbutanamide as a white powder: $R_t$=14.1 min; FAB-MS m/z=674 (M+H); HRMS: $C_{32}H_{48}N_7O_7S$ calcd. 674.3336 (M+H), found 674.3361.

EXAMPLE 55

Preparation of N-[2R-Hydroxy-3-[[(benzothiazol-6-yl)sulfonyl](2-methylpropyl)amino]-1S-(phenylmethyl)propyl]-2S-[(chloroacetyl)amino]-3,3-dimethylbutanamide

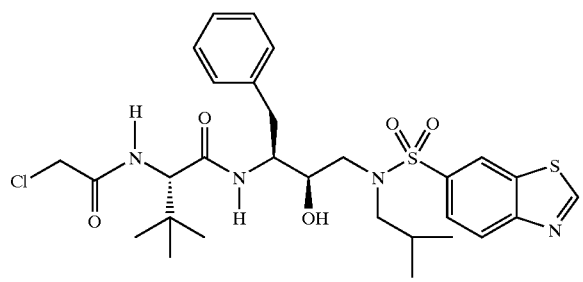

Part A: Preparation of [2R-Hydroxy-3-[(4-aminophenylsulfonyl)(2-methylpropyl)amino]-1S-(phenylmethyl)propylcarbamic Acid t-Butyl Ester

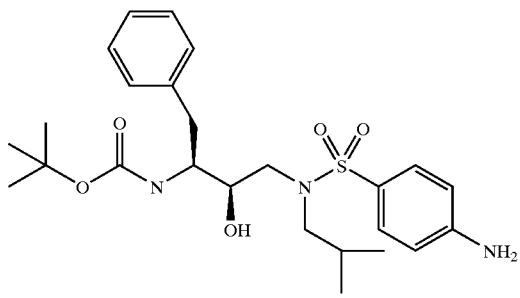

A mixture of [2R-hydroxy-3-[(4-aminophenylsulfonyl)(2-methylpropyl)-amino]-1S-(phenylmethyl)propylamine 3.7 g (9.45 mmol) and BOC-ON (2.33 g, 9.45 mmol) and triethylamine (0.954 g, 9.45 mmol) in tetrahydrofuran (60 mL) was stirred for 16 h and concentrated in vacuo. The residue was dissolved in dichloromethane (200 mL), washed with sodium hydroxide (1N, 100 mL), citric acid (5%, 100 mL), dried (MgSO4), and concentrated to afford 1.18 g (94%) of the desired product as a white solid.

Part B: Preparation of [2R-Hydroxy-3-[(2-aminobenzothiazole-6-sulfonyl)-(2-methylpropyl)amino]-1S-(phenylmethyl)propylcarbamic Acid t-Butyl Ester

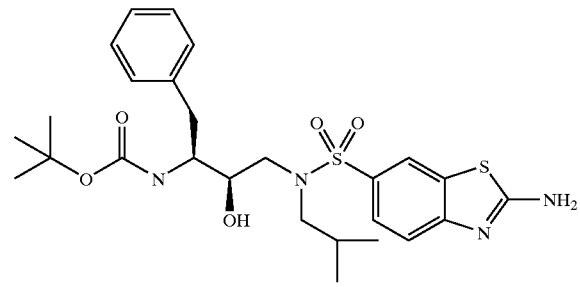

The [2R-hydroxy-3-[(4-aminophenylsulfonyl)(2-methylpropyl)]amino]-1S-(phenylmethyl)propylcarbamic acid t-butyl ester 1.12 g (2.279 mmol) was added to a well mixed powder of anhydrous copper sulfate (4.48 g) and potassium thiocyanate (5.60 g) followed by dry methanol (35 mL) and the rsulting black-brown suspension was heated at reflux for 2 h. The reaction mixture turned grey. The reaction mixture was filtered and the filtrate was diluted with water (50 mL) and heated at reflux. Ethanol was added to the reaction mixture, cooled and filtered. The filtrate upon concentration afforded a rseidue which was chromatographed (ethyl acetate:methanol 90:10) to afford 0.80 g (78%) of the deprotected compound as a solid. This was directly reprotected via the following procedure; (2.25 g, 5.005 mmol) BOC-ON (1.24 g), and triethylamine (0.505 g, 5.005 mmol) in tetrahydrofuran (20 mL) was stirred at room temperature for 18 h. The reaction mixture was concentrated and the residue was dissolved in dichloromethane (200 mL) and was washed with sodium hydroxide (1N, 100 mL), citric acid (5%, 100 mL) dried (MgSO4) and concentrated to afford a residue which was chromatographed (ethyl acetate:hexane 3:1) to afford 1.8 g (65%) of the desired product as a solid.

Part C: Preparation of [2R-Hydroxy-3-[(benzothiazole-6-sulfonyl)(2-methylpropyl)amino]-1S-(phenylmethyl) propylcarbamic Acid t-Butyl Ester

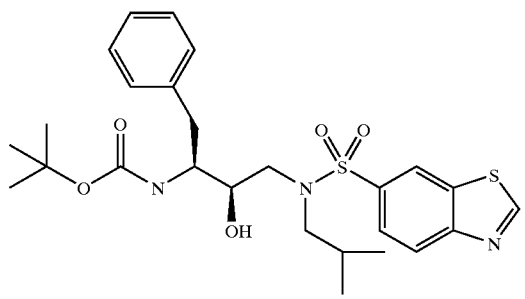

The product of part B above (1.80 g, 3.2755 mmol) was added to a solution of isoamylnitrite (0.88 mL) in dioxane (20 mL) and the mixture was heated at 85° C. After the cessation of evolution of nitrogen, the reaction mixture was concentrated and the residue was purified by chromatography (hexane:ethyl acetate 1:1) to afford 1.25 g (78%) of the desired product as a solid.

Part D: Preparation of [(2R-Hydroxy-3-[(benzothiazole-6-sulfonyl)(2-methylpropyl)amino]-1S-(phenylmethyl) propylamine.hydrochloride

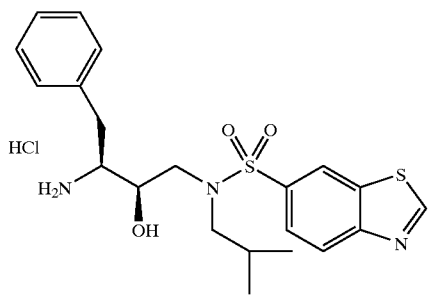

The product of part C above was deprotected via the following procedure; (1.25 g, 2.3385 mmol) was added dioxane/HCl (4N, 10 mL) and was stirred at room temperature for 2 h and concentrated. Excess HCl was chased with toluene to afford 1.0 g (quantitative yield) of the desired product as its HCl salt.

Part E: Preparation of N-[2R-Hydroxy-3-[[(benzothiazol-6-yl)sulfonyl](2-methylpropyl)-amino]-1S-(phenylmethyl) propyl]-2S-[[(N-benzyloxy)carbonyl]amino]-3,3-dimethylbutanamide

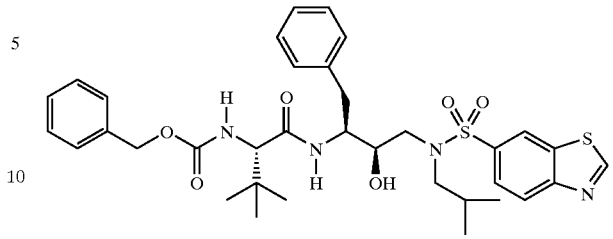

A mixture of N-benzyloxycarbonyl-t-butylglycine (2.0 g, 7.538 mmol), HOBT (1.02 g, 7.55 mmol), and EDC (1.45 g, 7.55 mmol) in DMF (20 mL) was stirred at room temperature for 1 hour. Then [2R-hydroxy-3-[[(benzothiazol-6-yl) sulfonyl](2-methylpropyl)amino]-1S-(phenylmethyl) propylamine hydrochloride (3.825 g, 7.54 mmol) and N-methylmorpholine (3.80 g) were added and the stirring continued for 18 hours. The DMF was removed in vacuo, the residue was dissolved in dichloromethane (500 mL), and washed with citric acid (1N, 100 mL), sodium bicarbonate (100 mL), brine (200 mL), dried, filtered, End concentrated to afford 4.69 g (91%) of pure N-[2R-hydroxy-3-[[(benzothiazol-6-yl)sulfonyl](2-methylpropyl)amino]-1S-(phenylmethyl)propyl]-2S-[N-(phenylmethoxycarbonyl) amino]-3,3-dimethylbutanamide.

Part F: Preparation of N-[2R-Hydroxy-3-[[(benzothiazol-6-yl)sulfonyl](2-methylpropyl)amino]-1S-(phenylmethyl) propyl]-2S-(amino)-3,3-dimethylbutanamide.dihydrobromide

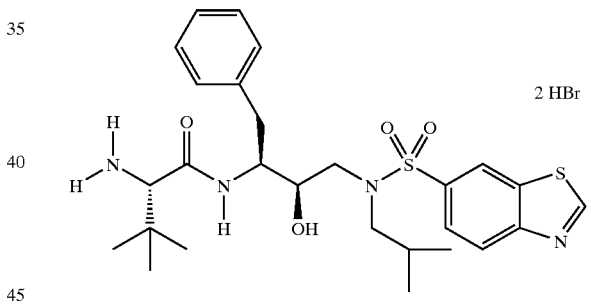

A solution of N-[2R-hydroxy-3-[[(benzothiazol-6-yl) sulfonyl](2-methylpropyl)amino]-1S-(phenylmethyl) propyl]-2S-[N-(phenylmethoxycarbonyl)amino]-3,3-dimethylbutanamide (4.69 g, 6.89 mmol) in dichloroethane (200 mL) was treated with HBr (48% in acetic acid, 7.1 mL), and the reaction mixture was stirred for 2 hours at room temperature. The reaction mixture was concentrated and the residue was washed with diethyl ether several times to afford 4.88 g of the desired dihydrobromide product as a powder: high resolution FAB-MS Calcd for $C_{27}H_{38}N_4O_4S_2$: 547.2413, found: 547.2429 (M+H).

Part G: Preparation of N-[2R-Hydroxy-3-[[(benzothiazol-6-yl)sulfonyl](2-methylpropyl)amino]-1S-(phenylmethyl) propyl]-2S-[(chloroacetyl)amino]-3,3-dimethylbutanamide A mixture of N-[2R-hydroxy-3-[[(benzothiazol-6-yl) sulfonyl](2-methylpropyl)amino]-1S-(phenylmethyl) propyl]-2S-(amino)-3,3-dimethylbutanamide dihydrobromide (3.5 g, 4.9388 mmol), chloroacetic anhydride (0.929 g, 5.44 mmol) and triethylamine (1.097 g, 10.86 mmol) in dichloromethane (35 mL) was stirred at room temperature for 16 hours. The reaction mixture was washed with citric acid (1N, 30 mL), sodium bicarbonate (30 mL), brine (30 mL), dried, filtered and concentrated to afford 3.0 g of the desired product.

EXAMPLE 56

Preparation of 2S-[[N-(Phenylmethyl)aminoacetyl]amino]-N-[2R-hydroxy-3-[[(1,3-benzodioxol-5-yl)sulfonyl](2-methylpropyl)amino]-1S-(phenylmethyl)propyl]-3,3-dimethylbutanamide.hydrochloride

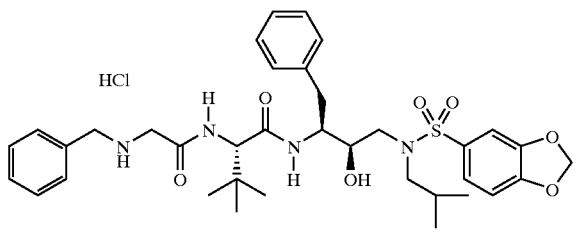

To a solution of 2.0 g (3.3 mmol) 2S-[[chloroacetyl]amino]-N-[2R-hydroxy-3-[[(1,3-benzodiox-5-yl)sulfonyl](2-methylpropyl)amino]-1S-(phenylmethyl)propyl]-3,3-dimethylbutanamide in 10 mL of tetrahydrofuran was added 2.2 mL of benzylamine. After 1 hour, an additional 2.0 mL of benzylamine was added. After 30 min, the reaction mixture was concentrated in vacuo, hexane was added and the heaxne decanted away from the oil. The oil was dissolved in ethyl acetate, washed with saturated sodium bicarbonate, brine, dried with magnesium sulfate, filtered and concentrated the crude product. This was dissolved in diethyl ether and hexane added, which resulted in an insoluble oil. The solvents were decanted from the oil and the oily residue concentrated under reduced pressure to afford 1.85 g. This was dissolved in ethyl acetate and poured into hexane which resulted in an insoluble oil. The solvents were decanted and the residue concentrated to afford 1.56 g of the desired product, m/e=687 (M+Li).

EXAMPLE 57

Preparation of 2S-[[N,N-(Dimethyl)aminoacetyl]amino]-N-[2R-hydroxy-3-[[(1,3-benzodioxol-5-yl)sulfonyl](2-methylpropyl)amino]-1S-(phenylmethyl)propyl]-3,3-dimethylbutanamide.hydrochloride

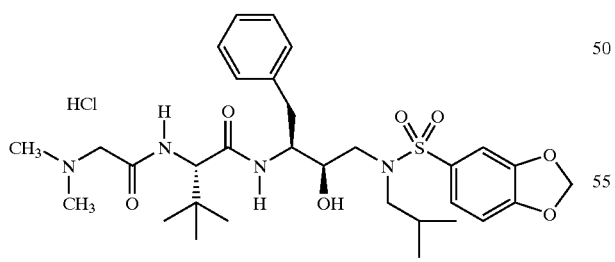

To a solution of 2.0 g (3.3 mmol) 2S-[[chloroacetyl]amino]-N-[2R-hydroxy-3-[[(1,3-benzodiox-5-yl)sulfonyl](2-methylpropyl)amino]-1S-(phenylmethyl)propyl]-3,3-dimethylbutanamide in 8 mL of tetrahydrofuran was added 8.2 mL of 40% aqueous dimethylamine. After 2 hours, the solvents were removed in vacuo. The residue was dissolved in ethyl acetate, washed with brine, dried with magnesium sulfate, filtered and concentrated in vacuo to afford 1.97 g of the desired product, m/e=619 (M+H).

EXAMPLE 58

Preparation of 2S-[[2R-(N-Methylamino)propionyl]amino]-N-[2R-hydroxy-3-[[(1,3-benzodioxol-5-yl)sulfonyl](2-methylpropyl)amino]-1S-(phenylmethyl)propyl]-3,3-dimethylbutanamide.hydrochloride

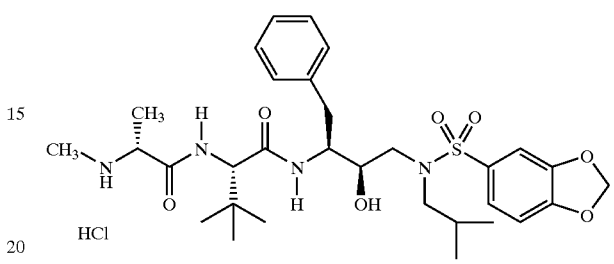

Part A: A solution of 1.0 grams (4.9 mmol) of N-t-BOC-N-methyl-D-alanine in 5 mL of anhydrous DMF was cooled to 0° C., charged with 0.9 grams (6.4 mmol) of HOBT and 0.9 grams (4.9 mmol) of EDC and stirred for four hours. The reaction solution was then charged with a solution of 2.3 grams (4.3 mmol) of 2S-amino-N-[2R-hydroxy-3-[[(1,3-benzodiox-5-yl)sulfonyl](2-methylpropyl)amino]-1S-(phenylmethyl)propyl]-3,3-dimethylbutaneamide and 1.3 grams (12.8 mmol) of 4-methylmorpholine in 5 mL of anhydrous DMF and stirred for 15 hours. The solvents were removed in vacuo and the residue was partitioned between 150 mL of ethyl acetate and 50 mL of 5% potassium hydrogen sulfate solution. The layers were separated, and the organic layer was washed with 50 mL each of saturated sodium bicarbonate solution, water and brine, then dried over anhydrous magnesium sulfate, filtered and concentrated to afford 2.9 grams of the desired product as a white solid, m/e=725 (M+Li).

Part B: A solution of 2.5 g of the compound from part A in 20 mL 4N HCl-dioxane and stirred for 1 hour at room temperature. Concentration in vacuo followed by trituration with Et₂O yielded 2.2 g white solid. The product was vacumn dried over P₂O₅ to yield 2.1 g final product.

EXAMPLE 59

Preparation of 2S-[[2R-Aminopropionyl]amino]-N-[2R-hydroxy-3-[[(1,3-benzodioxol-5-yl)sulfonyl](2-methylpropyl)amino]-1S-(phenylmethyl)propyl]-3,3-dimethylbutanamide

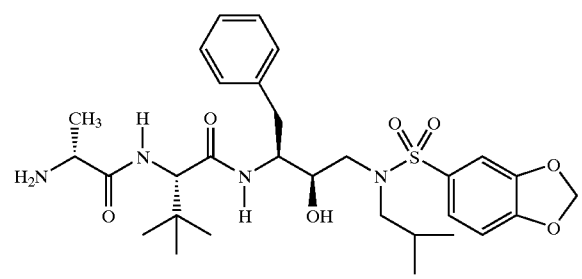

Part A: Preparation of 2S-[[2R-[(Phenylmethoxycarbonyl)amino]propionyl]amino]-N-[2R-hydroxy-3-[[(1,3-benzodioxol-5-yl)sulfonyl](2-methylpropyl)amino]-1S-(phenylmethyl)propyl]-3,3-dimethylbutanamide To a solution of 1.0 g (4.5 mmol) of N-carbobenzyloxycarbonyl-D-alanine and 1.03 g of HOBt in 9 mL of anhydrous N,N-dimtheylformamide at 0° C., was added 0.95 g of EDC coupling agent. After 2 hours at 0° C., 2.39 g (4.5 mmol) of 2S-amino-N-[2R-hydroxy-3-[[(1,3-benzodiox-5-yl)sulfonyl](2-methylpropyl)amino]-1S-(phenylmethyl)propyl]-3,3-dimethylbutanamide was added. After stirring overnite, the solvents were removed in vacuo. The residue was dissolved in ethyl acetate, washed with 5% potassium hydrogen sulfate, saturated sodium bicarbonate, brine, dried with magnesium sulfate, filtered and concentrated in vacuo to afford 3.2 g of crude material. This was chromatographed on 150 g of silica gel using 50–80% ethyl acetate/hexane as eluent to afford 2.3 g of the desired product, which was used directly in the next step.

Part B: Preparation of 2S-[[2R-Aminopropionyl]amino]-N-[2R-hydroxy-3-[[(1,3-benzodioxol-5-yl)sulfonyl](2-methylpropyl)amino]-1S-(phenylmethyl)propyl]-3,3-dimethylbutanamide A solution of 2.3 g of the product of Part A in 20 mL of methanol was hydrogenated over 1.0 g of 4% Palldium-on-carbon under 50 psig of hydrogen for 1 hour. The catalyst was removed by filtration. The solvents were removed in vacuo to afford 1.5 g of the desired product, m/e=611 (M+Li).

EXAMPLE 60

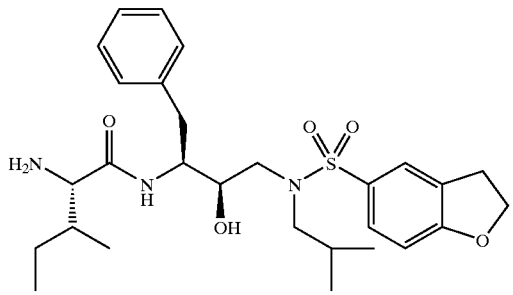

Preparation of N-[2R-Hydroxy-3-[[(2,3-dihydrobenzofuran-5-yl)sulfonyl](2-methylpropyl)amino]-1S-(phenylmethyl)propyl]-2S-amino-3S-methylpentanamide Part A: Preparation of N-[2R-Hydroxy-3-[[(2,3-dihydrobenzofuran-5-yl)sulfonyl](2-methylpropyl)amino]-1S-(phenylmethyl)propyl]-2S-[(phenylmethoxycarbonyl)amino]-3S-methylpentanamide A solution of 5.8 grams (22.0 mmol) of N-CBZ-L-isoleucine in 45 mL of anhydrous N,N-dimethylformamide (DMF) was cooled to 0° C. and charged with 3.9 grams (28.7 mmol) of N-hydroxybenzotriazole (HOBT) and 4.2 grams (22.0 mmol) of 1-(3-Dimethylaminopropyl)-3-ethylcarbodiimide hydrochloride (EDC). The ice bath was removed after 20 minutes and stirring was continued for an additional 40 minutes. The reaction solution was then charged with a solution of 8.0 grams (19.1 mmol) of 2R-hydroxy-3-[[(2,3-dihydrobenzofuran-5-yl)sulfonyl](2-methylpropyl)amino]-1S-(phenylmethyl)propylamine and 2.2 grams (22.0 mmol) of 4-methylmorpholine in 25 mL of anhydrous DMF and stirred for 15 hours. The solvents were removed in vacuo and the residue was partitioned between 300 mL of ethyl acetate and 120 mL of 5% potassium hydrogen sulfate solution. The layers were separated, and the organic layer was washed with 120 mL each of saturated sodium bicarbonate solution, water, and brine, then dried over anhydrous magnesium sulfate, filtered and concentrated to afford 16.7 grams of crude material. The crude material was crystallized from ethanol, the solid was isolated by filtration, rinsed with one 50 mL portion of hexane, and air-dried to yield 12.0 grams (94%) of the desired product, m/e=672 (M+Li).

Part B: Preparation of N-[2R-Hydroxy-3-[[(2,3-dihydrobenzofuran-5-yl)sulfonyl](2-methylpropyl)amino]-1S-(phenylmethyl)propyl]-2S-amino-3S-methylpentanamide A Fischer-Porter bottle equipped with a magnetic stir bar was charged with 11.9 grams (17.9 mmol) of the product from Part A and 75 mL of tetrahydrofuran (THF). The solution was hydrogenated in the presence of 5 grams of 10% palladium-on-carbon catalyst (50% water by weight) under 50 psig of hydrogen for 4 hours at room temperature. The catalyst was removed by filtration, and the solvents removed in vacuo. The residue was dissolved in 300 mL of ethyl acetate, washed with 120 mL each of saturated sodium bicarbonate solution and of brine, then dried over anhydrous magnesium sulfate, filtered and concentrated under reduced pressure to afford 8.8 grams of the desired product, m/e=532 (M+H).

EXAMPLE 61

Preparation of N-[2R-Hydroxy-3-[(phenylsulfonyl)(2-methylpropyl)amino]-1S-(phenylmethyl)propyl]-2S-amino-3S-methylpentanamide

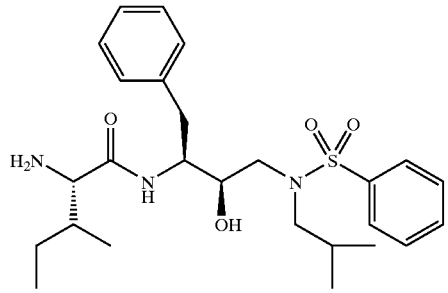

Part A: Preparation of N-[2R-Hydroxy-3-[(phenylsulfonyl)(2-methylpropyl)amino]-1S-(phenylmethyl)propyl]-2S-[(phenylmethoxycarbonyl)amino]-3S-methylpentanamide A solution of 6.0 grams (22.6 mmol) of N-CBZ-L-isoleucine in 45 mL of anhydrous DMF was cooled to 0° C. and charged with 4.0 grams (29.5 mmol) of HOBT and 4.3 grams (22.6 mmol) of EDC. The ice bath was removed after 20 minutes and stirring was continued for an additional 40 minutes. The reaction solution was then charged with a solution of 7.4 grams (19.7 mmol) of 2R-hydroxy-3-[(phenylsulfonyl)(2-methylpropyl)amino]-1S-(phenylmethyl)propylamine and 2.3 grams (22.6 mmol) of 4-methylmorpholine in 25 mL of anhydrous DMF and stirred for 18 hours. The solvents were removed in vacuo and the residue was partitioned between 300 mL of ethyl acetate and 120 mL of 5% potassium hydrogen sulfate solution. The layers were separated, and the organic layer was washed with 120 mL each of saturated sodium bicarbonate solution, water and brine, then dried over anhydrous magnesium sulfate, filtered and concentrated to afford 13 grams of crude material. The crude material crystallized from ethanol, the solid was isolated by filtration, rinsed with one 50 mL portion of hexane, and air-dried to yield 10.3 grams (84%) of the desired product, m/e=630 (M+Li).

Part B: Preparation of N-[2R-Hydroxy-3-[(phenylsulfonyl) (2-methylpropyl)amino]-1S-(phenylmethyl)propyl]-2S-amino-3S-methylpentanamide A Fischer-Porter bottle equipped with a magnetic stir bar was charged with 10.2 grams (16.4 mmol) of the product from Part A and 75 mL of tetrahydrofuran (THF). The solution was hydrogenated in the presence of 4 grams of 10% palladium-on-carbon catalyst (50% water by weight) under 50 psig of hydrogen for 3 hours at room temperature. The catalyst was removed by filtration, and the solvents removed in vacuo. The residue was dissolved in 300 mL of ethyl acetate and washed with 120 mL each of saturated sodium bicarbonate solution and brine, then dried over anhydrous magnesium sulfate, filtered and concentrated in vacuo to afford 7.4 grams of the desired product, m/e=490 (M+H).

EXAMPLE 62

Preparation of 2S-[[2S-(N-Methylamino)propionyl] amino]-N-[2R-hydroxy-3-[[(1,3-benzodioxol-5-yl) sulfonyl](2-methylpropyl)amino]-1S-(phenylmethyl) propyl]-3,3-dimethylbutanamide.hydrochloride

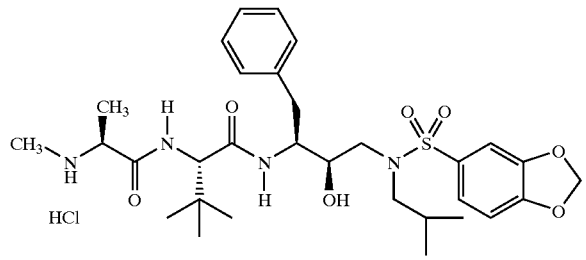

Part A: Preparation of 2S-[[2S-[N-(tert-Butoxycarbonyl)-N-(methyl)amino]propionyl]amino]-N-[(2R-hydroxy-3-[[(1,3-benzodioxol-5-yl)sulfonyl](2-methylpropyl)amino]-1S-(phenylmethyl)propyl]-3,3-dimethylbutanamide.hydrochloride A solution of 1.0 grams (4.9 mmol) of N-t-BOC-N-methyl-L-alanine in 5 mL of anhydrous DMF was cooled to 0° C., charged with 0.9 grams (6.4 mmol) of HOBT and 0.9 grams (4.9 mmol) of EDC and stirred for four hours. The reaction solution was then charged with a solution of 2.3 grams (4.3 mmol) of 2S-amino-N-[2R-hydroxy-3-[[(1,3-benzodiox-5-yl)sulfonyl](2-methylpropyl)amino]-1S-(phenylmethyl)propyl]-3,3-dimethylbutaneamide and 1.3 grams (12.8 mmol) of 4-methylmorpholine in 5 mL of anhydrous DMF and stirred for 15 hours. The solvents were removed in vacuo and the residue was partitioned between 150 mL of ethyl acetate and 50 mL of 5% potassium hydrogen sulfate solution. The layers were separated, and the organic layer was washed with 50 mL each of saturated sodium bicarbonate solution, water and brine, then dried over anhydrous magnesium sulfate, filtered and concentrated in vacuo to afford 3.1 grams (100%) of the desired product as a white solid, m/e=725 (M+Li).

Part B: Preparation of 2S-[[2S-(N-Methylamino)propionyl] amino]-N-[2R-hydroxy-3-[[(1,3-benzodioxol-5-yl)sulfonyl] (2-methylpropyl)amino]-1S-(phenylmethyl)propyl]-3,3-dimethylbutanamide.hydrochloride A solution of 3.1 grams (4.3 mmol) of the product from Part A in 10 mL of 1,4-dioxane was charged with 20 mL (40 mmol) of 4N HCl in dioxane solution and stirred for 2 hours. The solvents were removed in vacuo to yield a white solid. The solid was triturated with diethyl ether and isolated by filtration. This solid was triturated with 35% acetonitrile/65% water (both with 1% HCl) and again isolated by filtration. The solid was dried by sequentially adding then removing under reduced pressure three volume of ethanol then three volumes of water. Final drying was done over phosphorous pentaoxide ($P_2O_5$) under reduced pressure at room temperature and yielded 1.3 grams (46%) of the desired product as the HCl salt, m/e=625 (M+Li).

EXAMPLE 63

Preparation of 2S-[[2S-Aminopropionyl]amino]-N-[2R-hydroxy-3-[[(1,3-benzodioxol-5-yl)sulfonyl](2-methylpropyl)amino]-1S-(phenylmethyl)propyl]-3,3-dimethylbutanamide

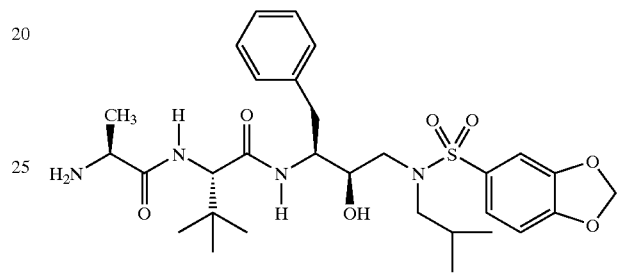

Part A: Preparation of 2S-[[2S-[(Phenylmethoxycarbonyl) amino]propionyl]amino]-N-[2R-hydroxy-3-[[(1,3-benzodioxol-5-yl)sulfonyl](2-methylpropyl)amino]-1S-(phenylmethyl)propyl]-3,3-dimethylbutanamide A solution of 1.1 grams (4.9 mmol) of N-CBZ-L-alanine in 5 mL of anhydrous DMF was cooled to 0° C., charged with 0.9 grams (6.4 mmol) of HOBT and 1.0 grams (4.9 mmol) of EDC and stirred for two hours. The reaction was then charged with a solution of 2.3 grams (4.3 mmol) of 2S-amino-N-[2R-hydroxy-3-[[(1,3-benzodiox-5-yl) sulfonyl](2-methylpropyl)amino]-1S-(phenylmethyl) propyl]-3,3-dimethylbutanamide and 1.3 grams (12.9 mmol) of 4-methylmorpholine in 5 mL of anhydrous DMF and stirred for 18 hours. The solvents were removed in vacuo and the residue was partitioned between 150 mL of ethyl acetate and 50 mL of 5% potassium hydrogen sulfate solution. The layers were separated, and the organic layer was washed with 50 mL each of saturated sodium bicarbonate solution, water and brine, then dried over anhydrous magnesium sulfate, filtered and concentrated to afford 3.2 grams of crude material. The crude material was crystallized from ethanol, the solid was isolated by filtration, rinsed with one 40 mL portion of hexane, and air-dried to yield 3.0 grams (84%) of the desired product, m/e=745 (M+Li).

Part B: Preparation of 2S-[[2S-Aminopropionyl]amino]-N-[2R-hydroxy-3-[[(1,3-benzodioxol-5-yl)sulfonyl](2-methylpropyl)amino]-1S-(phenylmethyl)propyl]-3,3-dimethylbutanamide A Fischer-Porter bottle equipped with a magnetic stir bar was charged with 2.9 grams (3.9 mmol) of the product from Part A and 20 mL of tetrahydrofuran (THF). The solution was hydrogenated in the presence of 1.3 grams of 10% palladium-on-carbon catalyst (50% water by weight) under 50 psig of hydrogen for 2 hours at room temperature. The catalyst was removed by filtration, and the solvents removed under reduced pressure. The residue was dissolved in 150 mL of ethyl acetate and washed with 50 mL each of saturated sodium bicarbonate solution and brine, then dried over anhydrous magnesium sulfate, filtered and concentrated under reduced pressure to afford 2.1 grams of crude material. Purification was accomplished by flash chromatography on silica gel using 2–6% methanol/methylene chloride and yielded 1.9 grams (83%) of the desired product as a white solid, m/e=605 (M+H).

EXAMPLE 64

Preparation of 2S-[[2R-(N-Methylamino)propionyl]amino]-N-[2R-hydroxy-3-[[(1,3-benzodioxol-5-yl)sulfonyl](2-methylpropyl)amino]-1S-(phenylmethyl)propyl]-2S-amino-3S-methylpentanamide.hydrochloride Salt

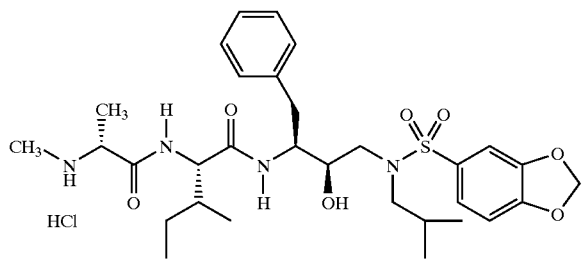

Part A: Preparation of 2S-[[2R-[N-(tert-Butoxycarbonyl)-N-(methyl)amino]propionyl]amino]-N-[2R-hydroxy-3-[[(1,3-benzodioxol-5-yl)sulfonyl](2-methylpropyl)amino]-1S-(phenylmethyl)propyl]-2S-amino-3S-methylpentanamide A solution of 0.7 grams (3.3 mmol) of N-t-BOC-N-methyl-D-alanine in 5 mL of anhydrous DMF was cooled to 0° C., charged with 0.7 grams (5.0 mmol) of HOBT and 0.7 grams (3.8 mmol) of EDC and stirred for three hours. The reaction solution was then charged with a solution of 1.8 grams (3.3 mmol) of 2S-amino-N-[2R-hydroxy-3-[[(1,3-benzodiox-5-yl)sulfonyl](2-methylpropyl)amino]-1S-(phenylmethyl)propyl]-3S-methylpentanamide and 1.0 grams (9.9 mmol) of 4-methylmorpholine in 5 mL of anhydrous DMF and stirred for 16 hours. The solvents were removed in vacuo and the residue was partitioned between 150 mL of ethyl acetate and 50 mL of 5% potassium hydrogen sulfate solution. The layers were separated, and the organic layer was washed with 50 mL each of saturated sodium bicarbonate solution, water, and brine, then dried over anhydrous magnesium sulfate, filtered and concentrated in vacuo to yield the crude material. Purification was accomplished using flash chromatography on silica gel using 30–50% ethyl acetate/methylene chloride and yielded 1.9 grams (79%) of the desired product as a white solid, m/e=725 (M+Li).

Part B: Preparation of 2S-[[2R-(N-Methylamino)propionyl]amino]-N-[2R-hydroxy-3-[[(1,3-benzodioxol-5-yl)sulfonyl](2-methylpropyl)amino]-1S-(phenylmethyl)propyl]-2S-amino-3S-methylpentanamide.hydrochloride Salt A solution of 1.9 grams (4.3 mmol) of the product from Part A in 10 mL of 1,4-dioxane was charged with 20 mL (40 mmol) of 4N HCl in dioxane solution and stirred for 2 hours. The solvents were removed in vacuo to yield a white solid. The solid was dried by sequentially adding then removing in vacuo three volumes of ethanol then three volumes of water. Final drying was done over phosphorous pentaoxide ($P_2O_5$) under reduced pressure at room temperature and yielded 1.5 grams (88%) of the desired product as the HCl salt, m/e=625 (M+Li).

EXAMPLE 65

Preparation of 2S-[[N-(Phenylmethyl)aminoacetyl]amino]-N-[2R-hydroxy-3-[[(1,3-benzodioxol-5-yl)sulfonyl](2-methylpropyl)amino]-1S-(phenylmethyl)propyl]-3S-methylpentanamide

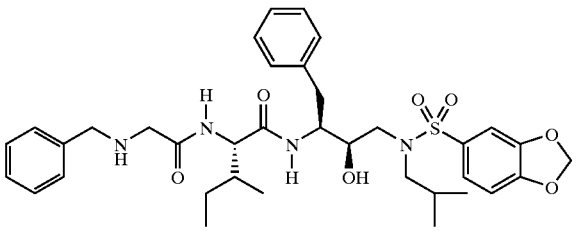

A solution of 1.5 grams (2.5 mmol) of 2S-[[chloroacetyl]amino]-N-[2R-hydroxy-3-[[(1,3-benzodiox-5-yl)sulfonyl](2-methylpropyl)amino]-1S-(phenylmethyl)propyl]-3S-methyl pentanamide in 10 mL of tetrahydrofuran (THF) and 0.5 mL of water was charged with 5.3 grams (49.2 mmol) of benzylamine and stirred for 17 hours. The solvents were removed in vacuo and the residue was partitioned between 150 mL of ethyl acetate and 50 mL of saturated sodium bicarbonate solution, the layers were separated and the organic layer was washed with 50 mL of brine, then dried over anhydrous magnesium sulfate, filtered and concentrated in vacuo to afford 2.5 grams of crude material. Purification was accomplished using flash chromatography on silica gel using 0–6% methanol/methylene chloride and yielded 1.6 grams (96%) of the desired product as a white solid, m/e=687 (M+Li).

EXAMPLE 66

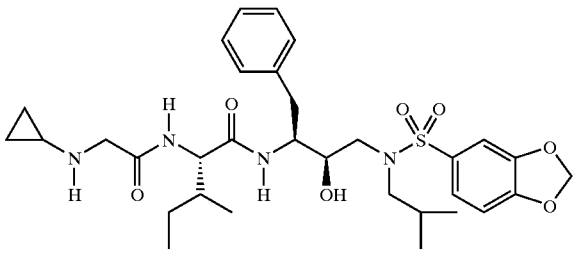

Preparation of N-[2R-Hydroxy-3-[[(1,3-benzodioxol-5-yl)sulfonyl](2-methylpropyl)amino]-1S-(phenylmethyl)propyl]-2S-[[(N-cyclopropylamino)acetyl]amino]-3S-methylpentanamide A solution of 1.5 grams (2.5 mmol) of 2S-[[chloroacetyl]amino]-N-[2R-hydroxy-3-[[(1,3-benzodiox-5-yl)sulfonyl](2-methylpropyl)amino]-1S-(phenylmethyl)propyl]-3S-methylpentanamide in 10 mL of THF and 0.5 mL of water was charged with 2.8 grams (49.2 mmol) of cyclopropylamine and stirred for 16 hours. The solvents were removed in vacuo and the residue was partitioned between 150 mL of ethyl acetate and 50 mL of saturated sodium bicarbonate solution, the layers were separated and the organic layer was washed with 50 mL of brine, then dried over anhydrous magnesium sulfate, filtered and concentrated in vacuo to afford 1.5 grams of the desired product as a white solid, m/e=637 (M+Li), 98% by HPLC.

EXAMPLE 67

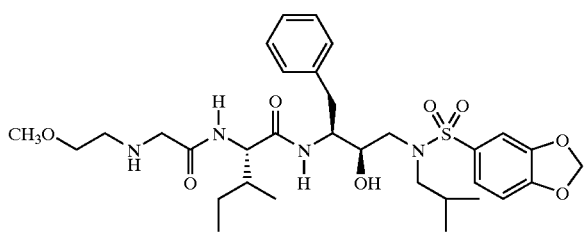

Preparation of 2S-[[N-(2-Methoxyethyl)aminoacteyl]amino]-N-[2R-hydroxy-3-[[(1,3-benzodioxol-5-yl)sulfonyl](2-methylpropyl)amino]-1S-(phenylmethyl)propyl]-3S-methylpentanamide A solution of 1.5 grams (2.5 mmol) of 2S-[[chloroacetyl]amino]-N-[2R-hydroxy-3-[[(1,3-benzodiox-5-yl)sulfonyl](2-methylpropyl)amino]-1S-(phenylmethyl)propyl]-3S-methylpentanamide in 10 mL of THF and 0.5 mL of water was charged with 3.7 grams (49.2 mmol) of 2-methoxyethylamine and stirred for 18 hours. The solvents were removed in vacuo and the residue was partitioned between 150 mL of ethyl acetate and 50 mL of saturated sodium bicarbonate solution, the layers were separated and the organic layer was washed with 50 mL of brine, then dried over anhydrous magnesium sulfate, filtered and concentrated in vacuo to afford 2 grams of crude material. Purification was accomplished using flash chromatography on silica gel using 0–6% methanol/methylene chloride and yielded 1.3 grams (81%) of the desired product as a white solid, m/e=655 (M+Li).

EXAMPLE 68

Preparation of 2S-[[2R-(N-Methylamino)propionyl]amino]-N-[2R-hydroxy-3-[[(4-methoxyphenyl)sulfonyl](2-methylpropyl)amino]-1S-(phenylmethyl)propyl]-3,3-dimethylbutanamide.hydrochloride

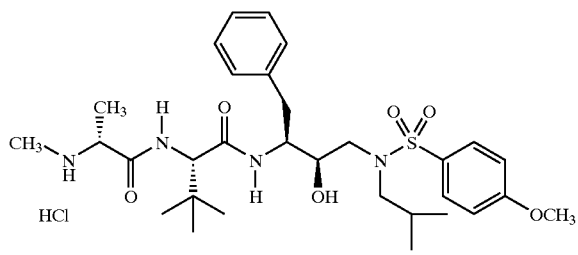

Part A: Preparation of 2S-[[2R-[N-(tert-Butoxycarbonyl)-N-(methyl)amino]propionyl]amino]-N-[2R-hydroxy-3-[[(4-methoxyphenyl)sulfonyl](2-methylpropyl)amino]-1S-(phenylmethyl)propyl]-3,3-dimethylbutanamide A solution of 0.7 grams (3.3 mmol) of N-t-BOC-N-methyl-D-alanine in 5 mL of anhydrous DMF was cooled to 0° C., charged with 0.7 grams (5.0 mmol) of HOBT and 0.7 grams (3.8 mmol) of EDC and stirred for three hours. The reaction solution was then charged with a solution of 1.7 grams (3.3 mmol) of 2S-amino-N-[2R-hydroxy-3-[[(4-methoxyphenyl)sulfonyl](2-methylpropyl)amino]-1S-(phenylmethyl)propyl]-3,3-dimethylbutanamide and 1.0 grams (9.9 mmol) of 4-methylmorpholine in 5 mL of anhydrous DMF and stirred for 18 hours. The solvents were removed in vacuo and the residue was partitioned between 150 mL of ethyl acetate and 50 mL of 5% potassium hydrogen sulfate solution. The layers were separated, and the organic layer was washed with 50 mL each of saturated sodium bicarbonate solution, water, and brine, then dried over anhydrous magnesium sulfate, filtered and concentrated in vacuo to yield 2.3 grams (100%) of the desired product as a white solid, m/e=711 (M+Li).

Part B: Preparation of 2S-[[2R-(N-Methylamino)propionyl]amino]-N-[2R-hydroxy-3-[[(4-methoxyphenyl)sulfonyl](2-methylpropyl)amino]-1S-(phenylmethyl)propyl]-3,3-dimethylbutanamide.hydrochloride A solution of 2.3 grams (3.2 mmol) of the product from Part A in 10 mL of 1,4-dioxane was charged with 20 mL (40 mmol) of 4N HCl in dioxane solution and stirred for 2 hours. The solvents were removed in vacuo to yield a white solid. The solid was dried by sequentially adding then removing in vacuo three volumes of ethanol then three volumes of water. Final drying was done over phosphorous pentaoxide ($P_2O^5$) under reduced pressure at room temperature and yielded 1.9 grams (90%) of the desired product as the HCl salt, m/e=611 (M+Li).

EXAMPLE 69

Preparation of 2S-[[N-(Phenylmethyl)aminoacteyl]amino]-N-[2R-hydroxy-3-[[(4-methoxyphenyl)sulfonyl](2-methylpropyl)amino]-1S-(phenylmethyl)propyl]-3,3-dimethylbutanamide

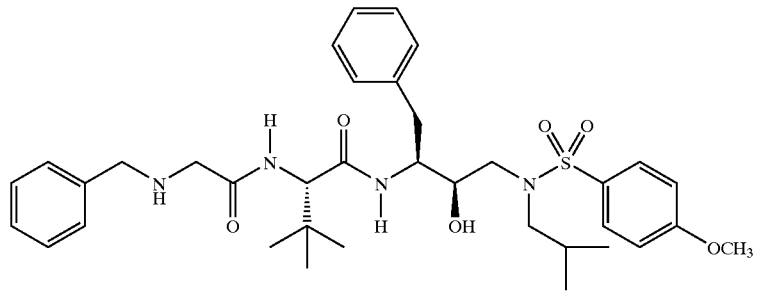

Part A: Preparation of N-[2R-Hydroxy-3-[[(4-methoxyphenyl)sulfonyl](2-methylpropyl)amino]-1S-(phenylmethyl)propyl]-2S-[(chloroacetyl)amino]-3,3-dimethylbutanamide A solution of 4.4 grams (8.4 mmol) of 2S-amino-N-[2R-hydroxy-3-[[(4-methoxybenzene)sulfonyl](2-methylpropyl)amino]-1S-(phenylmethyl)propyl]-3,3-dimethylbutanamide and 1.3 grams (10.1 mmol) of diisopropylethylamine in 30 mL of anhydrous methylene chloride was cooled in an ice bath and charged with 1.2 grams (7.1 mmol) of chloroacetic anhydride and stirred for one-half hour. HPLC analysis at this time showed the reaction to be 83% complete. The solution was charged with an additional 0.2 gram (1.2 mmol) of chloroacetic anhydride and stirred for 15 hours. The solvents were removed in vacuo and the residue was partitioned between 300 mL of ethyl acetate and 100 mL of 5% citric acid solution, the layers were separated and the organic layer was washed with 100 mL each of saturated sodium bicarbonate solution, water and brine, then dried over anhydrous magnesium sulfate, filtered and concentrated to afford 5.1 grams of crude material. Purification was accomplished using flash chromatography on silica gel using 30–50% ethyl acetate/hexane and yielded 4.1 grams (82%) of the desired product as a white solid, m/e=602 (M+Li).

Part B: Preparation of 2S-[[N-(Phenylmethyl)aminoacetyl]amino]-N-[2R-hydroxy-3-[[(4-methoxyphenyl)sulfonyl](2-methylpropyl)amino]-1S-(phenylmethyl)propyl]-3,3-dimethylbutanamide A solution of 1.3 grams (2.2 mmol) of the product from Part A in 12 mL of THF and 0.5 mL of water was charged with 4.8 grams (44.6 mmol) of benzylamine and stirred for 16 hours. The solvents were removed in vacuo and the residue was partitioned between 150 mL of ethyl acetate and 50 mL of saturated sodium bicarbonate solution, the layers were separated and the organic layer was washed with 50 mL of brine, then dried over anhydrous magnesium sulfate, filtered and concentrated to yield the crude material as an oil. Purification was accomplished using flash chromatography on silica gel using 0–4% methanol/methylene chloride and yielded 1.3 grams (87%) of the desired product as a white solid, m/e=673 (M+Li).

EXAMPLE 70

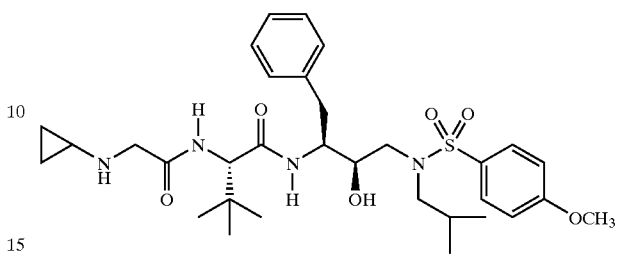

Preparation of 2S-[[(N-Cyclopropylamino)acteyl]amino]-N-[2R-hydroxy-3-[[(4-methoxyphenyl)sulfonyl](2-methylpropyl)amino]-1S-(phenylmethyl)propyl]-3,3-dimethylbutanamide A solution of 1.3 grams (2.2 mmol) of 2S-[[chloroacetyl]amino-N-[2R-hydroxy-3-[[(4-methoxybenzene)sulfonyl](2-methylpropyl)amino]-1S-(phenylmethyl)propyl]-3,3-dimethylbutanamide in 12 mL of THF and 0.5 mL of water was charged with 2.6 grams (44.6 mmol) of cyclopropylamine and stirred for 18 hours. The solvents were removed in vacuo and the residue was partitioned between 150 mL of ethyl acetate and 50 mL of saturated sodium bicarbonate solution, the layers were separated and the organic layer was washed with 50 mL of brine, then dried over anhydrous magnesium sulfate, filtered and concentrated in vacuo to yield 1.3 grams (93%) of the desired product as a white solid, m/e=623 (M+Li).

EXAMPLE 71

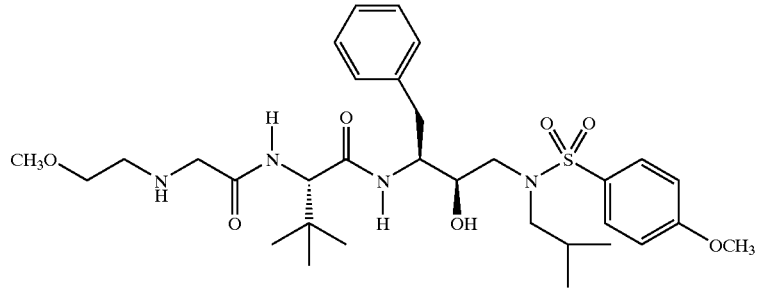

Preparation of 2S-[[N-(2-Methoxyethyl)aminoacetyl]amino]-N-[2R-hydroxy-3-[[(4-methoxyphenyl)sulfonyl](2-methylpropyl)amino]-1S-(phenylmethyl)propyl]-3,3-dimethylbutanamide A solution of 1.3 grams (2.2 mmol) of 2S-[[chloroacetyl]amino]-N-[2R-hydroxy-3-[[(4-methoxybenzene)sulfonyl](2-methylpropyl)amino]-1S-(phenylmethyl)propyl]-3,3-dimethylbutanamide in 12 mL of THF and 0.5 mL of water was charged with 3.4 grams (44.6 mmol) of 2-methoxyethylamine and stirred for 17 hours. The solvents were removed in vacuo and the residue was partitioned between 150 mL of ethyl acetate and 50 mL of saturated sodium bicarbonate solution, the layers were separated and the organic layer was washed with 50 mL of brine, then dried over anhydrous magnesium sulfate, filtered and concentrated in vacuo to yield the crude material. Purification was accomplished using flash chromatography on silica gel using 0–6% methanol/methylene chloride and yielded 1.1 grams (77%) of the desired product as a white solid, m/e=641 (M+Li).

EXAMPLE 72

Preparation of 2S-[[2R-(N-Methylamino)propionyl]amino]-N-[2R-hydroxy-3-[[(4-methoxyphenyl)sulfonyl](2-methylpropyl)amino]-1S-(phenylmethyl)propyl]-2S-amino-3S-methylpentanamide.hydrochloride Salt

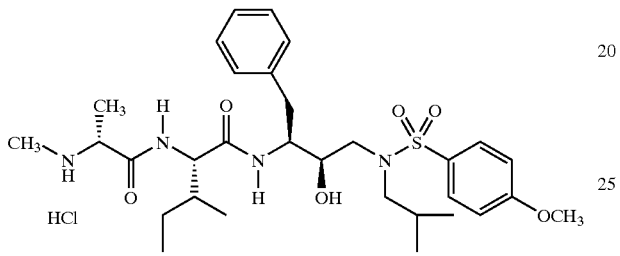

Part A: Preparation of 2S-[[2R-[N-(tert-Butoxycarbonyl)-N-(methyl)amino]propionyl]amino]-N-[2R-hydroxy-3-[[(4-methoxyphenyl)sulfonyl](2-methylpropyl)amino]-1S-(phenylmethyl)propyl]-2S-amino-3S-methylpentanamide A solution of 0.7 grams (3.3 mmol) of N-t-BOC-N-methyl-D-alanine in 5 mL of anhydrous DMF was cooled to 0° C., charged with 0.7 grams (5.0 mmol) of HOBT and 0.7 grams (3.8 mmol) of EDC and stirred for three hours. The reaction solution was then charged with a solution of 1.7 grams (3.3 mmol) of 2S-amino-N-[2R-hydroxy-3-[[(4-methoxyphenyl)sulfonyl](2-methylpropyl)amino]-1S-(phenylmethyl)propyl]-3S-methylpentanamide and 1.0 grams (9.9 mmol) of 4-methylmorpholine in 5 mL of anhydrous DMF and stirred for 16 hours. The solvents were removed in vacuo and the residue was partitioned between 150 mL of ethyl acetate and 50 mL of 5% potassium hydrogen sulfate solution. The layers were separated, and the organic layer was washed with 50 mL each of saturated sodium bicarbonate solution, water, and brine, then dried over anhydrous magnesium sulfate, filtered and concentrated in vacuo to yield the crude material. Purification was accomplished using flash chromatography on silica gel using 30–50% ethyl acetate/hexane and yielded 1.6 grams (70%) of the desired product as a white solid, m/e=711 (M+Li).

Part B: Preparation of Preparation of 2S-[[2R-(N-Methylamino)propionyl]amino]-N-[2R-hydroxy-3-[[(4-methoxyphenyl)sulfonyl](2-methylpropyl)amino]-1S-(phenylmethyl)propyl]-2S-amino-3S-methylpentanamide.hydrochloride Salt A solution of 1.6 grams (2.2 mmol) of the product from Part A in 10 mL of 1,4-dioxane was charged with 20 mL (40 mmol) of 4N HCl in dioxane solution and stirred for 2 hours. The solvents were removed in vacuo to yield a white solid. The solid was dried by sequentially adding then removing under reduced pressure three volumes of ethanol then three volumes of water. Final drying was done over phosphorous pentaoxide ($P_2O_5$) under reduced pressure at room temperature and yielded 1.2 grams (86%) of the desired product as the HCl salt, m/e=611 (M+Li).

EXAMPLE 73

Preparation of 2S-[[N-(Phenylmethyl)aminoacetyl]amino]-N-[2R-hydroxy-3-[[(4-methoxyphenyl)sulfonyl](2-methylpropyl)amino]-1S-(phenylmethyl)propyl]-3S-methylpentanamide

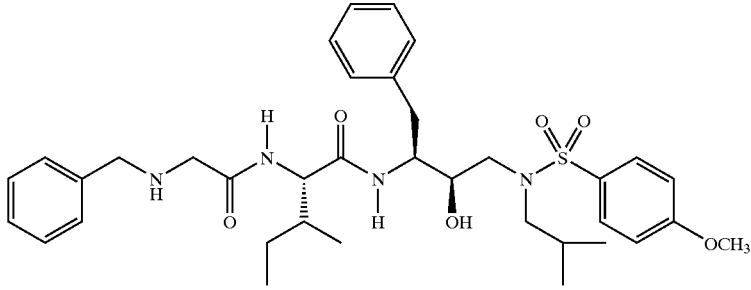

Part A: Preparation of 2S-[(Chloroacetyl)amino]-N-[2R-hydroxy-3-[[(4-methoxyphenyl)sulfonyl](2-methylpropyl)amino]-1S-(phenylmethyl)propyl]-3S-methylpentanamide A solution of 5.5 grams (10.6 mmol) of 2S-amino-N-[2R-hydroxy-3-[[(4-methoxybenzene)sulfonyl](2-methylpropyl)amino]-1S-(phenylmethyl)propyl]-3S-methylpentanamide and 1.6 grams (12.7 mmol) of diisopropylethylamine in 30 mL of anhydrous methylene chloride was cooled in an ice bath and charged with 1.5 grams (9.0 mmol) of chloroacetic anhydride and stirred for one-half hour. HPLC analysis at this time showed the reaction to be 82% complete. The solution was charged with an additional 0.3 gram (1.8 mmol) of chloroacetic anhydride and stirred for 16 hours. The solvents were removed in vacuo and the residue was partitioned between 300 mL of ethyl acetate and 100 mL of 5% citric acid solution, the layers were separated and the organic layer was washed with 100 mL each of saturated sodium bicarbonate solution, water and brine, then dried over anhydrous magnesium sulfate, filtered and concentrated in vacuo to afford 6.2 grams of the desired product as a white solid, m/e=602 (M+Li).

Part B: Preparation of 2S-[[N-(Phenylmethyl)aminoacetyl]amino]-N-[2R-hydroxy-3-[[(4-methoxyphenyl)sulfonyl](2-methylpropyl)amino]-1S-(phenylmethyl)propyl]-3S-methylpentanamide A solution of 2.0 grams (3.4 mmol) of the chloroacetyl product from Part A in 12 mL of THF and 0.5 mL of water was charged with 7.2 grams (67.1 mmol) of benzylamine and stirred for 64 hours. The solvents were removed in vacuo and the residue was partitioned between 150 mL of ethyl acetate and 50 mL of saturated sodium bicarbonate solution, the layers were separated and the organic layer was washed with 50 mL each of water and brine, then dried over anhydrous magnesium sulfate, filtered and concentrated in vacuo to yield the crude material as an oil. Purification was accomplished using flash chromatography on silica gel using 0–4% methanol/methylene chloride and yielded 1.8 grams (80%) of the desired product as a white solid, m/e=673 (M+Li).

EXAMPLE 74

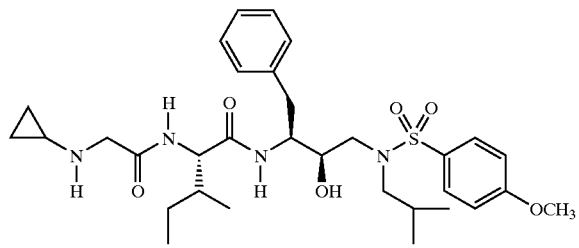

Preparation of N-[2R-Hydroxy-3-[[(4-methoxyphenyl)sulfonyl](2-methylpropyl)amino]-1S-(phenylmethyl)propyl]-2S-[[(N-cycloprorylamino)acetyl]amino]-3S-methylpentanamide A solution of 2.0 grams (3.4 mmol) of 2-S-[[chloroacetyl]amino]-N-[2R-hydroxy-3-[[(4-methoxybenzene)sulfonyl](2-methylpropyl)amino]-1S-(phenylmethyl)propyl]-3S-methylpentanamide in 12 mL of THF and 0.5 mL of water. The solution was charged with 3.8 grams (67.1 mmol) of cyclopropylamine and stirred for 64 hours. The solvents were removed in vacuo and the residue was partitioned between 150 mL of ethyl acetate and 50 mL of saturated sodium bicarbonate solution, the layers were separated and the organic layer was washed with 50 mL each of water and brine, then dried over anhydrous magnesium sulfate, filtered and concentrated in vacuo to yield the crude material as a white solid. Purification was accomplished using flash chromatography on silica gel using 1–4% methanol/methylene chloride and yielded 1.8 grams (81%) of the desired product as a white solid, m/e=623 (M+Li).

EXAMPLE 75

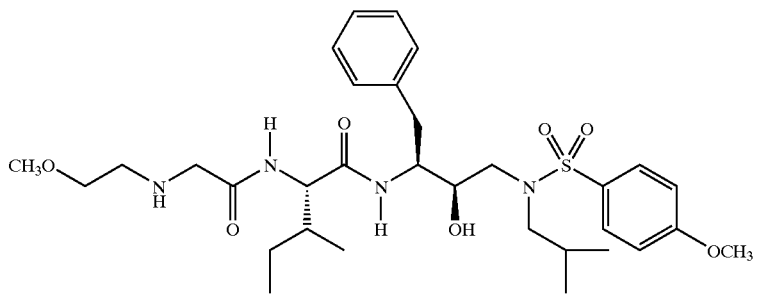

Preparation of 2S-[[N-(2-Methoxyethyl)aminoacetyl]amino]-N-[2R-hydroxy-3-[[(4-methoxyphenyl)sulfonyl](2-methylpropyl)amino]-1S-(phenylmethyl)propyl]-3S-methylpentanamide A solution of 2.0 grams (3.4 mmol) of 2S-[[chloroacetyl]amino]-N-[2R-hydroxy-3-[[(4-methoxybenzene)sulfonyl](2-methylpropyl)amino]-1S-(phenylmethyl)propyl]-3S-methylpentanamide in 12 mL of THF and 0.5 mL of water was charged with 5.0 grams (67.1 mmol) of 2-methoxyethylamine and stirred for 64 hours. The solvents were removed in vacuo and the residue was partitioned between 150 mL of ethyl acetate and 50 mL of saturated sodium bicarbonate solution, the layers were separated and the organic layer was washed with 50 mL each of water and brine, then dried over anhydrous magnesium sulfate, filtered and concentrated in vacuo to yield the crude material. Purification was accomplished using flash chromatography on silica gel using 0–6% methanol/methylene chloride and yielded 1.6 grams (76%) of the desired product as a white solid, m/e=641 (M+Li).

EXAMPLE 76

Following the procedures of the previous Examples, the compounds set forth in Tables 2 through 15 can be prepared.

TABLE 2

| Entry | $R^3$ | $R^4$ |
|---|---|---|
| 1 | isobutyl | 2-methyl-1,3-benzodioxol-5-yl |
| 2 | isobutyl | 2-methyl-1,3-benzodioxol-5-yl |
| 3 | cyclopentylmethyl | 2-methyl-1,3-benzodioxol-5-yl |
| 4 | cyclohexylmethyl | 2-methyl-1,3-benzodioxol-5-yl |
| 5 | cyclopentylmethyl | 1,3-benzodioxol-5-yl |
| 6 | cyclohexylmethyl | 1,3-benzodioxol-5-yl |
| 7 | cyclopentylmethyl | benzofuran-5-yl |
| 8 | cyclohexylmethyl | benzofuran-5-yl |
| 9 | cyclopentylmethyl | 2,3-dihydrobenzofuran-5-yl |
| 10 | cyclohexylmethyl | 2,3-dihydrobenzofuran-5-yl |

TABLE 2-continued

| Entry | R³ | R⁴ |
|---|---|---|
| 11 | isobutyl | 1,3-benzodioxol-5-yl |
| 12 | isobutyl | benzofuran-5-yl |
| 13 | isobutyl | 2,3-dihydrobenzofuran-5-yl |
| 14 | isobutyl | 1,4-benzodioxan-6-yl |
| 15 | isoamyl | 1,3-benzodioxol-5-yl |
| 16 | isoamyl | 2,3-dihydrobenzofuran-5-yl |

TABLE 2-continued

| Entry | R³ | R⁴ |
|---|---|---|
| 17 | isoamyl | 1,4-benzodioxan-6-yl |
| 18 | isobutyl | benzothiazol-6-yl |
| 19 | isobutyl | 2-ainino-benzothiazol-6-yl |
| 20 | isobutyl | benzoxazol-5-yl |
| 21 | cyclopentylmethyl | 2,2-difluoro-1,3-benzodioxol-5-yl |
| 22 | cyclohexylmethyl | 2,2-difluoro-1,3-benzodioxol-5-yl |

TABLE 3A

TABLE 3B
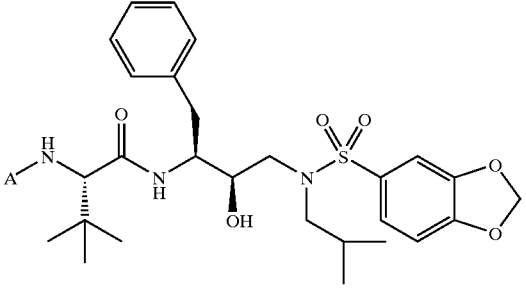
| Entry | A |
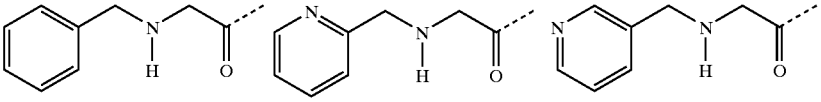
TABLE 3C
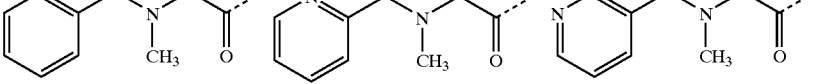
| Entry | A |

TABLE 3C-continued

TABLE 3D

TABLE 3D-continued
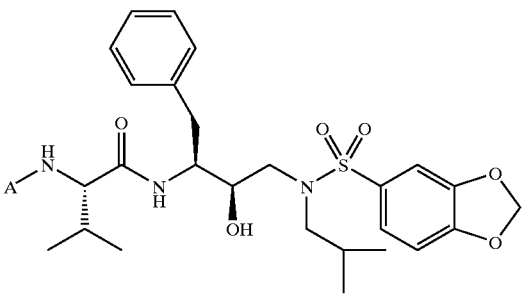
| Entry | A |
|---|---|
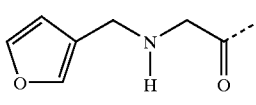
TABLE 3E
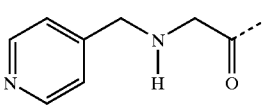
| Entry | A |
|---|---|
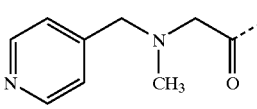

TABLE 3E-continued
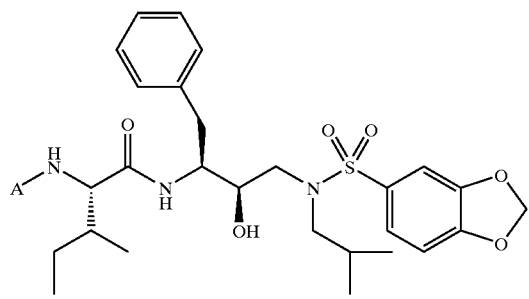
| Entry | A |
|---|---|
TABLE 3F
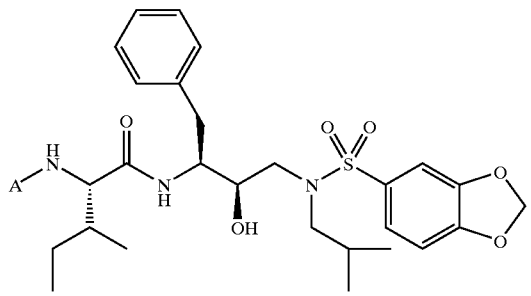
| Entry | A |
|---|---|

TABLE 3F-continued
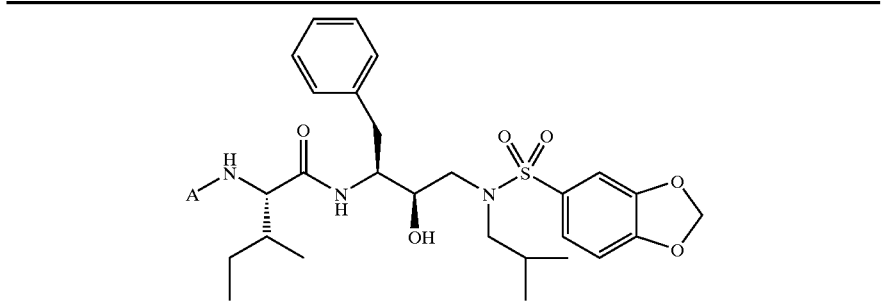
| Entry | A |
|---|---|
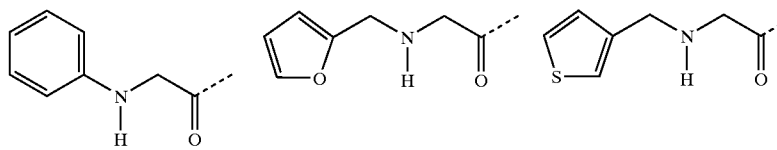
TABLE 3G
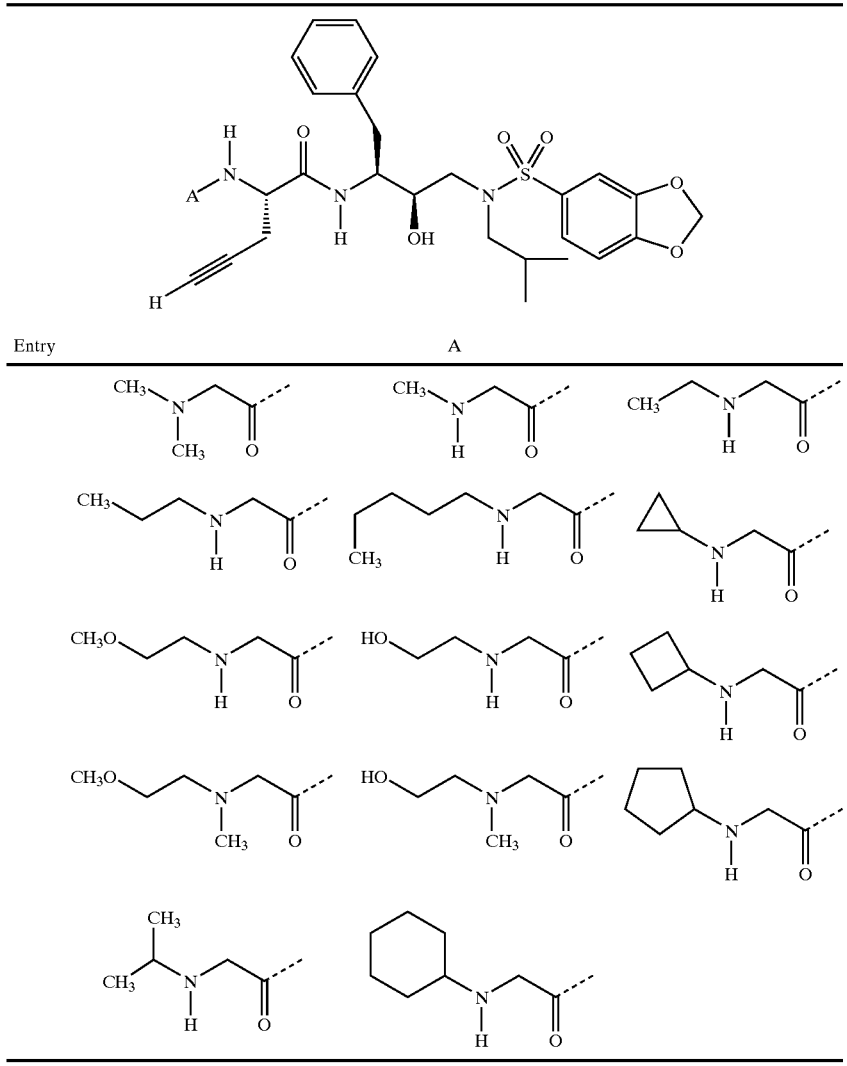
| Entry | A |
|---|---|
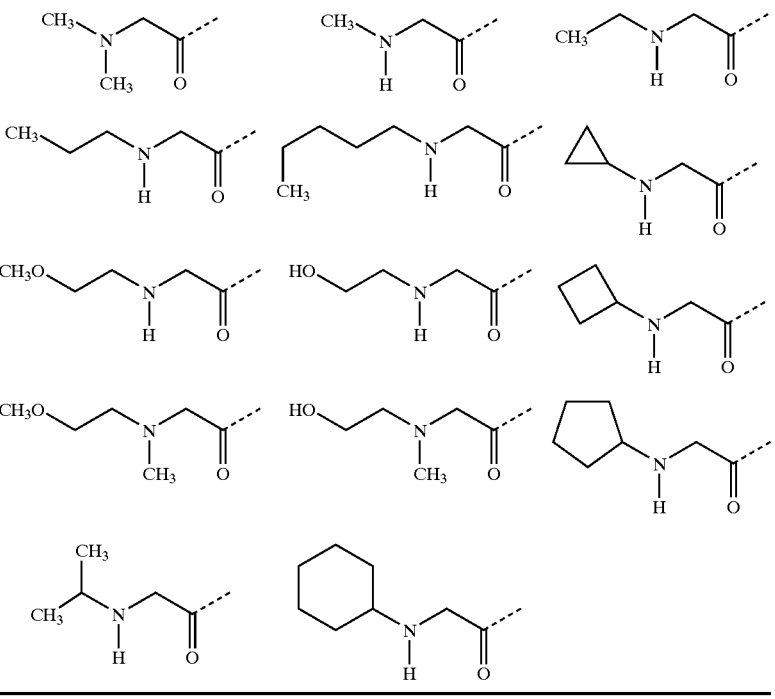

TABLE 3H

TABLE 4A

TABLE 4A-continued

TABLE 4B

TABLE 4B-continued
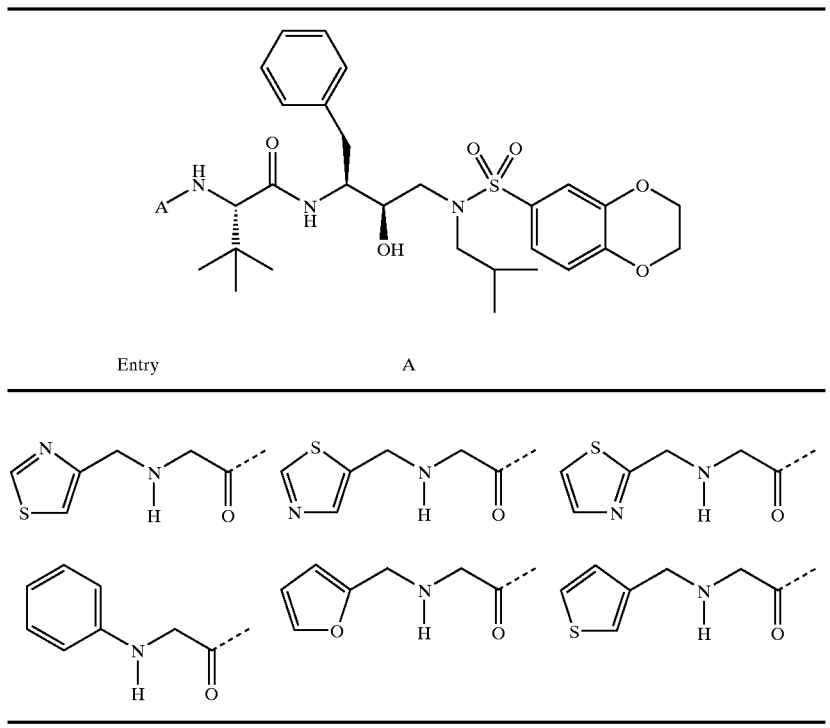
| Entry | A |
|---|---|
TABLE 4C
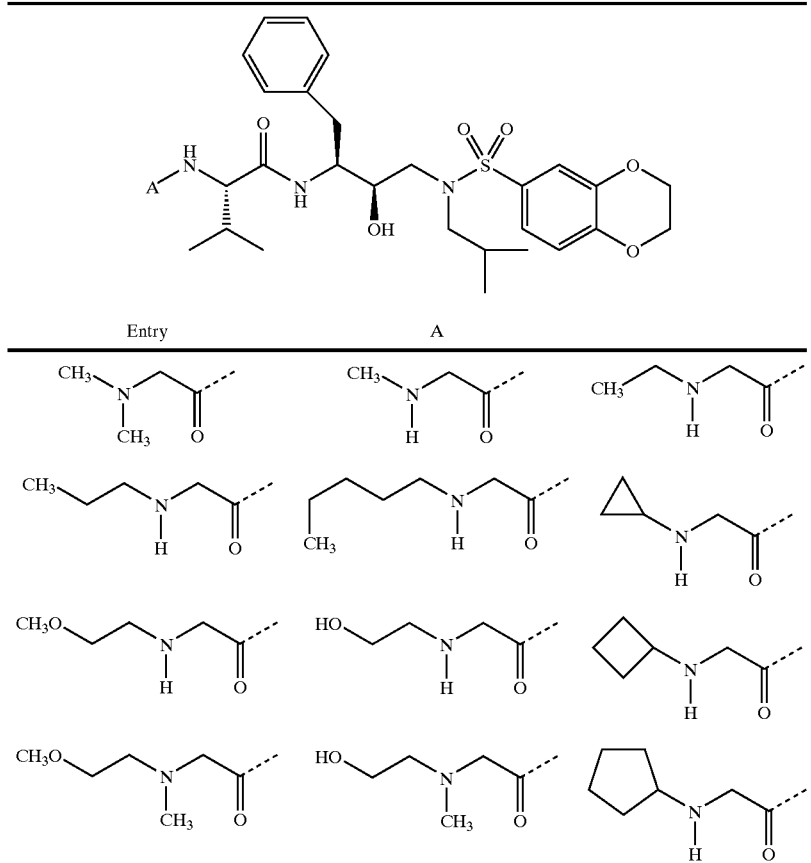
| Entry | A |
|---|---|

TABLE 4C-continued
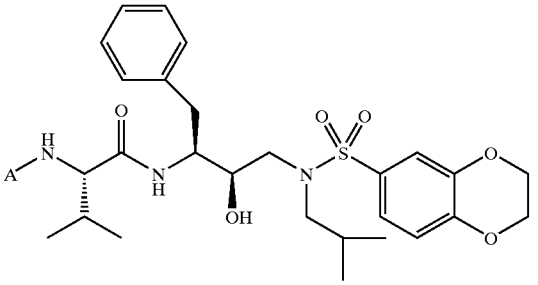
| Entry | A |
|---|---|
| 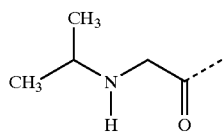 | 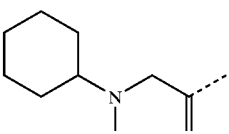 |
TABLE 4D
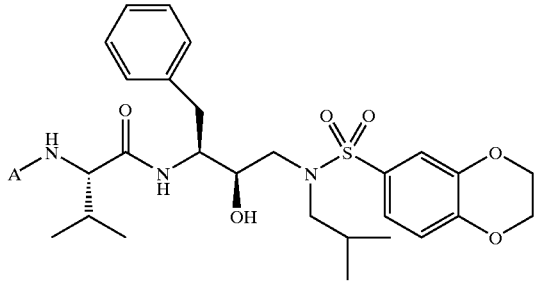
| Entry | A | |
|---|---|---|
| 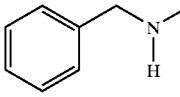 | 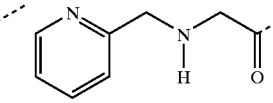 | 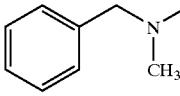 |
| 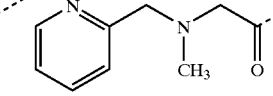 | 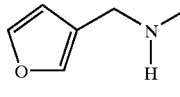 | 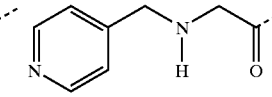 |
| 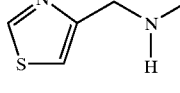 | 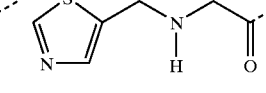 | 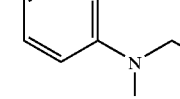 |
| 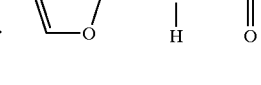 | | |

TABLE 4E

TABLE 4F

TABLE 4F-continued
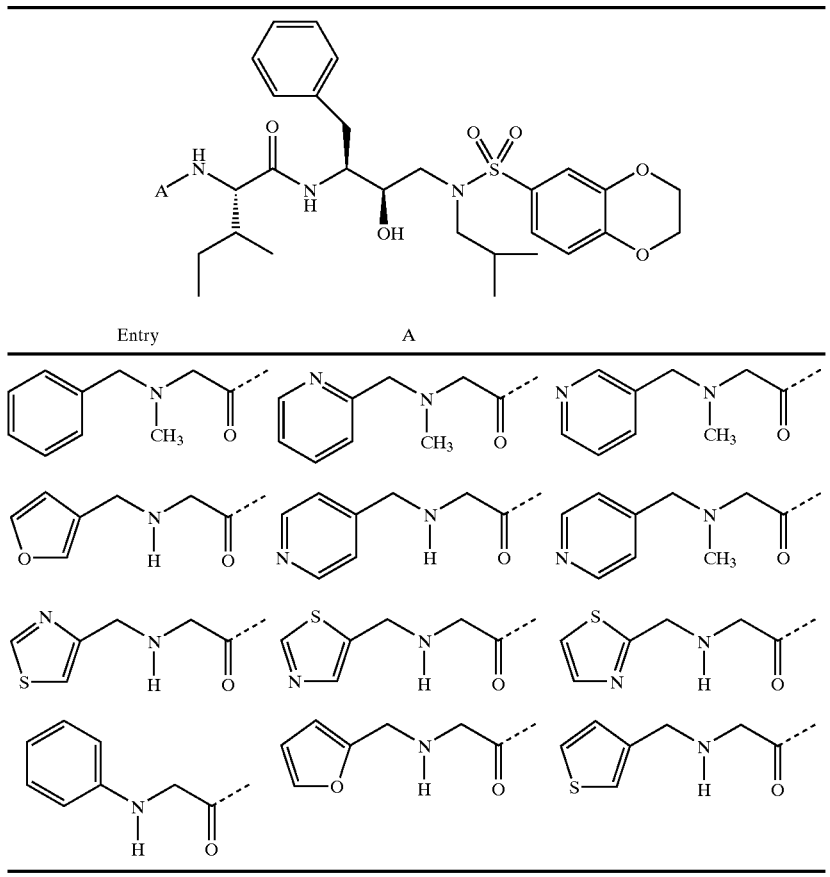
TABLE 4G
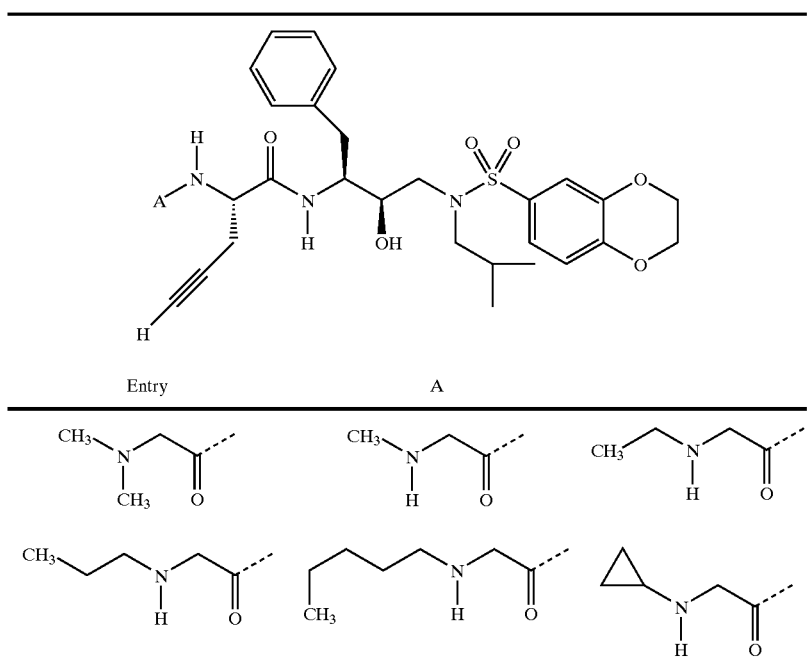

TABLE 4G-continued

[Chemical structure: peptidomimetic with A-NH group, phenyl side chain, propargyl group, OH, and benzodioxine sulfonamide with isobutyl]

| Entry | A |
|---|---|

[Structures of A groups:]
- CH₃O-CH₂CH₂-NH-CH₂-C(=O)-
- HO-CH₂CH₂-NH-CH₂-C(=O)-
- cyclobutyl-NH-CH₂-C(=O)-
- CH₃O-CH₂CH₂-N(CH₃)-CH₂-C(=O)-
- HO-CH₂CH₂-N(CH₃)-CH₂-C(=O)-
- cyclopentyl-NH-CH₂-C(=O)-
- (CH₃)₂CH-NH-CH₂-C(=O)-
- cyclohexyl-NH-CH₂-C(=O)-

TABLE 4H

[Chemical structure: similar peptidomimetic with propargyl group, OH, and benzodioxine sulfonamide with isobutyl]

| Entry | A |
|---|---|

[Structures of A groups:]
- benzyl-NH-CH₂-C(=O)-
- (pyridin-2-yl)methyl-NH-CH₂-C(=O)-
- (pyridin-3-yl)methyl-NH-CH₂-C(=O)-
- benzyl-N(CH₃)-CH₂-C(=O)-
- (pyridin-2-yl)methyl-N(CH₃)-CH₂-C(=O)-
- (pyridin-3-yl)methyl-N(CH₃)-CH₂-C(=O)-

TABLE 4H-continued
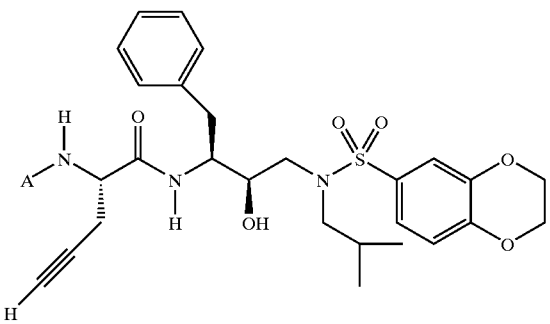
| Entry | A |
|---|---|
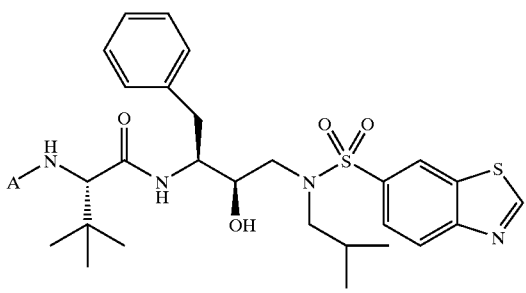
TABLE 5A
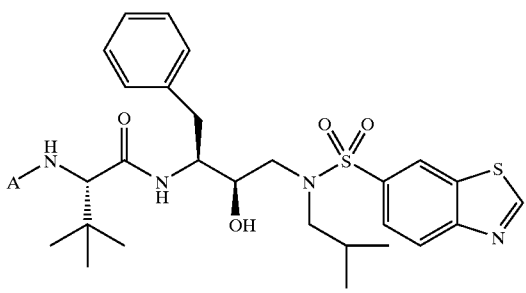
| Entry | A |
|---|---|

TABLE 5A-continued
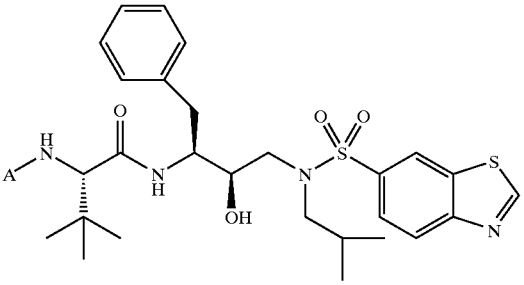
TABLE 5B
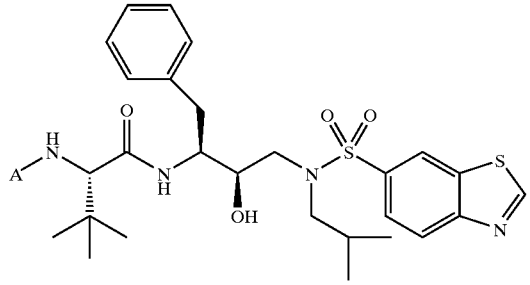

TABLE 5B-continued
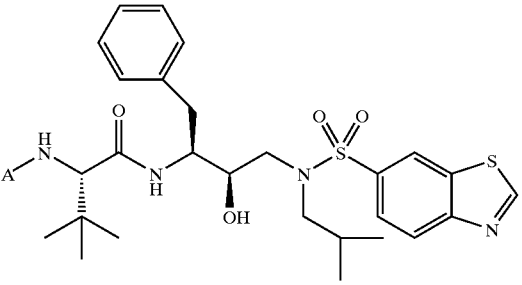
| Entry | A |
|---|---|
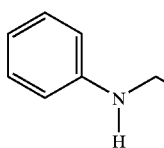 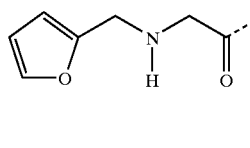 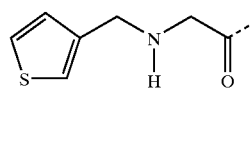
TABLE 5C
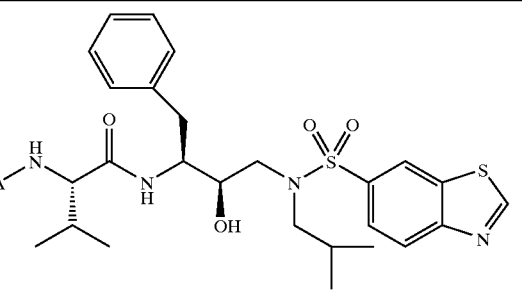
| Entry | A |
|---|---|
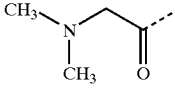 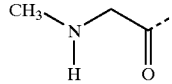 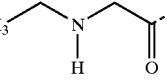
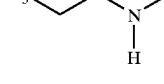 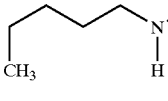 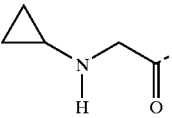
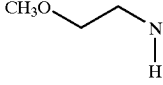 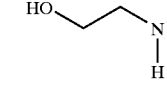 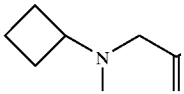
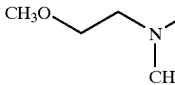 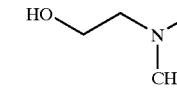 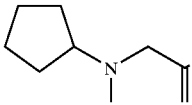
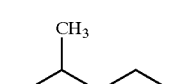 

TABLE 5D
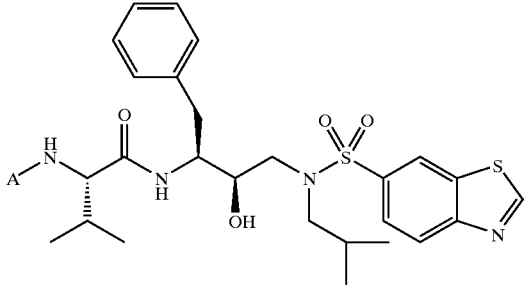
TABLE 5E
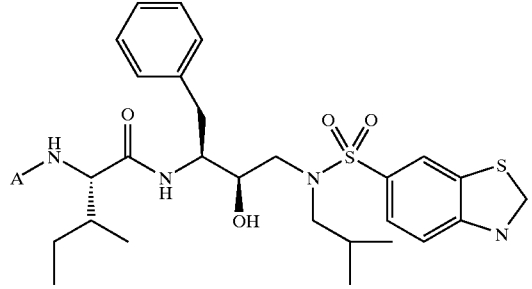

TABLE 5E-continued
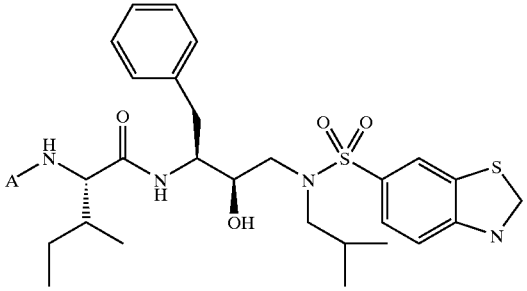
| Entry | A |
|---|---|
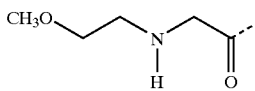
TABLE 5F
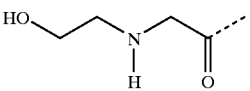
| Entry | A |
|---|---|
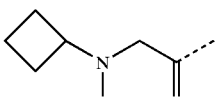

TABLE 5F-continued
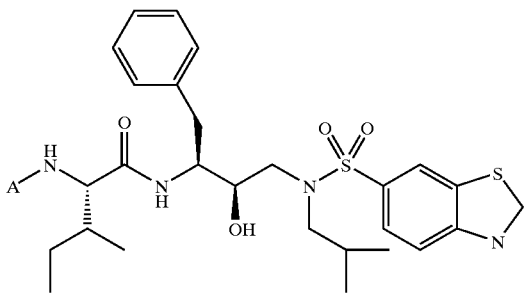
| Entry | A |
|---|---|
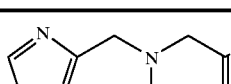 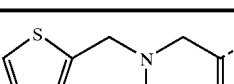 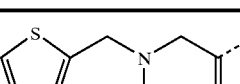
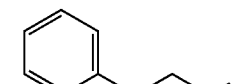 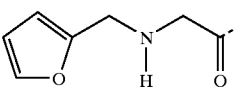 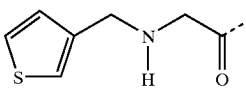
TABLE 5G
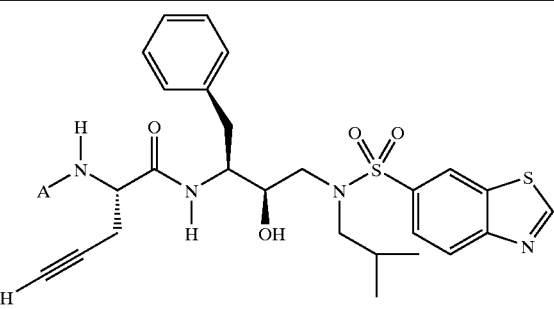
| Entry | A |
|---|---|
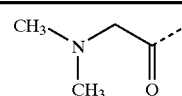 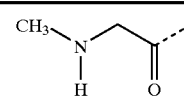 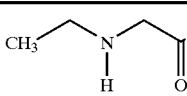
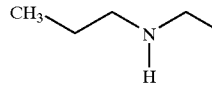 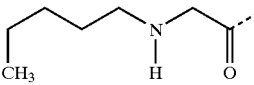 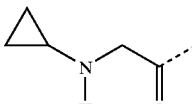
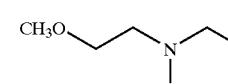 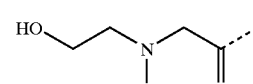 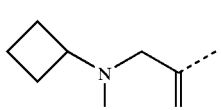
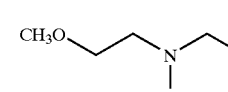 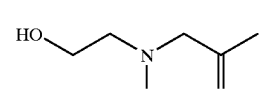 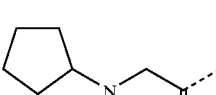

TABLE 5G-continued
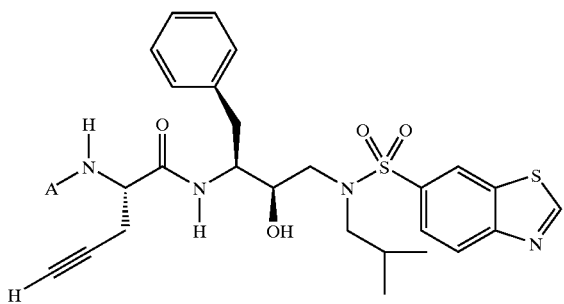
| Entry | A |
|---|---|
| |  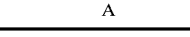 |
TABLE 5H
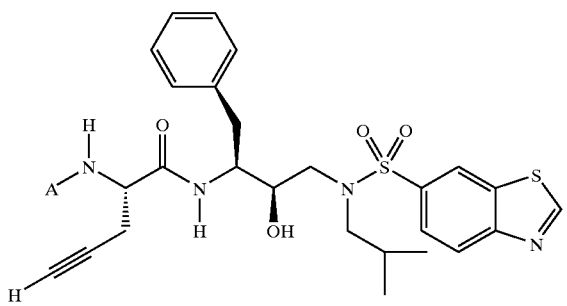
| Entry | A |
|---|---|

TABLE 6A
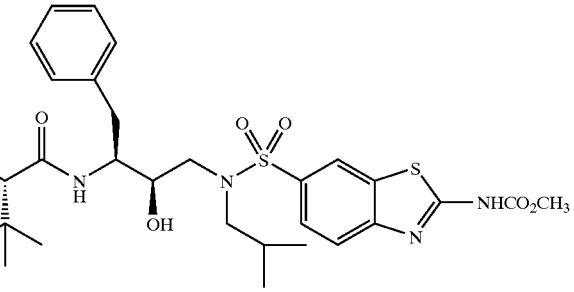
| Entry | A | | |
|---|---|---|---|
| | 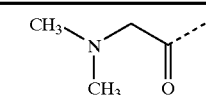 | 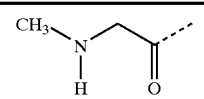 | 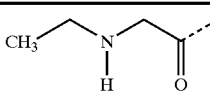 |
| | 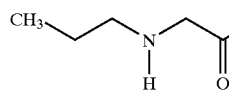 | 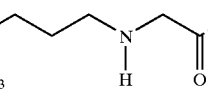 | 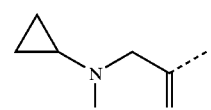 |
| | 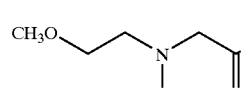 | 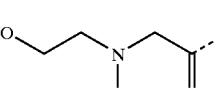 | 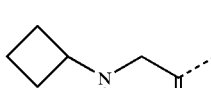 |
| | 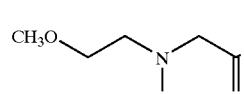 | 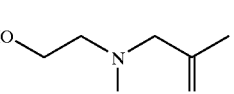 | 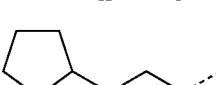 |
| | 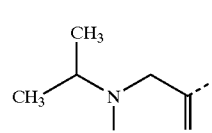 | 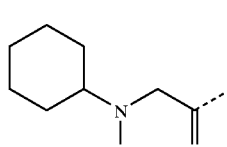 | |
TABLE 6B
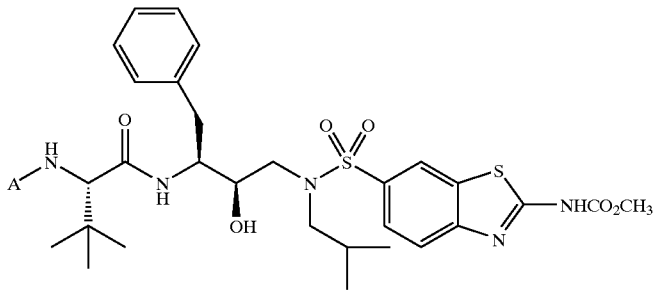
| Entry | A | | |
|---|---|---|---|
| | 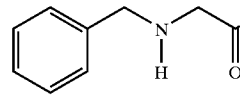 | 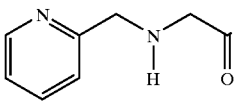 | 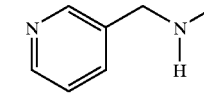 |

TABLE 6B-continued
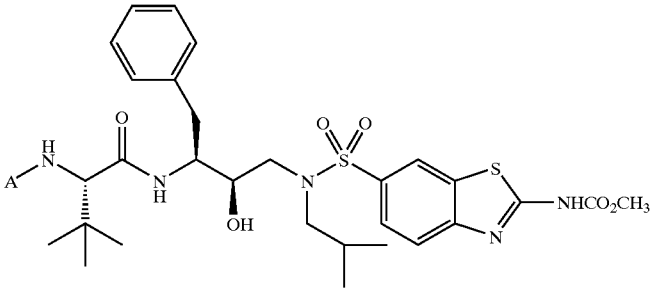
| Entry | A |
|---|---|
TABLE 6C
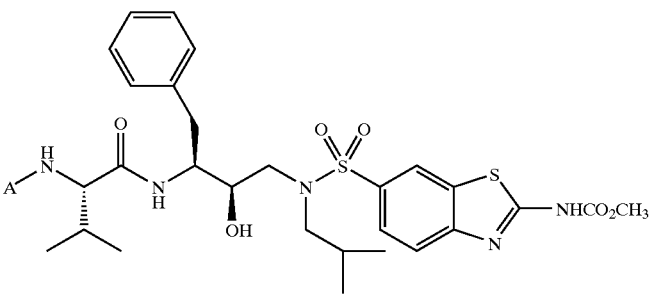
| Entry | A |
|---|---|

TABLE 6C-continued
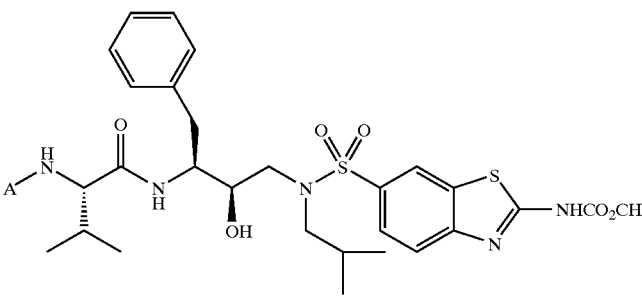
| Entry | A |
|---|---|
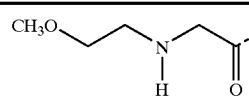
TABLE 6D
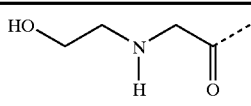
| Entry | A |
|---|---|
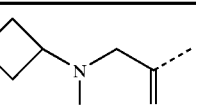

TABLE 6D-continued

TABLE 6E

TABLE 6E-continued
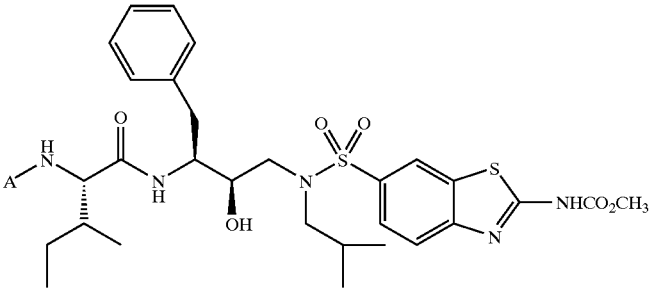
| Entry | A |
|---|---|
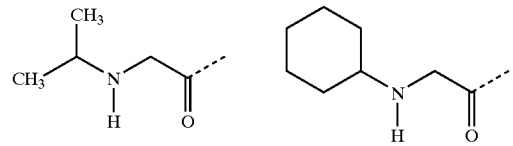 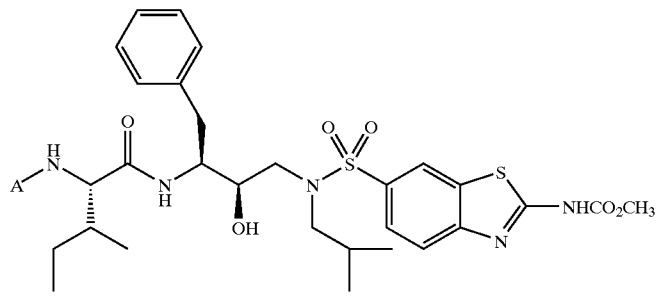
TABLE 6F
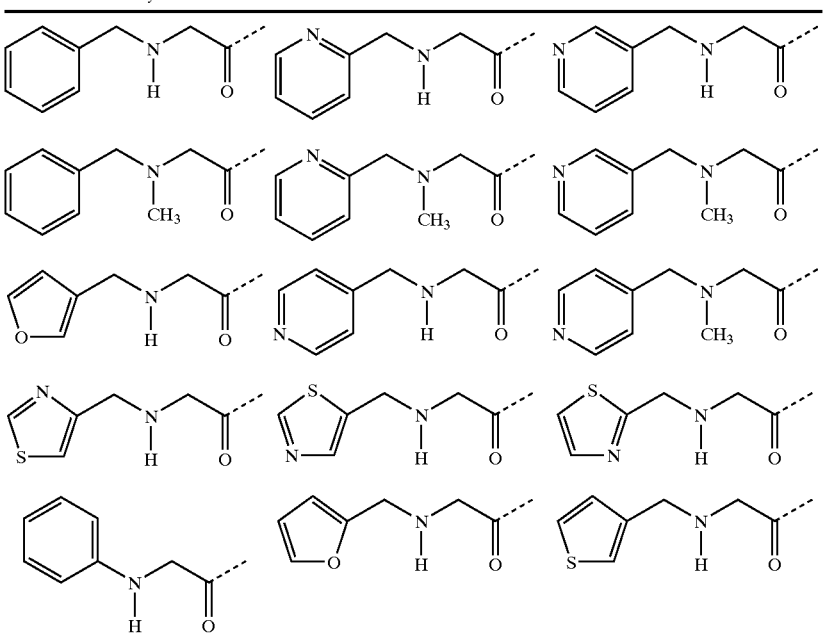
| Entry | A |
|---|---|
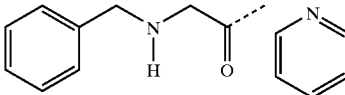 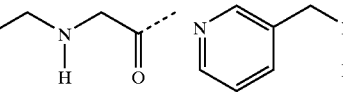 
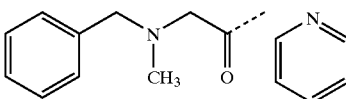 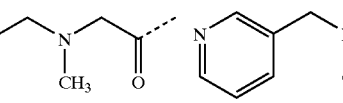 
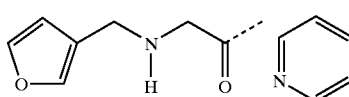 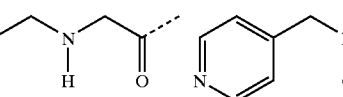 
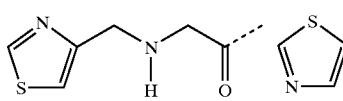 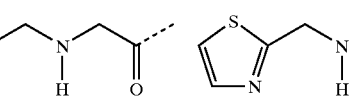 
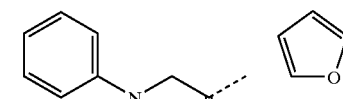 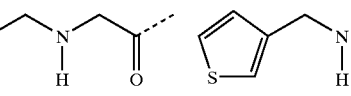 

TABLE 6G
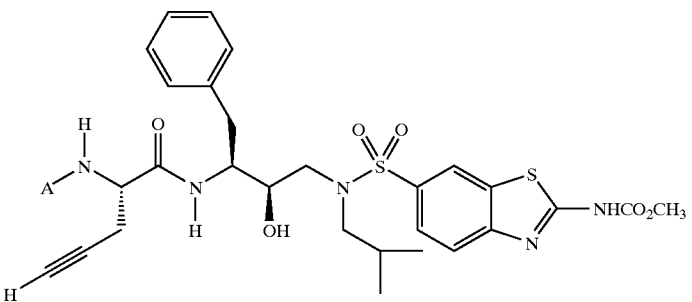
| Entry | A | | |
|---|---|---|---|
(table of A substituents shown as structures)
TABLE 6H
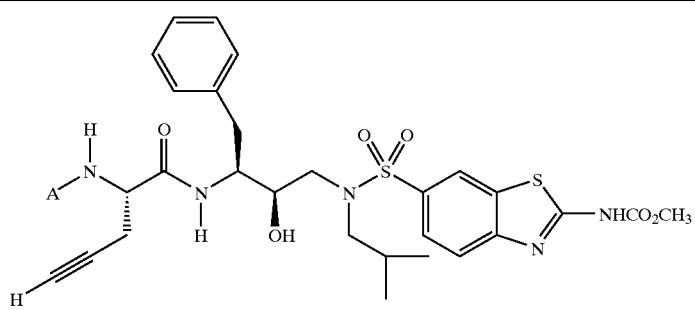
| Entry | A | | |
|---|---|---|---|

TABLE 6H-continued

TABLE 7A

TABLE 7A-continued
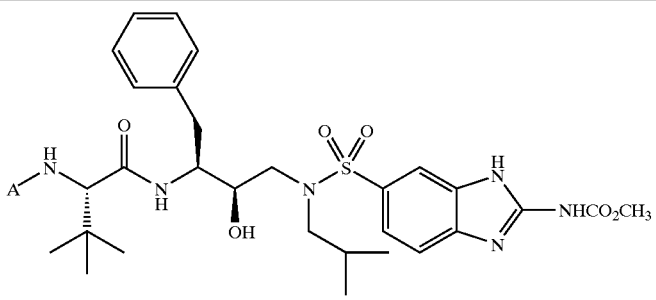
TABLE 7B
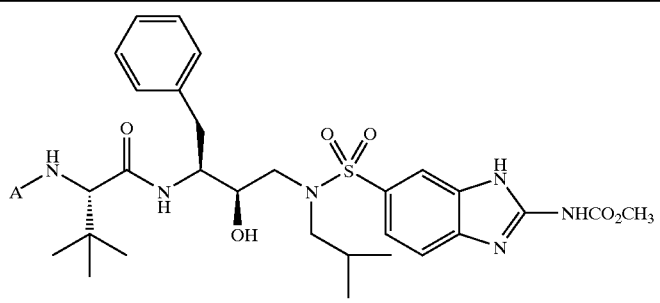

TABLE 7B-continued
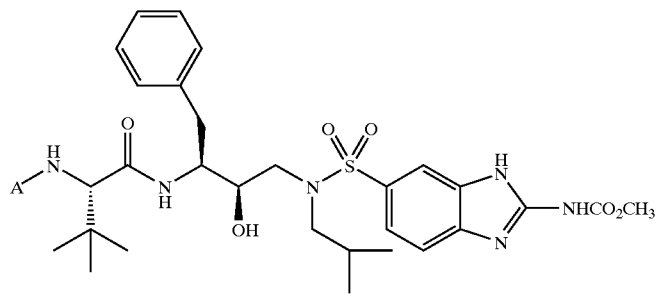
| Entry | A |
|---|---|
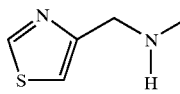 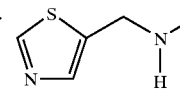 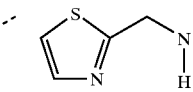
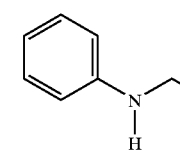 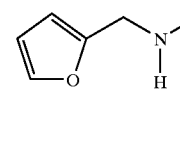 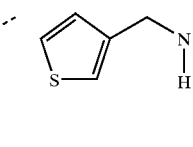
TABLE 7C
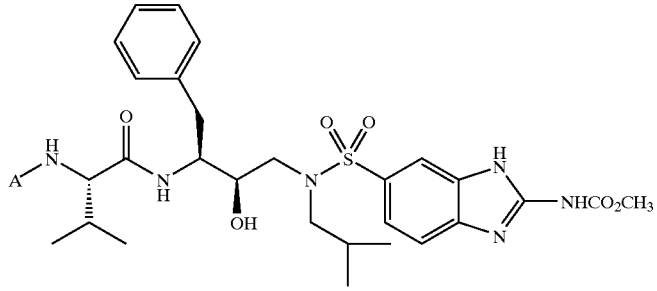
| Entry | A |
|---|---|
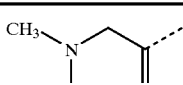 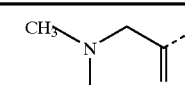 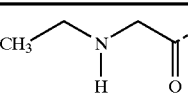
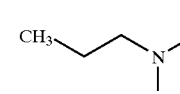 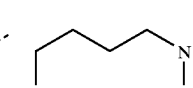 
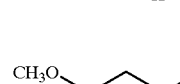 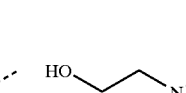 
  

TABLE 7C-continued

TABLE 7D

TABLE 7E (Structure: A-NH-CH(sec-butyl)-C(=O)-NH-CH(CH2Ph)-CH(OH)-CH2-N(iBu)-SO2-[2-(NHCO2CH3)-benzimidazol-5-yl])

| Entry | A | | |
|---|---|---|---|
| | (CH3)2N-CH2-C(=O)- | CH3-NH(H)-CH2-C(=O)- (N-methyl) | CH3-CH2-NH-CH2-C(=O)- |
| | CH3-CH2-CH2-NH-CH2-C(=O)- | CH3-CH2-CH2-CH2-NH-CH2-C(=O)- | cyclopropyl-NH-CH2-C(=O)- |
| | CH3O-CH2-CH2-NH-CH2-C(=O)- | HO-CH2-CH2-NH-CH2-C(=O)- | cyclobutyl-NH-CH2-C(=O)- |
| | CH3O-CH2-CH2-N(CH3)-CH2-C(=O)- | HO-CH2-CH2-N(CH3)-CH2-C(=O)- | cyclopentyl-NH-CH2-C(=O)- |
| | (CH3)2CH-NH-CH2-C(=O)- | cyclohexyl-NH-CH2-C(=O)- | |

TABLE 7F (Structure: A-NH-CH(sec-butyl)-C(=O)-NH-CH(CH2Ph)-CH(OH)-CH2-N(iBu)-SO2-[2-(NHCO2CH3)-benzimidazol-5-yl])

| Entry | A | | |
|---|---|---|---|
| | PhCH2-NH-CH2-C(=O)- | (2-pyridyl)CH2-NH-CH2-C(=O)- | (3-pyridyl)CH2-NH-CH2-C(=O)- |

TABLE 7F-continued
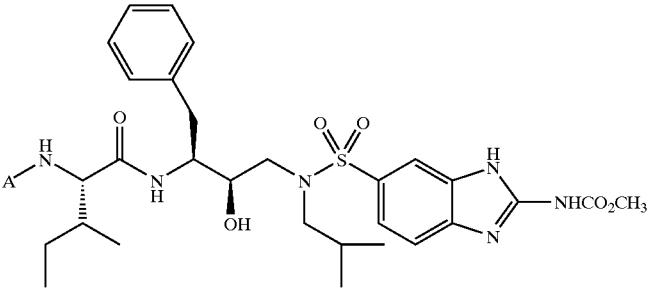
| Entry | A |
|---|---|
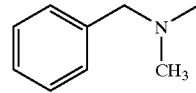 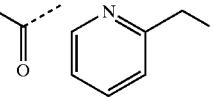 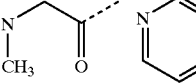
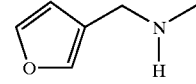 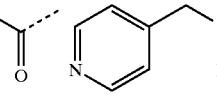 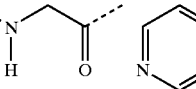
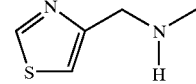 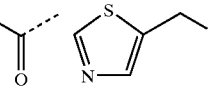 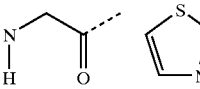
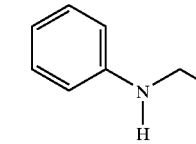 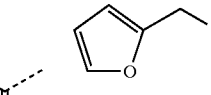 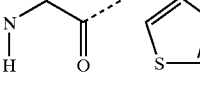
TABLE 7G
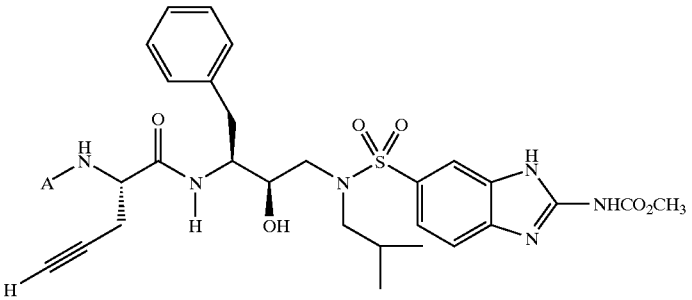
| Entry | A |
|---|---|
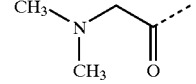 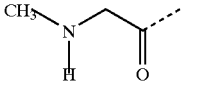 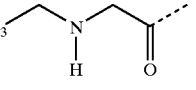
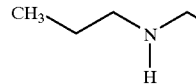 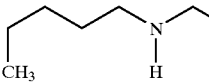 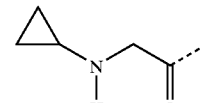

TABLE 7G-continued
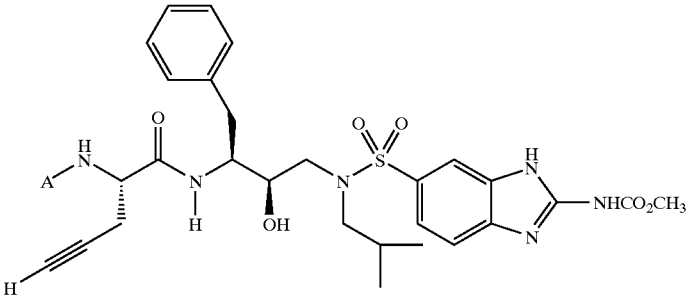
Entry | A
TABLE 7H
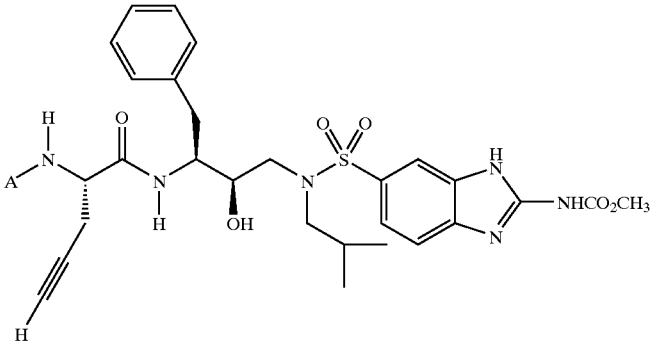
Entry | A

TABLE 7H-continued

| Entry | A |
|---|---|

TABLE 8A

| Entry | R² |
|---|---|
| (CH₃)₂CHCH₂— | (4-FC₆H₅)CH₂— |
| CH₃CH₂CH₂CH₂— | (naphth-2-yl)CH₂— |
| CH₃SCH₂CH₂— | C₆H₁₁CH₂— |
| C₆H₅CH₂— | C₆H₅SCH₂— |
| (4-CH₃OC₆H₅)CH₂— | (naphth-2-yl)SCH₂— |

TABLE 8B

| Entry | R² |
|---|---|
| (CH₃)₂CHCH₂— | (4-FC₆H₅)CH₂— |
| CH₃CH₂CH₂CH₂— | (naphth-2-yl)CH₂— |

TABLE 8B-continued

| Entry | R² |
|---|---|
| CH₃SCH₂CH₂— | C₆H₁₁CH₂— |
| C₆H₅CH₂— | C₆H₅SCH₂— |
| (4-CH₃OC₆H₅)CH₂— | (naphth-2-yl)SCH₂— |

TABLE 8C

| Entry | R² |
|---|---|
| (CH₃)₂CHCH₂— | (4-FC₆H₅)CH₂— |
| CH₃CH₂CH₂CH₂— | (naphth-2-yl)CH₂— |
| CH₃SCH₂CH₂— | C₆H₁₁CH₂— |

TABLE 8C-continued
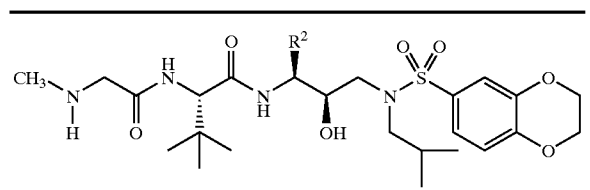
| Entry | R² |
|---|---|
| | C₆H₅CH₂— C₆H₅SCH₂— |
| | (4-CH₃OC₆H₅)CH₂— (naphth-2-yl)SCH₂— |
TABLE 8D
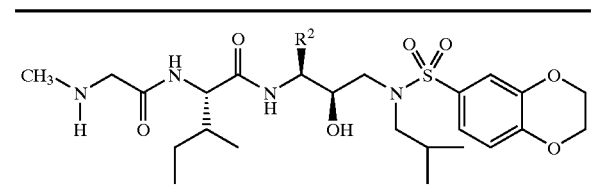
| Entry | R² |
|---|---|
| | (CH₃)₂CHCH₂— (4-FC₆H₅)CH₂— |
| | CH₃CH₂CH₂CH₂— (naphth-2-yl)CH₂— |
| | CH₃SCH₂CH₂— C₆H₁₁CH₂— |
| | C₆H₅CH₂— C₆H₅SCH₂— |
| | (4-CH₃OC₆H₅)CH₂— (naphth-2-yl)SCH₂— |
TABLE 9A
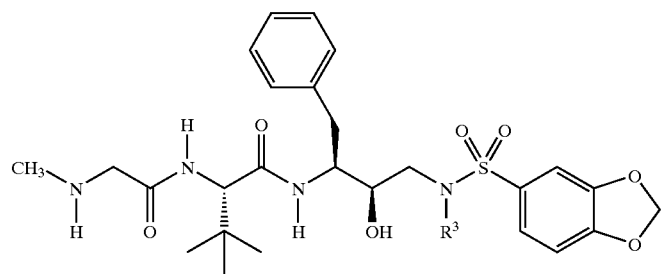
| Entry | R³ |
|---|---|
| —CH₂CH₂CH₃ | 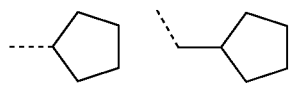 |
| —CH₂CH₂CH₂CH₃ | 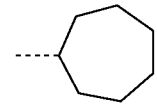 |
| —CH₂CH(CH₃)₂ | |
| —CH₂CH₂CH(CH₃)₂ | 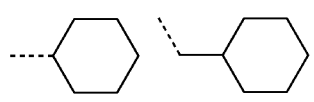 |

TABLE 9B

| Entry | R³ | | |
|---|---|---|---|
| —CH₂CH₂CH₃ | cyclopentyl | cyclopentylmethyl | |
| —CH₂CH₂CH₂CH₃ | | | |
| —CH₂CH(CH₃)₂ | | cycloheptyl | |
| —CH₂CH₂CH(CH₃)₂ | cyclohexyl | cyclohexylmethyl | |

30

TABLE 9C

| Entry | R³ | | |
|---|---|---|---|
| —CH₂CH₂CH₃ | cyclopentyl | cyclopentylmethyl | |
| —CH₂CH₂CH₂CH₃ | | | |
| —CH₂CH(CH₃)₂ | | cycloheptyl | |
| —CH₂CH₂CH(CH₃)₂ | cyclohexyl | cyclohexylmethyl | |

TABLE 9D

| Entry | R³ |
|---|---|
| —CH₂CH₂CH₃ | cyclopentyl, cyclopentylmethyl |
| —CH₂CH₂CH₂CH₃ | |
| —CH₂CH(CH₃)₂ | cycloheptyl |
| —CH₂CH₂CH(CH₃)₂ | cyclohexyl, cyclohexylmethyl |

TABLE 10A

| Entry | R¹ |
|---|---|
| | tert-butyl, sec-butyl, isobutyl, n-butyl, n-pentyl, propargyl, allyl |
| | isopropyl, —CH₂SO₂C(CH₃)₃, —CH(CH₃)SO₂CH₃, —CH₂SC(CH₃)₃, —CH(CH₃)SCH₃ |
| | —CH₂C(O)NH₂, —C(CH₃)₂C(O)NH₂, —C(CH₃)₂SO₂NH₂, —CH₂SO₂NH₂ |

TABLE 10B
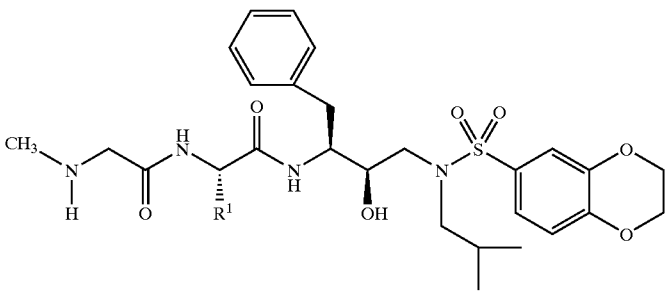
| Entry | R¹ |
| --- | --- |
TABLE 10C
| Entry | R¹ |
| --- | --- |

TABLE 10D
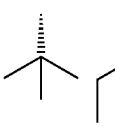
| Entry | R¹ |
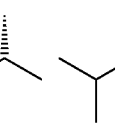
TABLE 10E
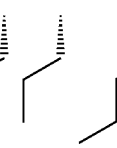
| Entry | R¹ |
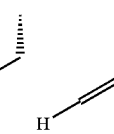

TABLE 10E-continued
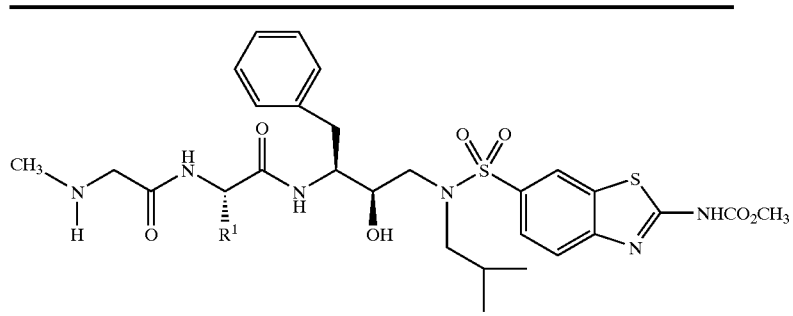
| Entry | R¹ |
TABLE 10F
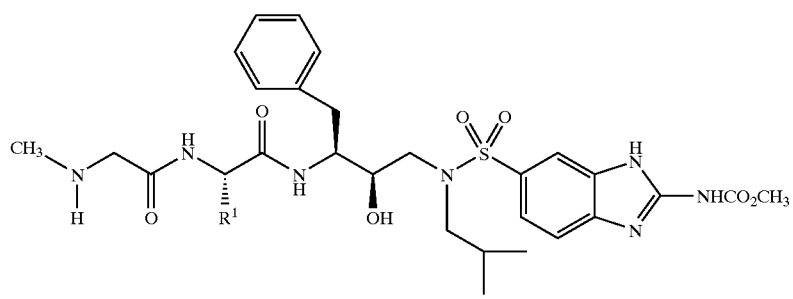
| Entry | R¹ |

TABLE 11A
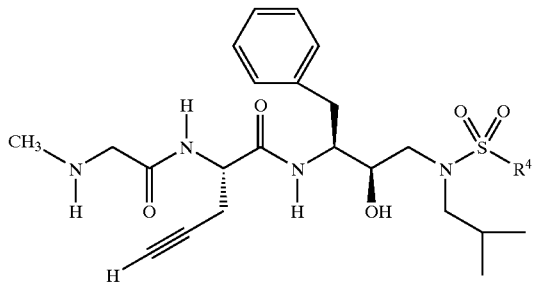
| Entry | R⁴ | | | |
|---|---|---|---|---|
| | 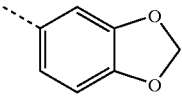 | 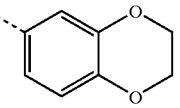 | 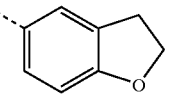 | 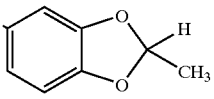 |
| | 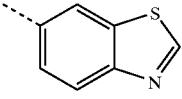 | 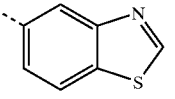 | 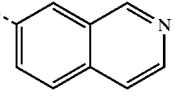 | 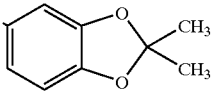 |
| | 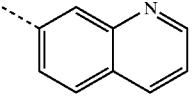 | 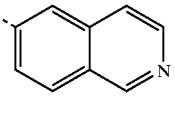 | 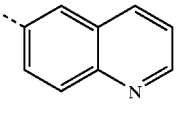 | 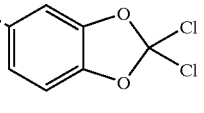 |
| | 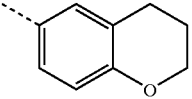 | 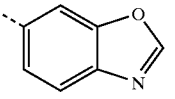 | 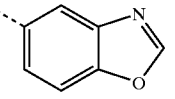 | 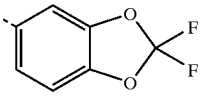 |
| | 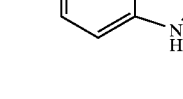 | 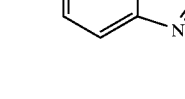 |  | |
| | 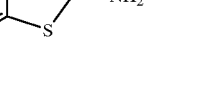 | 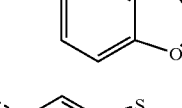 | 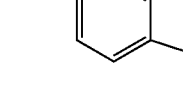 | |
| | 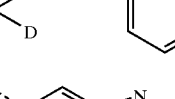 | 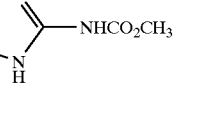 | | |

TABLE 11B
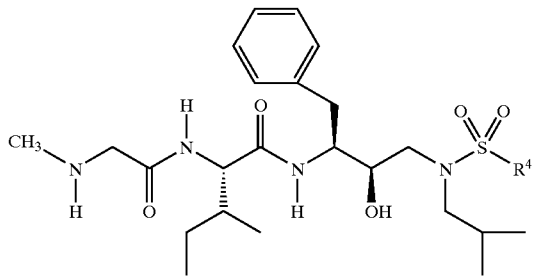
| Entry | R⁴ | | | |
|---|---|---|---|---|
| | 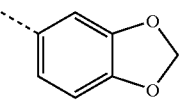 | 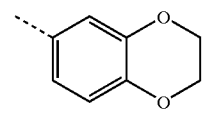 | 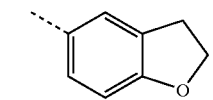 | 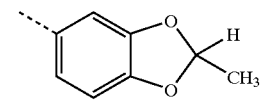 |
| | 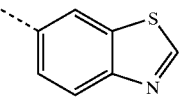 | 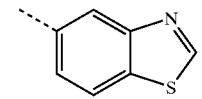 | 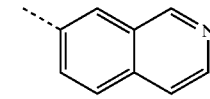 | 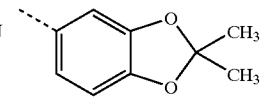 |
| | 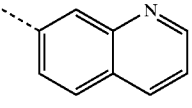 | 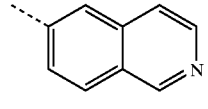 | 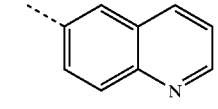 | 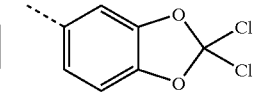 |
| | 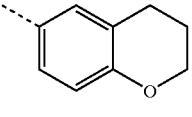 | 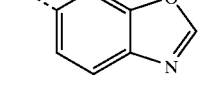 | 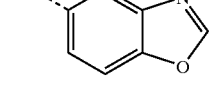 | 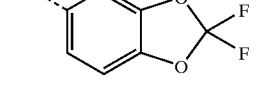 |
| | 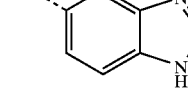 | 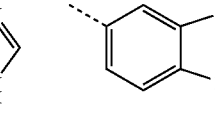 | 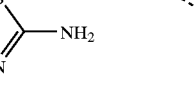 | |
| | 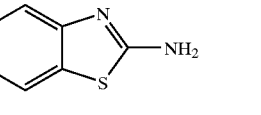 | 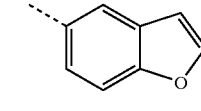 | 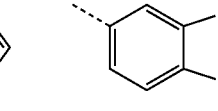 | |
| | 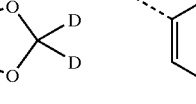 | 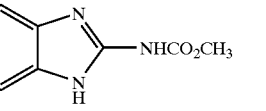 | | |

TABLE 11C
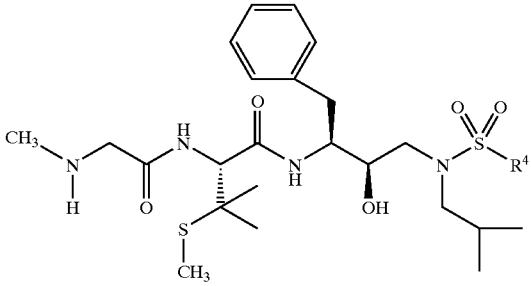
| Entry | R⁴ | | | |
|---|---|---|---|---|
| | 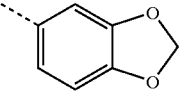 | 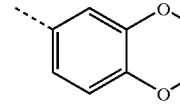 | 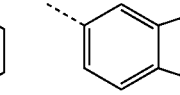 | 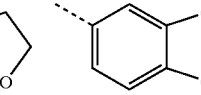 |
| | 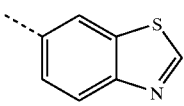 | 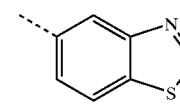 | 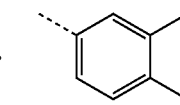 | 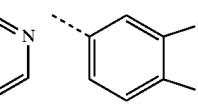 |
| | 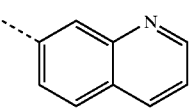 | 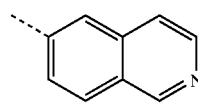 | 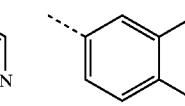 | 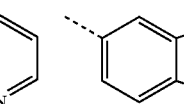 |
| | 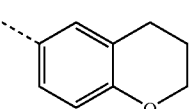 | 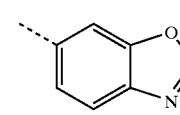 | 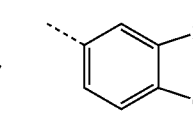 | 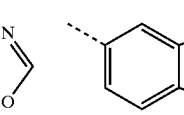 |
| | 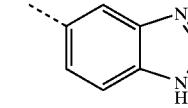 | 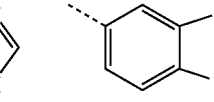 | 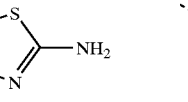 | |
| | 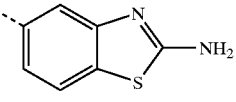 | 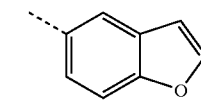 | 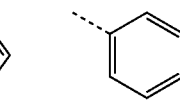 | |
| | 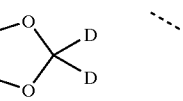 | 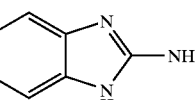 | | |

TABLE 11D
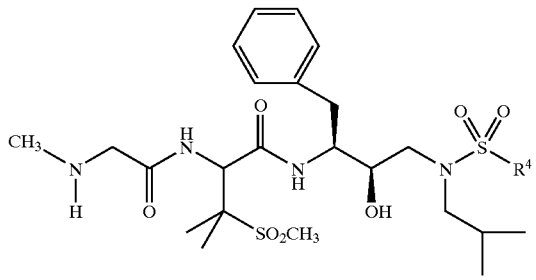
| Entry | R⁴ | | | |
|---|---|---|---|---|
| | 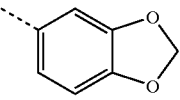 | 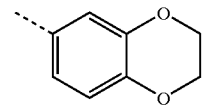 | 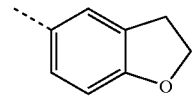 | 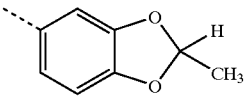 |
| | 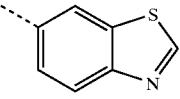 | 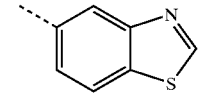 | 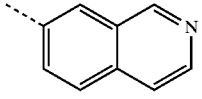 | 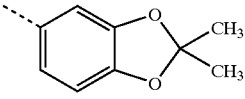 |
| | 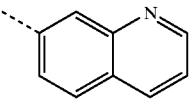 | 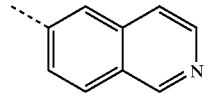 | 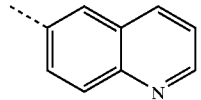 | 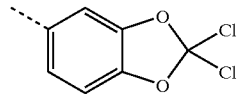 |
| | 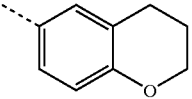 | 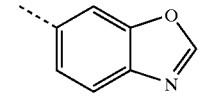 | 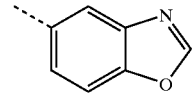 | 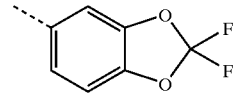 |
| | 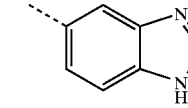 | 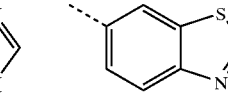 | 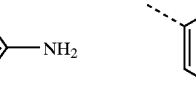 | |
| | 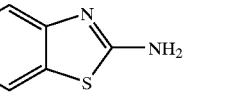 | 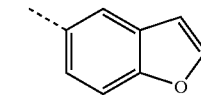 | 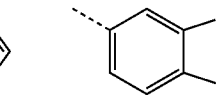 | |
| | 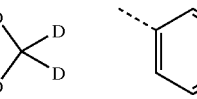 | 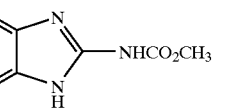 | | |

TABLE 11E

TABLE 11F

TABLE 12A
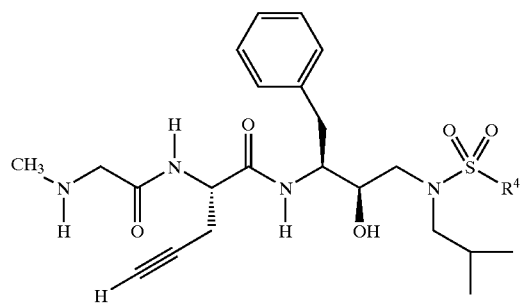

TABLE 12B

TABLE 12C
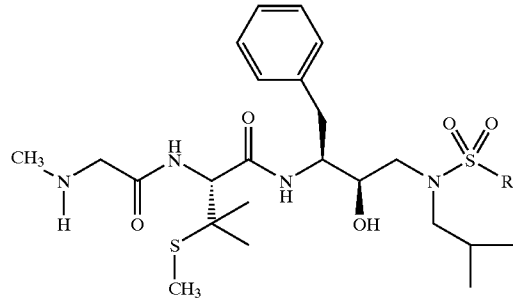
| Entry | R⁴ |
|---|---|
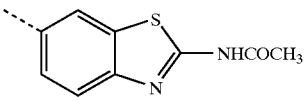 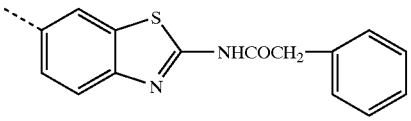
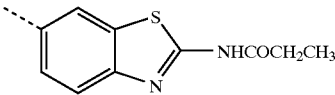 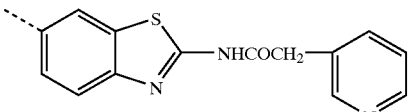
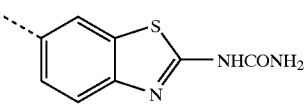 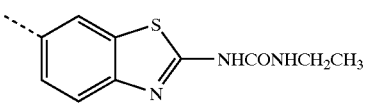
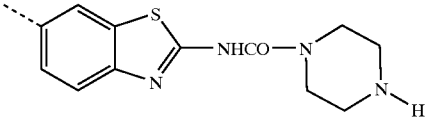 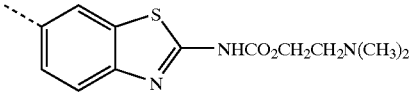
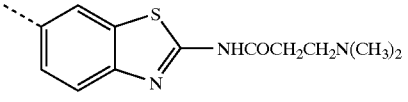 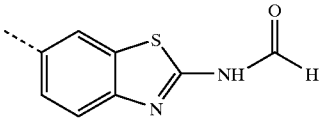
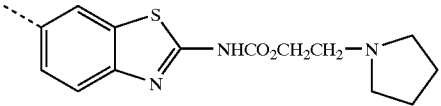 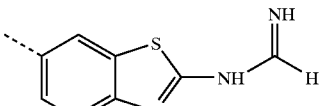
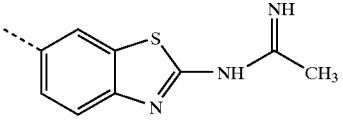 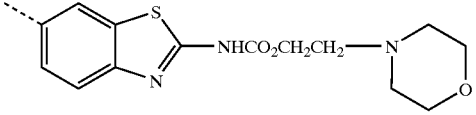
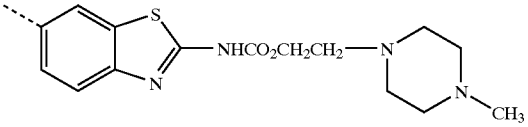 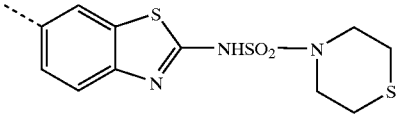
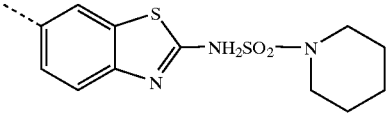 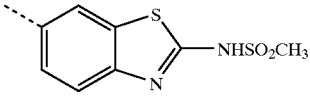

TABLE 12D

TABLE 12E

TABLE 12F

| Entry R⁴ (left) | R⁴ (right) |
|---|---|
| benzothiazol-6-yl-NHCOCH₃ | benzothiazol-6-yl-NHCOCH₂-phenyl |
| benzothiazol-6-yl-NHCOCH₂CH₃ | benzothiazol-6-yl-NHCOCH₂-(3-pyridyl) |
| benzothiazol-6-yl-NHCONH₂ | benzothiazol-6-yl-NHCONHCH₂CH₃ |
| benzothiazol-6-yl-NHCO-O-piperazin-1-yl | benzothiazol-6-yl-NHCO₂CH₂CH₂N(CH₃)₂ |
| benzothiazol-6-yl-NHCOCH₂CH₂N(CH₃)₂ | benzothiazol-6-yl-NH-CHO |
| benzothiazol-6-yl-NHCO₂CH₂CH₂-pyrrolidin-1-yl | benzothiazol-6-yl-NH-CH=NH |
| benzothiazol-6-yl-NH-C(=NH)CH₃ | benzothiazol-6-yl-NHCO₂CH₂CH₂-morpholin-4-yl |
| benzothiazol-6-yl-NHCO₂CH₂CH₂-(4-methylpiperazin-1-yl) | benzothiazol-6-yl-NHSO₂-thiomorpholin-4-yl |
| benzothiazol-6-yl-NH₂SO₂-piperidin-1-yl | benzothiazol-6-yl-NHSO₂CH₃ |

TABLE 13A
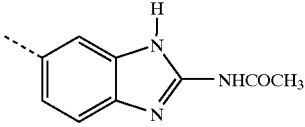
| Entry | R⁴ |
|---|---|
| 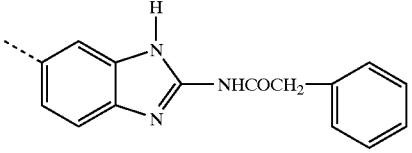 | 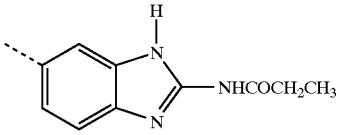 |
| 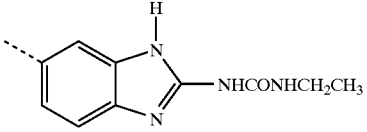 | 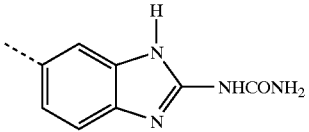 |
| 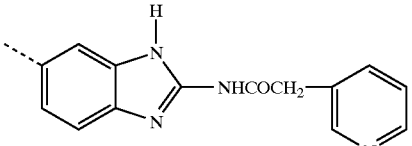 | 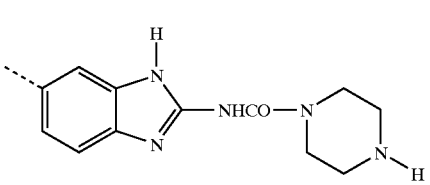 |
| 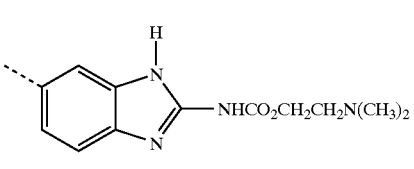 | 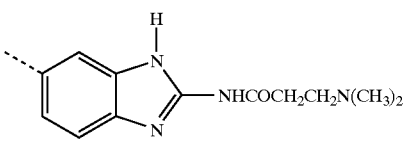 |
| 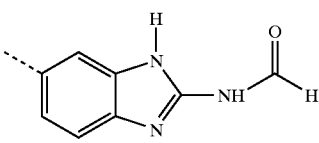 | 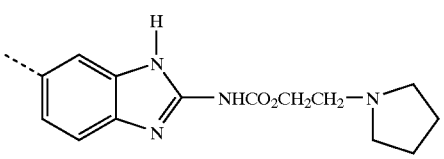 |
| 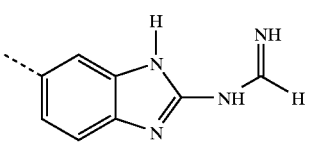 | 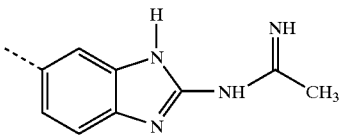 |
| 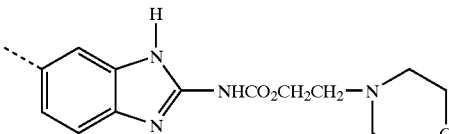 | |

TABLE 13A-continued

TABLE 13B

TABLE 13B-continued

| Entry | R⁴ |
|---|---|

TABLE 13C

TABLE 13C-continued

| Entry | R⁴ |
|---|---|

TABLE 13D

| Entry | R⁴ |
|---|---|

TABLE 13D-continued
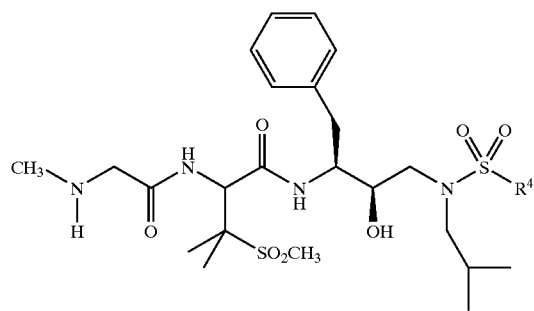
| Entry | R⁴ |
|---|---|

TABLE 13E

| Entry | R⁴ |
|---|---|
| | 6-(NHCOCH₃)-benzimidazol-2-yl |
| | 6-(NHCOCH₂Ph)-benzimidazol-2-yl |
| | 6-(NHCOCH₂CH₃)-benzimidazol-2-yl |
| | 6-(NHCONHCH₂CH₃)-benzimidazol-2-yl |
| | 6-(NHCONH₂)-benzimidazol-2-yl |
| | 6-(NHCOCH₂-(pyridin-3-yl))-benzimidazol-2-yl |
| | 6-(NHCO-piperazin-1-yl)-benzimidazol-2-yl |
| | 6-(NHCO₂CH₂CH₂N(CH₃)₂)-benzimidazol-2-yl |
| | 6-(NHCOCH₂CH₂N(CH₃)₂)-benzimidazol-2-yl |
| | 6-(NHCHO)-benzimidazol-2-yl |
| | 6-(NHCO₂CH₂CH₂-pyrrolidin-1-yl)-benzimidazol-2-yl |
| | 6-(NHCH=NH)-benzimidazol-2-yl |
| | 6-(NHC(=NH)CH₃)-benzimidazol-2-yl |
| | 6-(NHCO₂CH₂CH₂-morpholin-4-yl)-benzimidazol-2-yl |

TABLE 13E-continued

| Entry | R⁴ |
|---|---| benzimidazol-2-yl-NHCO₂CH₂CH₂-N(4-methylpiperazinyl)

benzimidazol-2-yl-NHSO₂-N(thiomorpholinyl)

benzimidazol-2-yl-NHSO₂-N(piperidinyl)

benzimidazol-2-yl-NHSO₂CH₃

TABLE 13F

| Entry | R⁴ |
|---|---| benzimidazol-2-yl-NHCOCH₃ benzimidazol-2-yl-NHCOCH₂-phenyl benzimidazol-2-yl-NHCOCH₂CH₃ benzimidazol-2-yl-NHCONHCH₂CH₃ benzimidazol-2-yl-NHCONH₂ benzimidazol-2-yl-NHCOCH₂-(pyridin-3-yl)

TABLE 13F-continued
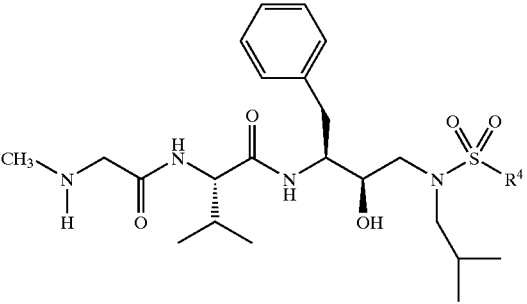
| Entry | R⁴ |
|---|---|
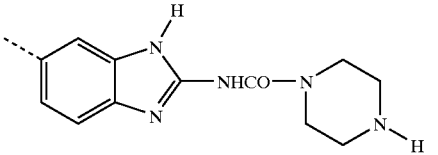 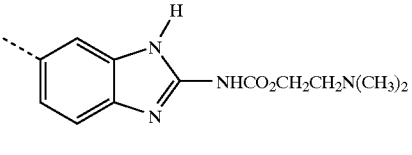
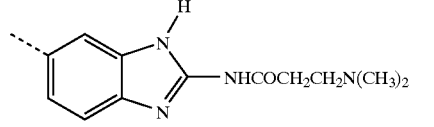 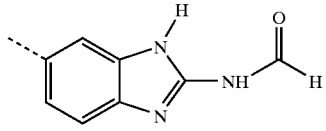
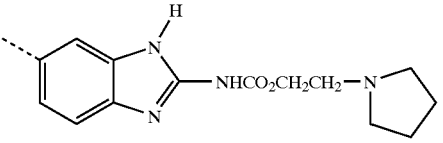 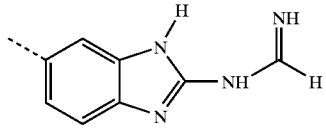
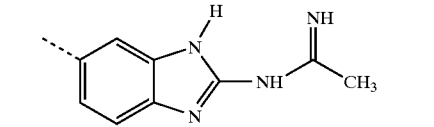 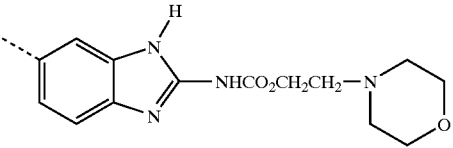
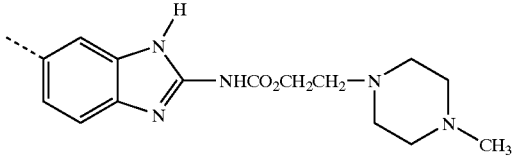 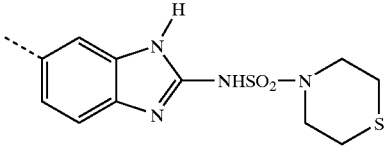
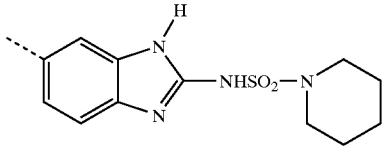 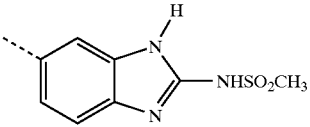

TABLE 14A

TABLE 14B
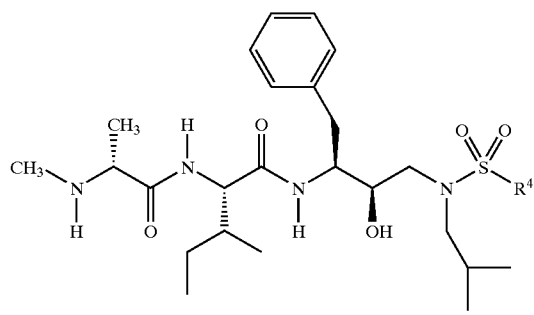
| Entry | R⁴ |
|---|---|

TABLE 14C

| Entry | R⁴ |
|---|---|

TABLE 14D
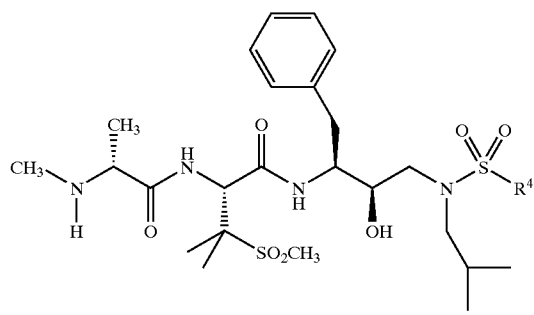
Entry      R⁴

TABLE 14E (Structure shown: a peptidomimetic core with CH₃NH-CH(CH₃)-C(O)-NH-CH(C(CH₃)₃)-C(O)-NH-CH(CH₂Ph)-CH(OH)-CH₂-N(iBu)-SO₂-R⁴)

| Entry | R⁴ |
|-------|-----|

R⁴ groups shown:
- benzo[1,3]dioxol-5-yl
- 2,3-dihydro-1,4-benzodioxin-6-yl
- 2,3-dihydrobenzofuran-5-yl
- 2-methyl-benzo[1,3]dioxol-5-yl (H, CH₃)
- benzothiazol-5-yl (S/N)
- benzothiazol-5-yl (N/S)
- isoquinolin-7-yl
- 2,2-dimethyl-benzo[1,3]dioxol-5-yl (CH₃, CH₃)
- quinolin-7-yl
- isoquinolin-6-yl
- quinolin-6-yl
- 2,2-dichloro-benzo[1,3]dioxol-5-yl (Cl, Cl)
- chroman-6-yl
- benzoxazol-5-yl
- benzoxazol-6-yl
- 2,2-difluoro-benzo[1,3]dioxol-5-yl (F, F)
- benzimidazol-5-yl
- 2-amino-benzothiazol-6-yl (NH₂)
- 2-amino-benzothiazol-5-yl (NH₂)
- benzofuran-5-yl
- 2,2-dideutero-benzo[1,3]dioxol-5-yl (D, D)
- 2-(NHCO₂CH₃)-benzimidazol-5-yl
- 2-(NHCO₂CH₃)-benzothiazol-6-yl
- 2-(NHCO₂CH₃)-benzothiazol-5-yl TABLE 14F
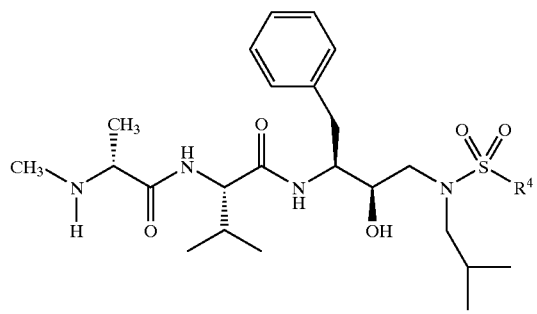
| Entry | R⁴ |
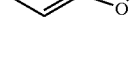 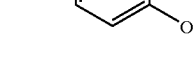 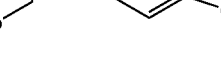 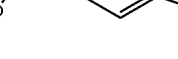
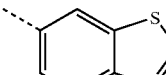   
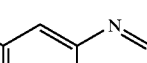 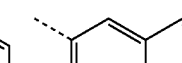  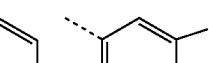
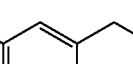 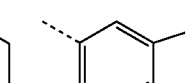 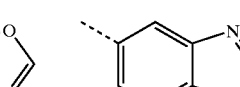 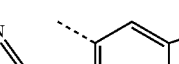
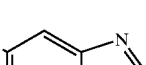 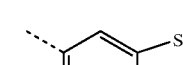 
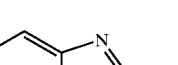 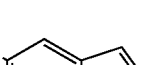 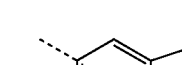
 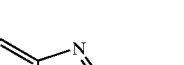

TABLE 15A
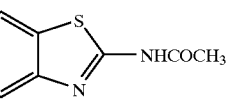
| Entry | R⁴ | | |
|---|---|---|---|
| | 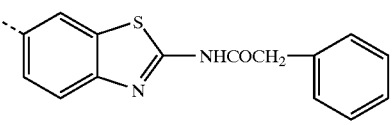 | |  |
| |  | |  |
| |  | | 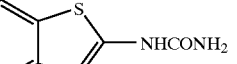 |
| | 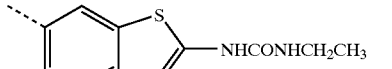 | |  |
| |  | |  |
| |  | |  |
| | 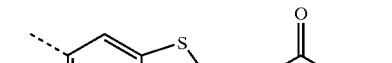 | |  |
| | 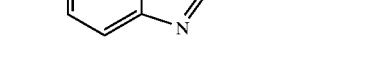 | |  |
| | 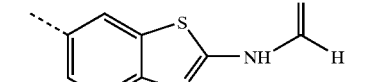 | |  |

TABLE 15B

| Entry | R⁴ | | R⁴ |
|---|---|---|---|
| | benzothiazol-6-yl-NHCOCH₃ | | benzothiazol-6-yl-NHCOCH₂-phenyl |
| | benzothiazol-6-yl-NHCOCH₂CH₃ | | benzothiazol-6-yl-NHCOCH₂-(pyridin-3-yl) |
| | benzothiazol-6-yl-NHCONH₂ | | benzothiazol-6-yl-NHCONHCH₂CH₃ |
| | benzothiazol-6-yl-NHCO-O-piperazinyl | | benzothiazol-6-yl-NHCO₂CH₂CH₂N(CH₃)₂ |
| | benzothiazol-6-yl-NHCOCH₂CH₂N(CH₃)₂ | | benzothiazol-6-yl-NH-CHO |
| | benzothiazol-6-yl-NHCO₂CH₂CH₂-pyrrolidinyl | | benzothiazol-6-yl-NH-C(=NH)H |
| | benzothiazol-6-yl-NH-C(=NH)CH₃ | | benzothiazol-6-yl-NHCO₂CH₂CH₂-morpholinyl |
| | benzothiazol-6-yl-NHCO₂CH₂CH₂-(4-methylpiperazin-1-yl) | | benzothiazol-6-yl-NHSO₂-thiomorpholinyl |
| | benzothiazol-6-yl-NHSO₂-piperidinyl | | benzothiazol-6-yl-NHSO₂CH₃ |

TABLE 15C
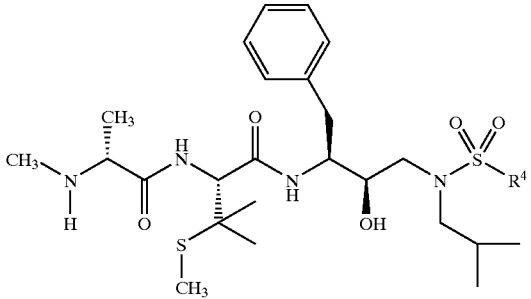
| Entry | R⁴ | | |
|---|---|---|---|
| | 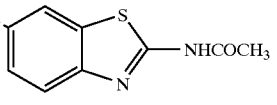 | | 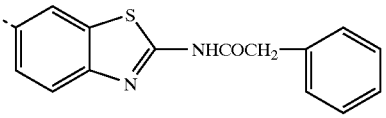 |
| | 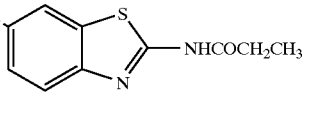 | | 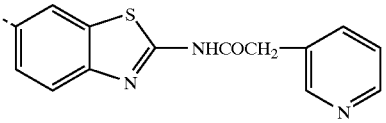 |
| | 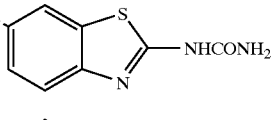 | | 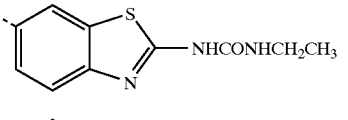 |
| |  | | 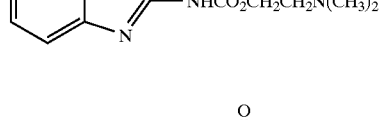 |
| |  | | 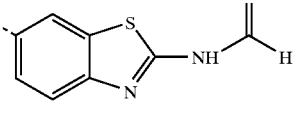 |
| | 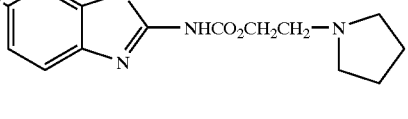 | | 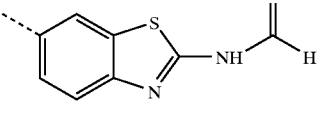 |
| | 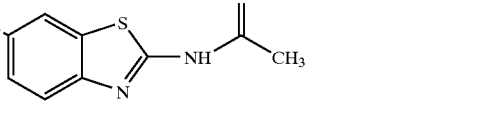 | | 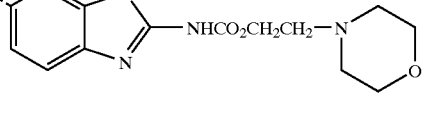 |
| | 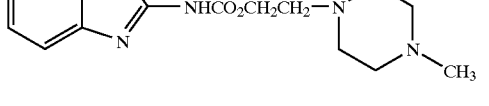 | | 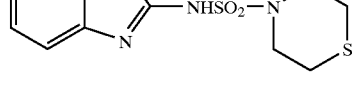 |
| | 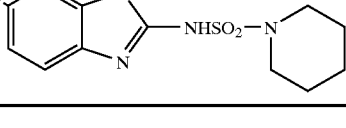 | | 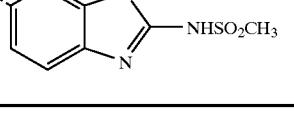 |

TABLE 15D

| Entry | R⁴ | | |
|---|---|---|---|
| | benzothiazol-6-yl-NHCOCH₃ | | benzothiazol-6-yl-NHCOCH₂-phenyl |
| | benzothiazol-6-yl-NHCOCH₂CH₃ | | benzothiazol-6-yl-NHCOCH₂-(3-pyridyl) |
| | benzothiazol-6-yl-NHCONH₂ | | benzothiazol-6-yl-NHCONHCH₂CH₃ |
| | benzothiazol-6-yl-NHCO-O-piperazin-1-yl | | benzothiazol-6-yl-NHCO₂CH₂CH₂N(CH₃)₂ |
| | benzothiazol-6-yl-NHCOCH₂CH₂N(CH₃)₂ | | benzothiazol-6-yl-NH-CHO |
| | benzothiazol-6-yl-NHCO₂CH₂CH₂-pyrrolidin-1-yl | | benzothiazol-6-yl-NH-C(=NH)H |
| | benzothiazol-6-yl-NH-C(=NH)CH₃ | | benzothiazol-6-yl-NHCO₂CH₂CH₂-morpholin-4-yl |
| | benzothiazol-6-yl-NHCO₂CH₂CH₂-(4-methylpiperazin-1-yl) | | benzothiazol-6-yl-NHSO₂-thiomorpholin-4-yl |
| | benzothiazol-6-yl-NHSO₂-piperidin-1-yl | | benzothiazol-6-yl-NHSO₂CH₃ |

TABLE 15E

| Entry | R⁴ | | R⁴ |
|---|---|---|---|
| | benzothiazol-2-yl-NHCOCH₃ | | benzothiazol-2-yl-NHCOCH₂-phenyl |
| | benzothiazol-2-yl-NHCOCH₂CH₃ | | benzothiazol-2-yl-NHCOCH₂-(pyridin-3-yl) |
| | benzothiazol-2-yl-NHCONH₂ | | benzothiazol-2-yl-NHCONHCH₂CH₃ |
| | benzothiazol-2-yl-NHCO-O-piperazin-1-yl | | benzothiazol-2-yl-NHCO₂CH₂CH₂N(CH₃)₂ |
| | benzothiazol-2-yl-NHCOCH₂CH₂N(CH₃)₂ | | benzothiazol-2-yl-NHCHO |
| | benzothiazol-2-yl-NHCO₂CH₂CH₂-pyrrolidin-1-yl | | benzothiazol-2-yl-NH-C(=NH)H |
| | benzothiazol-2-yl-NH-C(=NH)CH₃ | | benzothiazol-2-yl-NHCO₂CH₂CH₂-morpholin-4-yl |
| | benzothiazol-2-yl-NHCO₂CH₂CH₂-(4-methylpiperazin-1-yl) | | benzothiazol-2-yl-NHSO₂-thiomorpholin-4-yl |
| | benzothiazol-2-yl-NHSO₂-piperidin-1-yl | | benzothiazol-2-yl-NHSO₂CH₃ |

TABLE 15F

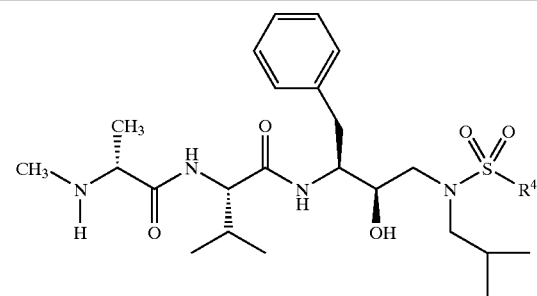

| Entry | R⁴ | | |
|---|---|---|---|
| | benzothiazol-6-yl-NHCOCH₃ | | benzothiazol-6-yl-NHCOCH₂-phenyl |
| | benzothiazol-6-yl-NHCOCH₂CH₃ | | benzothiazol-6-yl-NHCOCH₂-(3-pyridyl) |
| | benzothiazol-6-yl-NHCONH₂ | | benzothiazol-6-yl-NHCONHCH₂CH₃ |
| | benzothiazol-6-yl-NHCO-(piperazin-1-yl) | | benzothiazol-6-yl-NHCO₂CH₂CH₂N(CH₃)₂ |
| | benzothiazol-6-yl-NHCOCH₂CH₂N(CH₃)₂ | | benzothiazol-6-yl-NHCHO |
| | benzothiazol-6-yl-NHCO₂CH₂CH₂-(pyrrolidin-1-yl) | | benzothiazol-6-yl-NHC(=NH)H |
| | benzothiazol-6-yl-NHC(=NH)CH₃ | | benzothiazol-6-yl-NHCO₂CH₂CH₂-(morpholin-4-yl) |
| | benzothiazol-6-yl-NHCO₂CH₂CH₂-(4-methylpiperazin-1-yl) | | benzothiazol-6-yl-NHSO₂-(thiomorpholin-4-yl) |
| | benzothiazol-6-yl-NHSO₂-(piperidin-1-yl) | | benzothiazol-6-yl-NHSO₂CH₃ |

EXAMPLE 77

The compounds of the present invention are effective HIV protease inhibitors. Utilizing an enzyme assay as described below, the compounds set forth in the examples herein disclosed inhibited the HIV enzyme. The preferred compounds of the present invention and their calculated $IC_{50}$ (inhibiting concentration 50%, i.e., the concentration at which the inhibitor compound reduces enzyme activity by 50%) values are shown in Table 16. The enzyme method is described below. The substrate is 2-Ile-Nle-Phe(p-$NO_2$)-Gln-Arg$NH_2$. The positive control is MVT-101 (Miller, M. et al, *Science*, 246, 1149 (1989)] The assay conditions are as follows:

| Assay buffer: | 20 mM sodium phosphate, pH 6.4 |
|---|---|
| | 20% glycerol |
| | 1 mM EDTA |
| | 1 mM DTT |
| | 0.1% CHAPS |

The above described substrate is dissolved in DMSO, then diluted 10 fold in assay buffer. Final substrate concentration in the assay is 80 $\mu$M. HIV protease is diluted in the assay buffer to a final enzyme concentration of 12.3 nanomolar, based on a molecular weight of 10,780.

The final concentration of DMSO is 14% and the final concentration of glycerol is 18%. The test compound is dissolved in DMSO and diluted in DMSO to 10× the test concentration; 10 $\mu$l of the enzyme preparation is added, the materials mixed and then the mixture is incubated at ambient temperature for 15 minutes. The enzyme reaction is initiated by the addition of 40 $\mu$l of substrate. The increase in fluorescence is monitored at 4 time points (0, 8, 16 and 24 minutes) at ambient temperature. Each assay is carried out in duplicate wells.

The preceding examples can be repeated with similar success by substituting the generically or specifically described reactants and/or operating conditions of this invention for those used in the preceding examples.

EXAMPLE 78

The effectiveness of various compounds were determined in the above-described enzyme assay and in a CEM cell assay.

The HIV inhibition assay method of acutely infected cells is an automated tetrazolium based colorimetric assay essentially that reported by Pauwles et al, *J. Virol. Methods*, 20, 309–321 (1988). Assays were performed in 96-well tissue culture plates. CEM cells, a CD4+ cell line, were grown in RPMI-1640 medium (Gibco) supplemented with a 10% fetal calf serum and were then treated with polybrene (2 $\mu$l/ml).

An 80 $\mu$l volume of medium containing $1\times10^4$ cells was dispensed into each well of the tissue culture plate. To each well was added a 100 $\mu$l volume of test compound dissolved in tissue culture medium (or medium without test compound as a control) to achieve the desired final concentration and the cells were incubated at 37° C. for 1 hour. A frozen culture of HIV-1 was diluted in culture medium to a concentration of $5\times10^4$ $TCID_{50}$ per ml ($TCID_{50}$=the dose of virus that infects 50% of cells in tissue culture), and a 20 $\mu$L volume of the virus sample (containing 1000 $TCID_{50}$ of virus) was added to wells containing test compound and to wells containing only medium (infected control cells). Several wells received culture medium without virus (uninfected control cells). Likewise, the intrinsic toxicity of the test compound was determined by adding medium without virus to several wells containing test compound. In summary, the tissue culture plates contained the following experiments:

| | Cells | Drug | Virus |
|---|---|---|---|
| 1. | + | − | − |
| 2. | + | + | − |
| 3. | + | − | + |
| 4. | + | + | + |

In experiments 2 and 4 the final concentrations of test compounds were 1, 10, 100 and 500 $\mu$g/ml. Either azidothymidine (AZT) or dideoxyinosine (ddI) was included as a positive drug control. Test compounds were dissolved in DMSO and diluted into tissue culture medium so that the final DMSO concentration did not exceed 1.5% in any case. DMSO was added to all control wells at an appropriate concentration.

Following the addition of virus, cells were incubated at 37° C. in a humidified, 5% $CO_2$ atmosphere for 7 days. Test compounds could be added on days 0, 2 and 5 if desired. On day 7, post-infection, the cells in each well were resuspended and a 100 $\mu$l sample of each cell suspension was removed for assay. A 20 $\mu$L volume of a 5 mg/ml solution of 3-(4,5-dimethylthiazol-2-yl)-2,5-diphenyltetrazolium bromide (MTT) was added to each 100 $\mu$L cell suspension, and the cells were incubated for 4 hours at 27° C. in a 5% $CO_2$ environment. During this incubation, MTT is metabolically reduced by living cells resulting in the production in the cell of a colored formazan product. To each sample was added 100 $\mu$l of 10% sodium dodecylsulfate in 0.01 N HCl to lyse the cells, and samples were incubated overnight. The absorbance at 590 nm was determined for each sample using a Molecular Devices microplate reader. Absorbance values for each set of wells is compared to assess viral control infection, uninfected control cell response as well as test compound by cytotoxicity and antiviral efficacy.

TABLE 16
| Entry | Compound | IC$_{50}$ (nM) | EC$_{50}$ (nM) |
|---|---|---|---|
| 1 | 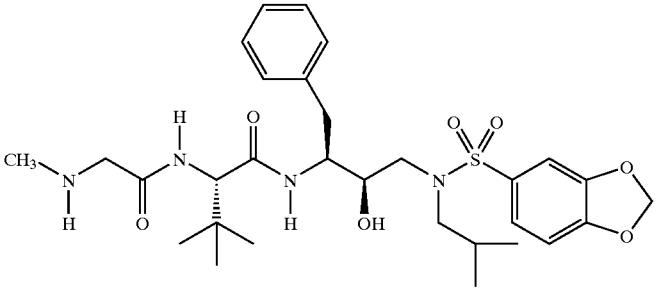 | 2 | 18 |
| 2 | 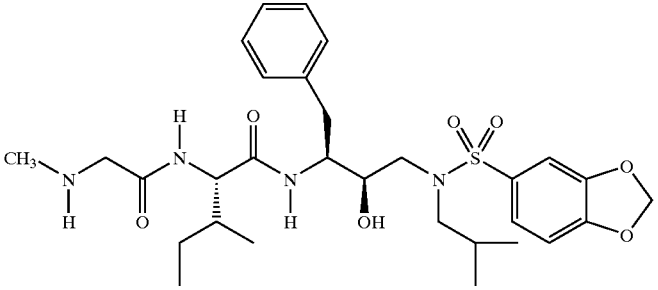 | 2 | 35 |
| 3 | 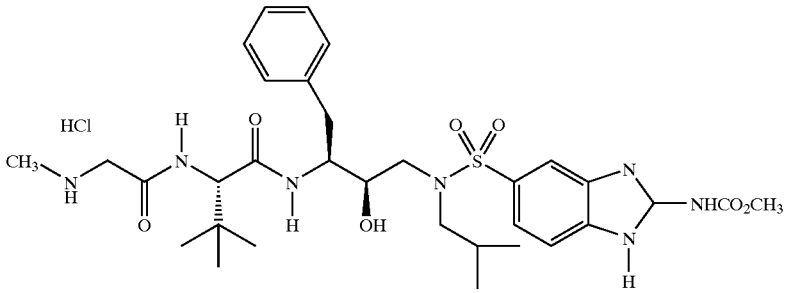 | 2 | |
| 4 | 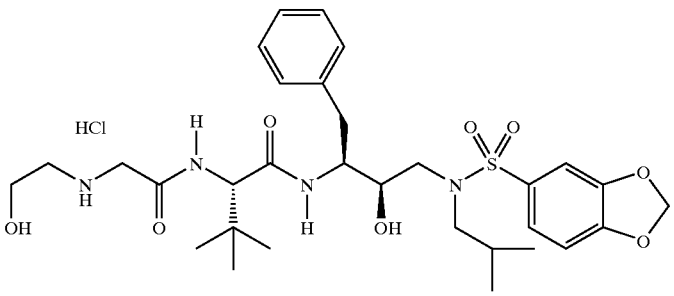 | 2 | 85 |
| 5 | 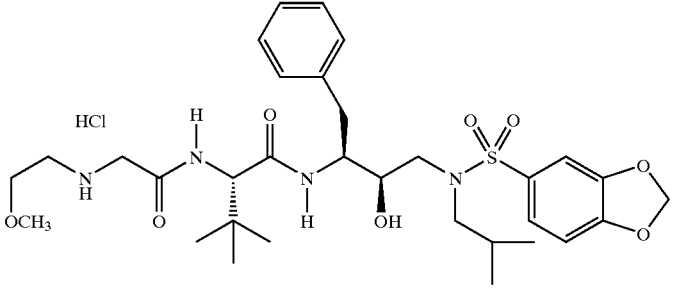 | 2 | 10 |

TABLE 16-continued

| Entry | Compound | IC$_{50}$ (nM) | EC$_{50}$ (nM) |
|---|---|---|---|
| 6 | | 3 | 24 |
| 7 | | 2 | 8 |
| 8 | | 2 | |
| 9 | | 3 | 17 |
| 10 | | 2 | 22 |

TABLE 16-continued

| Entry | Compound | IC$_{50}$ (nM) | EC$_{50}$ (nM) |
|---|---|---|---|
| 11 | | | 1 |
| 12 | | | 2 |
| 13 | | | 3 |
| 14 | | | 2 |
| 15 | | | 2 |

TABLE 16-continued

| Entry | Compound | IC$_{50}$ (nM) | EC$_{50}$ (nM) |
|---|---|---|---|
| 16 | | | 2 |
| 17 | | | 2 |
| 18 | | | 2 |
| 19 | | | 3 |

The compounds of the present invention are effective antiviral compounds and, in particular, are effective retroviral inhibitors as shown above. Thus, the subject compounds are effective HIV protease inhibitors. It is contemplated that the subject compounds will also inhibit other retroviruses such as other lentiviruses in articular other strains of HIV, e.g. HIV-2, human T-cell leukemia virus, respiratory syncitial virus, simia immunodeficiency virus, feline leukemia virus, feline immuno-deficiency virus, hepadnavirus, cytomegalovirus and picornavirus. Thus, the subject compounds are effective in the treatment, priplylaxis of retroviral infections and/or the prevention of the spread of retroviral infections.

The subject compounds are also effective in preventing the growth of retroviruses in a solution. Both human and animal cell cultures, such as T-lymphocyte cultures, are utilized for a variety of well known purposes, such as research and diagnostic procedures including calibrators and controls. Prior to and during the growth and storage of a cell culture, the subject compounds may be added to the cell culture medium at an effective concentration to prevent the unexpected or undesired replication of a retrovirus that may inadvertently, unknowingly or knowingly be present in the cell culture. The virus may be present originally in the cell culture, for example HIV is known to be present in human T-lymphocytes long before it is detectable in blood, or through exposure to the virus. This use of the subject compounds prevents the unknowing or inadvertent exposure of a potentially lethal retrovirus to a researcher or clinician.

Compounds of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose. The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more immunomodulators, antiviral agents or other antiinfective agents. For example, the compounds of the invention can be administered in combination with AZT, DDI, DDC or with glucosidase inhibitors, such as N-butyl-1-deoxynojirimycin or prodrugs thereof, for the prophylaxis and/or treatment of AIDS. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims. From the foregoing description, one skilled in the art can easily ascertain the essential characteristics of this invention, and without departing from the spirit and scope thereof, can make various changes and modifications of the invention to adapt it to various usages and conditions.

What is claimed is:

1. Compound represented by the formula:

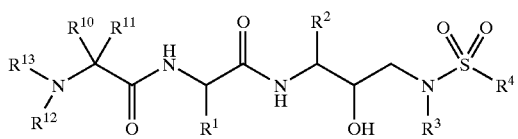

or a pharmaceutically acceptable salt, prodrug or ester thereof, wherein $R^1$ represents alkyl of 1–5 carbon atoms, alkenyl of 2–5 carbon atoms, alkynyl of 2–5 carbon atoms, hydroxyalkyl of 1–3 carbon atoms, alkoxyalkyl of 1–3 alkyl and 1–3 alkoxy carbon atoms, cyanoalkyl of 1–3 alkyl carbon atoms, imidazolylmethyl, —CH$_2$CONH$_2$, —CH$_2$CH$_2$CONH$_2$, —CH$_2$S(O)$_2$NH$_2$, —CH$_2$SCH$_3$, —CH$_2$S(O)CH$_3$, —CH$_2$S(O)$_2$CH$_3$, —C(CH$_3$)$_2$SCH$_3$, —C(CH$_3$)$_2$S(O)CH$_3$ or —C(CH$_3$)$_2$S(O)$_2$CH$_3$ radicals;

$R^2$ represents radicals of alkyl of 1–5 carbon atoms, aralkyl of 1–3 alkyl carbon atoms, alkylthioalkyl of 1–3 alkyl carbon atoms, arylthioalkyl of 1–3 alkyl carbon atoms or cycloalkylalkyl of 1–3 alkyl carbon atoms and 3–6 ring member carbon atoms;

$R^3$ represents radicals of alkyl radical of 1–5 carbon atoms, cycloalkyl of 5–8 ring members or cycloalkylmethyl radical of 3–6 ring members;

$R^{10}$ represents hydrogen, alkyl, hydroxyalkyl or alkoxyalkyl radicals, wherein alkyl and alkoxy are each 1–3 carbon atoms;

$R^{11}$ represents alkyl of 1–5 carbon atoms, hydroxyalkyl of 1–4 carbon atoms, alkoxyalkyl of 1–4 alkyl carbon atoms, benzyl, imidazolylmethyl, —CH$_2$CH$_2$CONH$_2$, —CH$_2$CONH$_2$, —CH$_2$CH$_2$SCH$_3$ or —CH$_2$SCH$_3$ radicals or the sulfone or sulfoxide derivatives thereof;

$R^4$ represents aryl; and, $R^{12}$ and $R^{13}$ each independently represent hydrogen, alkyl, aralkyl, heteroaralkyl, cycloalkyl, cycloalkylalkyl, hydroxyalkyl, alkoxyalkyl, aryl or heteroaryl radicals, wherein alkyl is 1–5 carbon atoms, cycloalkyl is 3–6 ring membered cycloalkyl optionally benzo fused, and heteroaryl is 5 to 6 ring membered heteroaryl optionally benzo fused.

2. Compound of claim 1, or a pharmaceutically acceptable salt, prodrug or ester thereof, wherein $R^1$ represents alkyl of 1–4 carbon atoms, alkenyl of 2–3 carbon atoms, alkynyl of 3–4 carbon atoms, cyanomethyl, imidazolylmethyl, —CH$_2$CONH$_2$, —CH$_2$CH$_2$CONH$_2$, —CH$_2$S(O)$_2$NH$_2$, —CH$_2$SCH$_3$, —CH$_2$S(O)CH$_3$, —CH$_2$S(O)$_2$CH$_3$, —C(CH$_3$)$_2$SCH$_3$, —C(CH$_3$)$_2$S(O)CH$_3$ or —C(CH$_3$)$_2$S(O)$_2$CH$_3$ radicals;

$R^2$ represents radicals of alkyl of 3–5 carbon atoms, arylmethyl, alkylthioalkyl of 1–3 alkyl carbon atoms, arylthiomethyl or cycloalkylmethyl of 5–6 ring member carbon atoms radicals;

$R^3$ represents alkyl of 1–5 carbon atoms, cycloalkylmethyl of 3–6 ring members, cyclohexyl, or cycloheptyl radicals; and, $R^{12}$ and $R^{13}$ each independently represent hydrogen, alkyl of 1–5 carbon atoms, phenylalkyl of 1–3 alkyl carbon atoms, 5 to 6 ring member heteroaralkyl of 1–3 alkyl carbon atoms, cycloalkyl of 3–6 ring members, cycloalkylmethyl of 3–6 ring members, hydroxyalkyl of 1–3 carbon atoms, methoxyalkyl of 1–3 alkyl carbon atoms or phenyl radicals.

3. Compound of claim 2, or a pharmaceutically acceptable salt, prodrug or ester thereof, wherein $R^1$ represents iso-propyl, sec-butyl, tert-butyl, 3-propynyl, cyanomethyl, imidazolylmethyl, —CH$_2$CONH$_2$, —CH$_2$SCH$_3$, —CH$_2$S(O)CH$_3$, —CH$_2$S(O)$_2$CH$_3$, —C(CH$_3$)$_2$SCH$_3$, —C(CH$_3$)$_2$S(O)CH$_3$, or —C(CH$_3$)$_2$S(O)$_2$CH$_3$ radicals;

$R^2$ represents isobutyl, n-butyl, CH$_3$SCH$_2$CH$_2$—, phenylthiomethyl, (2-naphthylthio)methyl, benzyl, 4-methoxyphenylmethyl, 4-hydroxyphenylmethyl, 4-fluorophenylmethyl, or cyclohexylmethyl radicals;

$R^3$ represents propyl, isoamyl, isobutyl, butyl, cyclohexyl, cycloheptyl, cyclopentylmethyl, or cyclohexylmethyl radicals;

$R^{10}$ represents hydrogen, methyl, ethyl, propyl, methoxymethyl, methoxyethyl, hydroxymethyl or hydroxyethyl radicals;

$R^{11}$ represents methyl, ethyl, propyl, isopropyl, butyl, secbutyl, isobutyl, tertbutyl, hydroxymethyl, hydroxyethyl, methoxymethyl or methoxyethyl radicals; and, $R^{12}$ and $R^{13}$ each independently represent hydrogen, methyl, ethyl, propyl, isopropyl, cyclopropyl, cyclobutyl, cyclopentyl, cyclohexyl, cyclohexylmethyl, benzyl, phenylmethyl, 2-pyridylmethyl, 3-pyridylmethyl, 4-pyridylmethyl, 2-(2-pyridyl)ethyl, 2-(3-pyridyl)ethyl, 2-(4-pyridyl)ethyl, furylmethyl, 2-furylethyl, 2-hydroxyethyl, 2-methoxyethyl or phenyl radicals.

4. Compound of claim 3, or a pharmaceutically acceptable salt, prodrug or ester thereof, wherein n represents 1;

$R^1$ represents sec-butyl, tert-butyl, iso-propyl, 3-propynyl, cyanomethyl, or —C(CH$_3$)$_2$S(O)$_2$CH$_3$ radicals;

$R^2$ represents benzyl, 4-fluorophenylmethyl, or cyclohexylmethyl radicals;

$R^{10}$ represents hydrogen, methyl, or ethyl radicals;

$R^{11}$ represents methyl or ethyl radicals;

$R^{12}$ represents hydrogen or methyl radicals; and, $R^{13}$ represents hydrogen, methyl, ethyl, propyl, cyclopropyl, isopropyl, benzyl, 2-phenylmethyl, 2-pyridylmethyl, 3-pyridylmethyl, 4-pyridylmethyl, 2-(2-pyridyl)ethyl, 2-(3-pyridyl)ethyl, 2-(4-pyridyl)ethyl, furylmethyl, 2-furylethyl or 2-methoxyethyl radicals.

5. Compound of claim 1 wherein said pharmaceutically acceptable salt is hydrochloric acid salt, sulphuric acid salt, phosphoric acid salt, oxalic acid salt, maleic acid salt, succinic acid salt, citric acid salt or methanesulfonic acid salt.

6. Compound of claim 5 wherein said pharmaceutically acceptable salt is hydrochloric acid salt, oxalic acid salt, citric acid salt or methanesulfonic acid salt.

7. Compound of claim 1 wherein the absolute stereochemistry about the hydroxyl group is designated as (R).

8. Compound of claim 7 wherein the absolute stereochemistry about the $R^2$ substituent is designated as (S).

9. Compound of claim 8 wherein the absolute stereochemistry about the $R^1$ substituent is designated as (S).

10. Composition comprising a compound of claim 1 and a pharmaceutically acceptable carrier.

11. Method of inhibiting, a retroviral protease comprising administering an effective amount of a compound of claim 1.

12. Method of treating a retroviral infection comprising administering an effective amount of a composition of claim 10.

13. Method of preventing replication of a retrovirus comprising administering an effective amount of a compound of claim 1.

14. Method of preventing replication of a retrovirus in vitro comprising administering an effective amount of a compound of claim 1.

15. Method of treating AIDS comprising administering an effective amount of a composition of claim 10.

16. Compound represented by the formula:

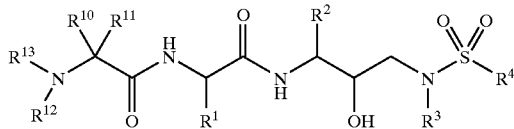

or a pharmaceutically acceptable salt thereof, wherein
$R^1$ represents alkyl of 1–5 carbon atoms, alkenyl of 2–5 carbon atoms, alkynyl of 2–5 carbon atoms, hydroxyalkyl of 1–3 carbon atoms, alkoxyalkyl of 1–3 alkyl and 1–3 alkoxy carbon atoms, cyanoalkyl of 1–3 alkyl carbon atoms, imidazolylmethyl, —$CH_2CONH_2$, —$CH_2CH_2CONH_2$, —$CH_2S(O)_2NH_2$, —$CH_2SCH_3$, —$CH_2S(O)CH_3$, —$CH_2S(O)_2CH_3$, —$C(CH_3)_2SCH_3$, —$C(CH_3)_2S(O)CH_3$ or —$C(CH_3)_2S(O)_2CH_3$ radicals;

$R^2$ represents radicals of alkyl of 1–5 carbon atoms, aralkyl of 1–3 alkyl carbon atoms, alkylthioalkyl of 1–3 alkyl carbon atoms, arylthioalkyl of 1–3 alkyl carbon atoms or cycloalkylalkyl of 1–3 alkyl carbon atoms and 3–6 ring member carbon atoms;

$R^3$ represents radicals of alkyl radical of 1–5 carbon atoms, cycloalkyl of 5–8 ring members or cycloalkylmethyl radical of 3–6 ring members;

$R^{10}$ represents hydrogen, alkyl, hydroxyalkyl or alkoxyalkyl radicals, wherein alkyl and alkoxy are each 1–3 carbon atoms;

$R^{11}$ represents alkyl of 1–5 carbon atoms, hydroxyalkyl of 1–4 carbon atoms, alkoxyalkyl of 1–4 alkyl carbon atoms, benzyl, imidazolylmethyl, —$CH_2CH_2CONH_2$, —$CH_2CONH_2$, —$CH_2CH_2SCH_3$ or —$CH_2SCH_3$ radicals or the sulfone or sulfoxide derivatives thereof;

$R^4$ represents aryl; and, $R^{12}$ and $R^{13}$ each independently represent hydrogen, alkyl, aralkyl, heteroaralkyl, cycloalkyl, cycloalkylalkyl, hydroxyalkyl, alkoxyalkyl, aryl or heteroaryl radicals, wherein alkyl is 1–5 carbon atoms, cycloalkyl is 3–6 ring membered cycloalkyl optionally benzo fused, and heteroaryl is 5 to 6 ring membered heteroaryl optionally benzo fused.

17. Compound of claim 16, or a pharmaceutically acceptable salt thereof, wherein $R^1$ represents alkyl of 1–4 carbon atoms, alkenyl of 2–3 carbon atoms, alkynyl of 3–4 carbon atoms, cyanomethyl, imidazolylmethyl, —$CH_2CONH_2$, —$CH_2CH_2CONH_2$, —$CH_2S(O)_2NH_2$, —$CH_2SCH_3$, —$CH_2S(O)CH_3$, —$CH_2S(O)_2CH_3$, —$C(CH_3)_2SCH_3$, —$C(CH_3)_2S(O)CH_3$ or —$C(CH_3)_2S(O)_2CH_3$ radicals;

$R^2$ represents radicals of alkyl of 3–5 carbon atoms, arylmethyl, alkylthioalkyl of 1–3 alkyl carbon atoms, arylthiomethyl or cycloalkylmethyl of 5–6 ring member carbon atoms radicals;

$R^3$ represents alkyl of 1–5 carbon atoms, cycloalkylmethyl of 3–6 ring members, cyclohexyl, or cycloheptyl radicals; and, $R^{12}$ and $R^{13}$ each independently represent hydrogen, alkyl of 1–5 carbon atoms, phenylalkyl of 1–3 alkyl carbon atoms, 5 to 6 ring member heteroaralkyl of 1–3 alkyl carbon atoms, cycloalkyl of 3–6 ring members, cycloalkylmethyl of 3–6 ring members, hydroxyalkyl of 1–3 carbon atoms, methoxyalkyl of 1–3 alkyl carbon atoms or phenyl radicals.

18. Compound of claim 17, or a pharmaceutically acceptable salt thereof, wherein $R^1$ represents iso-propyl, sec-butyl, tert-butyl, 3-propynyl, cyanomethyl, imidazolylmethyl, —$CH_2CONH_2$, —$CH_2SCH_3$, —$CH_2S(O)CH_3$, —$CH_2S(O)_2CH_3$, —$C(CH_3)_2SCH_3$, —$C(CH_3)_2S(O)CH_3$, or —$C(CH_3)_2S(O)_2CH_3$ radicals;

$R^2$ represents isobutyl, n-butyl, $CH_3SCH_2CH_2$—, phenylthiomethyl, (2-naphthylthio)methyl, benzyl, 4-methoxyphenylmethyl, 4-hydroxyphenylmethyl, 4-fluorophenylmethyl, or cyclohexylmethyl radicals;

$R^3$ represents propyl, isoamyl, isobutyl, butyl, cyclohexyl, cycloheptyl, cyclopentylmethyl, or cyclohexylmethyl radicals;

$R^{10}$ represents hydrogen, methyl, ethyl, propyl, methoxymethyl, methoxyethyl, hydroxymethyl or hydroxyethyl radicals;

$R^{11}$ represents methyl, ethyl, propyl, isopropyl, butyl, secbutyl, isobutyl, tertbutyl, hydroxymethyl, hydroxyethyl, methoxymethyl or methoxyethyl radicals; and, $R^{12}$ and $R^{13}$ each independently represent hydrogen, methyl, ethyl, propyl, isopropyl, cyclopropyl, cyclobutyl, cyclopentyl, cyclohexyl, cyclohexylmethyl, benzyl, phenylmethyl, 2-pyridylmethyl, 3-pyridylmethyl, 4-pyridylmethyl, 2-(2-pyridyl)ethyl, 2-(3-pyridyl)ethyl, 2-(4-pyridyl)ethyl, furylmethyl, 2-furylethyl, 2-hydroxyethyl, 2-methoxyethyl or phenyl radicals.

19. Compound of claim 18, or a pharmaceutically acceptable salt thereof, wherein n represents 1;

$R^1$ represents sec-butyl, tert-butyl, iso-propyl, 3-propynyl, cyanomethyl, or —$C(CH_3)_2S(O)_2CH_3$ radicals;

$R^2$ represents benzyl, 4-fluorophenylmethyl, or cyclohexylmethyl radicals;

$R^{10}$ represents hydrogen, methyl, or ethyl radicals;

$R^{11}$ represents methyl or ethyl radicals;

$R^{12}$ represents hydrogen or methyl radicals; and, $R^{13}$ represents hydrogen, methyl, ethyl, propyl, cyclopropyl, isopropyl, benzyl, 2-phenylmethyl, 2-pyridylmethyl, 3-pyridylmethyl, 4-pyridylmethyl, 2-(2-pyridyl)ethyl, 2-(3-pyridyl)ethyl, 2-(4-pyridyl)ethyl, furylmethyl, 2-furylethyl or 2-methoxyethyl radicals.

20. Compound of claim 16 wherein the absolute stereochemistry about the hydroxyl group is designated as (R).

21. Compound of claim 20 wherein the absolute stereochemistry about the $R^2$ substituent is designated as (S).

22. Compound of claim 21 wherein the absolute stereochemistry about the $R^2$ substituent is designated as (S).

23. Composition comprising a compound of claim 16, or a pharmaceutically acceptable salt thereof, and a pharmaceutically acceptable carrier.

24. Method of inhibiting a retroviral protease comprising administering an effective amount of a compound of claim 16 or a pharmaceutically acceptable salt thereof.

25. Method of treating a retroviral infection comprising administering an effective amount of a composition of claim 24.

26. Method of preventing replication of a retrovirus comprising administering an effective amount of a compound of claim 16, or a pharmaceutically acceptable salt thereof.

27. Method of preventing replication of a retrovirus in vitro comprising administering an effective amount of a compound of claim 16, or a pharmaceutically acceptable salt thereof.

28. Method of treating AIDS comprising administering an effective amount of a composition of claim 23.

* * * * *

UNITED STATES PATENT AND TRADEMARK OFFICE
CERTIFICATE OF CORRECTION

PATENT NO. : 6,683,210 B2
DATED : January 27, 2004
INVENTOR(S) : Daniel P. Getman et al.

It is certified that error appears in the above-identified patent and that said Letters Patent is hereby corrected as shown below:

Title page,
Item [56], References Cited, OTHER PUBLICATIONS, please insert
McQuade et al., *Science*, 274, 454 --

Column 263,
Line 10, please replace "$R^2$" with -- $R^1$ --

Signed and Sealed this

Thirty-first Day of August, 2004

JON W. DUDAS
*Director of the United States Patent and Trademark Office*